US012534496B2

(12) United States Patent
Olmstead et al.

(10) Patent No.: US 12,534,496 B2
(45) **Date of Patent: *Jan. 27, 2026**

(54) POLYMORPHIC FORMS OF CYCLO (-HIS-PRO) AND METHODS OF USE TO TREAT KIDNEY DISEASE

(71) Applicant: NovMetaPharma Co., Ltd., Seoul (KR)

(72) Inventors: Kay Olmstead, San Diego, CA (US); David Pearson, Lauder (GB); Elaine Mcpherson, Edinburgh (GB)

(73) Assignee: NovMetaPharma Co., Ltd., Seoul (KR)

(*) Notice: Subject to any disclaimer, the term of this patent is extended or adjusted under 35 U.S.C. 154(b) by 0 days.

This patent is subject to a terminal disclaimer.

(21) Appl. No.: 18/377,656

(22) Filed: Oct. 6, 2023

(65) Prior Publication Data

US 2024/0043472 A1 Feb. 8, 2024

Related U.S. Application Data

(63) Continuation of application No. 16/901,676, filed on Jun. 15, 2020, now Pat. No. 11,820,834, which is a continuation-in-part of application No. 16/448,083, filed on Jun. 21, 2019, now Pat. No. 10,683,300.

(60) Provisional application No. 62/696,190, filed on Jul. 10, 2018.

(51) Int. Cl.

| | |
|---|---|
| ***C07K 5/12*** | (2006.01) |
| ***A61K 9/19*** | (2006.01) |
| ***A61K 47/02*** | (2006.01) |

(52) U.S. Cl.
CPC .................. *C07K 5/12* (2013.01); *A61K 9/19* (2013.01); *A61K 47/02* (2013.01)

(58) Field of Classification Search
CPC ........................................................ C07K 5/12
See application file for complete search history.

(56) References Cited

U.S. PATENT DOCUMENTS

| | | | |
|---|---|---|---|
| 6,090,780 A | 7/2000 | Prasad | |
| 7,202,279 B1 | 4/2007 | Kozikowski et al. | |
| 10,683,300 B2 * | 6/2020 | Olmstead | C07D 487/04 |
| 11,820,834 B2 * | 11/2023 | Olmstead | A61K 9/19 |
| 2007/0161640 A1 | 7/2007 | Kozikowski et al. | |
| 2009/0004291 A1 | 1/2009 | Song et al. | |
| 2009/0297616 A1 | 12/2009 | Posten | |
| 2010/0144624 A1 | 6/2010 | Sinisterramillán et al. | |
| 2013/0331344 A1 | 12/2013 | Tsuruoka et al. | |
| 2020/0017509 A1 | 1/2020 | Olmstead et al. | |
| 2020/0237815 A1 | 7/2020 | Martin | |
| 2022/0193073 A1 | 6/2022 | Jung et al. | |

FOREIGN PATENT DOCUMENTS

| | | | |
|---|---|---|---|
| JP | 2003-525850 | A | 9/2003 |
| JP | 2004-518614 | A | 6/2004 |
| JP | 2007-500747 | A | 1/2007 |
| JP | 2011-521956 | A | 7/2011 |
| JP | 2013-537195 | A | 9/2013 |
| JP | 2018-510910 | A | 4/2018 |
| JP | 2022-528087 | A | 6/2022 |
| JP | 2022-528857 | A | 6/2022 |
| KR | 10-2010-0014736 | A | 2/2010 |
| KR | 10-2010-0127728 | A | 12/2010 |
| KR | 10-2012-0055095 | A | 5/2012 |
| KR | 10-2012-0055096 | A | 5/2012 |
| KR | 10-2013-0006170 | A | 1/2013 |
| KR | 10-2016-0040452 | A | 4/2016 |
| KR | 10-1617584 | B1 | 5/2016 |
| KR | 10-1734986 | B1 | 5/2017 |
| KR | 10-2018-0008305 | A | 1/2018 |
| KR | 10-2133151 | B1 | 7/2020 |
| KR | 10-2140910 | B1 | 8/2020 |
| WO | 95/29675 | A1 | 11/1995 |
| WO | 02/01956 | A1 | 1/2002 |
| WO | 2008/109445 | A1 | 9/2008 |
| WO | 2018/012901 | A1 | 1/2018 |
| WO | 2018/094023 | A2 | 5/2018 |
| WO | 2020/013974 | A1 | 1/2020 |

OTHER PUBLICATIONS

American Chemical Society. Chemical Abstract Service. RN 2254826-95-2. Entered into STN: Jan. 7, 2019. (Year: 2019).*
Kakkar, A.P. Drug Development and Industrial Pharmacy, 23(11), 1063-1067 (1997).
International Search Report mailed Mar. 22, 2022 in copending Application No. PCT/IB2021/061882.
A. Minelli, et al., "Focus on cyclo(His-Pro): history and perspectives as antioxidant peptide", Amino Acids, 2008, vol. 35, pp. 283-289.
J.C. Sible, et al., "Fibronectin gene expression differs in normal and abnormal human wound healing", Wound Repair Regen, Jan. 1994, vol. 2, No. 1 (1 page).
Pei-Hui Lin, et al., "Zinc in Wound Healing Modulation", Nutrients, 2018, vol. 10, No. 16, pp. 1-20.
Merriam-Webster online dictionary "aberrant" definition, accessed 2023, No. pagination (14 pages) https://www.merriam-webster.com/dictionary/aberrant.
Silvia Grottelli, et al., "The Role of Cyclo(His-Pro) in Neurodegeneration", Int. J. Mol. Sci., 2016, vol. 17, No. 1332, pp. 1-14 (16 pages).
Chao-Sheng Lo, et al., "Atrial Natriuretic Peptide Attenuates High Glucose-Activated Transforming Growth Factor-β, Smad and Collagen Synthesis in Renal Proximal Tubular Cells", Journal of Cellular Biochemistry, 2008, vol. 103, pp. 1999-2009.
Latha Muniappan, et al., "Calpain Inhibition Attenuates Adipose Tissue Inflammation and Fibrosis in Diet-induced Obese Mice", Scientific Reports, 2017, vol. 7, No. 14398, pp. 1-15.
(Continued)

*Primary Examiner* — John S Kenyon
(74) *Attorney, Agent, or Firm* — Sughrue Mion, PLLC

(57) ABSTRACT

The present disclosure relates to synthesis and characterization of novel polymorphic forms of Cyclo (-His-Pro) ("CHP").

18 Claims, 127 Drawing Sheets
(15 of 127 Drawing Sheet(s) Filed in Color)

(56) References Cited

OTHER PUBLICATIONS

Fumiko Nakazeki, et al., "Loss of periostin ameliorates adipose tissue inflammation and fibrosis in vivo", Scientific Reports, 2018, vol. 8, No. 8553, pp. 1-14.
Jeffrey E. Pessin, et al., "How Does High-Fat Diet Induce Adipose Tissue Fibrosis?", Journal of Investigative Medicine, Dec. 2012, vol. 60, No. 8, pp. 1147-1150 (5 pages total).
Matteo Rosselli, et al., "The Metabolic Syndrome and Chronic Liver Disease", Current Pharmaceutical Design, 2014, vol. 20, No. 31, pp. 5010-5024.
Simon Schenk, et al., "Insulin sensitivity: modulation by nutrients and inflammation", J Clin Invest, 2008, vol. 118, No. 9, pp. 2992-3002 (12 pages).
Kai Sun, et al., "Adipose tissue remodeling and obesity", J Clin Invest, 2011, vol. 121, No. 6, pp. 2094-2101 (9 pages).
Julien Ternacle, et al., "Short-term high-fat diet compromises myocardial function: a radial strain rate imaging study", European Heart Journal—Cardiovascular Imaging, 2017, vol. 18, pp. 1283-1291.
Elena Ulasova, et al., "Loss of interstitial collagen causes structural and functional alterations of cardiomyocyte subsarcolemmal mitochondria in acute volume overload", Journal of Molecular and Cellular Cardiology, 2011, vol. 50, pp. 147-156.
Kandy T. Velázquez, et al., "miR155 deficiency aggravates high-fat diet-induced adipose tissue fibrosis in male mice", Physiol Rep, 2017, vol. 5, Issue 18, e13412, pp. 1-11.
Lijun Wang, et al., "Berberine alleviates adipose tissue fibrosis by inducing AMP-activated kinase signaling in high-fat diet-induced obese mice", Biomedicine & Pharmacotherapy, 2018, vol. 105, pp. 121-129.
Davina Wu, et al., "Eosinophils sustain adipose alternatively activated macrophages associated with glucose homeostasis", Science, Apr. 8, 2011, vol. 332, No. 6026, pp. 243-247 (10 pages).
Ying Xia, et al., "Characterization of the inflammatory and fibrotic response in a mouse model of cardiac pressure overload", Histochem Cell Biol, 2009, vol. 131, pp. 471-481.
Zhou Xu, et al., "Bixin ameliorates high fat diet-induced cardiac injury in mice through inflammation and oxidative stress suppression", Biomedicine & Pharmacotherapy, 2017, vol. 89, pp. 991-1004.
Yi-chao Zhao, et al., "Nuclear receptor retinoid-related orphan receptor a deficiency exacerbates high-fat diet-induced cardiac dysfunction despite improving metabolic abnormality", Biochimica et Biophysica Acta, 2017, vol. 1863, pp. 1991-2000.
Michele Cavalera, et al., "Obesity, metabolic dysfunction and cardiac fibrosis: pathophysiologic pathways, molecular mechanisms and therapeutic opportunities", Translational Research, 2014, doi: 10.1016/j.trsl.2014.05.001 (36 pages).
Hong-Jun Chen, et al., "Actein ameliorates hepatic steatosis and fibrosis in high fat diet-induced NAFLD by regulation of insulin and leptin resistant", Biomedicine & Pharmacotherapy, 2018, vol. 97, pp. 1386-1396.
A. De Vries, et al., "High-fat feeding redirects cytokine responses and decreases allergic airway eosinophilia", Clinical & Experimental Allergy, 2009, vol. 39, pp. 731-739.
Stefan Fichtner-Feigl, et al., "IL-13 signaling through the IL-13α2 receptor is involved in induction of TGF-β1 production and fibrosis", Nature Medicine, Jan. 2006, vol. 12, No. 1, pp. 99-106 (9 pages).
Xiao Na Ge, et al., "High-fat diet promotes lung fibrosis and attenuates airway eosinophilia after exposure to cockroach allergen in mice", Exp Lung Res., Nov. 2013, vol. 39, No. 9, pp. 365-378 (21 pages).
Meilin Hu, et al., "The Role of Berberine in the Prevention of HIF-1α Activation to Alleviate Adipose Tissue Fibrosis in High-Fat-Diet-Induced Obese Mice", Evidence-Based Complementary and Alternative Medicine, 2018, vol. 2018, Article ID 4395137, pp. 1-12 (13 pages total).
Alfred J. Kaltman, et al., "Role of Circulatory Congestion in the Cardiorespiratory Failure of Obesity", The American Journal of Medicine, May 10, 1976, vol. 60, pp. 645-653.
In Hee Kim, et al., "Aging increases the susceptibility of hepatic inflammation, liver fibrosis and aging in response to high-fat diet in mice", Age, 2016, vol. 38, pp. 291-302.
Ping Kong, et al., "The Pathogenesis of Cardiac Fibrosis", Cell Mol Life Sci., Feb. 2014, vol. 71, No. 4, pp. 549-574 (43 pages).
Eun-Young Kwon, et al., "Luteolin Targets the Toll-Like Receptor Signaling Pathway in Prevention of Hepatic and Adipocyte Fibrosis and Insulin Resistance in Diet-Induced Obese Mice", Nutrients, 2018, vol. 10, No. 1415, pp. 1-17.
Andoni Lancha, et al., "Osteopontin Deletion Prevents the Development of Obesity and Hepatic Steatosis via Impaired Adipose Tissue Matrix Remodeling and Reduced Inflammation and Fibrosis in Adipose Tissue and Liver in Mice", PLoS One, May 2014, vol. 9, Issue 5, e98398, pp. 1-15.
Chun Geun Lee, et al., "Interleukin-13 Induces Tissue Fibrosis by Selectively Stimulating and Activating Transforming Growth Factor β1", J. Exp. Med., Sep. 17, 2001, vol. 194, No. 6, pp. 809-821.
Wei Li, et al., "Folic acid prevents cardiac dysfunction and reduces myocardial fibrosis in a mouse model of high-fat diet-induced obesity", Nutrition & Metabolism, 2017, vol. 14, No. 68, pp. 1-8.
International Search Report of PCT/KR2020/004354 dated Jul. 17, 2020 [PCT/ISA/210].
Takahiro Tsuburai, et al., "Adenovirus-Mediated Transfer and Overexpression of Heme Oxygenase 1 cDNA in Lung Prevents Bleomycin-Induced Pulmonary Fibrosis via a Fas-Fas Ligand-Independent Pathway," Human Gene Therapy, Nov. 1, 2002, vol. 13, pp. 1945-1960.
Silvia Grottelli, et al., "Cyclo(His-Pro) inhibits NLRP3 inflammasome cascade in ALS microglial cells", Molecular and Cellular Neuroscience, 2019, vol. 94, pp. 23-31 (10 pages).
International Search Report of PCT/KR2020/004343 dated Jul. 17, 2020 [PCT/ISA/210].
Zhen Zhang, et al., "Strategies for preventing peritoneal fibrosis in peritoneal dialysis patients: new insights based on peritoneal inflammation and angiogenesis", Front. Med., 2017, vol. 11, No. 3, pp. 349-358.
Extended European Search Report dated Jan. 16, 2023 from the European Patent Office in EP20776685.8.
Fang Tian, et al., "Factors affecting crystallization of hydrates", JPP, 2010, vol. 62, pp. 1534-1546.
International Search Report issued Aug. 28, 2019 in International Application No. PCT/US2019/038391.
International Preliminary Report on Patentability issued Jan. 12, 2021 in International Application No. PCT/US2019/038391.
"AKI: Mechanisms—Primary Injury and Repair—II", J Am Soc Nephrol: Kidney Week Edition (Abstract Supplement), 2019, vol. 30, p. 786 (1 page).
Kwang Bon Koo, et al., "Protective Effect of Cyclo(His-Pro) on Streptozotocin-Induced Cytotoxicity and Apoptosis In Vitro", J. Microbiol. Biotechnol., 2011, vol. 21, No. 2, pp. 218-227.
Office Action issued Nov. 18, 2023 in Chinese Application No. 201980046575.8.

* cited by examiner

Non-Polarised

Polarised

Non-Polarised

Polarised

| **Run** | **% RH** | **Temperature** | **Identity** |
|---|---|---|---|
| 1 | 40 | Ambient | Pattern 2 |
| 2 | 0 | | Pattern 2 |
| 3 | 0 | 80°C | Pattern 1 |
| 4 | 0 | | Pattern 1 |

FIG. 33

| | Solvent | Approximate Solubility (mg/mL) |
|---|---|---|
| 1 | 1-Butanol | ≤5 |
| 2 | 2-Butanol | ≤5 |
| 3 | 1-Propanol | 14.3 ≥ x ≥ 12.5 |
| 4 | 2-Propanol | 5.6 ≥ x ≥ 5.3 |
| 5 | 40 % Methanol : 60 % Water (% v/v) (calc. aw 0.8) | 20 ≥ x ≥ 16.7 |
| 6 | 95 % Methanol : 5 % Water (% v/v) (calc. aw 0.2) | 33.3 ≥ x ≥ 25 |
| 7 | Acetone | ≤5 |
| 8 | Acetonitrile | ≤5 |
| 9 | Dichloromethane | ≤5 |
| 10 | Ethanol | 100 ≥ x ≥ 50 |
| 11 | Ethyl Acetate | ≤5 |
| 12 | Ethyl Formate | ≤5 |
| 13 | Heptane | ≤5 |
| 14 | Isopropyl Acetate | ≤5 |
| 15 | Methanol | 100 ≥ x ≥ 50 |
| 16 | Methylethyl Ketone | ≤5 |
| 17 | Methylisobutyl Ketone | ≤5 |
| 18 | N,N'-Dimethylacetamide | 33.3 ≥ x ≥ 25 |
| 19 | Nitromethane | ≤5 |
| 20 | tert-Butylmethyl Ether | ≤5 |
| 21 | THF | ≤5 |
| 22 | Toluene | ≤5 |
| 23 | Water | 25 ≥ x ≥ 20 |
| 24 | Trifluoroethanol | 25 ≥ x ≥ 20 |
| 25 | Benzyl Alcohol | 7.7 ≥ x ≥ 7.1 |
| 26 | Chloroform | ≤5 |
| 27 | Chlorobenzene | ≤5 |
| 28 | 1,4-Dioxane | ≤5 |
| 29 | 2-Methoxyethanol | 11.1 ≥ x ≥ 10 |
| 30 | Dimethylsulfoxide | 20 ≥ x ≥ 16.7 |

FIG. 43

| Number | Solvent | Volume of solvent added (100µL) | | | | | | | | | | | | | | | | | | | |
|---|---|---|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 | 17 | 18 | 19 | 20 |
| 1 | 1-Butanol | | | | | | | | | | | | | | | | | | | | |
| 2 | 2-Butanol | | | | | | | | | | | | | | | | | | | | |
| 3 | 1-Propanol | | | | | | | | | | | | | | | | | | | | |
| 4 | 2-Propanol | | | | | | | | | | | | | | | | | | | | |
| 5 | 40% Methanol : 60 % Water (% v/v) (calc. aw 0.8) | | | | | | | | | | | | | | | | | | | | |
| 6 | 95% Methanol : 5 % Water (% v/v) (calc. aw 0.2) | | | | | | | | | | | | | | | | | | | | |
| 7 | Acetone | | | | | | | | | | | | | | | | | | | | |
| 8 | Acetonitrile | | | | | | | | | | | | | | | | | | | | |
| 9 | Dichloromethane | | | | | | | | | | | | | | | | | | | | |
| 10 | Ethanol | | | | | | | | | | | | | | | | | | | | |
| 11 | Ethyl Acetate | | | | | | | | | | | | | | | | | | | | |
| 12 | Ethyl Formate | | | | | | | | | | | | | | | | | | | | |
| 13 | Heptane | | | | | | | | | | | | | | | | | | | | |
| 14 | Isopropyl Acetate | | | | | | | | | | | | | | | | | | | | |
| 15 | Methanol | | | | | | | | | | | | | | | | | | | | |
| 16 | Methylethyl ketone | | | | | | | | | | | | | | | | | | | | |
| 17 | Methylisobutyl Ketone | | | | | | | | | | | | | | | | | | | | |
| 18 | N, N'-Dimethylacetamide | | | | | | | | | | | | | | | | | | | | |
| 19 | Nitromethane | | | | | | | | | | | | | | | | | | | | |
| 20 | tert-Butylmethyl Ether | | | | | | | | | | | | | | | | | | | | |
| 21 | THF | | | | | | | | | | | | | | | | | | | | |
| 22 | Toluene | | | | | | | | | | | | | | | | | | | | |
| 23 | Water | | | | | | | | | | | | | | | | | | | | |
| 24 | Trifluoroethanol | | | | | | | | | | | | | | | | | | | | |
| 25 | Benzyl Alcohol | | | | | | | | | | | | | | | | | | | | |
| 26 | Chloroform | | | | | | | | | | | | | | | | | | | | |
| 27 | Chlorobenzene | | | | | | | | | | | | | | | | | | | | |
| 28 | 1,4-Dioxane | | | | | | | | | | | | | | | | | | | | |
| 29 | 2-Methoxyethanol | | | | | | | | | | | | | | | | | | | | |
| 30 | Dimethylsulfoxide | | | | | | | | | | | | | | | | | | | | |

| | |
|---|---|
| | Did not dissolve |
| | Dissolved on heating to 40° C |
| | Dissolved |

FIG. 44

| | Solvent | XRPD Results | |
|---|---|---|---|
| 1 | 1-Butanol | N/A - no solid produced | |
| 2 | 2-Butanol | N/A - no solid produced | |
| 3 | 1-Propanol | Pattern 1 | |
| 4 | 2-Propanol | Pattern 2 | |
| 5 | 40 % Methanol: 60 % Water (% v/v) (calc. aw 0.8) | Pattern 2 | |
| 6 | 95% Methanol: 5 % Water (% v/v) (calc. aw 0.2) | Pattern 2 | |
| 7 | Acetone | Pattern 2 | |
| 8 | Acetonitrile | Pattern 2 | |
| 9 | Dichloromethane | Pattern 2 | |
| 10 | Ethanol | Pattern 1 | Pattern 2 |
| 11 | Ethyl Acetate | Pattern 2 | |
| 12 | Ethyl Formate | Pattern 2 | |
| 13 | Heptane | Pattern 2 | |
| 14 | Isopropyl Acetate | Pattern 2 | |
| 15 | Methanol | N/A - colourless gel | |
| 16 | Methylethyl Ketone | Pattern 2 | |
| 17 | Methylisobutyl Ketone | Pattern 2 | |
| 18 | N, N'-Dimethylacetamide | N/A - no solid produced | |
| 19 | Nitromethane | Pattern 2 | |
| 20 | tert-Butylmethyl Ether | Pattern 2 | |
| 21 | THF | Amorphous with pattern 2 peaks | |
| 22 | Toluene | Pattern 2 | |
| 23 | Water | N/A - no solid produced | |
| 24 | Trifluoroethanol | Pattern 2 | |
| 25 | Benzyl Alcohol | N/A - no solid produced | |
| 26 | Chloroform | N/A - no solid produced | |
| 27 | Chlorobenzene | Pattern 2 | Pattern 3 |
| 28 | 1,4-Dioxane | N/A - no solid produced | |
| 29 | 2-Methoxyethanol | N/A - no solid produced | |
| 30 | Dimethylsulfoxide | N/A - no solid produced | |

FIG. 45

| Solvent |
|---|
| 1-Propanol |
| 2-Propanol |
| 95 % Methanol : 5 % Water (% v/v) |
| 50% Methanol / 50% TBME (%v/v) |
| 10% Methanol / 90% TBME |
| Acetone |
| Acetonitrile |
| Dichloromethane |
| Ethanol |
| 50% Ethanol / 50% TBME (%v/v) |
| 10% Ethanol / 90% TBME |
| Ethyl Acetate |
| Ethyl Formate |
| Heptane |
| Isopropyl Acetate |
| Methylethyl Ketone |
| Methylisobutyl Ketone |
| Nitromethane |
| tert-Butylmethyl Ether |
| Toluene |
| Trifluoroethanol |
| Chlorobenzene |
| THF |
| Methanol |

FIG. 46

*Table 5: Primary Polymorph Screen Temperature Cycling*

| **Solvent** | **Pattern 1** |
|---|---|
| 1-Propanol | N/A - solution |
| 2-Propanol | N/A - solution |
| 95 % Methanol: 5% Water (% v/v) | N/A - solution |
| 50 % Methanol / 50% TBME (%v/v) | Pure Pattern 1 |
| 10% Methanol / 90% TBME | Pure Pattern 1 |
| Acetone | N/A - solution |
| Acetonitrile | Pattern 1 |
| Dichloromethane | Preferred orientation - unable to assign |
| Ethanol | N/A - Solution |
| 50% Ethanol / 50% TBME (%v/v) | Pure Pattern 1 |
| 10% Ethanol / 90% TBME | Pure Pattern 1 |
| Ethyl Acetate | Pure Pattern 1 (preferred orientation) |
| Ethyl Formate | Pattern 1 - poorly crystalline |
| Heptane | Pattern 2 |
| Isopropyl Acetate | Pattern 2 |
| Methylethyl Ketone | Pattern 1 |
| Methylisobutyl Ketone | Pattern 2 |
| Nitromethane | N/A - solution |
| tert-Butylmethyl Ether | Pattern 2 |
| Toluene | Pattern 2 (preferred orientation) |
| Trifluoroethanol | N/A - solution |
| Chlorobenzene | N/A - insufficient solid |
| THF | Pattern 1 |
| Methanol | N/A - oil |

FIG. 50

*C1601736-D designate CHP (Anhydrous as well as Hydrate)
**Known impurities marked with code names Integration Results

| No. | Peak Name | Manipulated? | Retention Time min |
|---|---|---|---|
| 1 | Unknown | FALSE | 1.957 |
| 2 | Unknown | FALSE | 5.157 |
| 3 | Main Peak | FALSE | 5.543 |
| Total: | | | |

| Rel. Ret. Time. | Area mAU*min | Height mAU | Relative Area % | Amount %w/w |
|---|---|---|---|---|
| 0.35 | 0.592 | 6.831 | 0.42 | 0.39 |
| 0.93 | 0.161 | 3.156 | 0.11 | 0.11 |
| 1.00 | 140.011 | 1473.080 | 99.47 | 91.64 |
| | 140.763 | 1483.067 | 100.00 | 92.14 |

Chromatogram

Integration Results

| No. | Peak Name | Manipulated? | Retention Time min |
|---|---|---|---|
| 1 | Unknown | FALSE | 1.778 |
| 2 | Unknown | FALSE | 4.978 |
| 3 | Main Peak | FALSE | 5.355 |
| Total: | | | |

| Rel. Ret. Time. | Area mAU*min | Height mAU | Relative Area % | Amount %w/w |
|---|---|---|---|---|
| 0.33 | 0.574 | 8.911 | 0.40 | 0.44 |
| 0.93 | 0.141 | 2.058 | 0.10 | 0.11 |
| 1.00 | 142.529 | 1350.717 | 99.50 | 110.12 |
| | 143.244 | 1361.687 | 100.00 | 110.67 |

Chromatogram

D

Integration Results

| No. | Peak Name | Manipulated? | Retention Time min |
|---|---|---|---|
| 1 | Unknown | FALSE | 1.780 |
| 2 | Unknown | FALSE | 4.511 |
| 3 | Unknown | FALSE | 4.690 |
| 4 | Unknown | FALSE | 4.985 |
| 5 | Main Peak | FALSE | 5.356 |
| Total: | | | |

| Rel. Ret. Time. | Area mAU*min | Height mAU | Relative Area % | Amount %w/w |
|---|---|---|---|---|
| 0.33 | 0.569 | 8.381 | 0.38 | 0.44 |
| 0.84 | 0.103 | 1.730 | 0.07 | 0.08 |
| 0.88 | 0.114 | 1.974 | 0.08 | 0.09 |
| 0.93 | 0.107 | 1.938 | 0.07 | 0.08 |
| 1.00 | 147.250 | 1379.502 | 99.40 | 113.77 |
| | 148.144 | 1393.525 | 100.00 | 114.46 |

Integration Results

| No. | Peak Name | Manipulated? | Retention Time min |
|---|---|---|---|
| 1 | Unknown | FALSE | 1.783 |
| 2 | Unknown | FALSE | 4.990 |
| 3 | Main Peak | FALSE | 5.358 |
| Total: | | | |

E

| Rel. Ret. Time. | Area mAU*min | Height mAU | Relative Area % | Amount %w/w |
|---|---|---|---|---|
| 0.33 | 0.531 | 7.631 | 0.38 | 0.41 |
| 0.93 | 0.106 | 1.806 | 0.08 | 0.08 |
| 1.00 | 137.739 | 1304.452 | 99.54 | 106.42 |
| | 138.376 | 1313.889 | 100.00 | 106.91 |

Chromatogram

Integration Results

| No. | Peak Name | Manipulated? | Retention Time min |
|---|---|---|---|
| 1 | | FALSE | 12.676 |
| 2 | | FALSE | 14.605 |
| 3 | C16081735-D | FALSE | 16.908 |
| Total: | | | |

| Rel. Ret. Time. | Area mAU*min | Height mAU | Chiral purity % |
|---|---|---|---|
| n.a. | 1.806 | 3.526 | 0.17 |
| n.a. | 1.181 | 1.748 | 0.11 |
| n.a. | 1066.568 | 1337.842 | 99.72 |
| | 1069.555 | 1343.115 | 100.00 |

Integration Results

| No. | Peak Name | Manipulated? | Retention Time min |
|---|---|---|---|
| 1 | | FALSE | 11.116 |
| 2 | | FALSE | 11.216 |
| 3 | | FALSE | 12.080 |
| 4 | | FALSE | 13.601 |
| 5 | | FALSE | 14.273 |
| 6 | | FALSE | 15.741 |
| 7 | C16081735-D | FALSE | 16.245 |
| Total: | | | |

| Rel. Ret. Time. | Area mAU*min | Height mAU | Chiral purity % |
|---|---|---|---|
| n.a. | 0.171 | 0.777 | ND |
| n.a. | 0.394 | 0.837 | ND |
| n.a. | 2.372 | 4.555 | 0.23 |
| n.a. | 0.806 | 1.373 | 0.08 |
| n.a. | 0.510 | 0.964 | 0.05 |
| n.a. | 0.131 | 0.554 | ND |
| n.a. | 1014.890 | 1391.863 | 99.57 |
| | 1019.273 | 1400.923 | 99.93 |

Chromatogram

Integration Results

| No. | Peak Name | Manipulated? | Retention Time min |
|---|---|---|---|
| 1 | | FALSE | 12.998 |
| 2 | | FALSE | 14.741 |
| 3 | | FALSE | 17.011 |
| 4 | C16081735-D | FALSE | 17.578 |
| Total: | | | |

| Rel. Ret. Time. | Area mAU*min | Height mAU | Chiral purity % |
|---|---|---|---|
| n.a. | 1.548 | 3.411 | 0.15 |
| n.a. | 1.068 | 1.676 | 0.11 |
| n.a. | 0.270 | 0.810 | ND |
| n.a. | 996.309 | 1300.420 | 99.71 |
| | 999.195 | 1306.317 | 99.97 |

Chromatogram

Integration Results

| No. | Peak Name | Manipulated? | Retention Time min |
|---|---|---|---|
| 1 | | FALSE | 18.910 |
| 2 | | FALSE | 19.653 |
| 3 | | FALSE | 24.543 |
| 4 | C16081735-D | FALSE | 26.570 |
| Total: | | | |

I

| Rel. Ret. Time. | Area mAU*min | Height mAU | Chiral purity % |
|---|---|---|---|
| n.a. | 0.171 | 0.291 | ND |
| n.a. | 0.075 | 0.168 | ND |
| n.a. | 0.063 | 0.135 | ND |
| n.a. | 1623.359 | 1211.727 | 99.98 |
| | 1623.667 | 1212.321 | 99.98 |

Chromatogram

Integration Results

| No. | Peak Name | Manipulated? | Retention Time min |
|---|---|---|---|
| 1 | | FALSE | 13.248 |
| 2 | | FALSE | 13.501 |
| 3 | | FALSE | 14.095 |
| 4 | | FALSE | 15.020 |
| 5 | | FALSE | 16.538 |
| 6 | | FALSE | 17.525 |
| 7 | C16081735-D | FALSE | 18.051 |
| Total: | | | |

| Rel. Ret. Time. | Area mAU*min | Height mAU | Chiral purity % |
|---|---|---|---|
| n.a. | 0.790 | 1.941 | 0.07 |
| n.a. | 0.518 | 1.864 | ND |
| n.a. | 2.745 | 6.705 | 0.26 |
| n.a. | 10.413 | 16.917 | 0.98 |
| n.a. | 1.408 | 2.903 | 0.13 |
| n.a. | 6.104 | 16.100 | 0.57 |
| n.a. | 1042.087 | 1238.892 | 97.93 |
| | 1064.065 | 1285.323 | 99.95 |

Integration Results

| No. | Peak Name | Manipulated? | Retention Time min |
|---|---|---|---|
| 1 | | FALSE | 12.710 |
| 2 | C16081735-D | FALSE | 16.931 |
| Total: | | | |

K

| Rel. Ret. Time. | Area mAU*min | Height mAU | Chiral purity % |
|---|---|---|---|
| n.a. | 0.911 | 1.951 | 0.08 |
| n.a. | 1137.427 | 1393.406 | 99.92 |
| | 1138.338 | 1395.357 | 100.00 |

Chromatogram

Integration Results

| No. | Peak Name | Manipulated? | Retention Time min |
|---|---|---|---|
| 1 | | FALSE | 11.320 |
| 2 | | FALSE | 11.690 |
| 3 | | FALSE | 12.106 |
| 4 | | FALSE | 14.700 |
| 5 | C16081735-D | FALSE | 16.281 |
| Total: | | | |

| Rel. Ret. Time. | Area mAU*min | Height mAU | Chiral purity % |
|---|---|---|---|
| n.a. | 0.332 | 0.817 | ND |
| n.a. | 0.141 | 1.037 | ND |
| n.a. | 2.231 | 4.029 | 0.22 |
| n.a. | 0.142 | 0.335 | ND |
| n.a. | 992.018 | 1348.422 | 99.71 |
| | 994.864 | 1354.640 | 99.94 |

| Solvent | Pattern |
|---|---|
| 1-Propanol | N/A - colourless film on vial wall |
| 2-Propanol | N/A - colourless film on vial wall |
| 95% Methanol: 5 % Water (%v/v) | N/A - colourless film on vial wall |
| 50% Methanol / 50% TBME (%v/v) | N/A -no solution after temp cycling |
| 10% Methanol / 90% TBME | N/A - insufficient solid |
| Acetone | N/A - oily residue on vial wall |
| Acetonitrile | Pattern 1 (poorly crystalline) |
| Dichloromethane | amorphous |
| Ethanol | N/A - insufficient solid |
| 50% Ethanol / 50% TBME(%v/v) | N/A - insufficient solid |
| 10% Ethano / 90% TBME | N/A - colourless film on vial wall |
| Ethyl Acetate | N/A - colourless film on vial wall |
| Ethyl Formate | N/A - colourless film on vial wall |
| Heptane | N/A - colourless film on vial wall |
| Isopropyl Acetate | N/A - colourless film on vial wall |
| Methylethyl Ketone | N/A - colourless film on vial wall |
| Methylisobutyl Ketone | N/A - insufficient solid |
| Nitromwthane | Pattern 2 (poorly crystalline) |
| tert-Butylmethyl Either | N/A - colourless film on vial wall |
| Toluene | N/A - colourless film on vial wall |
| Trifluoroethanol | Pattern 2 |
| Chlorobenzene | N/A - colourless film on vial wall |
| THF | amorphous |
| Methanol | N/A - oil produced after temp cycle |

FIG. 113

| | |
|---|---|
| | Pure Pattern 1 |
| | Pattern 1 |
| | Pattern 2 |
| | Solution |
| | Insufficient solid |
| | Oil |
| | Amorphous |
| | Colourless film / oily residue |
| | Experiment not performed |
| 1 | Preferred orientation |
| * | Poorly crystalline |

| No. | Solvent | Temperature Cycling | Evaporations | Cooling (2-8°C) | Cooling (-20°C) | Anti-Solvent Addition |
|---|---|---|---|---|---|---|
| 1 | 1-Propanol | | | | | |
| 2 | 2-Propanol | | | | | |
| 3 | 95% Methanol: 5 % Water (%v/v) | | | | | |
| 4 | 50% Methanol / 50% TBME (%v/v) | | | | | |
| 5 | 10% Methanol / 90% TBME | | | | | |
| 6 | Acetone | | * | | | |
| 7 | Acetonitrile | 1 | | | | |
| 8 | Dichloromethane | | | | | |
| 9 | Ethanol | | | | | |
| 10 | 50% Ethanol / 50% TBME(%v/v) | | | | | |
| 11 | 10% Ethanol / 90% TBME | | | | | |
| 12 | Ethyl Acetate | 1 | | | | |
| 13 | Ethyl Formate | * | | | | |
| 14 | Heptane | | | | | |
| 15 | Isopropyl Acetate | | | | | |
| 16 | Methylethyl Ketone | | | | | |
| 17 | Methylisobutyl Ketone | | | | | |
| 18 | Nitromethane | | * | | | |
| 19 | tert-Butylmethyl Ether | | | | | |
| 20 | Toluene | 1 | | | | |
| 21 | Trifluoroethanol | | | | | |
| 22 | Chlorobenzene | | | | | |
| 23 | THF | | | | | |
| 24 | Methanol | | | | | |

FIG. 114

| Input Pattern | Timepoint | Appearance |
|---|---|---|
| Pure Pattern 1 | Initial | Faint beige |
| Pure Pattern 1 | 2-week | Faint beige |
| Pure Pattern 1 | 4-week | Faint beige |
| Pure Pattern 1 | 8-week | Faint beige |
| Pattern 2 | Initial | White |
| Pattern 2 | 2-week | White |
| Pattern 2 | 4-week | White |
| Pattern 2 | 8-week | White |

FIG. 115

POLYMORPHIC FORMS OF CYCLO (-HIS-PRO) AND METHODS OF USE TO TREAT KIDNEY DISEASE

RELATED APPLICATIONS

This application is a continuation application of U.S. application Ser. No. 16/901,676 (allowed) filed Jun. 15, 2020 which is a continuation-in-part application of U.S. application Ser. No. 16/448,083 filed Jun. 21, 2019 (now U.S. Pat. No. 10,683,300) which claims priority to U.S. Provisional Appl. Ser. No. 62/696,190 filed on Jul. 10, 2018, which is incorporated herein by reference in its entirety to the full extent permitted by law.

TECHNICAL FIELD

The present disclosure is directed to novel polymorphic forms of Cyclo (-His-Pro) ("CHP").

BACKGROUND

Cyclo (-His-Pro), $C_{11}H_{14}N_4O_2$, has been known as an anhydrous dipeptide having the CAS Registry Number 53109-32-3. It is an endogenous cyclic dipeptide derived in vivo from the hydrolytic removal of the amino-terminal pyroglutamic acid residue of the hypothalamic thyrotropin-releasing hormone. Cyclo (-His-Pro) can all be synthesized ex-vivo by conventional chemical methods. It may be important in regulating the nature of the glial cell contribution. Grotelli et al., *The Role of Cyclo(His-Pro) in Neurodegeneration*, Int J Mol Sci. 2016 August; 17(8): 1332. Cyclo (His-Pro) is ubiquitous in the central nervous system and is a key substrate of organic cation transporters, which are strongly linked to neuroprotection. The cyclic dipeptide can also cross the brain-blood-barrier and, once in the brain, can affect diverse inflammatory and stress responses by modifying the Nrf2-NF-κB signaling axis.

The crystalline anhydrous form of cyclo (-His-Pro) ("anhydrous CHP" or "Pattern 1") is the form that has heretofore been reported in literature and has potential therapeutic applications. However, certain anhydrous forms may be unstable. Possible disadvantages of using Pattern 1 include: (1) apparent physical instability at ambient to high humidity conditions; and (2) potential chemical instability due to water activity resulting in the formation of diastereomers of the desired L,L-dipeptides such as D,L-CHP, L,D-CHP, or D,D-CHP. Thus, there is a need in the art for more stable forms of CHP.

SUMMARY

The present disclosure provides Cyclo(-His-Pro) hydrate crystalline form ("CHP Hydrate" or "Pattern 2" compound) that may be characterized and distinguished from other solid forms of CHP using various analytical techniques including, but not limited to, X-ray powder diffraction (XRPD), solid-state nuclear magnetic resonance (NMR, or $^{13}C$ SSNMR), Raman spectroscopy, differential scanning calorimetry (DSC), dynamic vapor sorption (DVS), and thermogravimetric analysis (TGA).

Applicant has unexpectedly discovered that CHP hydrate (CAS RN: 2254826-95-2 (January 2019)) has superior stability over amorphous cyclo (-His-Pro) or Pattern 1. Based on this surprising discovery, Pattern 2 can be used alone as a single component drug rather than using Pattern 1 or a mixture of Pattern 1 and Pattern 2.

In one embodiment, the present disclosure relates to a process for isolating Pattern 2 by crystallization using solvents rather than column chromatography currently used to isolate the anhydrous CHP.

In another embodiment, Pattern 2 is stable at typical room temperature storage conditions for about 6 months, or about 12 months, or about 18 months, or about 24 months, or about 36 months.

In yet another embodiment, the present disclosure is directed to substantially pure Pattern 2 material. In some embodiments, the Pattern 2 material is at least about 90% pure, or at least about 95%, 96%, 97%, 98%, 99%, or 100% pure.

In one embodiment, the purity of a sample is measured by any analytical method. In one embodiment, the purity is measured by high pressure liquid chromatography (HPLC), X-ray powder diffraction (XRPD), pKa analysis, polarized light microscopy (PLM), thermogravimetric analysis/differential thermal analysis (TG/DTA), differential scanning calorimetry (DSC), Fourier-transform infrared spectroscopy (FT-IR), dynamic vapor sorption (DVS), variable temperature and humidity X-ray powder diffractometry (VT-/VH-XRPD), $^1H$ nuclear magnetic resonance (NMR), and/or heteronuclear single quantum coherence (HSQC) NMR. In another embodiment, the purity of the sample is measured by HPLC.

In one embodiment, the Pattern 2 material is at least about 90% pure, or at least about 95%, 96%, 97%, 98%, 99%, or 100% pure as measured by HPLC.

In another embodiment, Pattern 2 material may be characterized by at least two of the following:

(a) an X-ray powder diffractogram comprising at least two peaks chosen from the following list: 10, 13.7, 17, 18.1, 20.2 and 27.3 degrees (±0.2° in 2θ);
(b) pKa of about 6.4;
(c) birefringent with a fragmented, rod-like morphology when analyzed by polarized light microscopy;
(d) an initial weight loss of about 6.5% (0.9 equivalent of water), followed by sample degradation at about 280° C. when analyzed by thermogravimetric analysis technique;
(e) an endotherm with an onset of about 99° C. and a peak at about 102° C. in the first heat cycle of DSC;
(f) start of dehydration below about 10% relative humidity (RH), loss of about 5.8 wt % from 10 to 0% RH (0.8 equivalent of water) and hydration from 0 to about 40% RH in the 40° C. dynamic vapor sorption analysis;
(g) start of dehydration below about 20% RH, loss of about 6.1 wt % from about 20 to 0% RH (0.8 equivalent of water) and rehydration from 0 to about 40% RH in the 50° C. dynamic vapor sorption analysis; and
(h) start of dehydration below about 20% RH, loss of about 7 wt % from about 20 to 0% RH (1.0 equivalent of water), and rehydration from 0 to about 40% RH in the 60° C. dynamic vapor sorption analysis.

The present disclosure also encompasses a pharmaceutical composition comprising Pattern 2 material and excipients. Such composition may comprise about 1% to about 50%, about 5% to about 45%, about 10% to about 40%, about 15% to about 35%, about 20% to about 30%, at least about 10%, at least about 20%, at least about 30%, at least about 40%, at least about 50%, about 1%, about 2%, about 2%, about 3%, about 4%, about 5%, about 6%, about 7%, about 8%, about 9% or about 10% (w/w) CHP Hydrate. In one embodiment, the composition may comprise about 1% to about 10% (w/w) CHP Hydrate. In one specific embodiment, the composition may comprise about 4% (w/w) CHP Hydrate.

In another embodiment, the composition may be made to be in the form of a tablet, capsule, caplet, liquigel, trouche, injectable sterile solution and the like.

Alternatively, the compositions taught herein may be formulated in powder form for reconstitution with a suitable vehicle, such as sterile pyrogen-free water, before use. For example, a compound suitable for parenteral administration may comprise a sterile isotonic saline solution containing between 0.1 percent and 90 percent weight per volume of the compound. By way of example, a solution may contain from about 5 percent to about 20 percent, more preferably from about 5 percent to about 17 percent, more preferably from about 8 to about 14 percent, and still more preferably about 10 percent of the compound.

Additional embodiments of the present compositions, methods and the like will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment or aspect. Additional aspects and embodiments are set forth in the following description and claims, particularly when considered in conjunction with the accompanying examples and drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing features of embodiments will be more readily understood by reference to the following detailed description, taken with reference to the accompanying drawings, in which:

FIG. 7 is an XRPD analysis of CHP Hydrate or Pattern 2 (blue line: the sample from FIG. 5) that was returned to the vacuum oven for a further 30 minutes. In other words, purple line in FIG. 7 is an XRPD analysis of the product after storing CHP Hydrate (Pattern 2 Material) for 1.5 hour at 50° C. under vacuum, showing mostly Pattern 2 with some Pattern 1 mixed in.

FIG. 8 is an XRPD analysis of CHP Hydrate or Pattern 2 (blue line: the sample from FIG. 5) that was returned to the oven, in which the temperature was increased to 80° C. The vial was placed inside the oven for an additional 18 hours. In other words, pink line in FIG. 8 is an XRPD analysis of the product after storing CHP Hydrate (Pattern 2 Material) for 18 hour at 80° C., showing mostly Pattern 1 with some Pattern 2 mixed in.

FIG. 33 illustrates the results of the VT-/VH-XRPD analysis of CHP Hydrate, Pattern 2 and Pattern 1.

FIG. 43 illustrates the approximate solubility of Pattern 1 in various solvents.

FIG. 44 illustrates the solvent solubility results of Pattern 1 based on volume of solvent added.

FIG. 45 illustrates the polymorph (Pattern 1 or Pattern 2) when Pattern 1 was treated with various solvents.

FIG. 46 illustrates the primary polymorph screening solvents.

FIG. 50 illustrates the primary polymorph screen temperature cycling.

FIG. 113 is the primary polymorph screen evaporations.

FIG. 114 is the primary polymorph screen summary table.

FIG. 115 is the 8-week stability appearance results summary.

DETAILED DESCRIPTION OF THE SPECIFIC EMBODIMENTS

Figure 1:
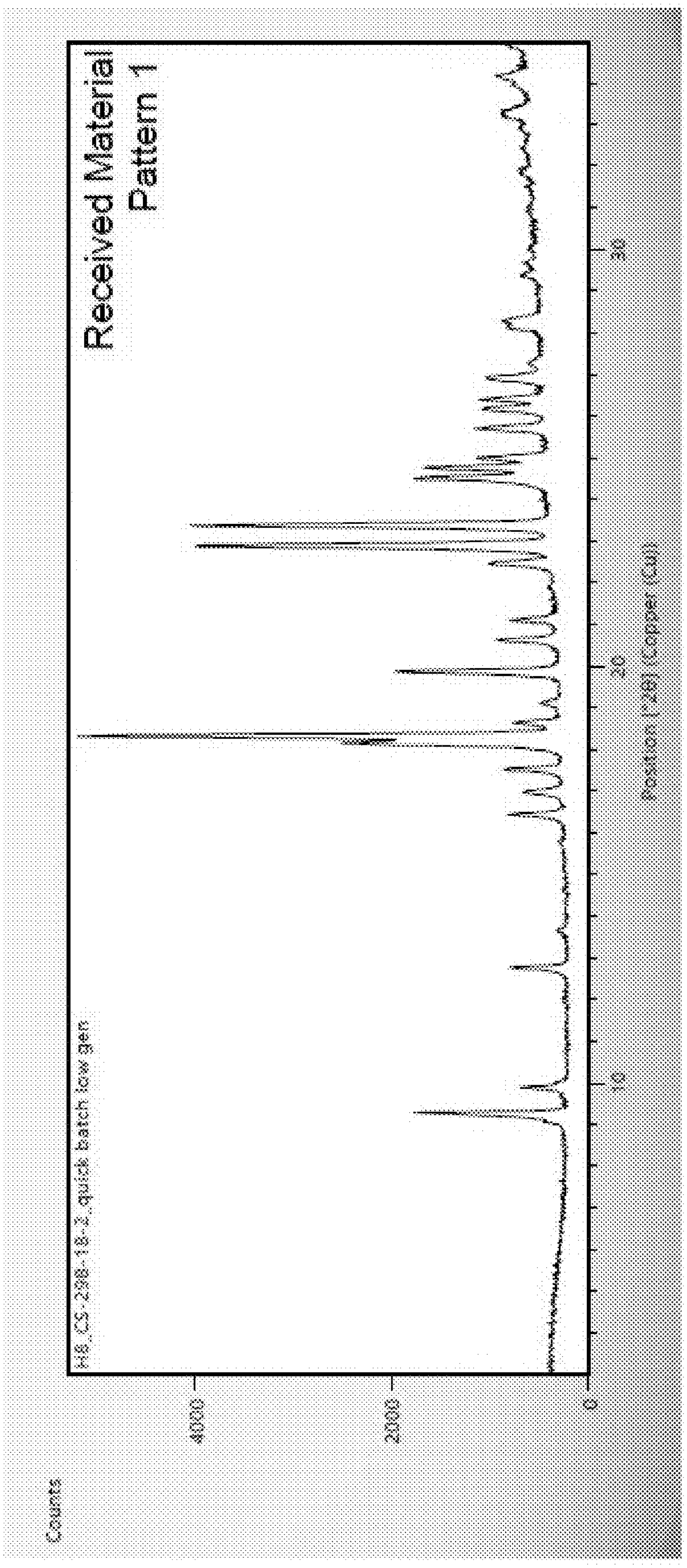
FIG. 1 is X-ray powder diffractogram of crystalline Pattern 1.

The various aspects and embodiments will now be fully described herein. These aspects and embodiments may, however, be embodied in many different forms and should not be construed as limiting; rather, these embodiments are provided so the disclosure will be thorough and complete, and will fully convey the scope of the present subject matter to those skilled in the art. All publications, patents and patent applications cited herein, whether supra or infra, are hereby incorporated by reference in their entirety.

A. Definitions

Unless defined otherwise, all terms and phrases used herein include the meanings that the terms and phrases have attained in the art, unless the contrary is clearly indicated or clearly apparent from the context in which the term or phrase is used. Although any methods and materials similar or equivalent to those described herein can be used in the practice or testing of the present invention, particular methods and materials are now described.

Unless otherwise stated, the use of individual numerical values are stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or"approximately." Consequently, recitation of ranges of values herein are merely intended to serve as a shorthand method of referring individually to each separate value falling within the range, and each separate value is incorporated into the specification as if it were individually recited herein.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, and intrasternal injection.

The term "active agent" or "drug," as used herein, refers to any chemical that elicits a biochemical response when administered to a human or an animal. The drug may act as a substrate or product of a biochemical reaction, or the drug may interact with a cell receptor and elicit a physiological response, or the drug may bind with and block a receptor from eliciting a physiological response.

The term "bioequivalent," as used herein, refers to two compositions, products or methods where the 90% Confidence Intervals (CI) for AUC, partial AUC and/or $C_{max}$ are between 0.80 to 1.25.

The terms "CHP Hydrate" (a/k/a "Pattern 2") means the compound identified by CAS Registry Number: 2254826-95-2 issued Jan. 7, 2019.

The phrase "substantially pure" refers to a substance having total purity of greater than 90%, or greater than 95%, or greater than 96%, or greater than 97%, or greater than 98%, or greater than 99%, or greater than 99.5%. For example, the phrase "substantially pure substance A" means substance A is at least 90% pure with respect to all impurities, or substance A is at least 95% pure with respect to all impurities, or substance A is at least 98% pure with respect to all impurities, or substance A is at least 99% pure with respect to all impurities.

In one embodiment, the purity of a sample is measured by any analytical method. In one embodiment, the purity is measured by HPLC, X-ray powder diffraction (XRPD), pKa analysis, polarized light microscopy (PLM), thermogravimetric analysis/differential thermal analysis (TG/DTA), differential scanning calorimetry (DSC), Fourier-transform infrared spectroscopy (FT-IR), dynamic vapor sorption (DVS), variable temperature and humidity X-ray powder diffractometry (VT-/VH-XRPD), $^{1}H$ nuclear magnetic resonance (NMR), and/or heteronuclear single quantum coherence (HSQC) NMR.

In some embodiments, the term "substantially as shown in" when referring to an X-ray powder diffraction pattern or a differential scanning calorimetry pattern means that a pattern that is not necessarily identical to those depicted herein, but that falls within the limits of experimental error or deviations, when considered by one of ordinary skill in the art.

The term "therapeutically effective amount" refers to an amount that is sufficient to effect treatment, as defined below, when administered to a human in need of such treatment. The therapeutically effective amount will vary depending upon the human subject being treated, the weight and age of the human subject, the severity of the disease condition, the manner of administration and the like, which can readily be determined by one of ordinary skill in the art.

B. Introduction

The present disclosure is directed to the novel compound CHP Hydrate, its uses and the manufacture thereof. It is illustrated below:

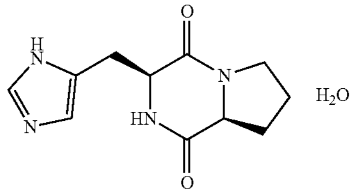

On Jan. 7, 2019, CHP Hydrate was assigned CAS Registry Number (CAS RN): 2254826-95-2 having the CA Index Name: Pyrrolo [1, 2-a]pyrazine-1,4-dione, hexahydro-3-(1H-imidazol-5-ylmethyl)-, hydrate (1:1), (3S, 8aS)-. CHP hydrate has a molecular weight of 252.3 g/mol.

One skilled in the art understands that the compound structure may be named or identified using other commonly recognized nomenclature systems and symbols. By way of example, the compound may be named or identified with common names, systematic or non-systematic names. The nomenclature systems and symbols that are commonly recognized in the art of chemistry including, but not limited to, Chemical Abstract Service (CAS) and International Union of Pure and Applied Chemistry (IUPAC). Accordingly, the compound structure provided above identified as Pyrrolo [1, 2-a]pyrazine-1,4-dione, hexahydro-3-(1H-imidazol-5-ylmethyl)-, hydrate (1:1), (3S, 8aS)- under CAS may be identified by other names that are equivalent to the CAS name.

C. General Characterization of CHP Hydrate

In one embodiment, CHP Hydrate has an X-ray powder diffraction pattern (XRPD) that includes characteristic peaks at about 13.7 degrees 2θ, 17 degrees 2θ, and about 27.3 degrees 2θ. In some embodiments, the X-ray powder diffraction pattern further includes any one or more of characteristic peaks at about 10 degrees 2θ, about 13.7 degrees 2θ, about 17 degrees 2θ, about 18.1 degrees 2θ, and 24.5 degrees 2θ.

In some embodiments, CHP Hydrate has a melting temperature of about 170° C. to about 172° C. In one variation, CHP Hydrate has an X-ray powder diffraction pattern that includes any one or more characteristic peaks at about 10 degrees 2θ, about 13.7 degrees 2θ, about 17 degrees 2θ, about 18.1 degrees 2θ, about 20.2 degrees 2θ, and about 27.3 degrees 2θ.

It should be understood that relative XRPD intensities can vary depending on a number of factors, including sample preparation, mounting, and the instrument and analytical procedure and settings used to obtain the spectrum. As such, the peak assignments listed herein are intended to encompass variations of plus or minus 0.2 degrees 2θ. In another embodiment, the characteristic XRPD pattern of the CHP Hydrate may be defined as a range such as 9.7°-10.1°, 13.5°-13.9°, 16.8°-17.3°, 18.2°-18.5°, 22.4°-22.6°, 24.1°-24.5°, and 27.2°-27.5°. [00147] In other embodiments, CHP Hydrate is characterized as having a melting temperature onset as determined by differential scanning calorimetry at about 170° C. In yet other embodiments, CHP Hydrate is substantially free of solvent.

Figure 2:
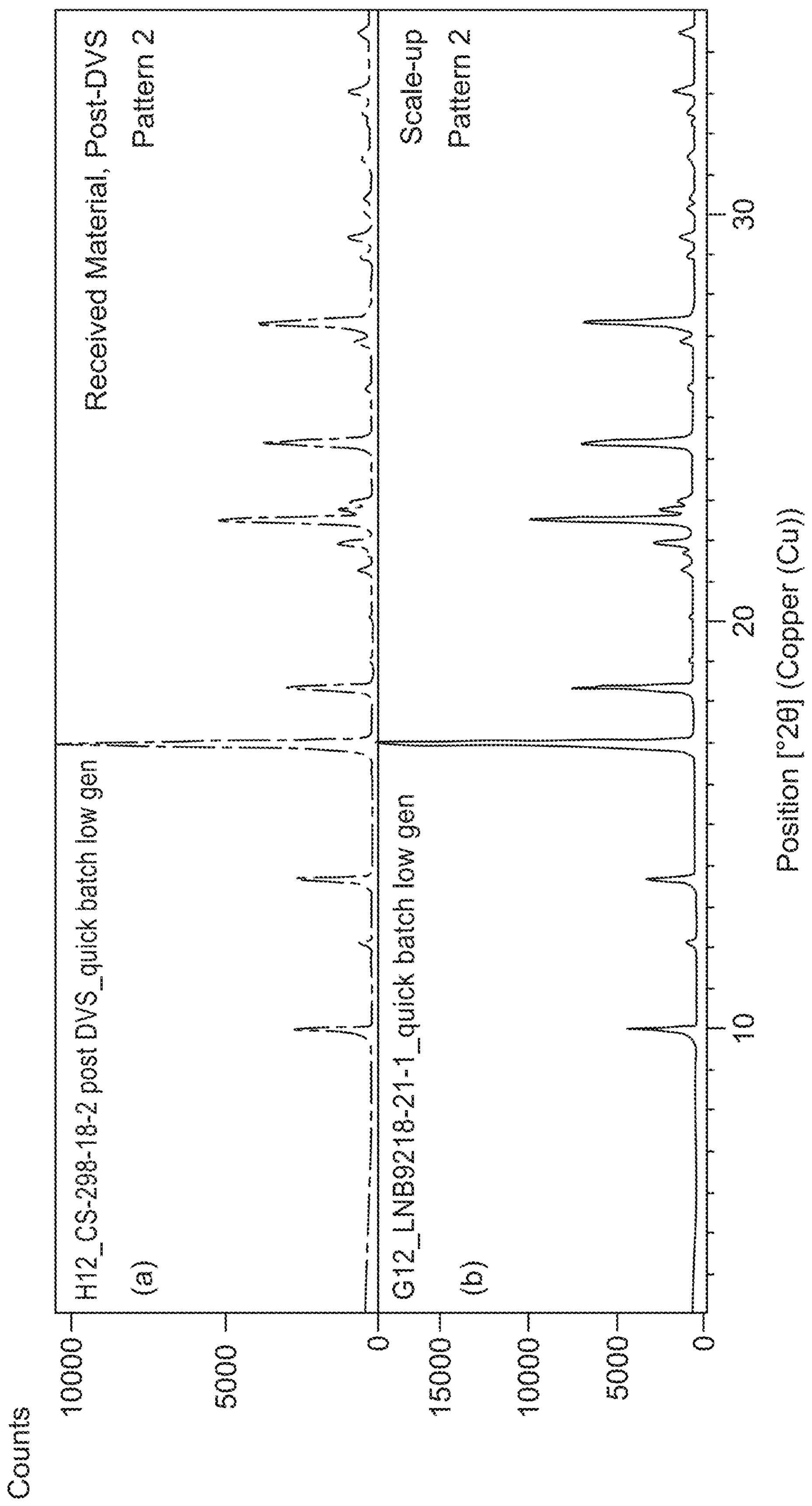
FIG. 2 is a comparison of the XRPD of (a) Pattern 1 post dynamic vapor sorption (DVS) and (b) Pattern 2 of CHP. These results confirm that the prepared CHP material is Pattern 2. (i.e., CHP Hydrate) and that Pattern 1 changed to Pattern 2 post-DVS.
Figure 19:
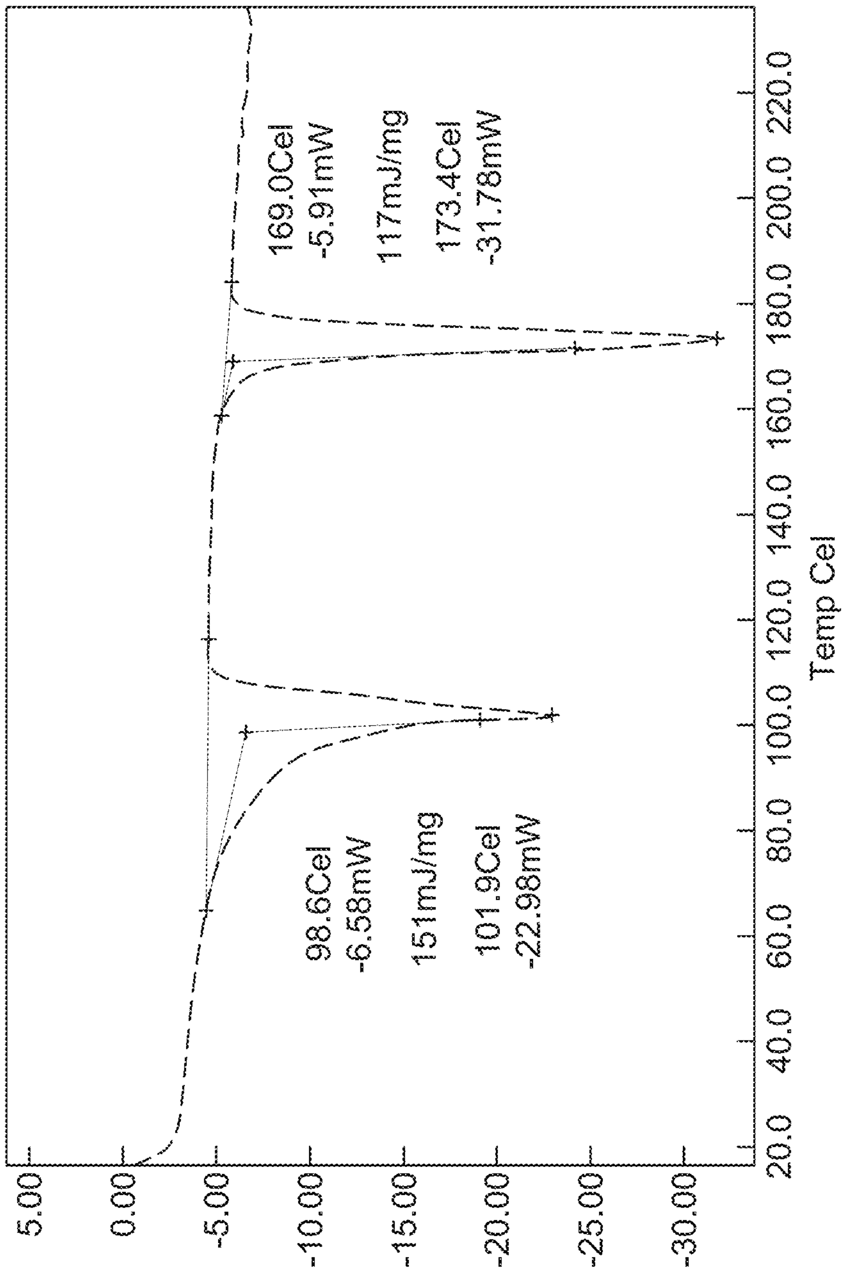
FIG. 19 illustrates the DSC analysis of Pattern 2 in the first heat cycle.
Figure 20:
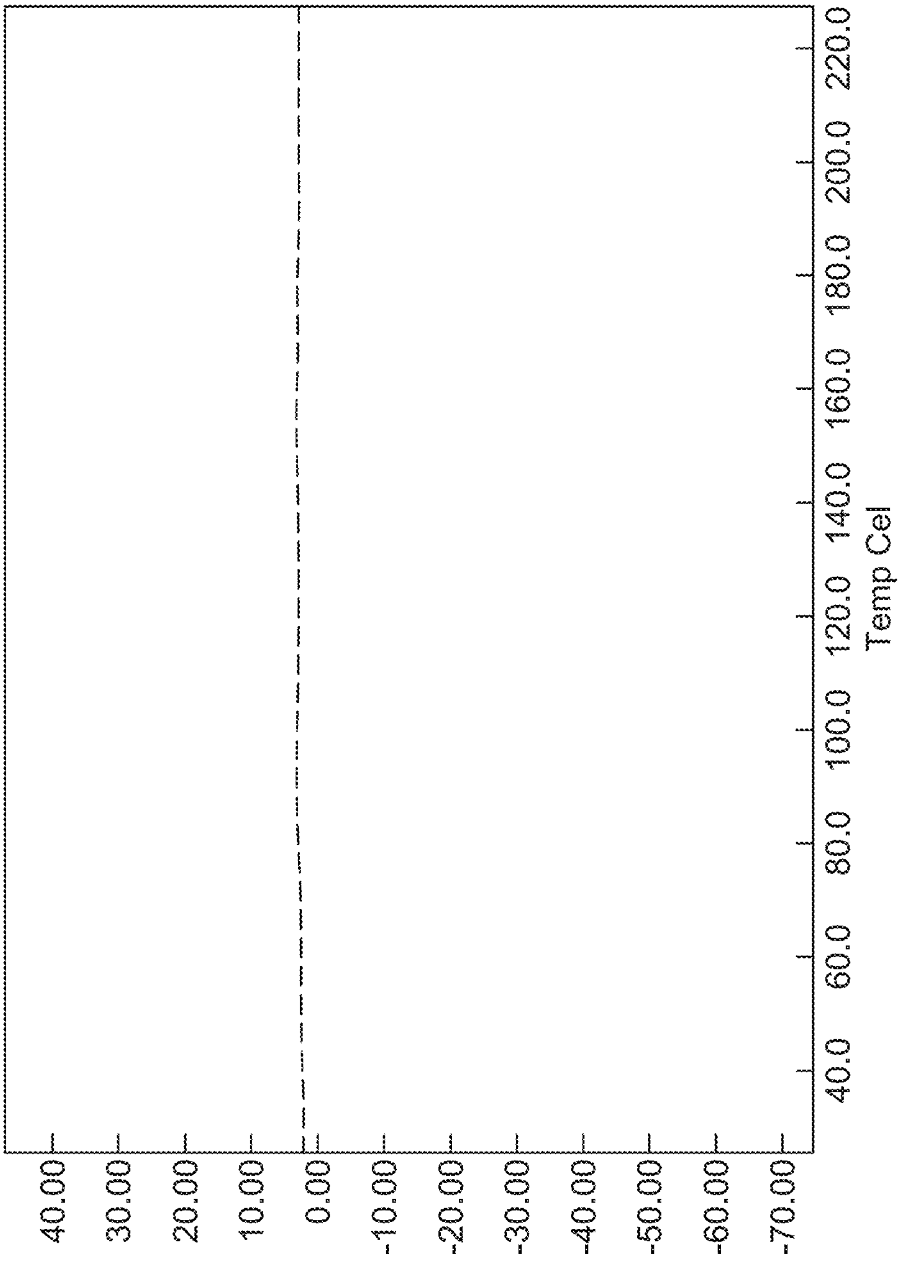
FIG. 20 illustrates the DSC analysis of Pattern 2 in the cooling cycle.
Figure 21:
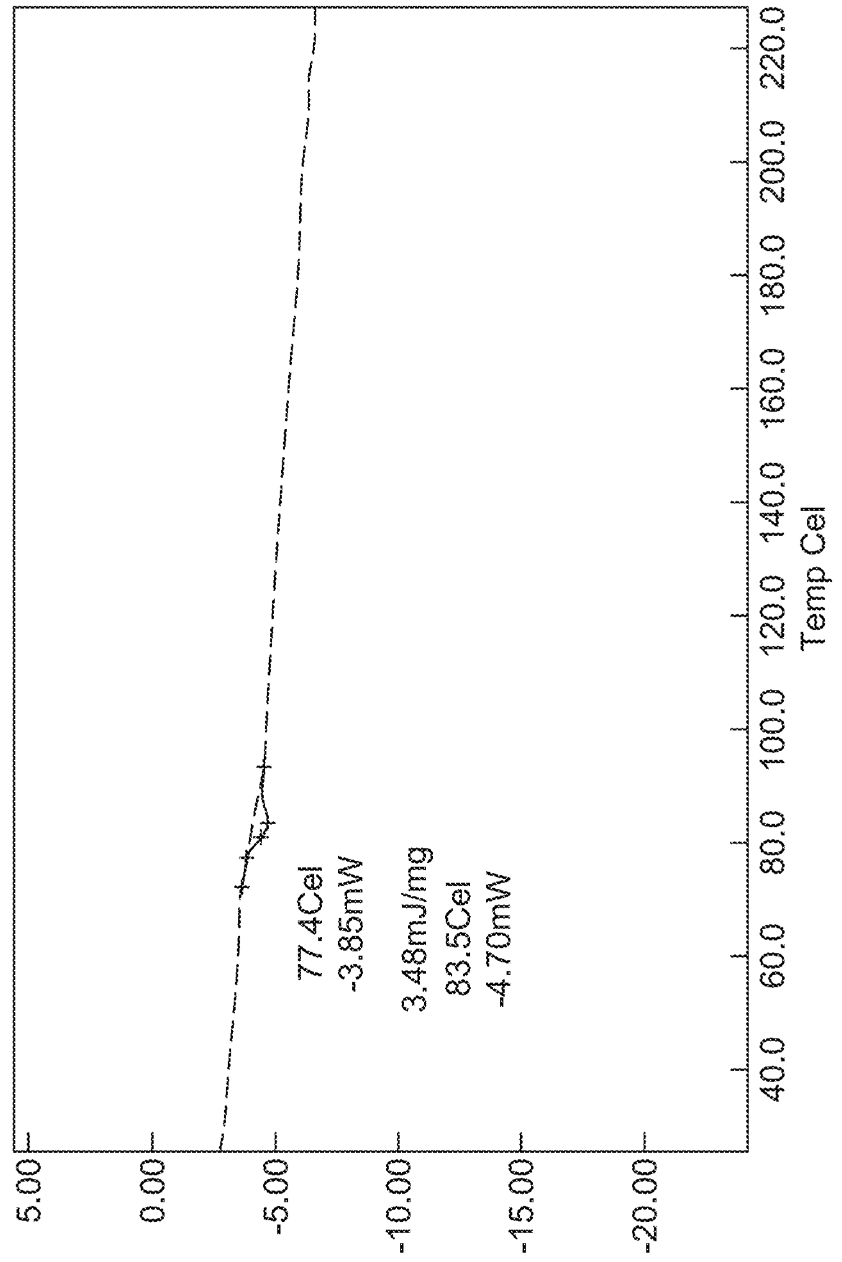
FIG. 21 illustrates the DSC analysis of Pattern 2 in the second heat cycle.

In some embodiments of CHP Hydrate, at least one, at least two, at least three, at least four, or all of the following (a)-(f) apply: (a) CHP Hydrate is substantially free of solvent; (b) CHP Hydrate is crystalline; (c) CHP Hydrate has an X-ray powder diffraction pattern substantially as shown in FIG. 2(*b*); (d) CHP Hydrate has a differential scanning calorimetry thermogram substantially as shown in FIGS. 19-21; (e) CHP Hydrate has a melting temperature onset as determined by differential scanning calorimetry at about 170° C.; and (f) CHP Hydrate is stable at room temperature storage conditions.

In some embodiments, CHP Hydrate comprises at least one, at least two, or all of the following properties:

(a) an X-ray powder diffraction pattern substantially as shown in FIG. 2(*b*);

(b) a differential scanning calorimetry thermogram substantially as shown in FIGS. 19-21; and (c) a melting temperature onset as determined by differential scanning calorimetry at about 170° C.

In some embodiments, the CHP Hydrate has an X-ray powder diffraction pattern displaying at least two of the largest peaks as the X-ray powder diffraction pattern substantially as shown in FIG. 2(*b*). In some embodiments, the CHP Hydrate has an X-ray powder diffraction pattern displaying at least three of the largest peaks as the X-ray powder diffraction pattern substantially as shown in FIG. 2(*b*). In some embodiments, the CHP Hydrate has an X-ray powder diffraction pattern displaying at least four of the largest peaks as the X-ray powder diffraction pattern substantially as shown in FIG. 2(*b*). In some embodiments, the CHP Hydrate has an X-ray powder diffraction pattern displaying at least five of the largest peaks as the X-ray powder diffraction pattern substantially as shown in FIG. 2(*b*). In some embodiments, the CHP Hydrate has an X-ray powder diffraction pattern displaying at least six of the largest peaks as the X-ray powder diffraction pattern substantially as shown in FIG. 2(*b*).

D. Pharmaceutical Compositions

In one embodiment, there is provided a pharmaceutical composition comprising substantially pure Pattern 2 compound and a pharmaceutically acceptable carrier. For example, a pharmaceutical composition can comprise substantially pure Pattern 2 compound at about 1 to about 20 percent (wt %) (i.e., about 1 percent, about 2 percent, about 3 percent, about 4 percent, about 5 percent, about 6 percent, about 7 percent, about 8 percent, about 9 percent, about 10 percent, about 11 percent, about 12 percent, about 13 percent, about 14 percent, about 15 percent, about 16 percent, about 17 percent, about 18 percent, about 19 percent, about 20 percent) of the total amount of pharmaceutical composition. By way of further example, a pharmaceutical composition can comprise Pattern 2 compound at about 1 to about 100 percent, about 1 to about 10 percent, about 10 to about 20 percent, about 20 to about 30 percent, about 30 to about 40 percent, about 40 to about 50 percent, about 50 to about 60 percent, about 60 to about 70 percent, about 70 to about 80 percent, about 80 to about 90 percent, about 90 to about 100 percent (wt %) of the total amount of the pharmaceutical composition. For example, a pharmaceutical composition can comprise Pattern 2 compound at about 1 to about 40 percent (wt %) of the total amount of the pharmaceutical composition. In a specific example, a pharmaceutical composition can comprise Pattern 2 compound at about 4 percent (wt %) of the total amount of the pharmaceutical composition.

In another embodiment, there is provided a pharmaceutical composition comprising substantially pure Pattern 2 compound, another therapeutically active agent and a pharmaceutically acceptable carrier. In one embodiment, the active agent is selected from a biomolecule, bioactive agent, small molecule, drug, prodrug, drug derivative, protein, peptide, vaccine, adjuvant, imaging agent (e.g., a fluorescent moiety), polynucleotide or a metal. In yet another embodiment, the active agent is a metal element, metal cation, a metal complex, or a metal compound wherein the metal can be copper, zinc, magnesium, manganese, iron, cobalt, chromium, or a combination thereof. In an embodiment, the metal is zinc and a zinc compound may be zinc gluconate, zinc acetate, zinc sulfate, zinc picolinate, zinc orotate, or zinc citrate. In another embodiment, the metal is magnesium and a magnesium compound such as magnesium oxide, magnesium citrate, magnesium chloride, magnesium glycinate, magnesium biglycinate, magnesium aspartate, magnesium lactate, or magnesium chloride can be employed. In another embodiment, the metal is manganese and a manganese compound may include manganese amino acid chelates (e.g., manganese bisglycinate chelate, manganese glycinate chelate, manganese aspartate, manganese gluconate, manganese picolinate, manganese sulfate, manganese citrate, or manganese chloride. In an embodiment, the metal is copper and a copper compound may include a cupric oxide, cupric sulfate, copper amino acid chelates, and copper gluconate. In still another embodiment, the metal is iron and iron may exist in various forms such as ferrous and ferric iron salts (for example, ferrous sulfate, ferrous gluconate, ferric citrate, or ferric sulfate cobalt). In an embodiment, the metal is cobalt and a cobalt compound may include cobalt acetate, cobalt sulfate, cobalt picolinate, cobalt orotate, or cobalt citrate. In an embodiment, the metal is chromium and a chromium compound may include chromium chloride, chromium nicotinate, chromium picolinate, high-chromium yeast, or chromium citrate.

In one embodiment, the Pattern 2 drug substance meets the ICH organic impurity guidelines Q3A for the structurally related organic impurity levels in CHP.

In another embodiment, the composition of the present invention can be administered in a variety of ways, including orally, topically, parenterally, intravenously, intradermally, colonically, rectally, intramuscularly or intraperitoneally.

The composition may be formulated for parenteral administration by injection, e.g., by bolus injection or continuous infusion. Formulations for injection may be presented in unit dosage form in ampoules or in multi-dose containers with an optional preservative added. The parenteral preparation can be enclosed in ampoules, disposable syringes or multiple dose vials made of glass, plastic or the like. The formulation may take such forms as suspensions, solutions or emulsions in oily or aqueous vehicles, and may contain agents such as suspending, stabilizing and/or dispersing agents.

For example, a parenteral preparation may be a sterile injectable solution or suspension in a nontoxic parenterally acceptable diluent or solvent. Among the acceptable vehicles and solvents that may be employed are water, 0.9% saline solution, or other suitable aqueous media.

In one embodiment, the concentration of the intravenous "solution" formulation is from about 1 mg/liter to about 200 mg/ml, from about 5 mg/ml to about 150 mg/ml, from about 10 mg/ml to about 100 mg/ml. In another embodiment, the concentration of the intravenous "solution" formulation is about 1 mg/liter, about 2 mg/liter, about 3 mg/liter, about 4 mg/liter, about 5 mg/liter, about 6 mg/liter, about 7 mg/liter, about 8 mg/liter, about 9 mg/liter, about 10 mg/liter, about 11 mg/liter, about 12 mg/liter, about 13 mg/liter, about 14 mg/liter, about 15 mg/liter, about 20 mg/liter, about 25 mg/liter, about 30 mg/liter, about 35 mg/liter, about 40 mg/liter, about 45 mg/liter, about 50 mg/liter, about 55 mg/liter, about 60 mg/liter, about 65 mg/liter, about 70 mg/liter, about 75 mg/liter, about 80 mg/liter, about 85 mg/liter, about 90 mg/liter, about 95 mg/liter, about 100 mg/liter, about 110 mg/liter, about 120 mg/liter, about 130 mg/liter, about 140 mg/liter, about 150 mg/liter, about 160 mg/liter, about 170 mg/liter about 180 mg/liter, about 190 mg/liter, or about 200 mg/liter.

In another embodiment, the composition may be formulated into a diffusion (slow drip) formulation or an intravenous bolus injection.

In yet another embodiment, Pattern 2 compound may be administered orally or formulated for oral administration. Administration may be via immediate release tablets and capsule or enteric coated tablets or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, sterile injectable solutions and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, hydroxypropyl cellulose, polyvinylpyrrolidone, cellulose, USP or sterile water, syrup base and methyl cellulose. The formulations can additionally include: lubricating agents such as talc, magnesium stearate, and stearic acid; wetting agents; emulsifying and suspending agents; preserving agents such as methyl and propylhydroxy-benzoates; sweetening agents; and flavoring agents.

In some embodiments, the compositions are formulated in a unit dosage form. The term "unit dosage forms" refers to physically discrete units suitable as unitary dosages for human subjects and other mammals, each unit containing a predetermined quantity of active material (therapeutically effective amount) calculated to produce the desired therapeutic effect, in association with a suitable pharmaceutical excipient (e.g., a tablet, capsule, ampoule). The compounds are generally administered in a pharmaceutically effective amount. In some embodiments, each dosage unit contains from about 1 mg to about 100 mg of Pattern 2 compound.

In some embodiments, each dosage unit contains from about 2 mg to about 60 mg, from about 3 mg to about 50 mg, from about 4 mg to about 40 mg, from about 5 mg to about 30 mg, from about 6 mg to about 20 mg, from about 8 mg to about 15 mg, or from about 8 mg to about 10 mg of Pattern 2 compound.

In other embodiments, each dosage unit contains about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 30 mg, about 40 mg, about 50 mg, about 60 mg, about 70 mg, about 80 mg, about 90 mg, or about 100 mg of Pattern 2 compound.

In one embodiment, the subject receives one or more dosage units per day. In yet another embodiment, the subject receives 15 mg of Pattern 2 compound per day.

For preparing solid compositions such as tablets, the active principle ingredient is mixed with a pharmaceutical excipient to form a solid mixed-blend composition containing a homogeneous mixture of a compound of the present disclosure. When referring to these mixed-blend compositions as homogeneous, it is meant that the active ingredient is dispersed evenly throughout the composition so that the composition may be readily subdivided into equally effective unit dosage forms such as tablets, pills and capsules.

The tablets or pills of the present disclosure may be powder-coated or otherwise compounded to provide a dosage form affording the advantage of prolonged action or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate. In one embodiment, the film coating is a polyvinyl alcohol-based coating.

Compounds useful in the compositions and methods include those described herein in any of their pharmaceutically acceptable forms, including isomers such as diastereomers and enantiomers, salts, solvates, and polymorphs, as well as racemic mixtures and pure isomers of the compounds described herein, where applicable.

Suitable excipients include binders, fillers, disintegrants, lubricants, antioxidants, chelating agents, and color agents.

Table 1 provides exemplary formulations for oral dosage forms include (based on weight % of the stated ingredients):

Table 1: Exemplary formulations for oral dosage forms include (based on weight % of the stated ingredients)

TABLE 1

Exemplary formulations for oral dosage forms include (based on weight % of the stated ingredients)

| Ingredient | 1 | 2 | 3 | 4 | 5 | 6 | 7 | 8 | 9 | 10 |
|---|---|---|---|---|---|---|---|---|---|---|
| CHP Hydrate | 85 | 70 | 60 | 50 | 40 | 30 | 20 | 10 | 5 | 2 |
| Binder | 9 | 10 | 20 | 30 | 30 | 40 | 40 | 40 | 40 | 40 |
| Disintegrant | 5 | 5 | 5 | 5 | 5 | 5 | 5 | 5 | 5 | 5 |
| Lubricant | 1 | 1 | 1 | 1 | 1 | 1 | 1 | 1 | 1 | 1 |
| Filler | 0 | 14 | 14 | 14 | 24 | 24 | 34 | 44 | 49 | 52 |

E. Preparation of CHP Hydrate

In some embodiments, CHP Hydrate is obtained by crystallization. CHP anhydrate was dissolved in 2-2.5 v of EtOH/water or Acetone/water at 50° C. and then the system was cooled to 35° C. Next, 0.5 v Methyl tert-butyl ether (MtBE) was added and then 0.5% seed (CHP hydrate) was added. After stirring for 2 h, the system was cooled to 5° C. in 2 h. Finally, 7 v MtBE was added in 8 h and was then stirred for 8 h.

Solubility assessments carried out a batch of CHP pattern 1 indicated high solubility in all solvent mixtures that contained water with the exception of ethanol:water:MtBE blends with the highest percentage of MtBE. Particularly high solubility was observed in water and water:acetone blends. The material was poorly soluble in acetone, acetonitrile and THF (≤10 mg/mL). Two-point solubility experiments indicated that out of the two solvent systems assessed (ethanol:water:MtBE and acetone:water), ethanol:water: MtBE allowed for slightly better yield, but there was a risk of Pattern 1 formation; while acetone:water allowed for pattern 2 exclusivity but there was a risk of reducing the yield.

Two sets of small-scale crystallization trials (500 mg scale) were carried out using CHP pattern 1. The first set utilized an acetone:water solvent system and the second set an ethanol:water:MtBE solvent system. Anti-solvent additions were carried out at either 5° C. or 50° C. Pattern 2 was returned exclusively by XRPD regardless of solvent system or anti-solvent addition temperature. Ethanol:water/MtBE produced larger particles, particularly when the solid was isolated at higher temperature (50° C.). Solvent loss due to evaporation (particularly in ethanol:water:MtBE) resulted in a much lower calculated yield in comparison to the mass of solid recovered post-filtration.

These crystallization development studies explored a combination of cooling and anti-solvent addition protocols with the aim of obtaining a good yield and particle uniformity. These studies indicated that on a 20 g scale, using 2% ground seed load, step-wise anti-solvent addition, use of an eight-hour hold period at 29° C. followed by cooling to 5° C. proved to be the most promising protocol with respect to particle uniformity (assessed by light microscopy and FBRM) and yield.

F. X-Ray Powder Diffraction (XRPD)

In one embodiment, the present disclosure relates to substantially pure cyclo(-His-Pro) hydrate (Pattern 2) compound as follows:

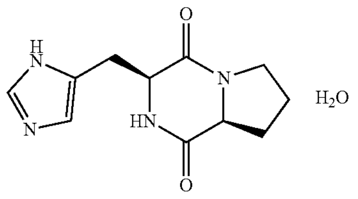

characterized by an XRPD diffractogram comprising peaks at about 17 and about 27.3 degrees (±0.2° in 2θ).

One embodiment of substantially pure Pattern 2 is characterized by an X-ray powder diffractogram comprising at least three peaks chosen from the following list: 13.7, 17, 18.1, 20.2 and 27.3 degrees (+0.2° in 2θ). Another embodiment is characterized by an XRPD diffractogram comprising at least two peaks chosen from the following list: 10, 13.7, 17, 18.1, 20.2 and 27.3 degrees (+0.2° in 2θ). Another embodiment is characterized XRPD diffractogram comprising three or more peaks at 20 values selected from the group consisting of 13.5°-13.9°, 16.9°-17.3°, 22.4°-22.6°, 24.1°-24.5°, and 27.2°-27.5°. Still in another embodiment, the compound is characterized by XRPD diffractogram further comprising peaks at 20 values at 17.90-18.40.

G. Nuclear Magnetic Resonance (NMR) or $^{13}$CSSNMR

In one embodiments, the $^{1}$H NMR spectrum of Pattern 2 displays the following chemical shifts: $^{1}$H NMR (400 MHz, $D_2O$) δ 7.58 (d, 1H, J=3.2 Hz), 6.82 (d, 1H, J=3.2 Hz), 4.42 (m, 1H), 4.12 (m, 1H), 3.36-3.47 (m, 2H), 3.05-3.09 (m, 2H), 2.12 (br, 1H), 1.80-1.84 (m, 2H), 1.37-1.40 (m, 1H).

In one embodiment, the CHP hydrate of the present disclosure exhibits essentially the same $^{1}$H-NMR as the CHP-anhydrous in DMSO-$d_6$ solvent. This includes the following values: 1.7 ppm (m, 3H), 2.1 ppm (m, 1H), 2.5 ppm (s, 3H), 3.2 ppm (d, 1H), 3.5 ppm (m, 1H), 4.2 ppm (m, 2H), 7.0 ppm (s, 1H), 7.6 ppm (s, 1H), 8.1 ppm (s, 1H).

H. Solid Infra-Red Spectroscopy

In one embodiment, the solid infra-red spectrum of Pattern 2 displays signals at 3457, 3411 (m); 3292, 3211 (m); 2976; 1658; 1633 (m); and 1445-1424 (m) $cm^{-1}$.

I. Differential Scanning Calorimetry (Dsc)

In another embodiment, the onset endotherm of Pattern 2 was found to be about 100±2° C. and 171±2° C. In other embodiments, the Pattern 2 (CHP hydrate) of the present disclosure exhibits an endotherm onset at about 75° C. to about 100° C.

J. Dynamic Vapor Sorption (Dvs)

In yet another embodiment, the dynamic vapor sorption of Pattern 2 shows one or more of:

- dehydrating below 10% RH losing 6±0.2 weight % loss, and rehydrating from 0 to 40% RH at 40° C.;
- dehydrating below 20% RH losing 6±0.2 weight % loss, and rehydrating from 0 to 40% RH at 50° C.; and
- dehydrating below 20% RH losing 7±0.2 weight % loss, and rehydrating from 0 to 40% RH at 60° C.

In other embodiments, the CHP hydrate of the present disclosure exhibits a weight loss of about 3% to about 9%, or about 4% to about 8.5%, or about 5% to about 8%. In another embodiments, the CHP hydrate of the present disclosure exhibits a weight loss of about 5.5 to about 7.3%.

In yet another embodiment, the CHP hydrate of the present disclosure exhibits a weight loss of about 5.8 to about 7.0%.

K. Thermogravimetric Analysis (Tga)

In another embodiment, the TGA of Pattern 2 shows a 6±0.5% weight loss before degradation.

In other embodiments, the CHP hydrate of the present disclosure exhibits at least one endothermic event at about 75-85° C. which is loss of water. In another embodiment, the CHP hydrate of the present disclosure exhibits at least one exothermic event at about 115 to about 120° C., which is a recrystallization event to Pattern 1.

L. Melting Temperature

In another embodiment, the melting temperature of Pattern 2 is 170±2° C.

M. Metastable Zone Width (Mszw) Measurements

In yet another embodiment, the lack of precipitation at 0% MtBE indicated that anti-solvent addition was required for crystallization to occur. At 10% MtBE, a metastable zone width of about 43.2° C. was observed. At 20% MtBE, CHP remained in solution until the starting concentration was >100 mg/mL. The metastable zone widths for the 325 and 425 mg/mL experiments were determined to be about 35.2 and about 30.7° C., respectively. Increasing the MtBE content to 30% v/v, gave a MSZW of about 30±0.5° C. (at 325 mg/mL). Furthermore, at 60 MtBE %, the MSZW was 51.4° C. (at 100 mg/mL). At 80% MtBE, samples prepared at a concentration of 100 mg/mL and 425 mg/mL remained as slurries through the duration of the experiment, even at higher temperatures. Throughout the metastable zone width analysis, a trend was noted whereby a temperature of approximately 56-61° C. was required to obtain a clear point.

P. Methods of Treatment

The Pattern 2 compound of the present disclosure may be used in therapeutically effective amounts to treat a variety of diseases and disorders, such as diabetes and other metabolic diseases, neurodegenerative diseases, Alzheimer's disease, Parkinson's disease, Huntington's disease, Acute Kidney Injury (AKI), Chronic Kidney Disease (CKD), kidney fibrosis, to provide cytoprotection against oxidative damage, to suppress inflammatory responses in the PC12 cell line, and as an appetite suppressant.

EXAMPLES

The following examples are included to demonstrate certain embodiments of the present disclosure. Those of skill in the art should, however, in light of the present disclosure, appreciate that modifications can be made in the specific embodiments that are disclosed and still obtain a like or similar result without departing from the spirit and scope of the intention. Therefore, all matter set forth is to be interpreted as illustrative and not in a limiting sense.

Example 1—Conversion of Pattern 1 (Anhydrous Chp) to Pattern 2 (CHP Hydrate)

An amount of 2 g of Pattern 1 material (Lot No PS00726-55-D) was dissolved in 1 mL water at 80° C. In order to counter a significant amount of evaporation, another 1 mL of water was added. At 80° C., this resulted in a clear, dark brown solution. Next, the solution was rapidly cooled to 50° C. and 9.5 volumes (19 mL) of acetone was added to the solution, to yield a pale yellow solution. No oiling or precipitation was detected. The solution was cooled to room temperature, resulting in a noticeable quantity of solid precipitation. The solution was cooled to 6° C. (to boost yield) and the slurry was filtered. The solid was dried on the filter to prevent dehydration. Because the dehydration to Patten 1 happens at 80° C. or higher under vacuum, drying at 50° C. under vacuum was considered to be safe to preserve Pattern 2. XRPD confirmed that the product is Pattern 2, with a yield of approximately 72%.

A batch of CHP Hydrate was analyzed by various techniques including: X-ray powder diffraction (XRPD), pKa analysis, polarized light microscopy (PLM), thermogravimetric analysis/differential thermal analysis (TG/DTA), differential scanning calorimetry (DSC), Fourier-transform infrared spectroscopy (FT-IR), dynamic vapor sorption (DVS), variable temperature and humidity X-ray powder diffractometry (VT-/VH-XRPD), $^1$H nuclear magnetic resonance (NMR), and heteronuclear single quantum coherence (HSQC) NMR.

A. X-Ray Powder Diffraction (XRPD)

XRPD analysis was carried out on a PANalytical X'pert pro, scanning the samples between 3 and 35° 2θ. The material was gently ground to release any agglomerates and loaded onto a multi-well plate with Kapton or Mylar polymer film to support the sample. The multi-well plate was then placed into the diffractometer and analysed using Cu K radiation (α1λ=1.54060 Å; α2=1.54443 Å; β=1.39225 Å; α1:α2 ratio=0.5) running in transmission mode (step size 0.0130° 2θ) using 40 kV/40 mA generator settings.

Figure 3:
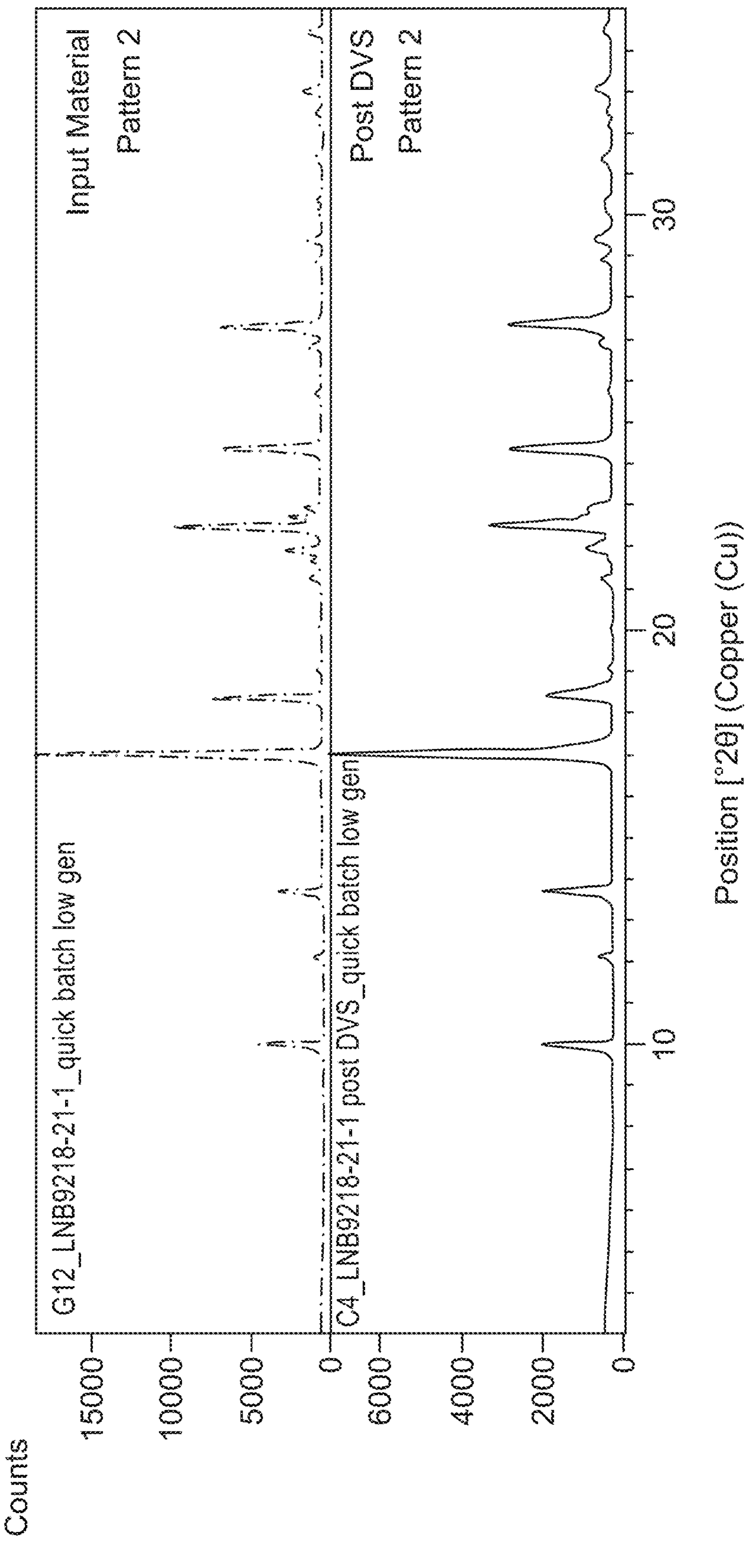
FIG. 3 is a comparison of the X-ray powder diffractograms of Pattern 2 at 40% RH pre-DVS and post-DVS.
Figure 4:
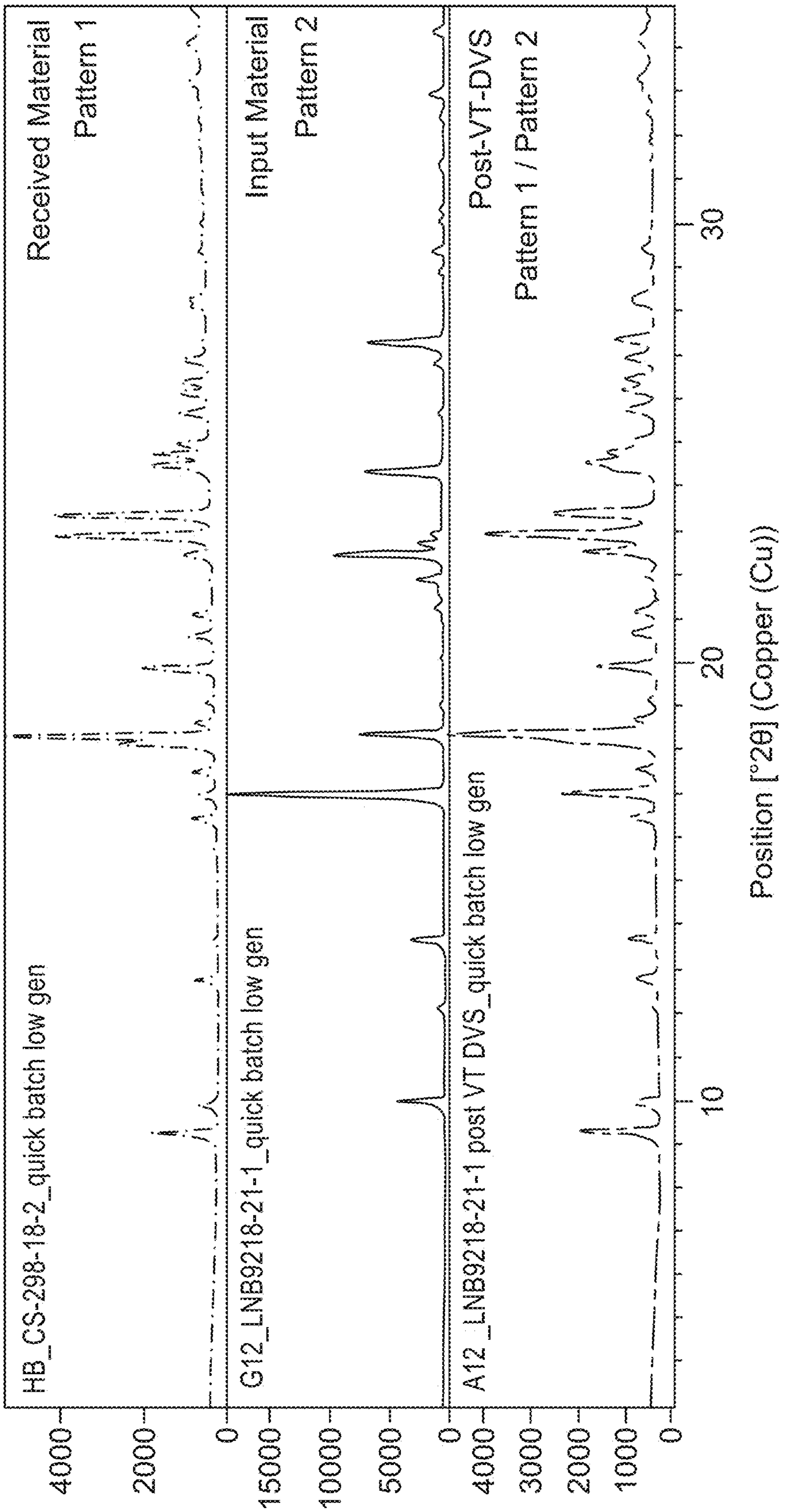
FIG. 4 is the analysis of the X-ray powder diffractograms of Pattern 2 post-VT-DVS. It shows that the material was a mixture of Patterns 1 and 2.
Figure 5:
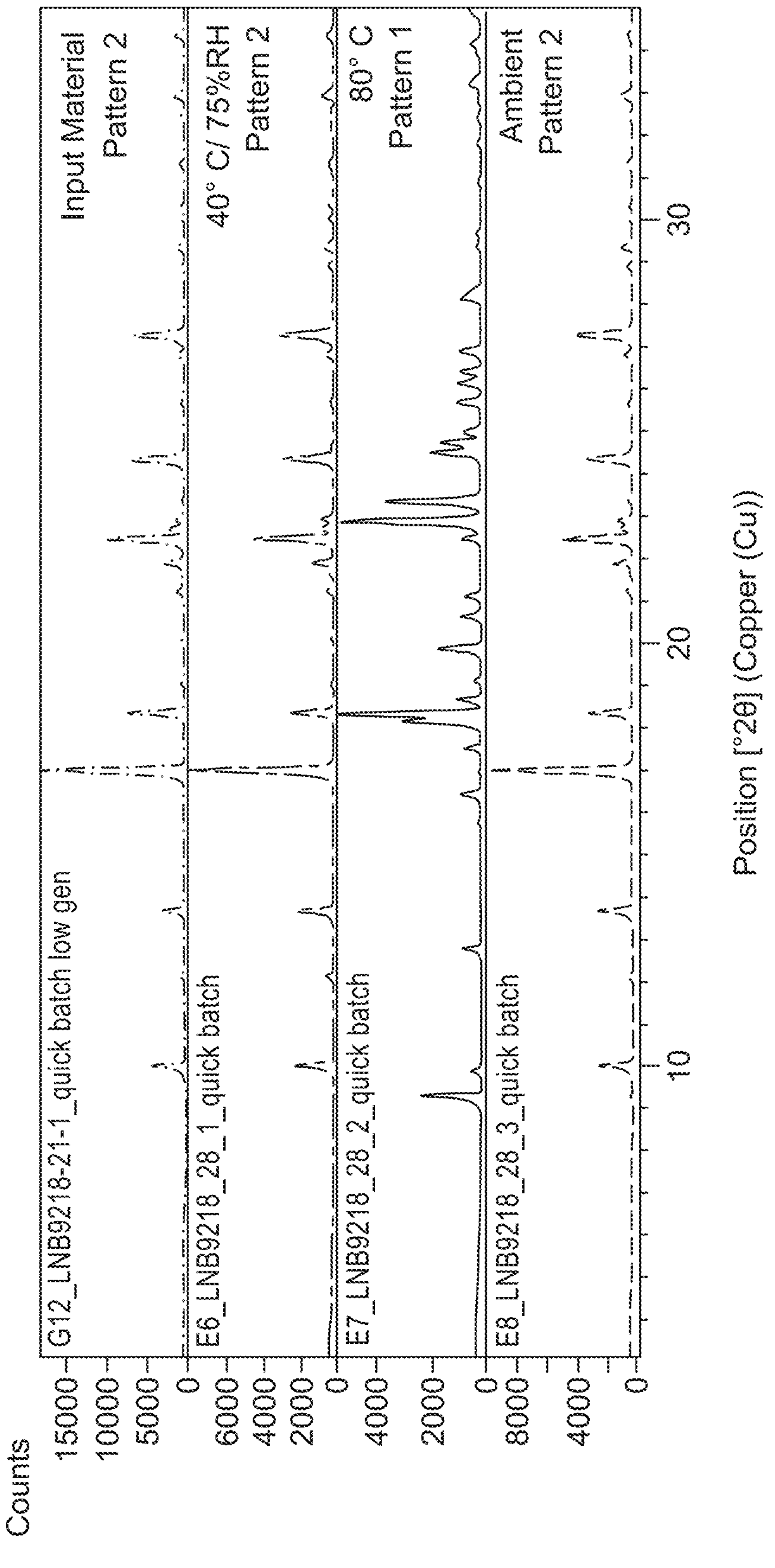
FIG. 5 is a comparison of the X-ray powder diffractograms of about 30 mg of Pattern 2 that was stored under three conditions for seven days: 40° C./75% RH, 80° C., and ambient light.
Figure 7:
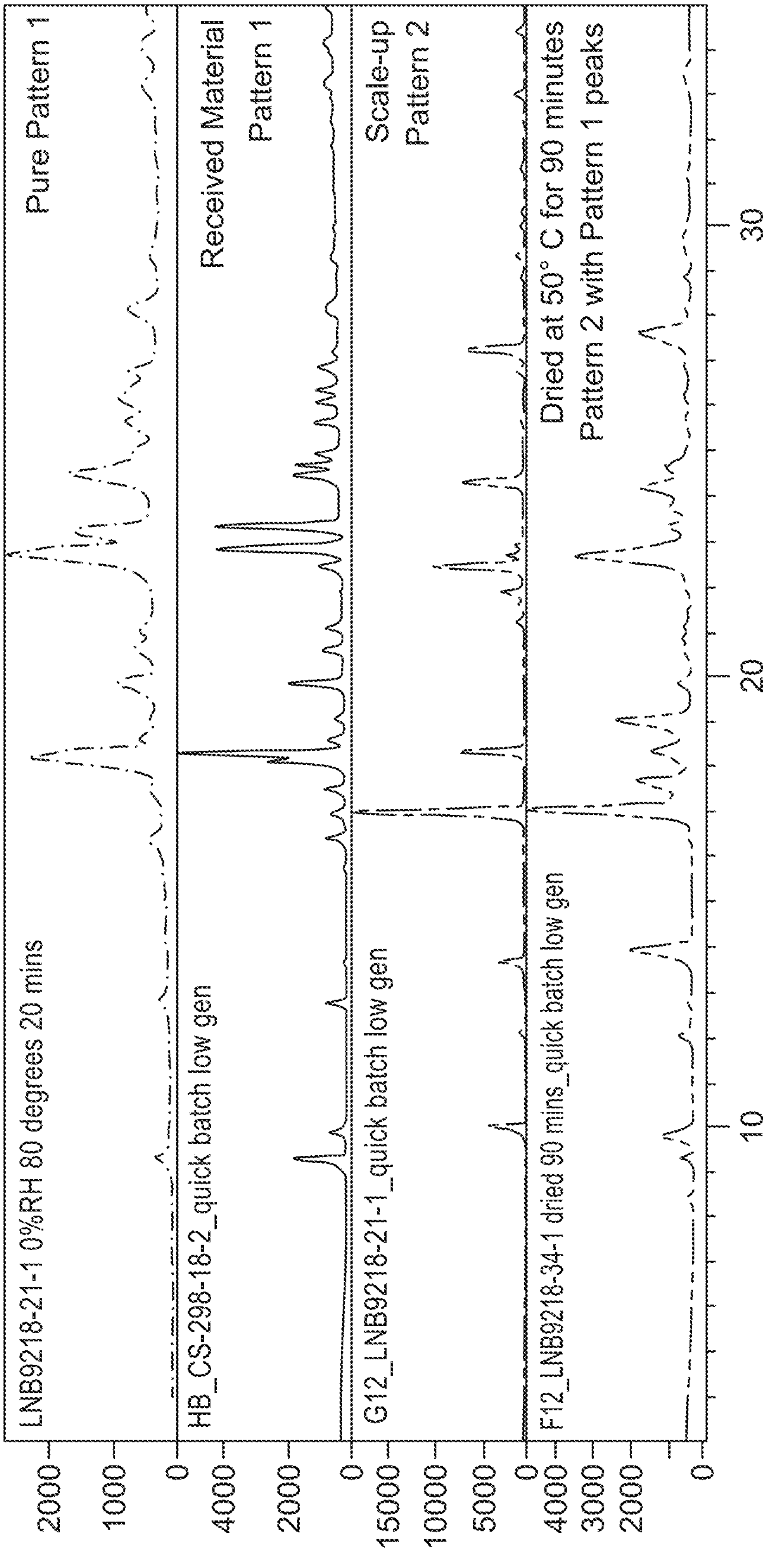

As shown in FIG. 1, the batch was crystalline by XRPD and was assigned as Pattern 1. XRPD analysis was carried out on a sample of 5 g of CHP Hydrate. The sample was weighed in a glass vial, and 6 mL of a 90:10 ethanol/water mixture was added to make a slurry. The mixture was then agitated for approximately 24 hours at ambient temperature and then analyzed by XRPD. As shown in FIG. 2, this material was confirmed as Pattern 2 (FIG. 2(*b*)). As shown in FIG. 3, the analysis of Pattern 2 following DVS showed no change in form at 40% RH post-DVS. As shown in FIG. 4, the analysis of Pattern 2 showed that post various temperature DVS (VT-DVS), the material was a mixture of Patterns 1 and 2. As shown in FIG. 5, approximately 30 mg of Pattern 2 (black line, FIG. 5) was stored under three conditions for seven days: 40° C./75% RH, 80° C., and ambient light. XPRD analysis was carried out to assess any change in the form of the material. After seven days, no change was observed in the samples stored at 40° C./75% RH (blue line, FIG. 5) and those stored at ambient light (green line, FIG. 5). The sample stored at 80° C. converted to Pattern 1 (red line, FIG. 5). As shown in FIG. 7, the Pattern 2 sample (blue line of FIG. 7) was returned to the vacuum oven for a further 30 minutes. XRPD analysis (purple line of FIG. 7) showed the material was still predominantly Pattern 2 with some Pattern 1 peaks.

Figure 6:
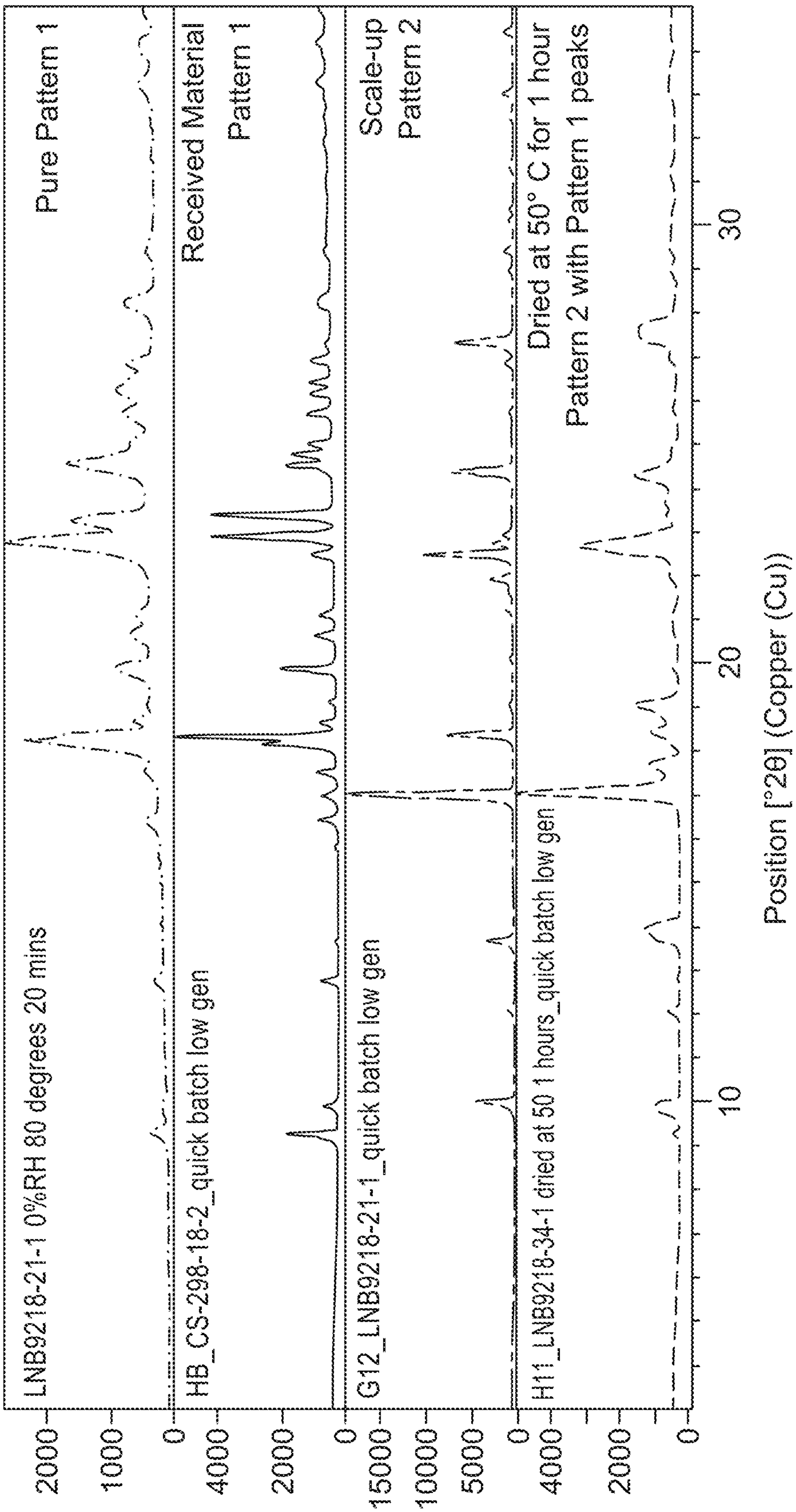
FIG. 6 is an XRPD analysis of about 2.2 g of CHP Hydrate (Pattern 2) that was weighed in a glass vial and placed inside a vacuum oven set to 50° C. for 1 hour.

As shown in FIG. 6, CHP Hydrate (Pattern 2) was weighed in a glass vial and placed inside a vacuum oven set to 50° C. for 1 hour. XRPD analysis (green line) showed that the material was still predominately Pattern 2 with some Pattern 1 peaks.

Figure 8:
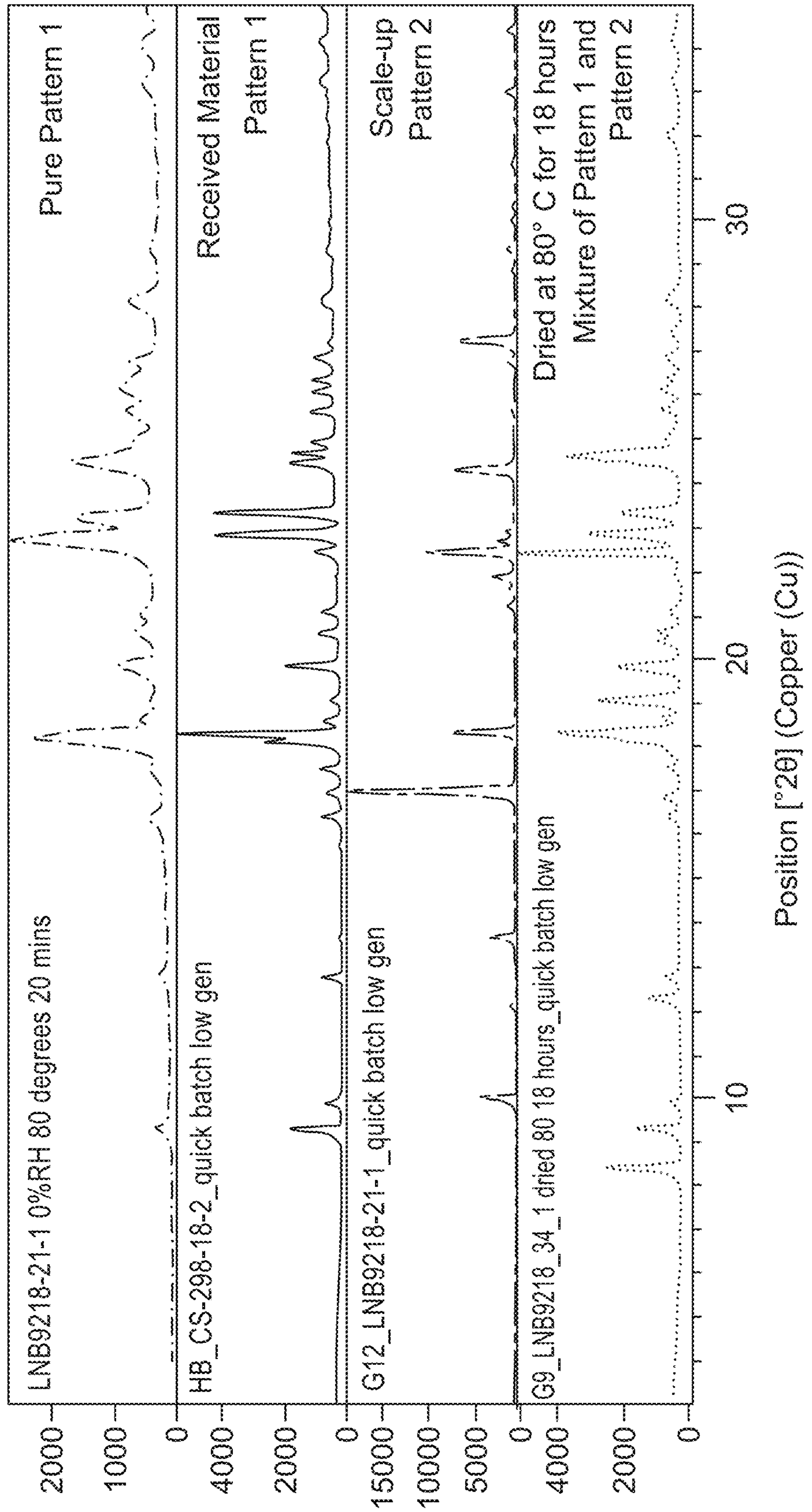
Figure 9:
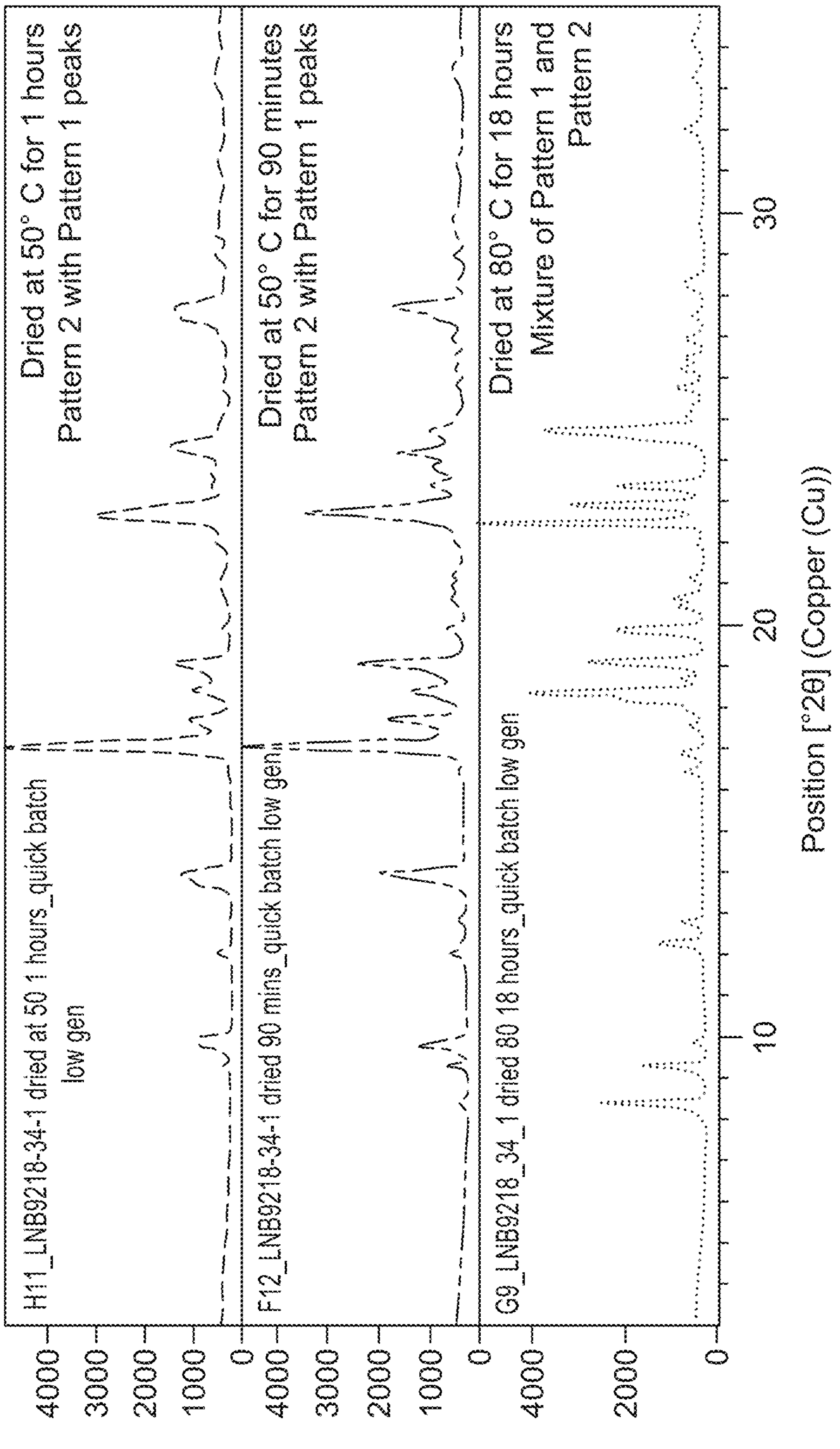
FIG. 9 is comparison of changes in Pattern 2 at different temperatures. It is an overlay of the product XRPD analysis of the sample from FIGS. 5-7 that was dried for three different time periods, and the results were analyzed by XRPD. The green line represents Pattern 2 sample stored at 50° C. for 1 hour, the purple line represents Pattern 2 sample stored at 50° C. for 90 min, and the pink line represents the Pattern 2 sample stored at 80° C. for 18 hours (pink line).

As shown in FIG. 8, the input material from FIG. 5 (black line) was returned to the oven, in which the temperature was increased to 80° C. The vial was placed inside the oven for an additional 18 hours. XRPD analysis (pink line) showed that the material was a mixture of Pattern 1 and 2. There was an extra peak at 8° 20 that had not been previously seen in any pattern. As shown in FIG. 9, the Pattern 2 from FIG. 5 was dried for three different time periods, and the results were analyzed by XRPD. Drying the sample at 50° C. for 1 hour produced Pattern 2 with Pattern 1 peaks (green line), drying the sample at 50° C. for 90 minutes also produced Pattern 2 with Pattern 1 peaks (purple line), and drying the sample at 80° C. for 18 hours showed a mixture of Pattern 1 and Pattern 2 (pink line).

Figure 34:
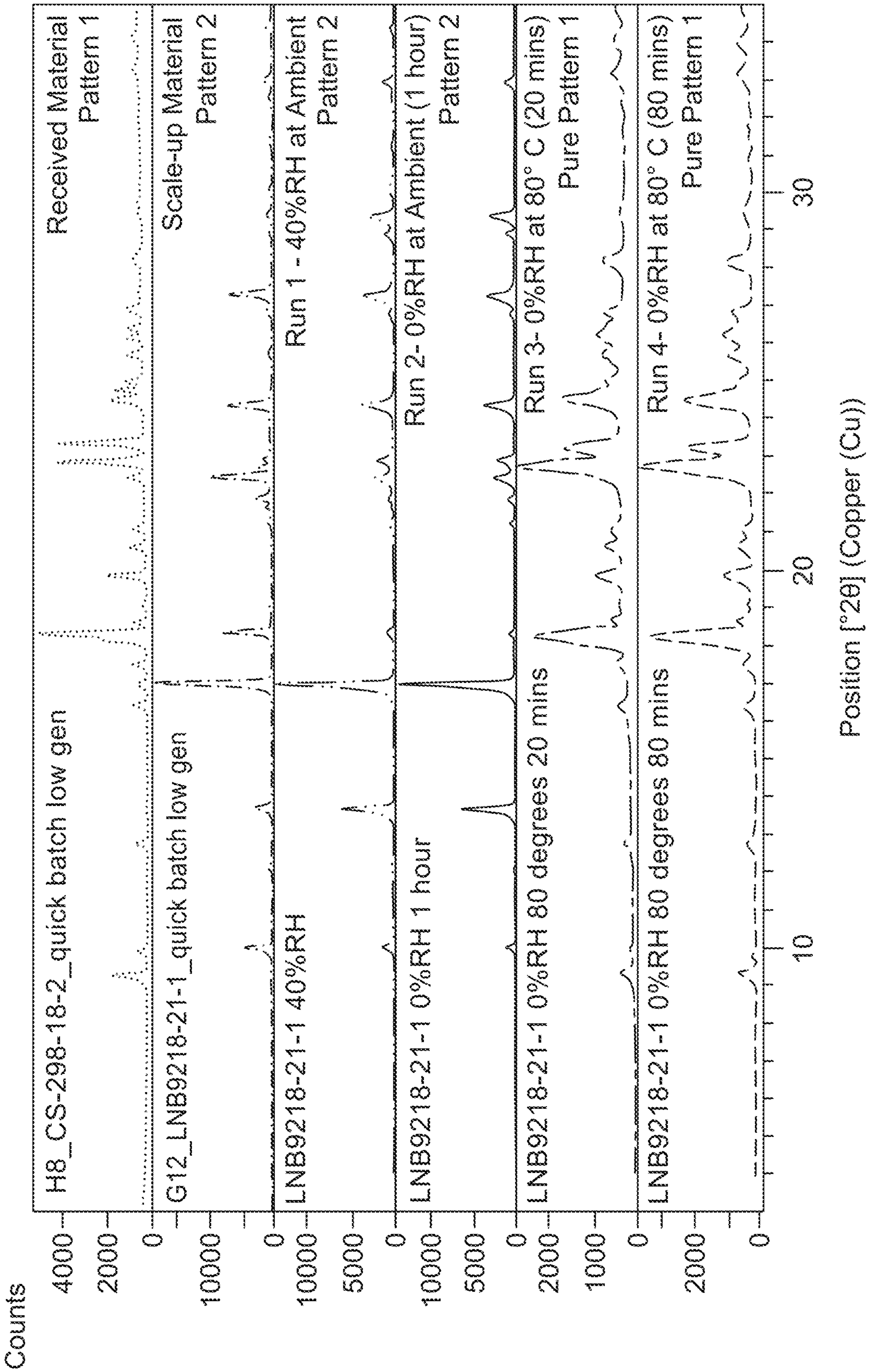
FIG. 34 illustrates XRPD diffractograms of CHP Hydrate, Pattern 2 material after various conditions of VT/DVS. The XRPD diffractogram of Pattern 1 is provided for comparison.

FIG. 34 summarized different conditions in which Pattern 2 changes to Pattern 1. Treating a sample of Pattern 2 (black line, FIG. 34) at (run 2, red line) 80° C. in 0% RH converted Pattern 2 to Pattern 1 within 20 minutes (run 3, blue line), while it remains as Pattern 2 at 0% RH at ambient temperature even after 1 hour (red line). The pattern 2 is stable at ambient temperature at 40% RH (run 1, brown line).

B. pKa Analysis pKa analysis was carried out on Pattern 1 via a potentiometric technique which is acid/base titration to determine the pKa point.

Figure 10:
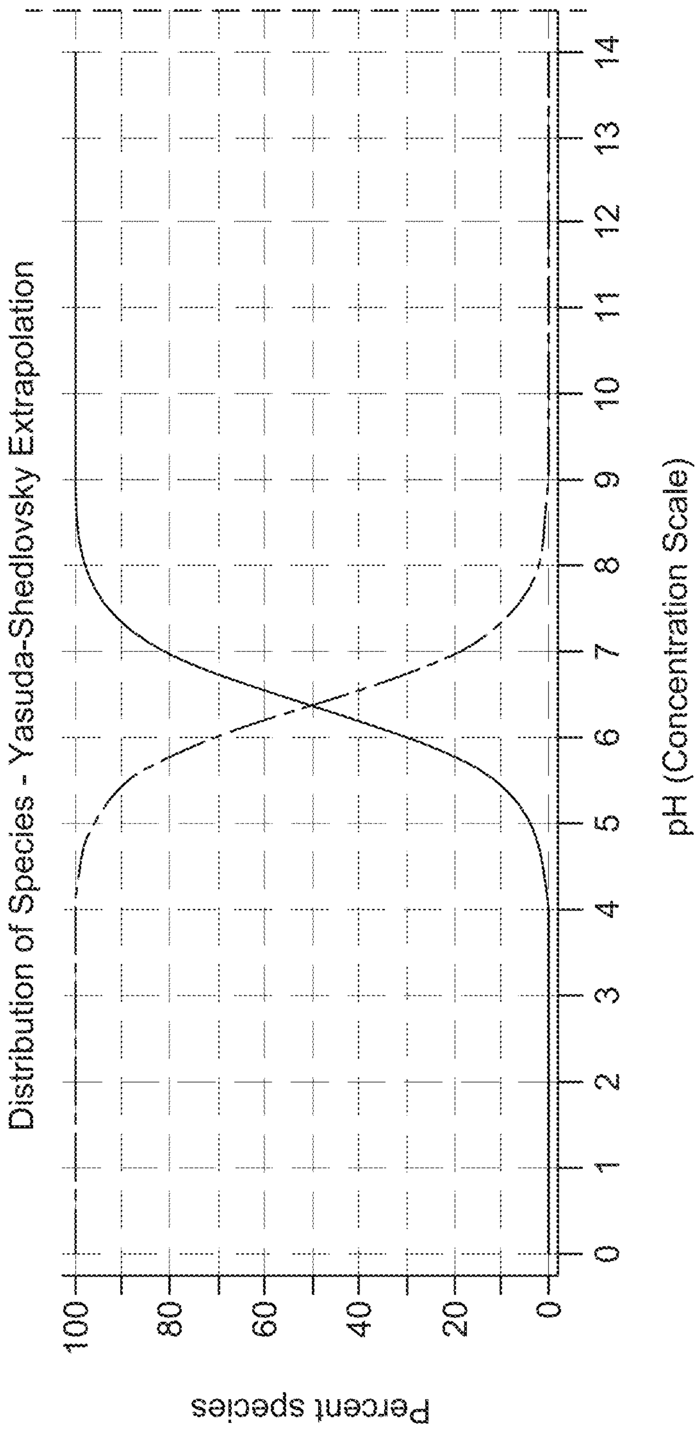
FIG. 10 illustrates the initial analysis of the received material (mostly Pattern 1). The pKa value is 6.4.

As shown FIG. 10, the analysis of the anhydrous CHP (Pattern 1) resulted in a pKa value of 6.4.

C. Optical Microscopy (Non-Polarized) and Polarized Light Microscopy (PLM)

Optical Microscopy was measured visually using a calibrated Linkam THM600 hostage with connected controller unit coupled to an Olympus BX50 polarising microscope equipped with a Motic camera and image capture software (Motic Images Plus 2.0). Approximately 0.5 mg of material was placed onto a microscope coverslip and heated at a rate of 10° C./min with images taken at routine intervals to document any thermal transitions. All images were recorded using the 10× objective, unless otherwise stated.

(PLM) analysis was carried out using an Olympus BX50 polarising microscope, equipped with a Motic camera and image capture software (Motic Images Plus 2.0). All images were recorded using the 20× objective, unless otherwise stated. The presence of crystallinity (birefringence) was determined by PLM. The polarized light microscope is designed to observe and photograph specimens that are visible primarily due to their optically anisotropic character.

Figure 11:
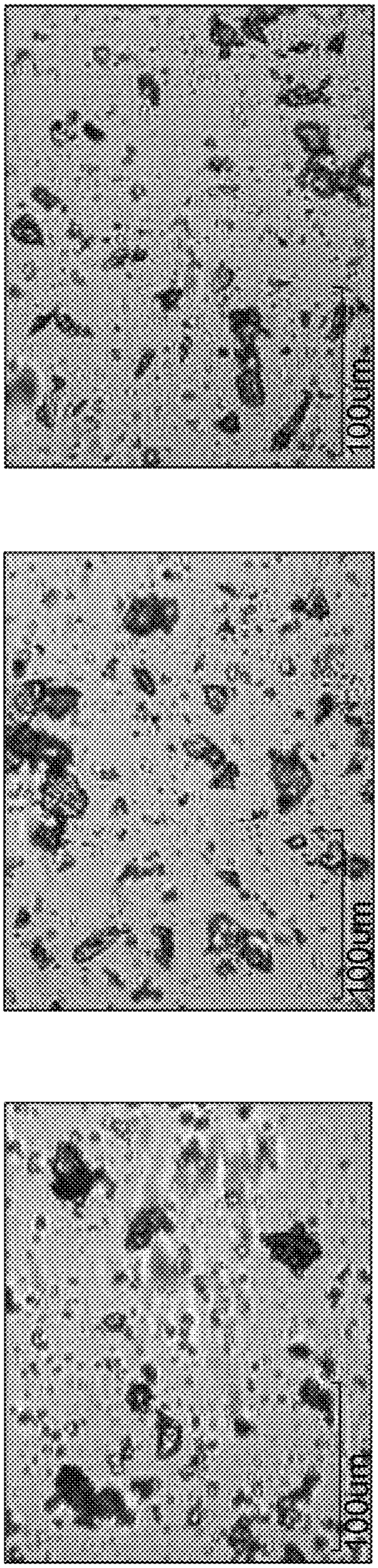
FIG. 11 illustrates the non-polarized microscope analysis of the received CHP (mostly Pattern 1).
Figure 13:
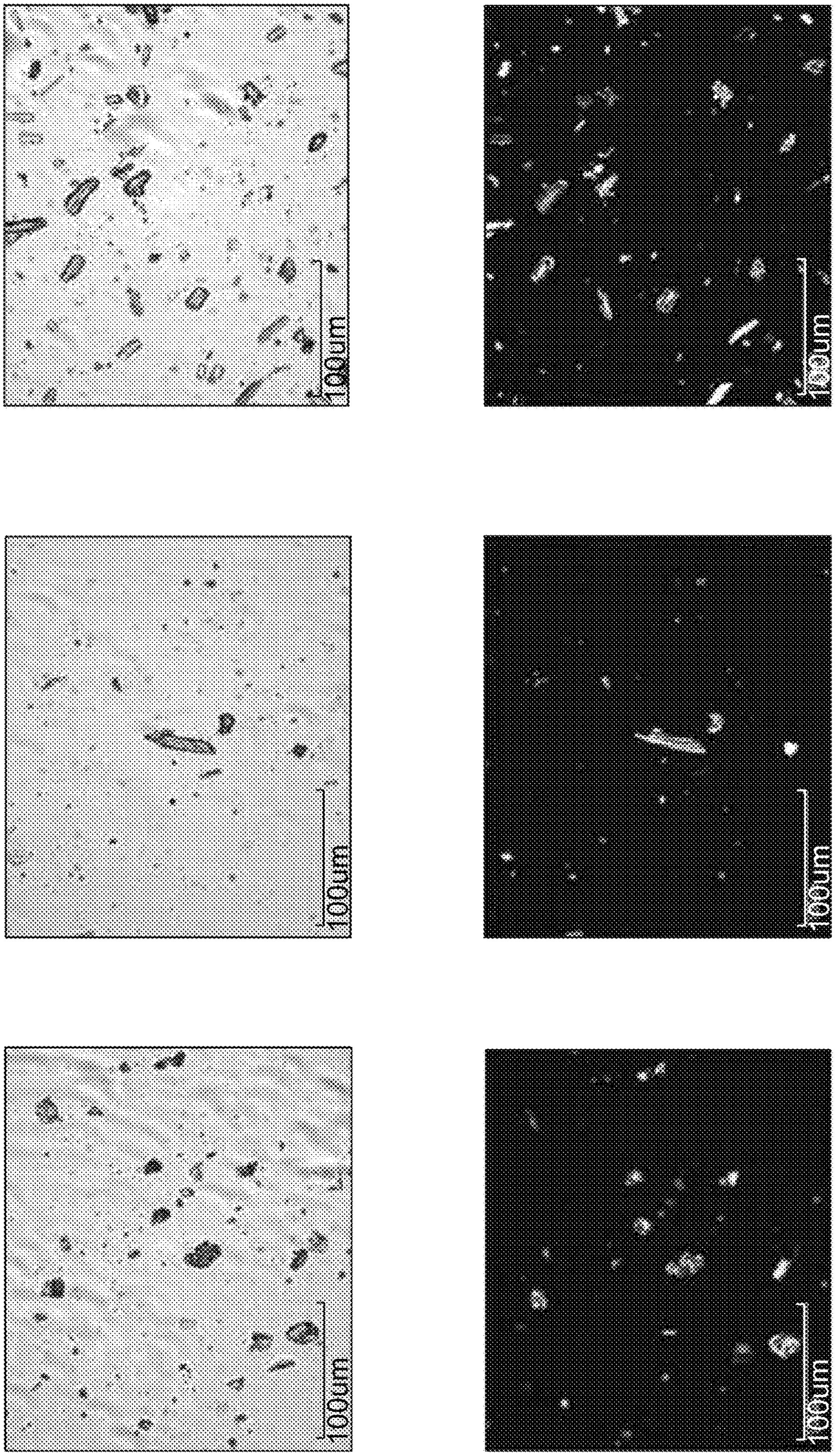
FIG. 13 illustrates the non-polarized microscope and PLM analysis of Pattern 2.

FIGS. 11 (non-polarized microscope) and 12 (polarized light microscope) demonstrated that the supplied CHP (mostly Pattern 1) was birefringent with no clear morphology. As shown in FIG. 13, Pattern 2 was found to be birefringent with a fragmented, rod-like morphology. In other embodiments, the CHP hydrate (Pattern 2) of the present disclosure shows a fragmented rod-like morphology under PLM.

D. Thermogravimetric Analysis/Differential Thermal Analysis (TG/DTA)

Approximately 5 mg of material was weighed into an open aluminum pan and loaded into a Seiko 6200/7200 simultaneous thermogravimetric/differential thermal analyzer (TG/DTA) and held at room temperature. The sample was then heated at a rate of 10° C./min from 20° C. to 300° C. during which time the change in sample weight was recorded along with any differential thermal events (DTA). Nitrogen was used as the purge gas, at a flow rate of 300 $cm^3$/min.

Figure 14:
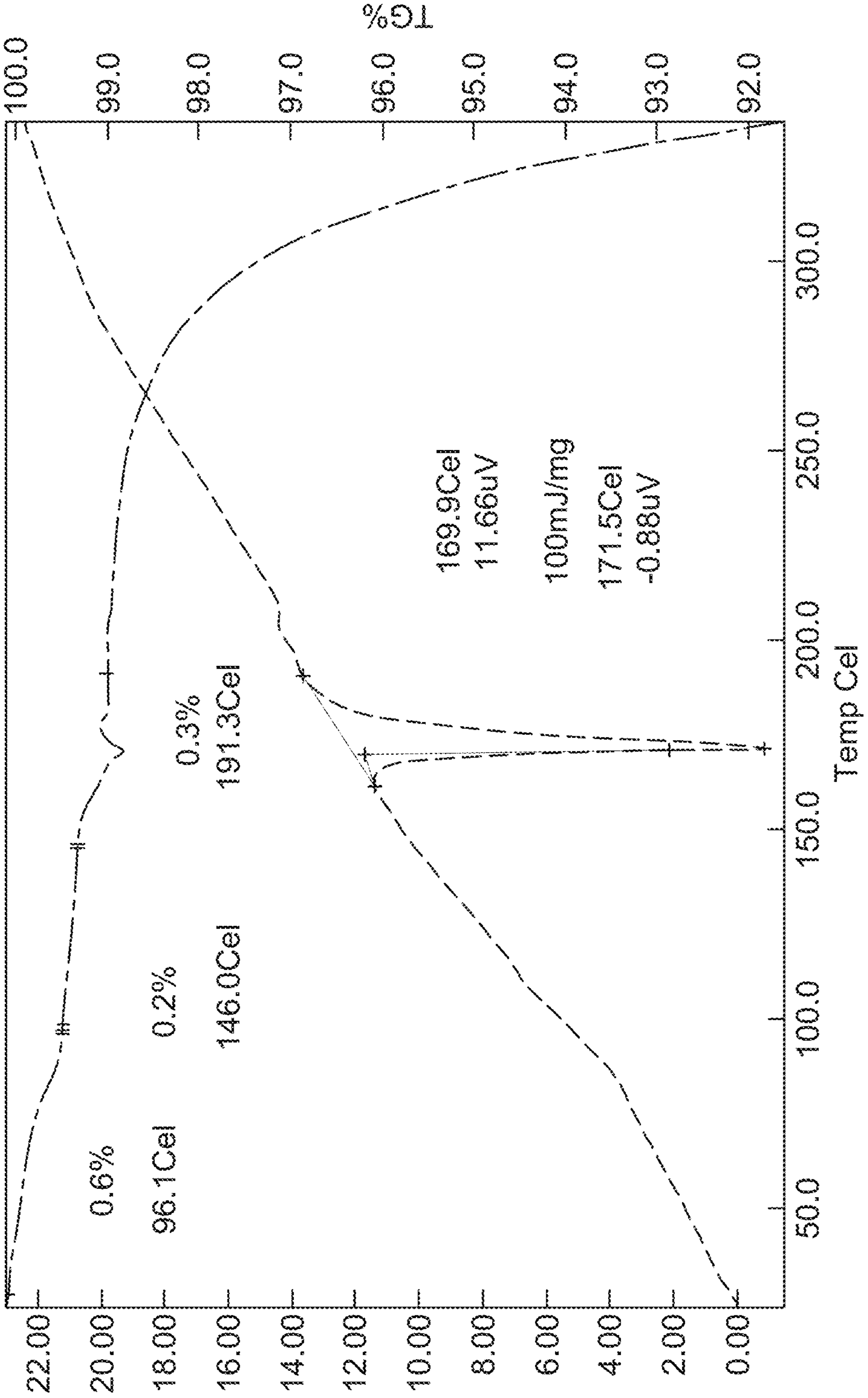
FIG. 14 illustrates the thermogravimetric analysis of the received CHP (mostly Pattern 1).

As shown in FIG. 14, a TGA analysis of Pattern 1 revealed an initial weight loss of 0.6% (0.08 equiv. water) at approximately 75-85° C. This 0.6% water was attributed to the surface water-non bound water. Two further weight losses were observed, 0.2% and 0.3% (0.03 and 0.04 equiv. water, respectively), before the sample degraded at ca. 260° C. The first weight loss may be due to small amount of Pattern 2 material mixed in the material lost water to become Pattern 1. The quantity is estimated to be 8% based on the weight loss. The second water loss at approximately 100° C. may be due to the evaporation of non-bound surface water. A DT analysis identified one sharp endothermic event with an onset of 170° C. and a peak at 172° C.

Figure 15:
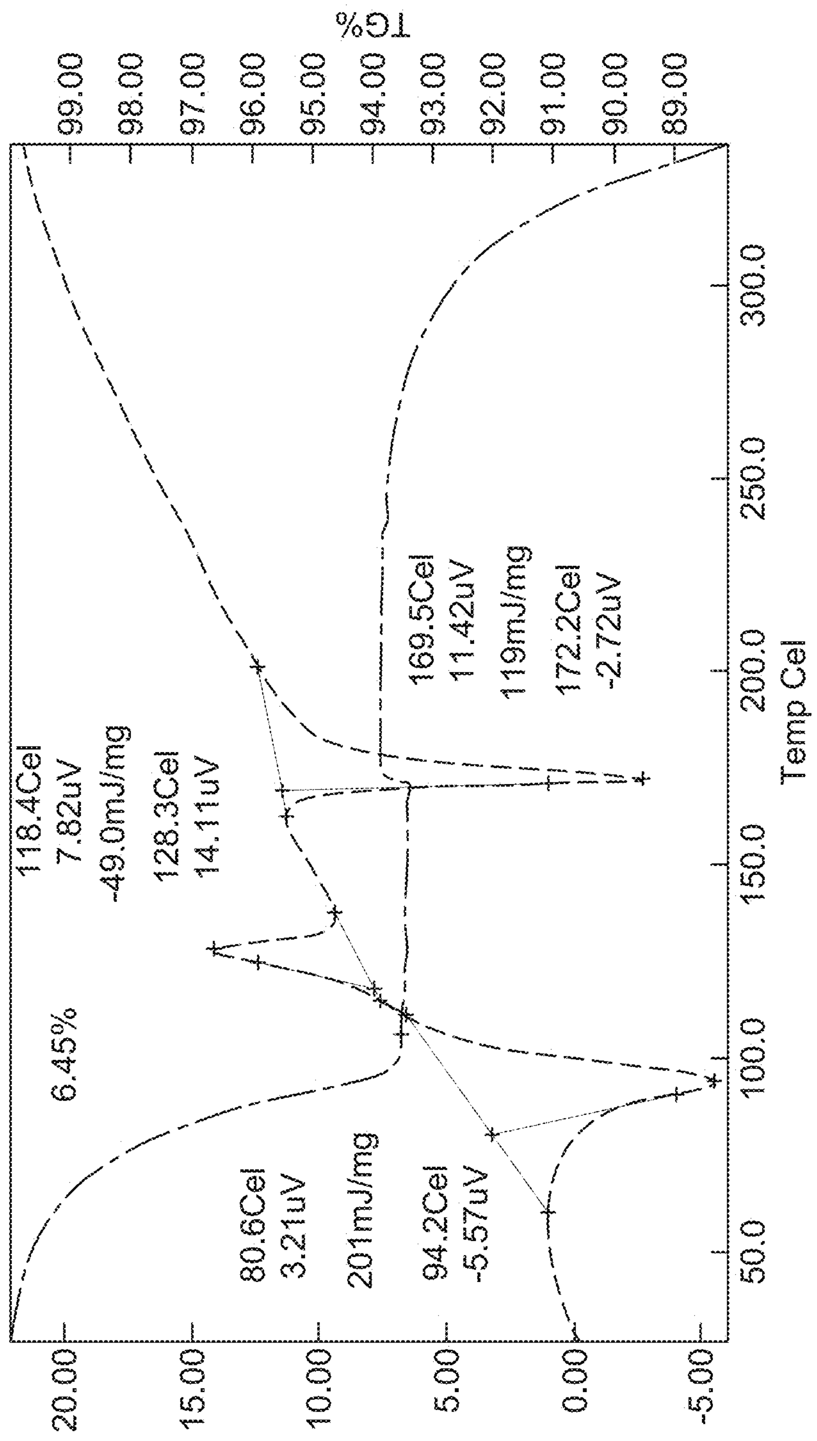
FIG. 15 illustrates the thermogravimetric analysis/differential thermal analysis (TG/DTA) of Pattern 2.

As shown in FIG. 15, a TGA analysis of Pattern 2 showed an initial weight loss of 6.5% (0.9 equivalent of water), followed by sample degradation at around 280° C. The DT trace identified an endothermic event associated with the initial weight loss. This was followed by an exothermic event (re-crystallization to Pattern 1) at 118° C. A second endotherm, thought to be a sample melt, was observed at 170° C. and a peak at 172° C. In other embodiments, the CHP hydrate of the present disclosure exhibits at least one endothermic event at about 75-85° C. which is loss of water. In another embodiment, the CHP hydrate of the present disclosure exhibits at least one exothermic event at about 115 to about 120° C. which is recrystallization event to Pattern 1.

E. Differential Scanning Calorimetry (DSC)

DSC was carried out by adding approximately 5 mg of material which was weighed into an aluminum DSC pan and sealed non-hermetically with a pierced aluminum lid. The sample pan was then loaded into a Seiko DSC6200 (equipped with a cooler) cooled and held at 20° C. Once a stable heat-flow response was obtained, the sample and reference were heated to 250° C. at scan rate of 10° C./min and the resulting heat flow response monitored. Nitrogen was used as the purge gas, at a flow rate of 50 $cm^3$/min.

Figure 16:
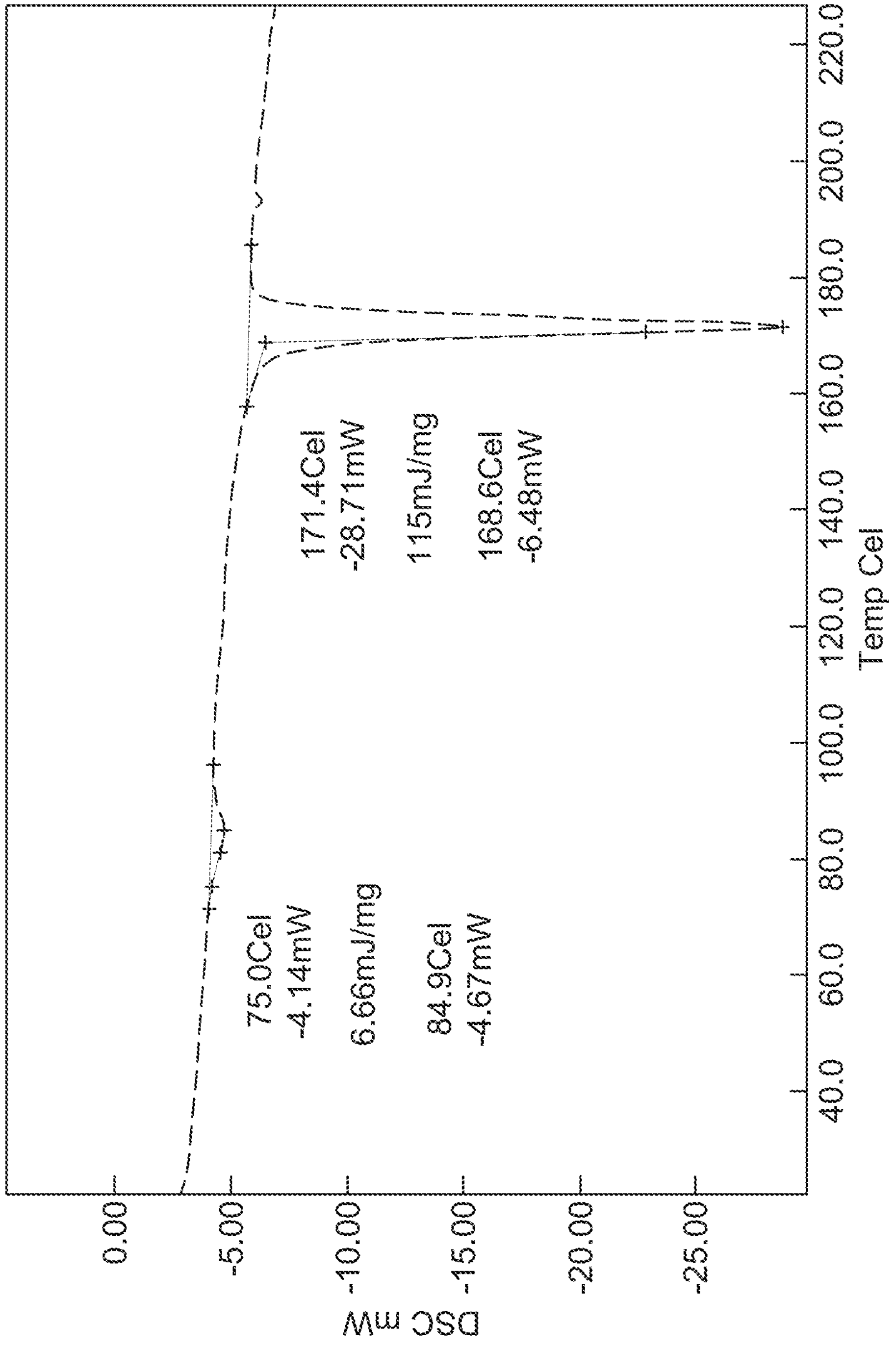
FIG. 16 illustrates the DSC analysis of the received CHP (mostly Pattern 1) in the first heat cycle.

As shown in FIG. 16 the first heat cycle of Pattern 1 showed a small, broad endotherm starting at 75° C. with a peak at 85° C. This is consistent with 0.6% weight loss observed in the TG/DTA seen in FIG. 14. A second, large endothermic event was observed at 169° C. with a peak of 171° C. This is consistent with the melt seen in the TG/DTA. The first broad peak in FIG. 16 may be due to dehydration of Pattern 2 to Pattern 1. The second peak in FIG. 16 may be a melt of Pattern 1.

Figure 17:
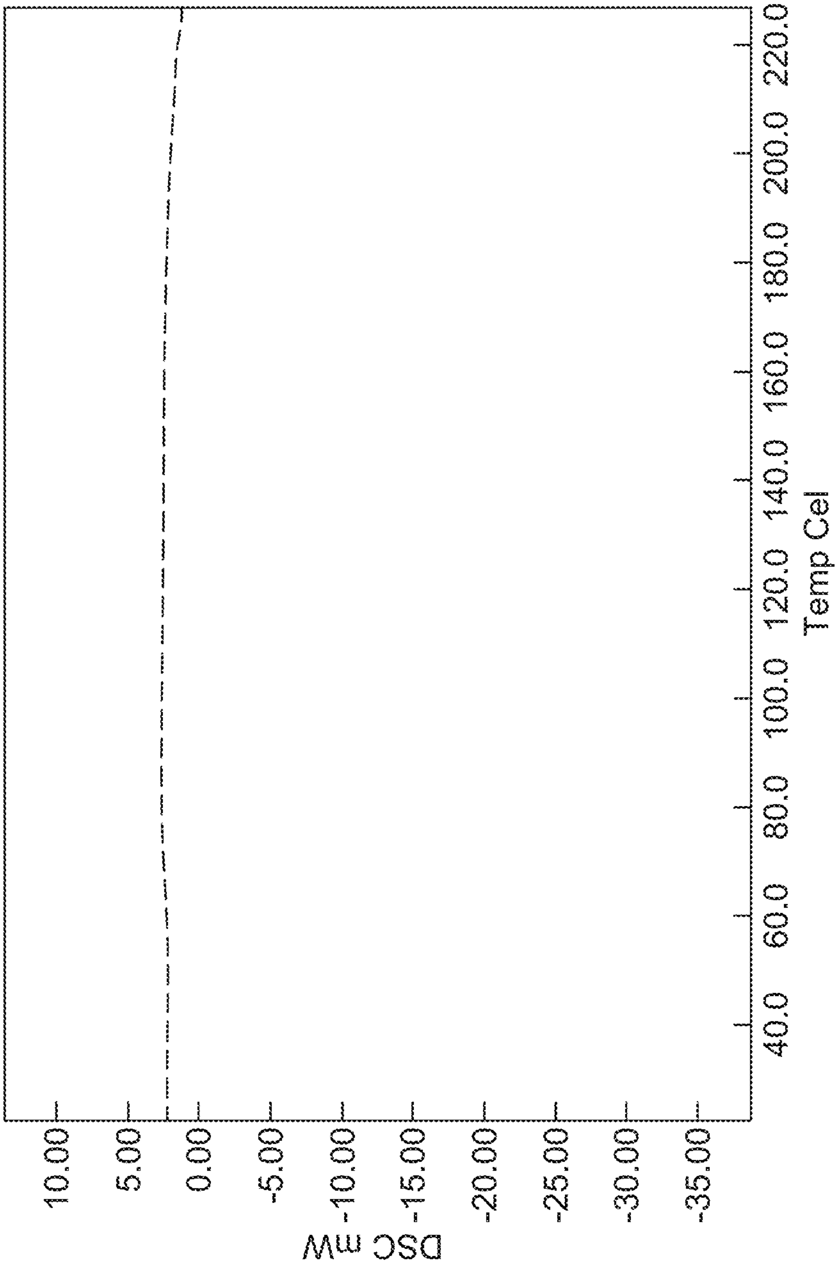
FIG. 17 illustrates the DSC analysis of the received CHP (mostly Pattern 1) in the cooling cycle.
Figure 18:
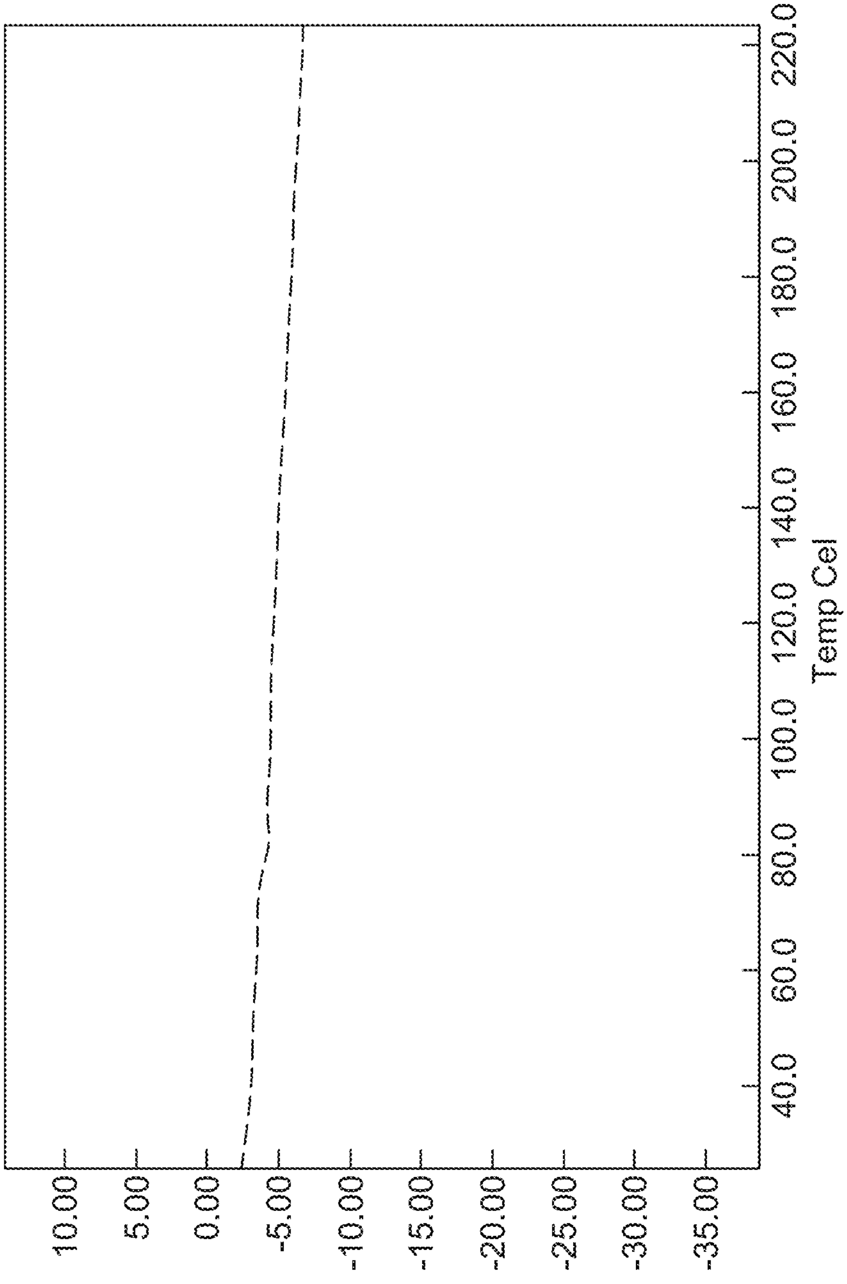
FIG. 18 illustrates the DSC analysis of the received CHP (mostly Pattern 1) in the second heat cycle.

As shown in FIG. 17, no thermal events were observed in the cool cycle. As shown in FIG. 18, very small broad peak, a potential glass transition point was observed approximately 80° C. in the second heat cycle.

As shown in FIG. 19, the first heat cycle of Pattern 2 identified an endotherm with an onset of 99° C. and a peak at 102° C. A sample melt was observed in starting at 170° C. with a peak at 173° C. This is consistent with the data seen in the TG/DTA. As shown in FIG. 20 no thermal events were observed in the cool cycle of Pattern 2.

As shown in FIG. 21 a possible glass transition point was observed in the second heat cycle at 77° of CHP hydrate.

In one embodiment, the CHP hydrate of the present disclosure exhibits an endotherm onset at about 75° C. to about 100° C.

F. Fourier-Transform Infrared Spectroscopy (FT-IR)

FR-IR was carried out on a Bruker ALPHA P spectrometer. Sufficient material was placed onto the center of the plate of the spectrometer and the spectra were obtained using the following parameters: Resolution: 4 $cm^{-1}$, Background Scan Time: 16 scans, Sample Scan Time: 16 scans, Data Collection: 4000 to 400 $cm^{-1}$, Result Spectrum: Transmittance, and Software: OPUS version 6.

Figure 22:
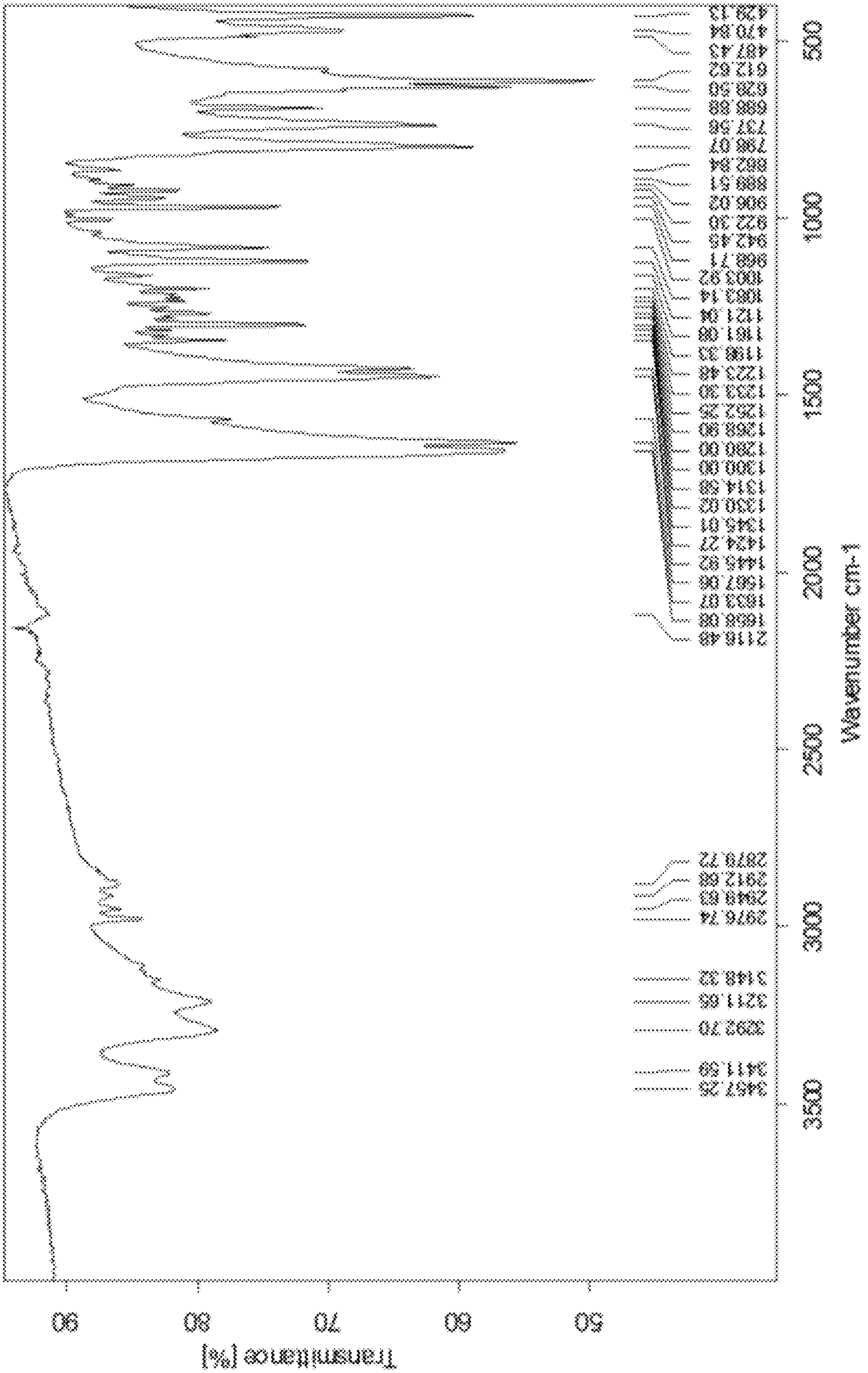
FIG. 22 illustrates the results of the FR-IR spectroscopy of the CHP hydrate.

As shown in FIG. 22, the FT-IR of Pattern 2 is consistent with the structure. The solid infra-red spectrum of Pattern 2 displays signals at 3457, 3411 (m); 3292, 3211 (m); 2976; 1658; 1633 (m); and 1445-1424 (m) $cm^{-1}$. In other embodiments, the CHP and CHP hydrate of the present disclosure shows essentially same IR spectrum that exhibits at least nine bands from about 500 $cm^{-1}$ to about 1660 $cm^{-1}$. Pattern 2 has stretching at 3457 and 3411 cm-1 due to water (hydrate) in the crystal lattice whereas Pattern 1 does not.

G. Dynamic Vapor Sorption (DVS)

DVS was carried out by placing an approximately 10-20 mg sample into a mesh vapour sorption balance pan and loaded into a DVS Intrinsic Dynamic Vapour Sorption Balance by Surface Measurement Systems. The sample was subjected to a ramping profile from 40 to 90% relative humidity (RH) at 10% increments, maintaining the sample at each step until a stable weight had been achieved (dm/dt 0.004%, minimum step length 30 minutes, maximum step length 500 minutes) at 25° C. After completion of the sorption cycle, the sample was dried using the same procedure to 0% RH and then a second sorption cycle back to 40% RH. Two cycles were performed. The weight change during the sorption/desorption cycles were plotted, allowing for the hygroscopic nature of the sample to be determined. XRPD analysis was then carried out on any solid retained.

Figure 23:
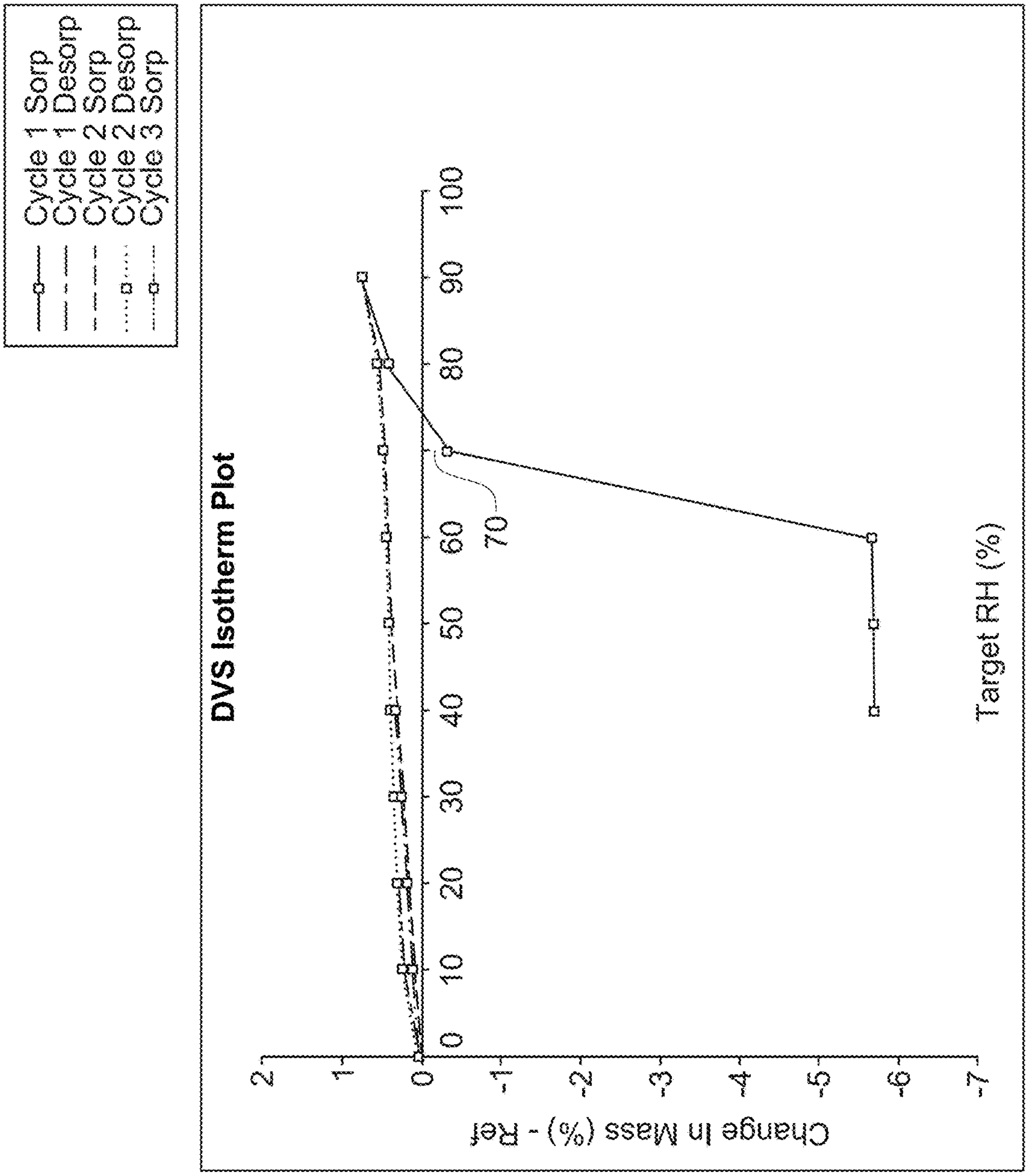
FIG. 23 illustrates the results of the isotherm plot of DVS of Pattern 1 showing 6.3% weight gain between 60% RH and 90% RH.
Figure 24:
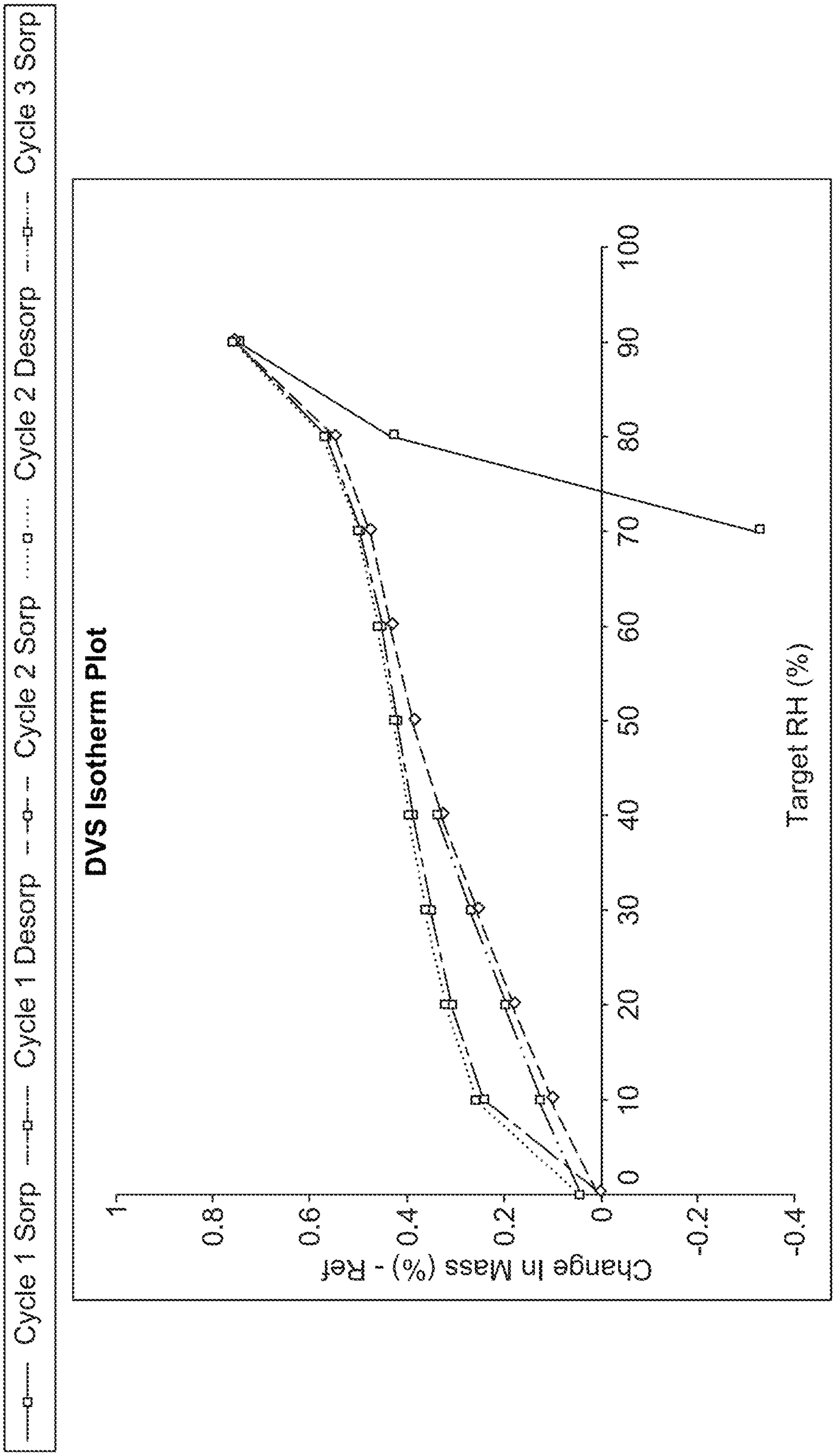
FIG. 24 illustrates the results of the isotherm plot of DVS of Pattern 1 following re-crystallization in the first heating cycle showing slightly hygroscopic with weight gain of 0.8% between 0-90% RH.
Figure 25:
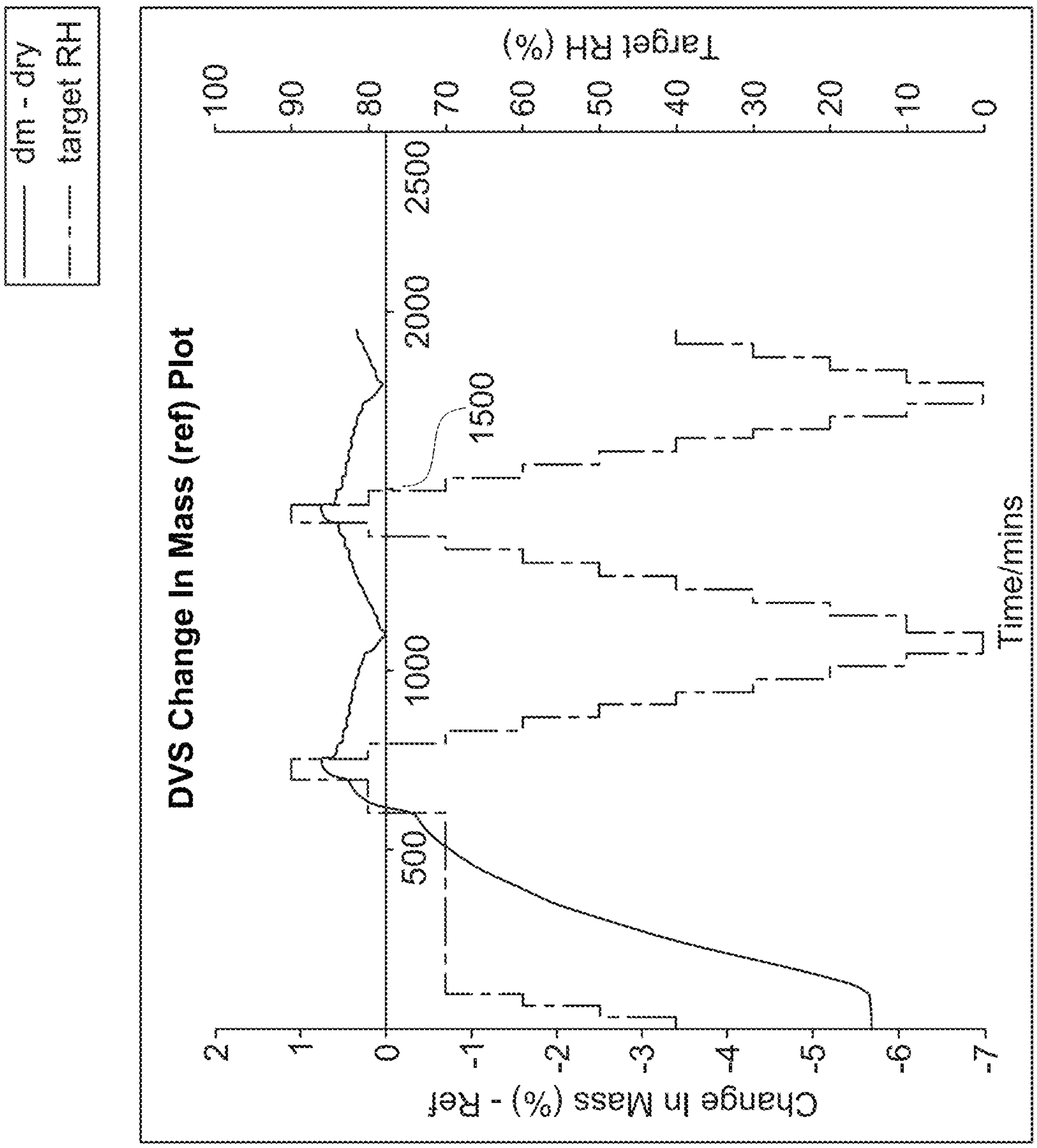
FIG. 25 illustrates the results of the kinetic plot of DVS of Pattern 1.

As shown in FIG. 23, the isotherm plot of DVS of Pattern 1 showed a 6.3% weight gain from 60% RH to 90% RH, indicating conversion to CHP hydrate, Pattern 2. As shown in FIG. 24, following conversion to Pattern 2, the material appeared only slightly hygroscopic with a maximum uptake of 0.8 wt % between 0 and 90% RH, which is assumed to be surface water, not a part of the crystal structure. This phenomenon is shown in FIG. 25, the kinetic plot of DVS of Pattern 1 that shows that Pattern 1 hydrates initially to form Pattern 2 but does not give up water during desorption phase, indicating the slight weight gain of 0.8% is not a part of the solid structure.

Figure 26:
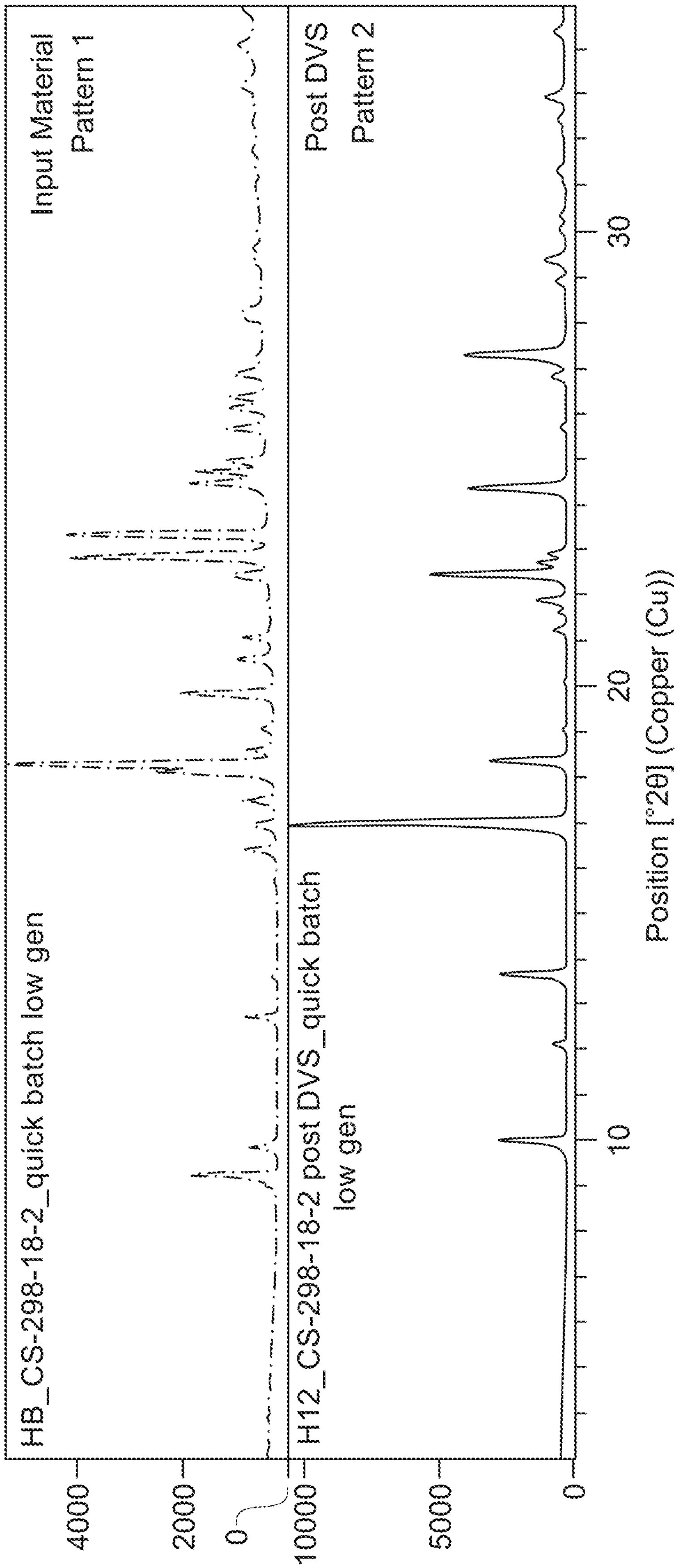
FIG. 26 illustrates the XRPD of Material before and after DVS. The post-DVS XRPD analysis shows a new form, assigned as Pattern 2.
Figure 27:
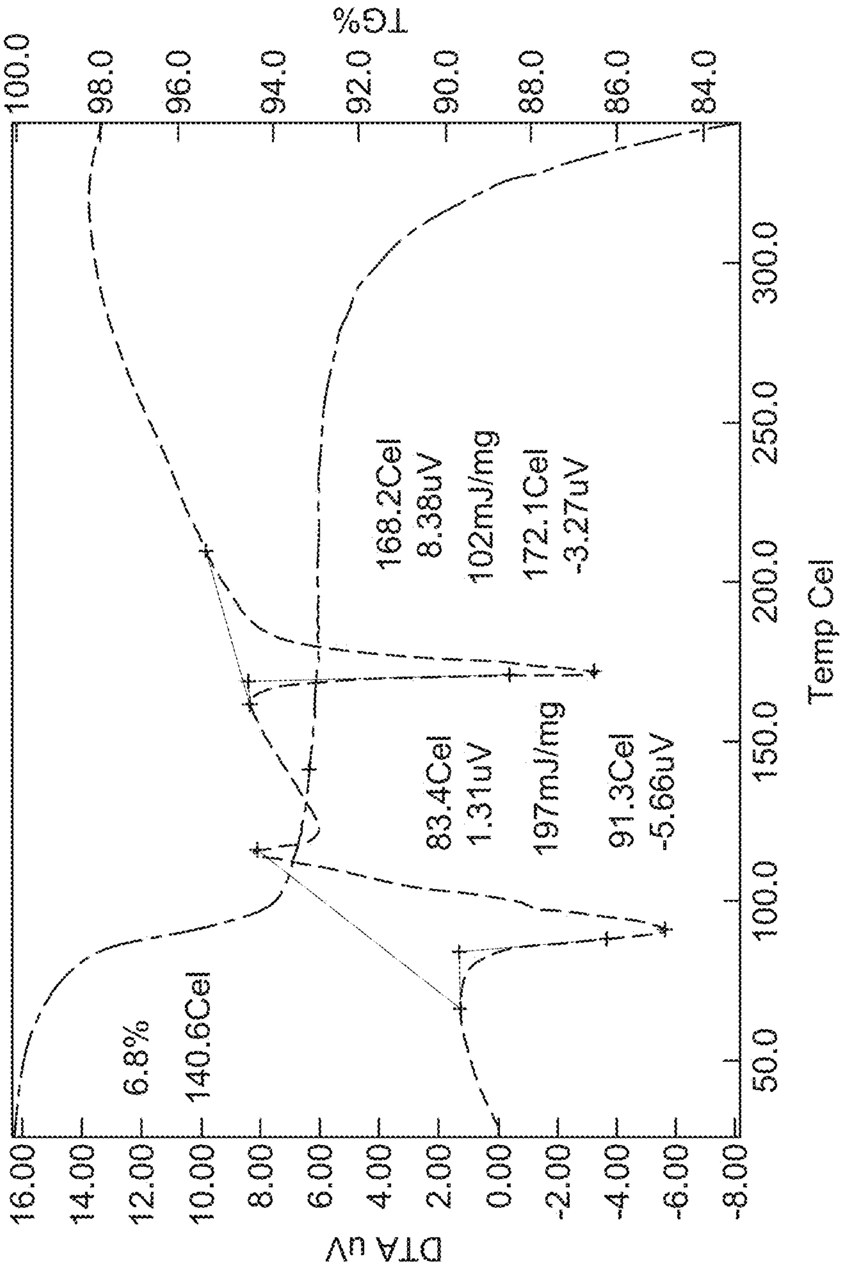
FIG. 27 illustrates TG/DTA of CHP Hydrate, Pattern 2.

As shown in FIG. 26, the post-DVS XRPD analysis of Pattern 1 showed a new form, assigned as pattern 2. As shown in FIG. 27, the post-DVS TG/DTA analysis of Pattern 2 showed an initial weight loss of 6.8% (0.95 equiv. water), followed by sample degradation at approximately 280° C. The DT trace identified an endothermic event associated with the weight loss, followed by re-crystallization (to Pattern 1), an exothermic event at approximately 120° C., then a melt with an onset of 168° C. and a peak at 172° C.

Figure 31:
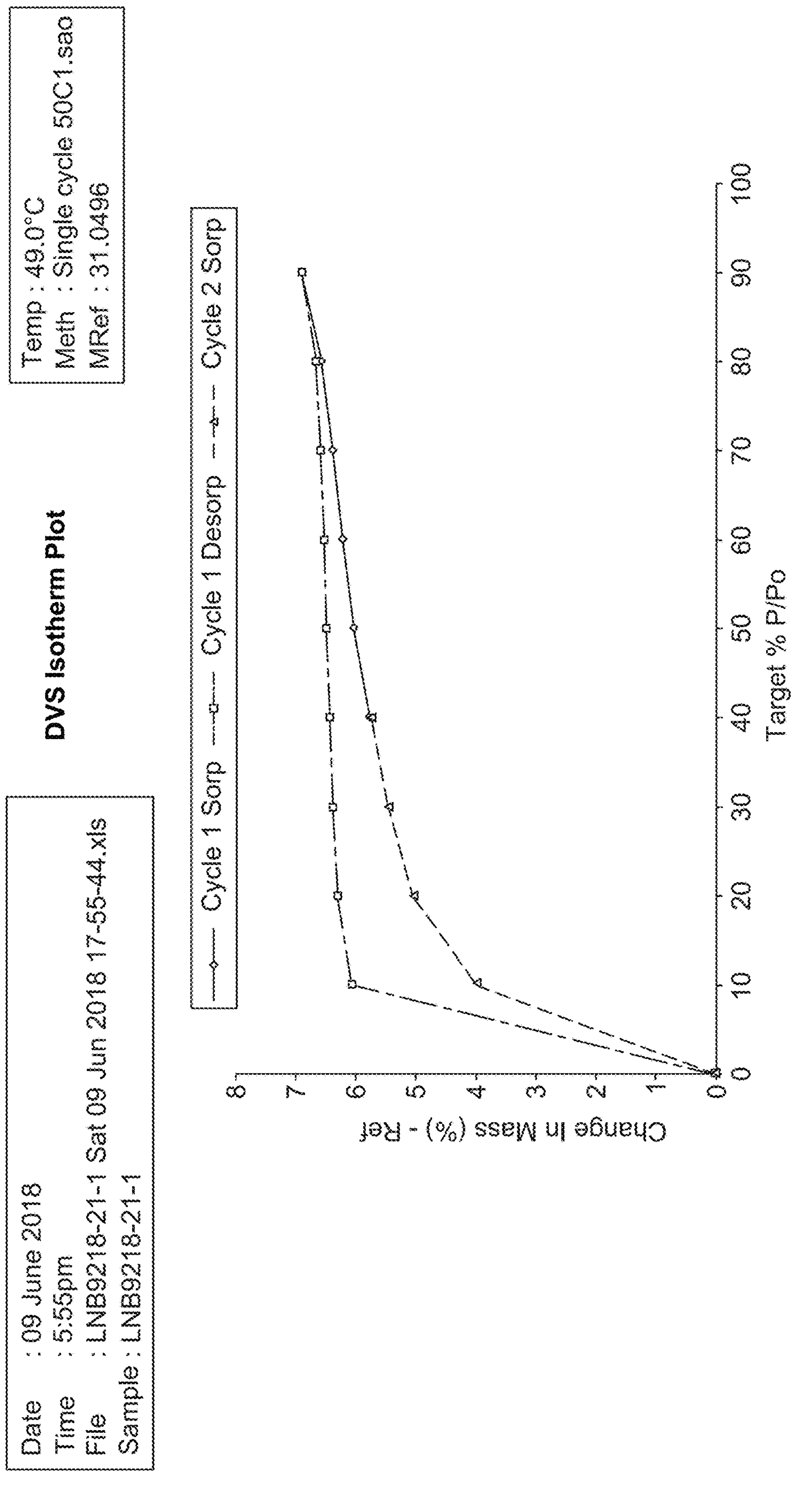
FIG. 31 illustrates the VT-DVS analysis after CHP Hydrate, Pattern 2 was subjected to a single cycle at 50° C. showing material started dehydrating below 20%, losing 6.1% weight (equivalent to 0.8 mole of water). The material rehydrated from 0-40% RH.
Figure 32:
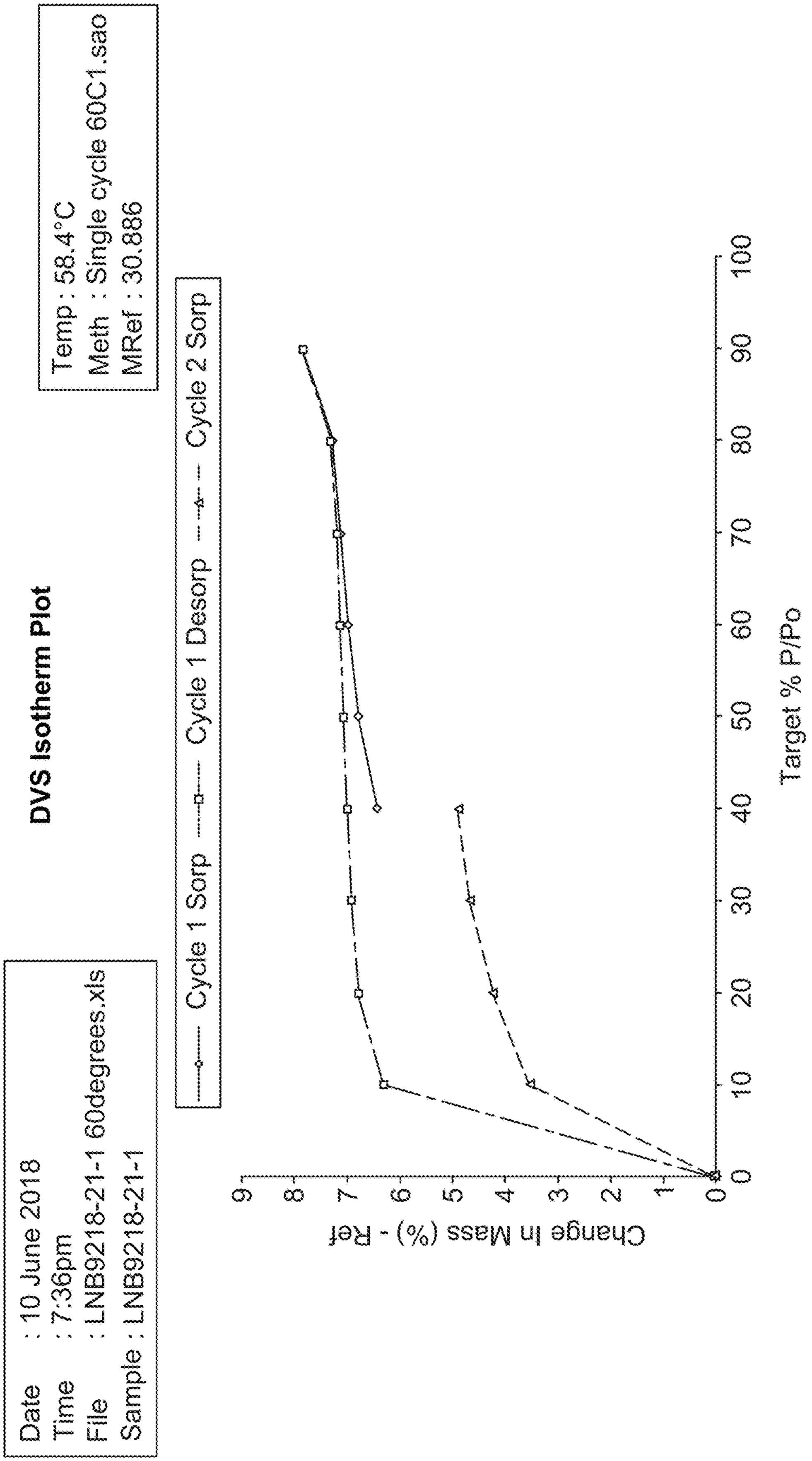
FIG. 32 illustrates the VT-DVS analysis after CHP Hydrate, Pattern 2 was subjected to a single cycle at 60° C., showing material started dehydrating below 20%, losing 7% weight (equivalent to 1.0 mole of water). The material rehydrated from 0-40% RH.

CHP pattern 2 was placed in the several higher temperature conditions for checking dehydrate/rehydrate under 0%-90% humidity: 25° C. (FIG. 28); 40° C. (FIG. 30); 50° C. (FIG. 31); and 60° C. (FIG. 32).

Figure 28:
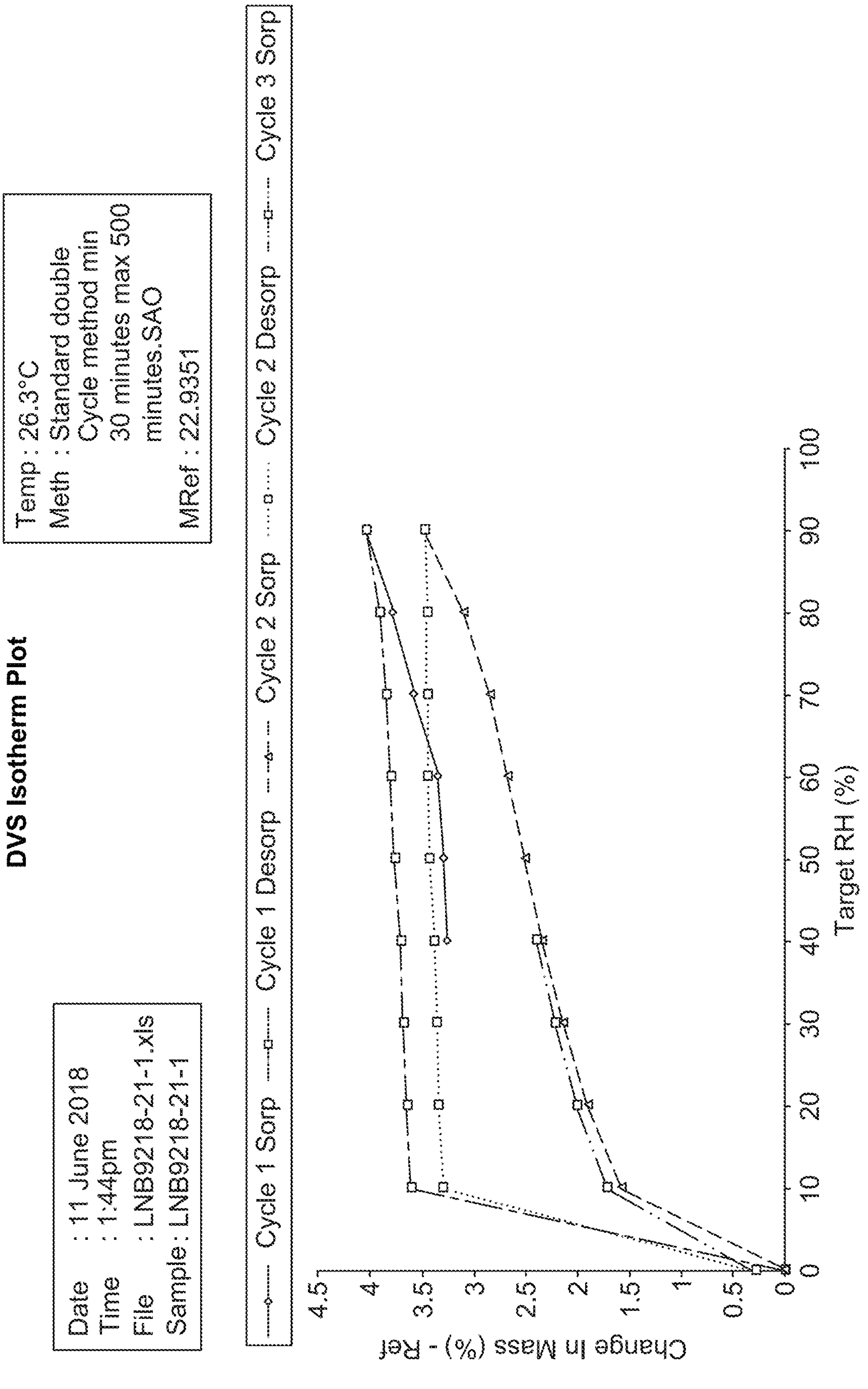
FIG. 28 is an isotherm plot of DVS showing that CHP Hydrate, Pattern 2 material did not change from 40 to 90% RH and 10 to 90% RH.
Figure 29:
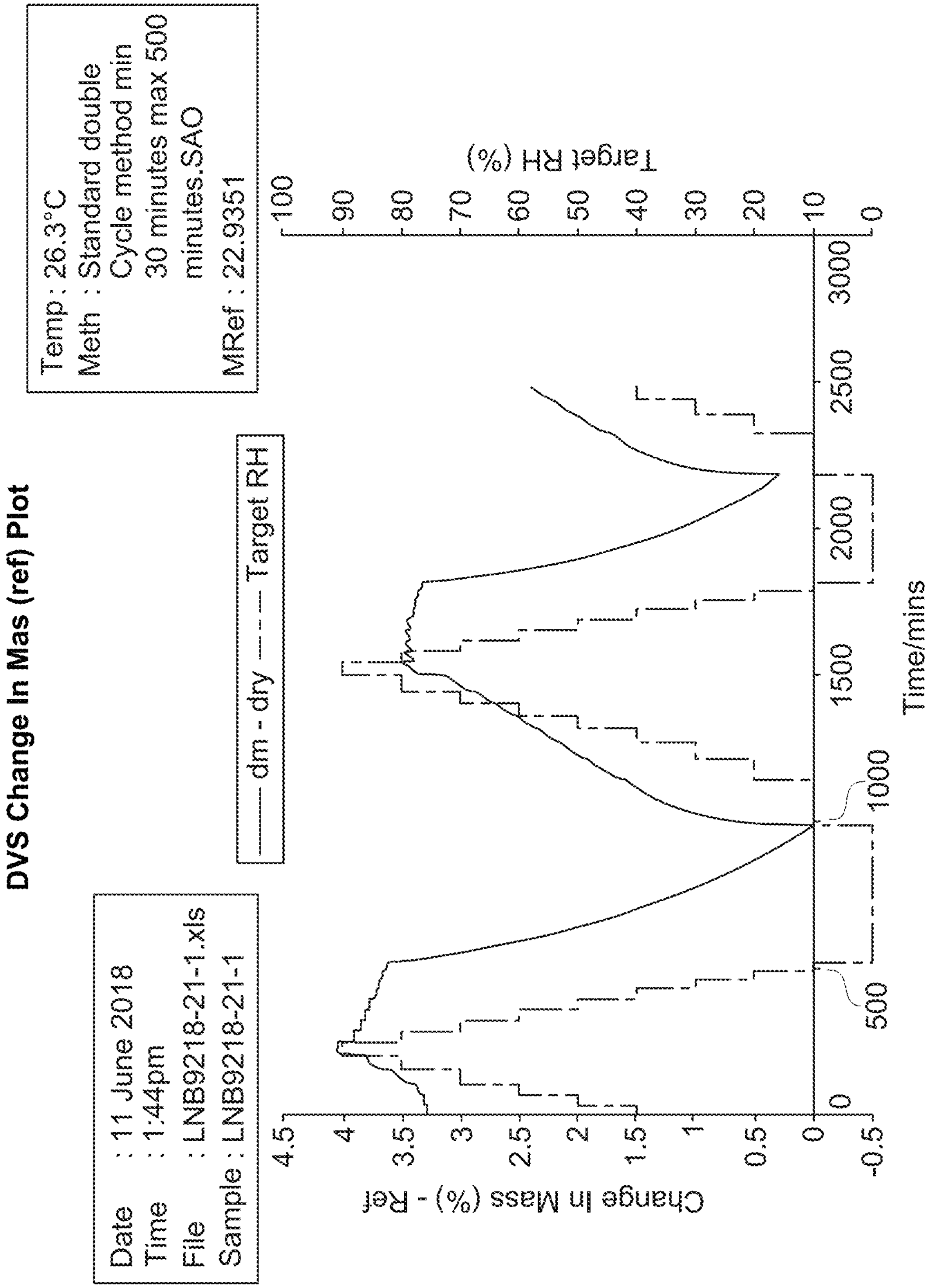
FIG. 29 illustrates a kinetic plot of DVS of CHP Hydrate, Pattern 2.
Figure 30:
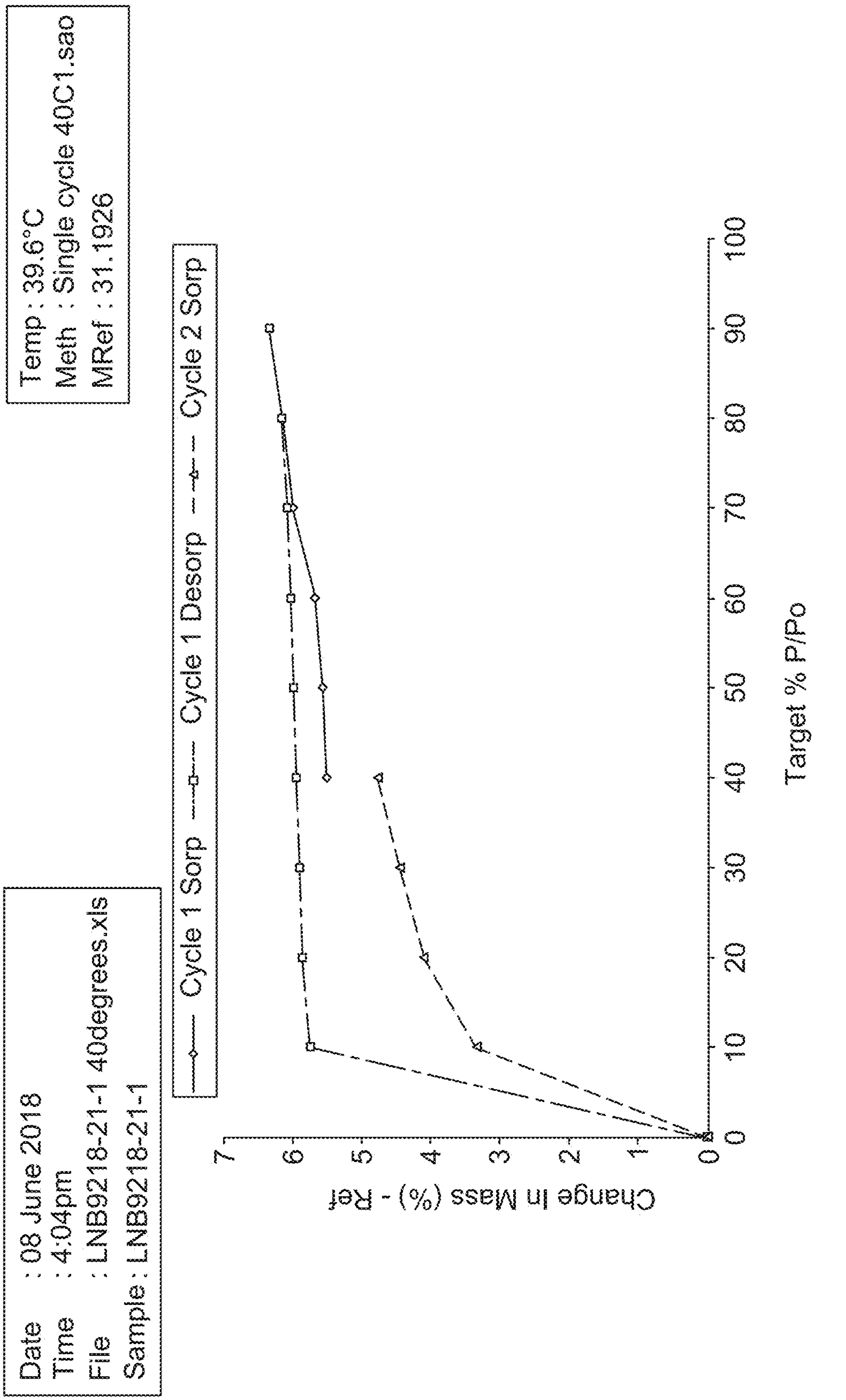
FIG. 30 illustrates the VT-DVS analysis after CHP Hydrate, Pattern 2 was subjected to a single cycle at 40° C., showing material started dehydrating below 10%, losing 5.8% weight (equivalent to 0.8 mole of water). The material rehydrated from 0-40% RH.

As shown in FIG. 28, an isotherm plot of DVS showed the Pattern 2 material did not change from 40 to 90% RH and 10 to 90% RH. The material then lost 3.5% wt. below 10% RH, and rehydrated from 0 to 90% RH. As shown in FIG. 29, a kinetic plot of DVS shows that CHP hydrate loses 3.5% of water (red line) during the desorption phase from 80% to 0% RH in 500 min. As shown in FIGS. 30, 31, and 32, Pattern 2 was subjected to a single cycle at 40° C., 50° C., and 60° C. The 40° C. showed that the material started dehydrating below 10% RH losing approx. 5.8 wt % from 10 to 0% RH (0.8 equiv water). The material hydrates from 0 to 40% RH (FIG. 30). The 50° C. showed that the material started dehydrating below 20% RH losing approximately 6.1 wt % from 20 to 0% RH (0.8 equiv water). The material rehydrates from 0 to 40% RH (FIG. 31). The 60° C. analysis showed that the material started dehydrating below 20% RH losing approximately 7 wt % from 20 to 0% RH (1.0 equiv water). The material rehydrates from 0 to 40% RH (FIG. 32).

In other embodiments, the CHP hydrate of the present disclosure exhibits a weight loss of about 3% to about 9%, or about 4% to about 8.5%, or about 5% to about 8%. In another embodiments, the CHP hydrate of the present disclosure exhibits a weight loss of about 5.5 to about 7.3%.

In yet another embodiments, the CHP hydrate of the present disclosure exhibits a weight loss of about 5.8 to about 7.0%.

H. Variable Temperature and Humidity X-Ray Powder Diffractometry (VT-/VH-XRPD)

VT-/VH-XRPD analysis was carried out on the Pattern 2 material. Pattern 2 was present for the initial scan at 40% RH and ambient temperature. Pattern 2 remained for Run 2 when the RH was lowered to 0% at ambient temperature. The temperature was increased to 80° C. and the sample left for 20 minutes before a scan was taken. The resulting diffractogram suggests that the material produced was pure Pattern 1. The pure Pattern 1 remained after 80 minutes at 80° C. and 0% RH. FIG. 33 indicates these results.

FIG. 34 shows the XRPD of Pattern 2 material after various VT/DVS. In other embodiments, the CHP hydrate of the present disclosure is present from at least about 0% to about 90% RH at room temperature. In yet another embodiment, 100% of Pattern 2 is converted to Pattern 1 in 0% RH at 80° C.

I. $^{1}$H Nuclear Magnetic Resonance (NMR)

Figure 35:
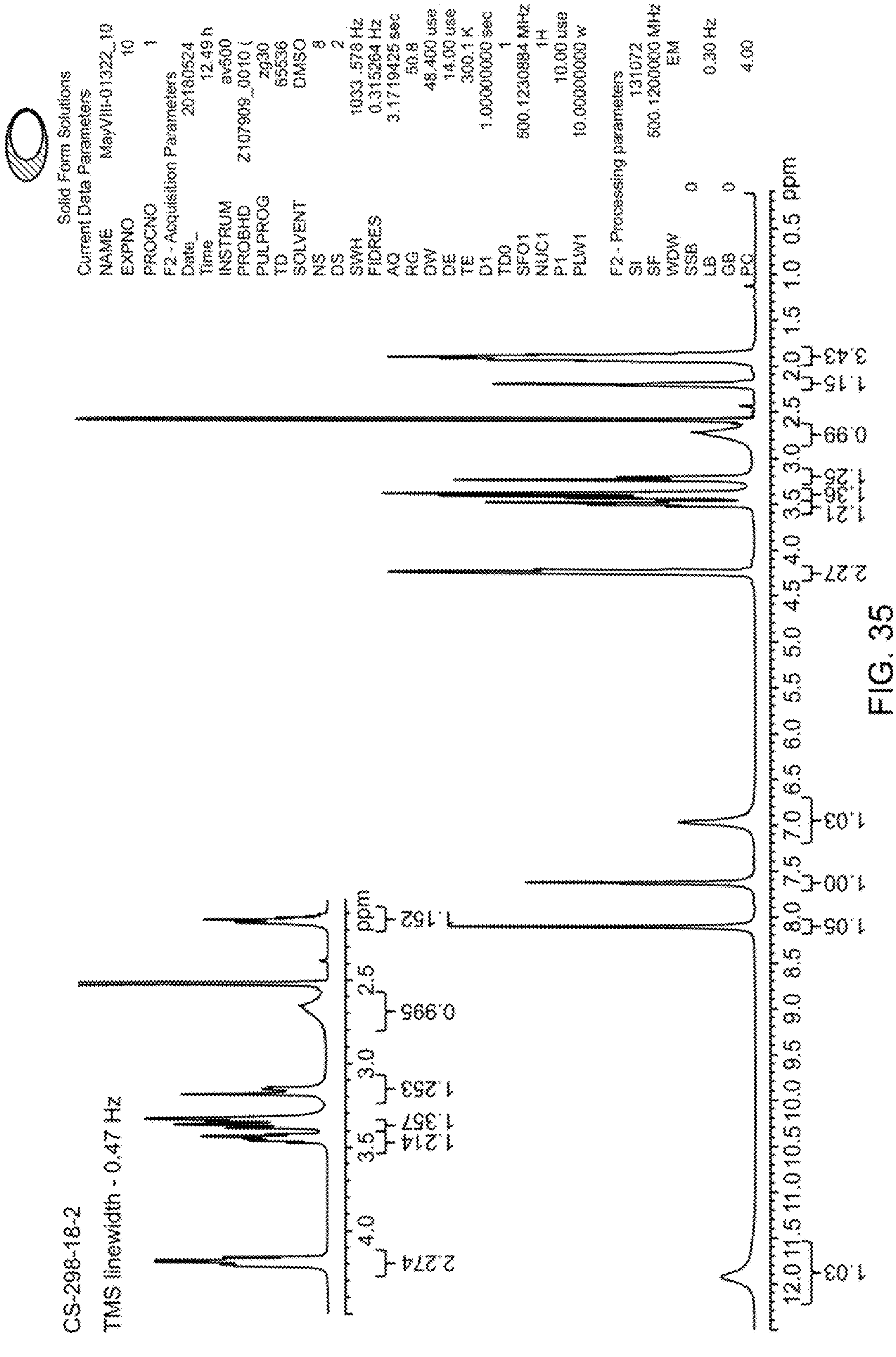
FIG. 35 illustrates the $^1$H-NMR spectrum of Pattern 1 in DMSO-$d_6$.
Figure 36:
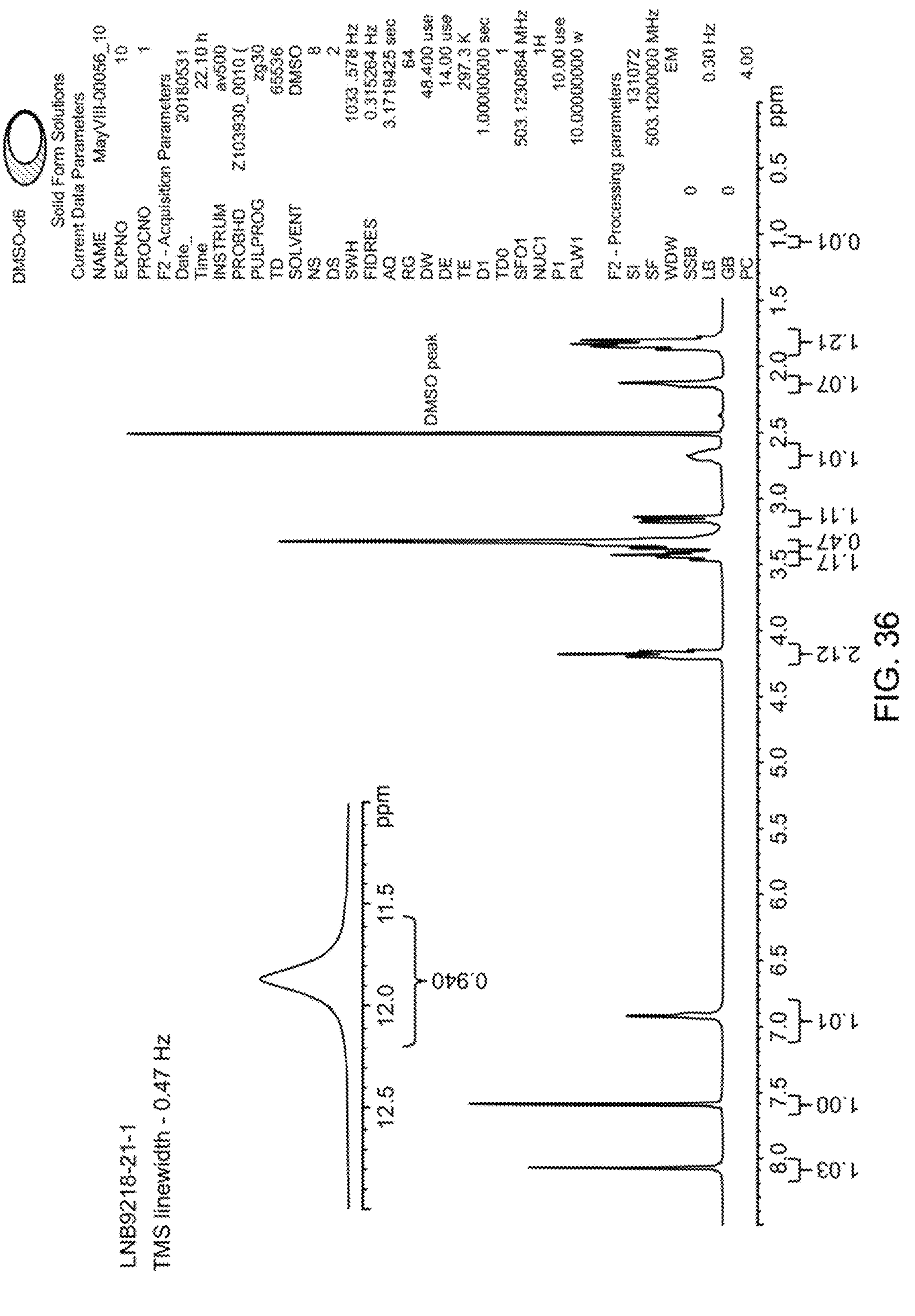
FIG. 36 illustrates the $^1$H-NMR spectrum of Pattern 2 in DMSO-$d_6$.
Figure 37:
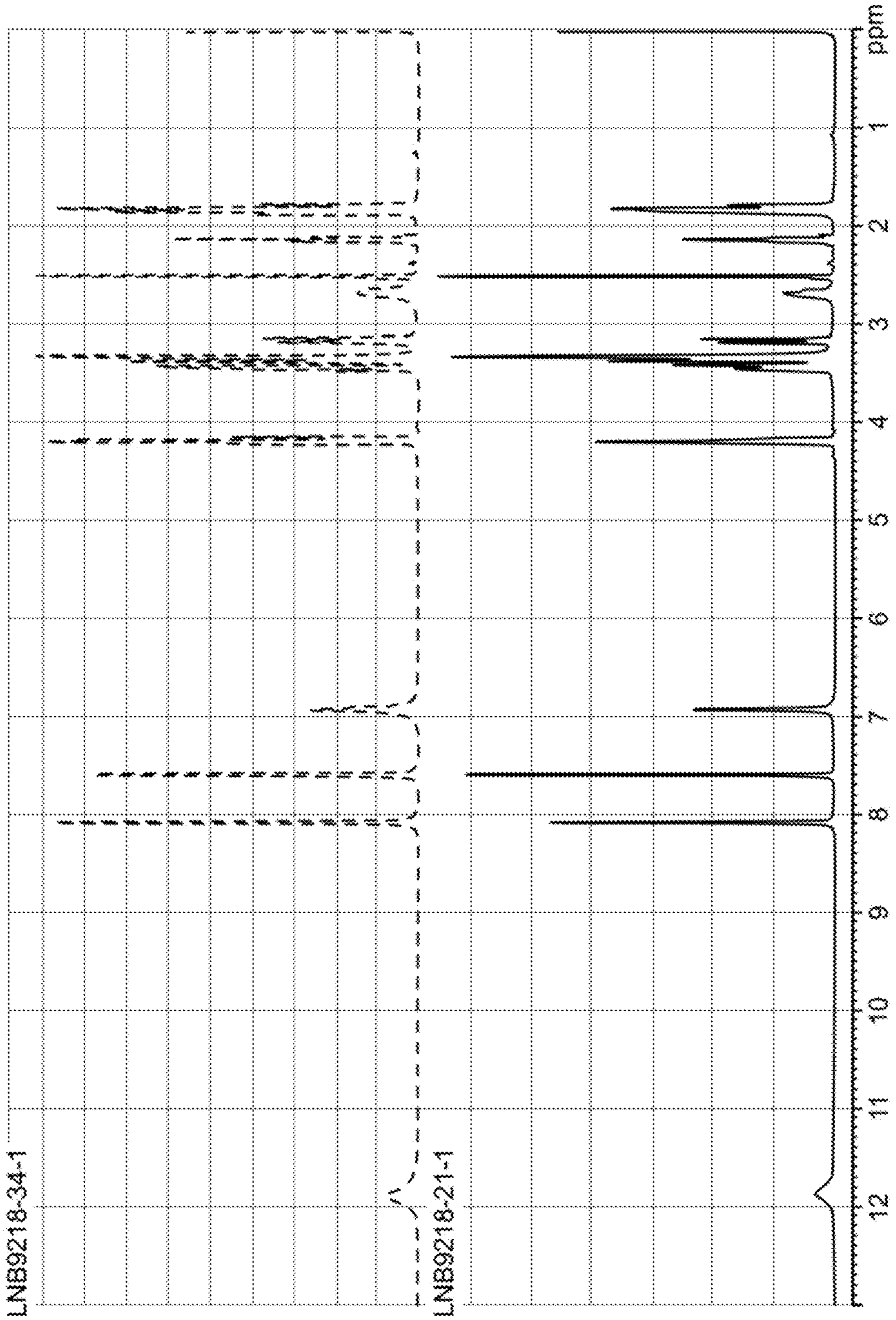
FIG. 37 illustrates the $^1$H-NMR spectrum comparison of Pattern 1 (blue line) and Pattern 2 (red line).

NMR was carried out by using Bruker AVIIIHID spectrometer equipped with a DCH cryoprobe operating at 500.12 MHz for protons. Experiments were performed in deuterated DMSO and each sample was prepared to ca. 10 mM concentration. The $^{1}$H-NMR spectrum of Pattern 1 CHP (DMSO-d6) shows that the results are consistent with the structure of the compound (FIG. 35). The $^{1}$H-NMR spectrum of Pattern 2 (DMSO-d6) is provided in FIG. 36. The Pattern 2 and Pattern 1 CHP showed the same NMR spectrum, as both are fully dissolved in the solvent. As shown in FIG. 37, NMR was carried out on the dried material, Pattern 2 (pink line from FIG. 9). No change was observed in the dried material from the Pattern 2 input material.

In one embodiment, the CHP hydrate of the present disclosure exhibits essentially the same $^{1}$H-NMR as the CHP-anhydrous in DMSO-$d_6$ solvent.

J. Heteronuclear Single Quantum Coherence (HSQC) NMR

Figure 38:
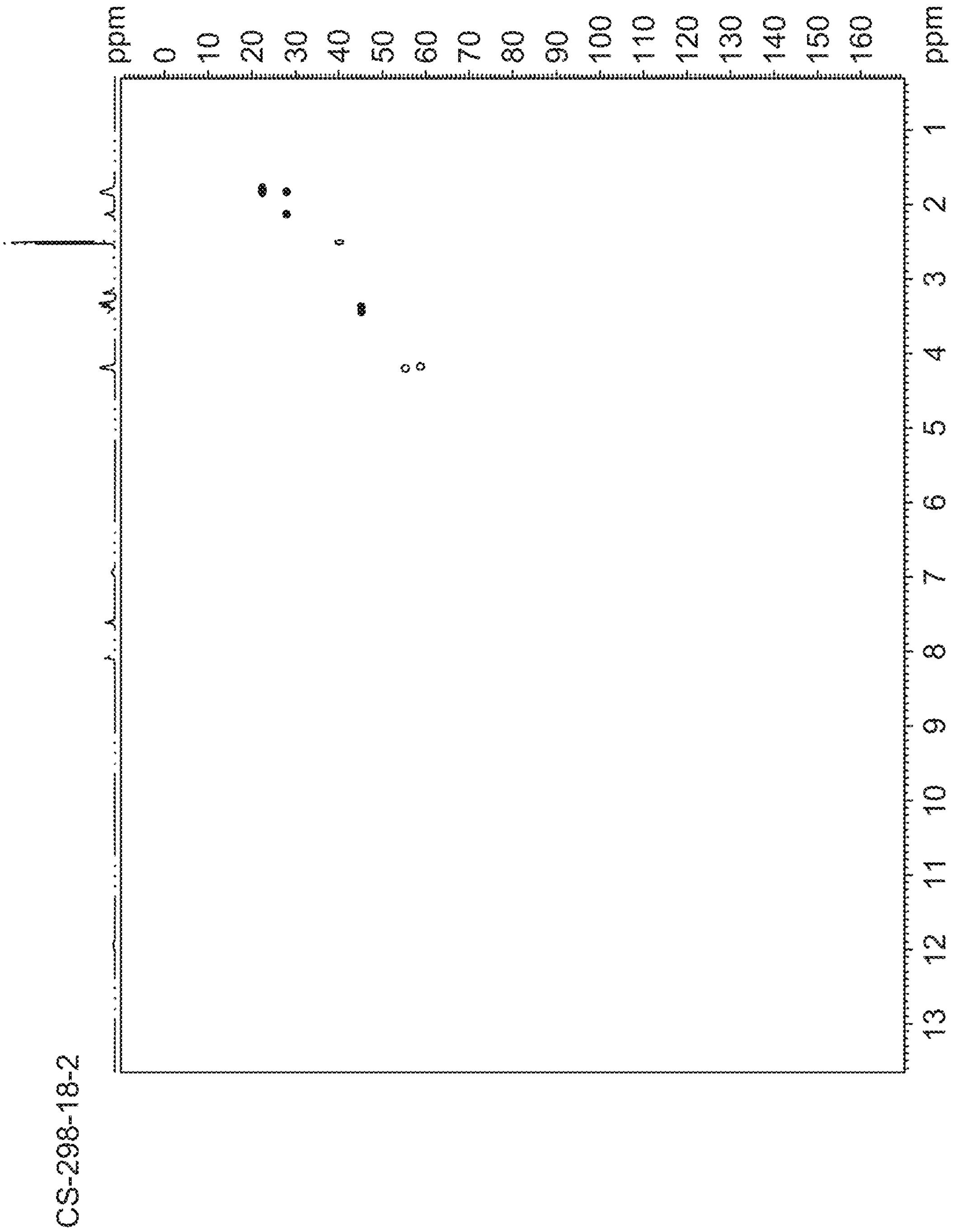
FIG. 38 illustrates the HSQC-NMR spectrum of Pattern 1.

HSQC-NMR was carried out on Pattern 2 using Bruker 500 MHz NMR equipment. DMSO-$d_6$ was used as the NMR sample solvent. As shown in FIG. 38, the results of Pattern 1 indicated two imidazole C-H's chemical shifts are at 4.2 ppm.

Figure 39:
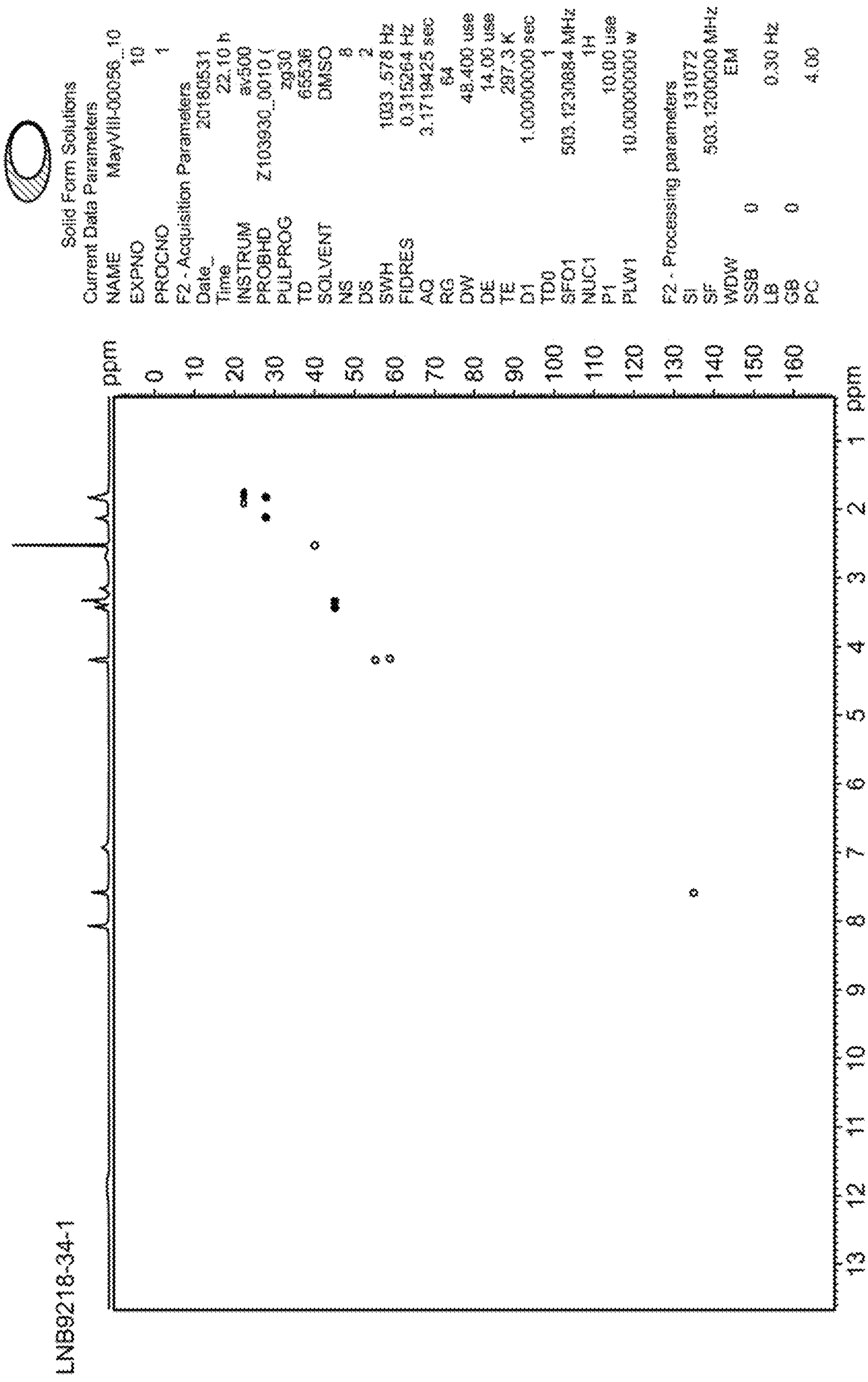
FIG. 39 illustrates the HSQC-NMR spectrum of a mixture of Pattern 1 and 2.

HSQC-NMR experiment was carried out on the dried material, Pattern 2 (pink line from FIG. 9). As shown in FIG. 39, the results indicated that the dried material (mixture of Pattern 1 and Pattern 2) and the NMR of Pattern 2 material are identical.

K. Lyophilization

For the solubility screen: 330 mg of CHP Pattern 1 was dissolved (with gentle heating) in water (3.3 mL) and split equally into 33 vials. These vials were then frozen at −50° C., before freeze drying overnight. It is widely known that lyophilization of crystalline compounds generates amorphous material which is routinely more soluble than crystalline forms of the given compound.

Figure 40:
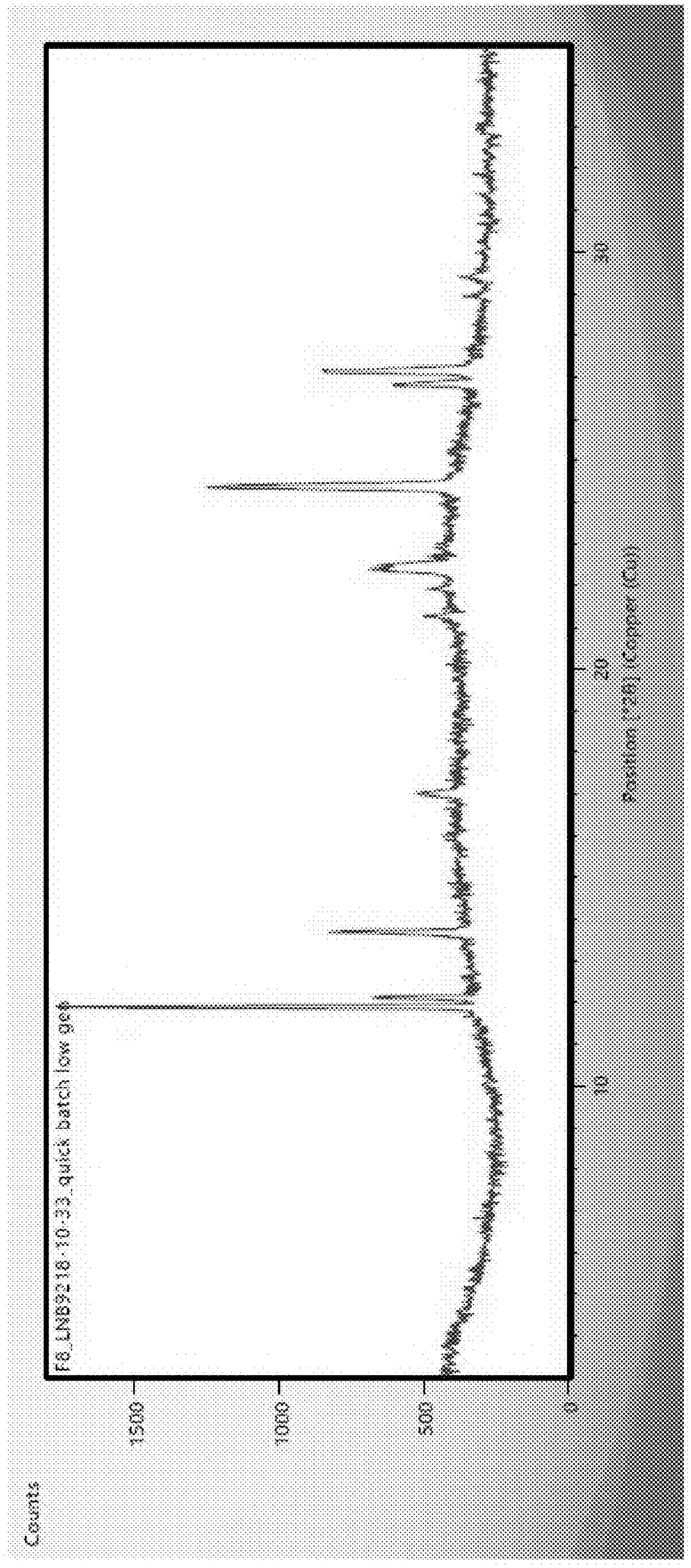
FIG. 40 illustrates the XRPD after initial lyophilization of Pattern 1.

As shown in FIG. 40, the material returned from freeze drying of Pattern 1 displayed some crystalline peaks when analyzed by XRPD. Applicant believes that the initial peaks indicate a mixture of hydrates and anhydrous forms mixed in with amorphous forms.

Figure 41:
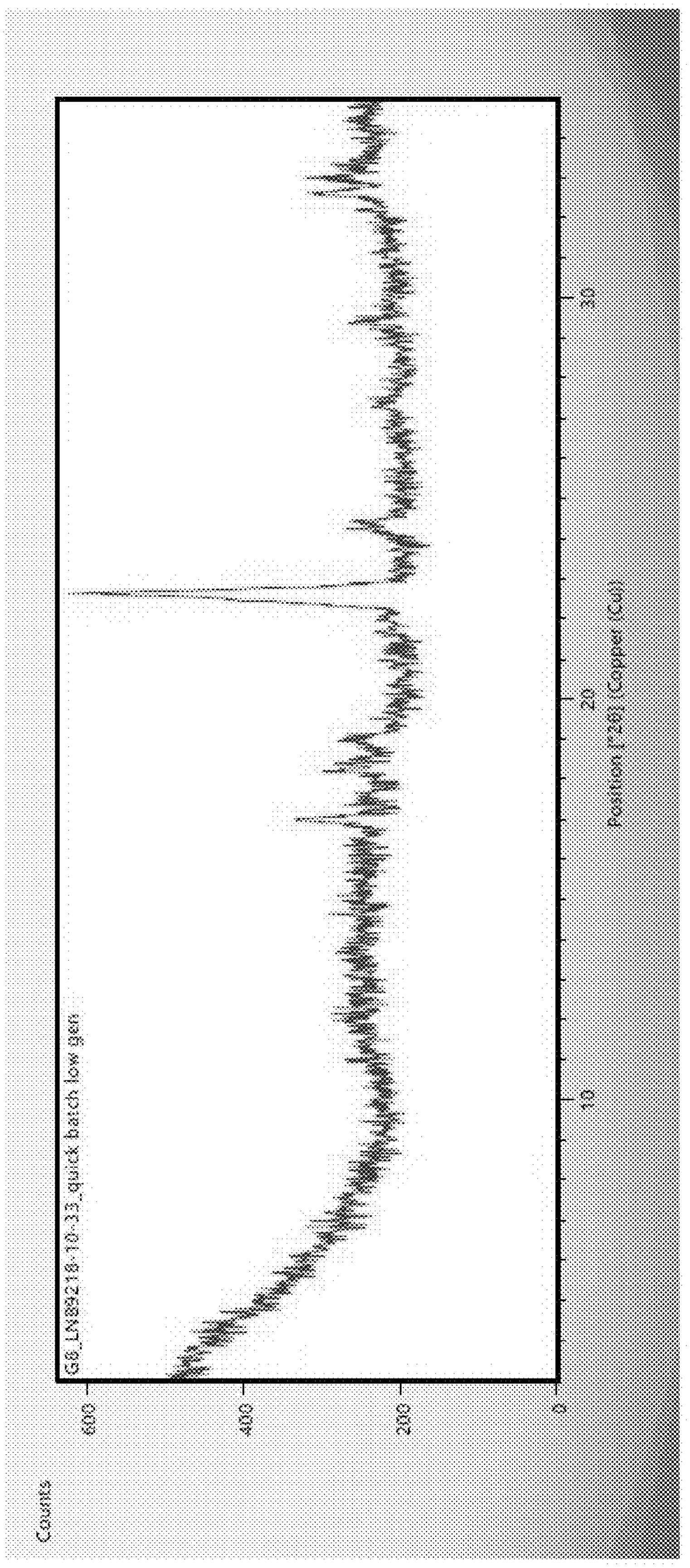
FIG. 41 illustrates the XRPD after prolonged lyophilization (72 hr) of Pattern 1 that the material returned from freeze drying was predominately amorphous by XRPD.

For another round of lyophilization, each 10 mg sample of FIG. 40 was re-dissolved in 200 μL of water. Vials were again frozen at −50° C. before being freeze dried for 72 hours. The material returned from freeze drying was predominately amorphous by XRPD, as shown in FIG. 41.

Figure 42:
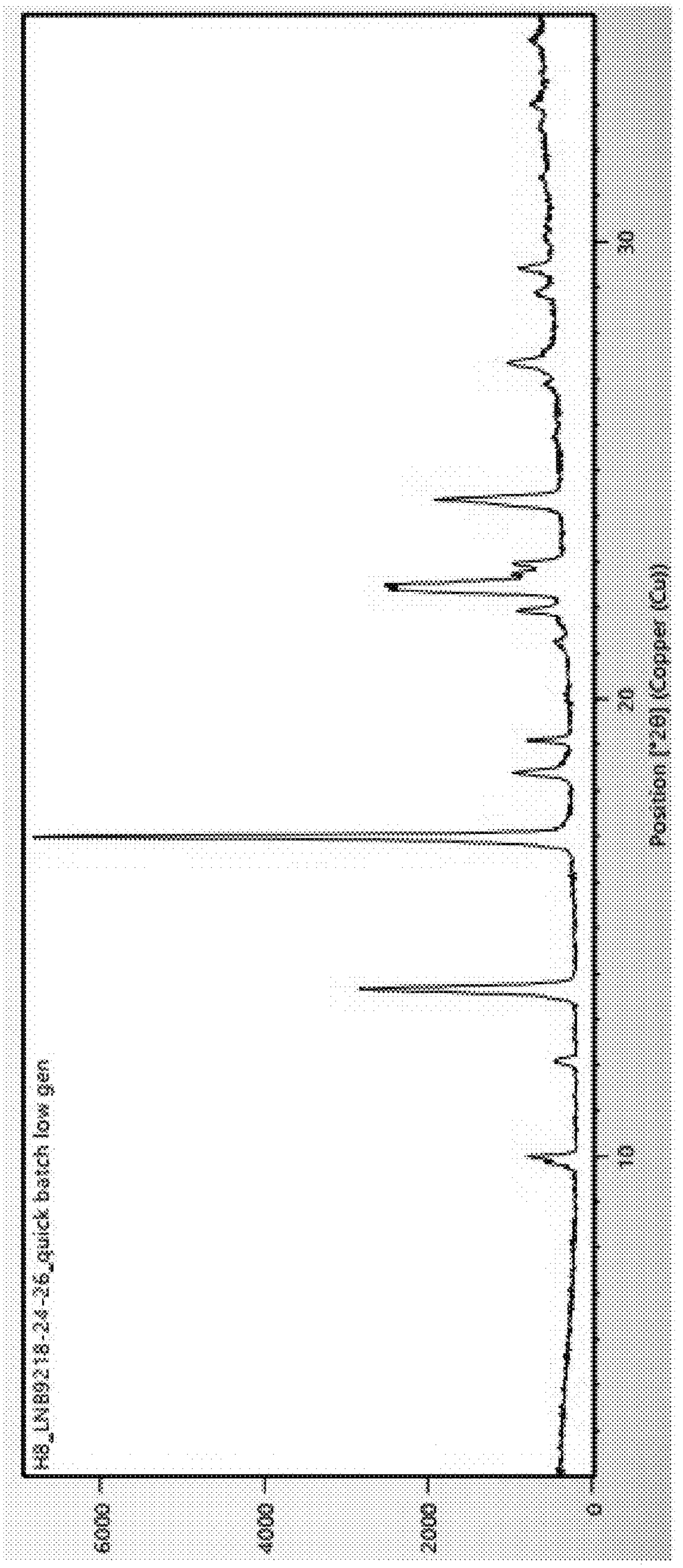
FIG. 42 illustrates the XRPD after initial lyophilization of Pattern 2 (72 hours drying) that the material returned from freeze drying was found to be Pattern 2 after 72 hours of drying.
Figure 47:
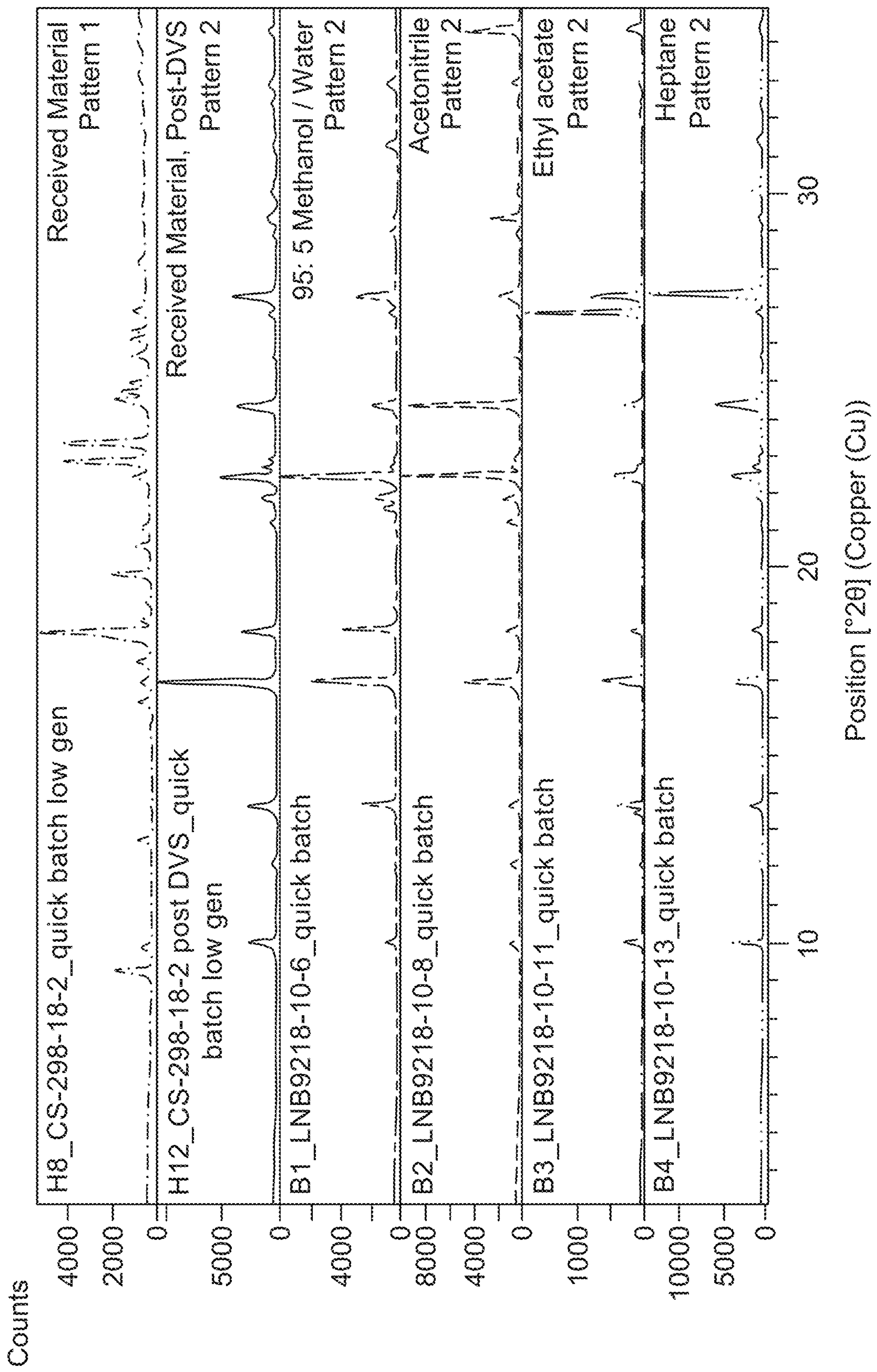
FIG. 47 illustrates the XRPD diffractograms of polymorph formed in various solvents-Part 1.
Figure 48:
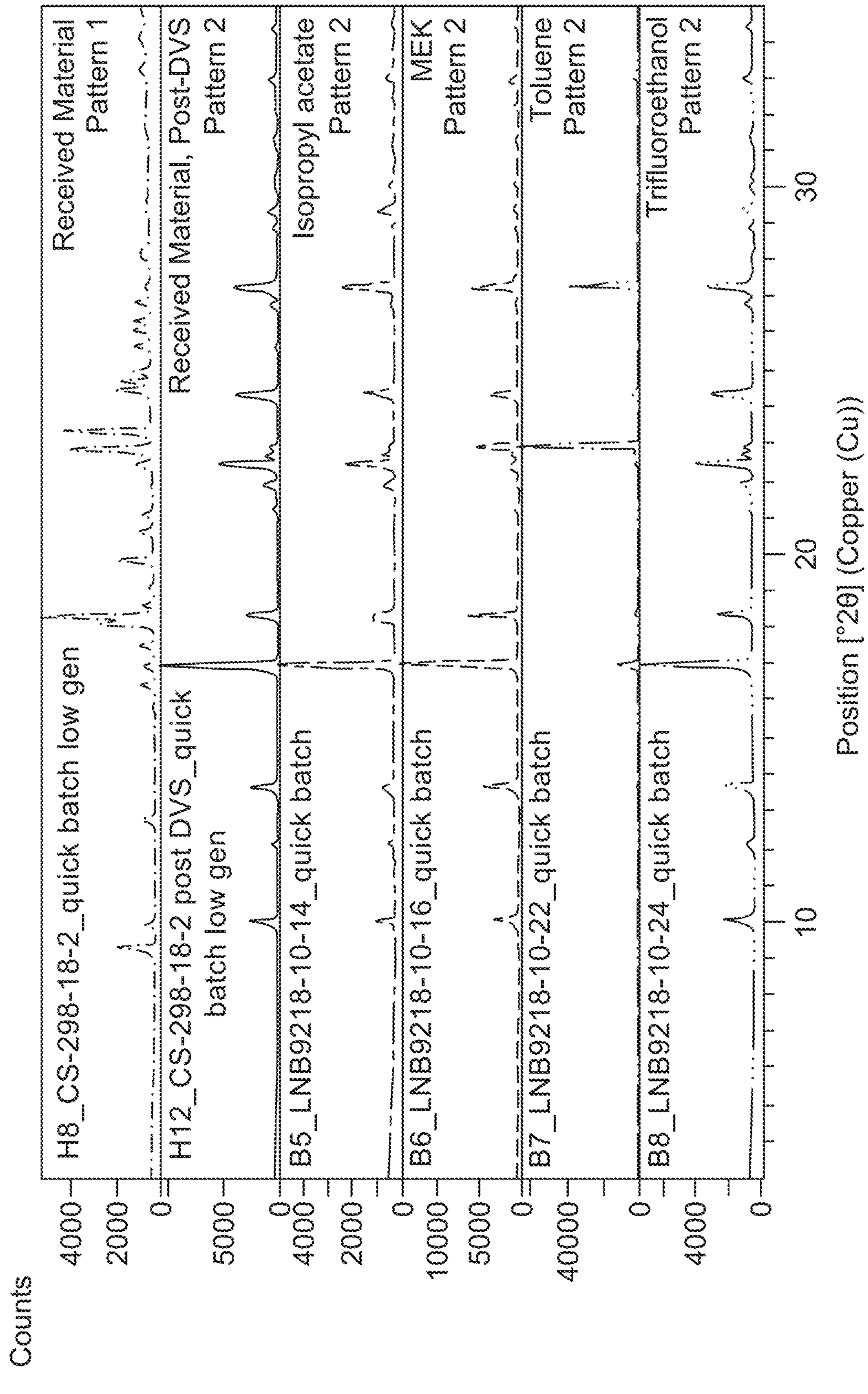
FIG. 48 illustrates the XRPD diffractograms of polymorph formed in various solvents—Part 2.
Figure 49:
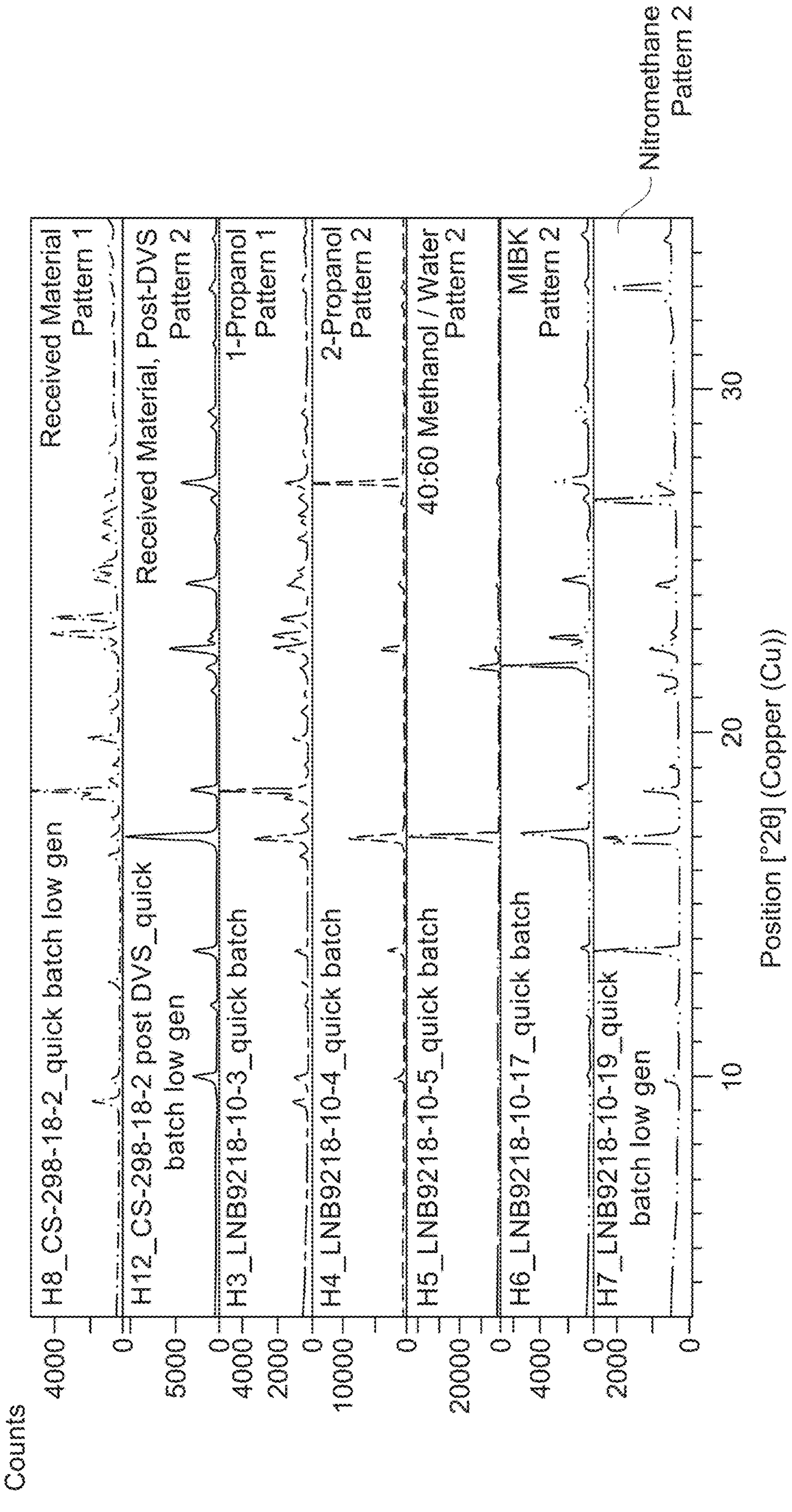
FIG. 49 illustrates the XRPD diffractograms of polymorph formed in various solvents—Part 3.
Figure 51:
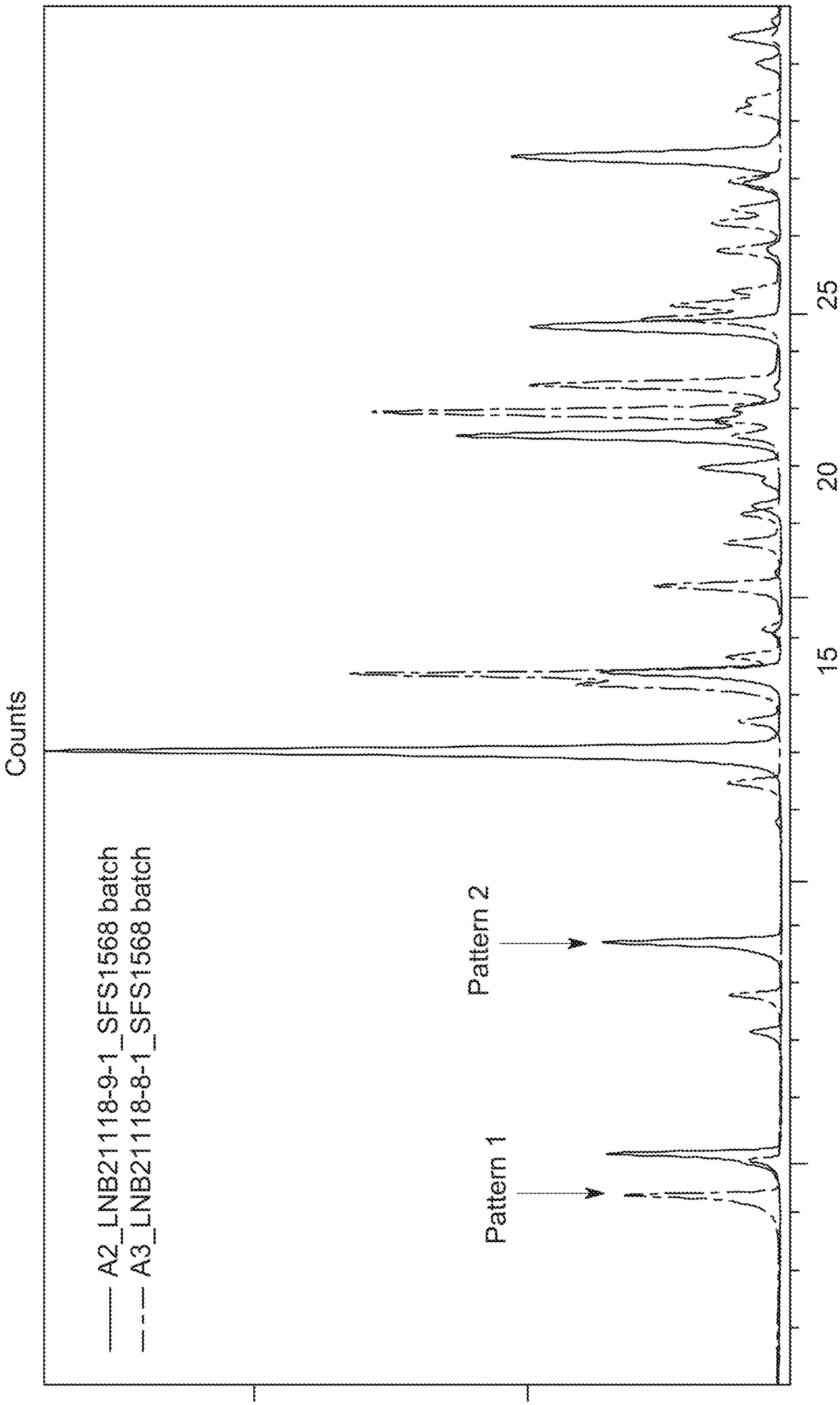
FIG. 51 is a superimposition of the XRPD diffractograms of Pattern 1 (in blue) and Pattern 2 (in red).

For the amorphization test: CHP hydrate (Pattern 2) was dissolved in distilled water. This solution was equally divided into 26 glass vials and the vials were frozen at −50° C. in preparation for freeze drying. Once frozen, the samples were placed in desiccators attached to a freeze dryer and dried for approximately 48 hours. As shown in FIG. 42, the material returned from freeze drying of Pattern 2 was found to be Pattern 2 when analyzed by XRPD.

For another round of amorphization, the samples were re-dissolved by adding 1 mL of distilled water to each vial. Solutions were then pipetted into 26, 20 mL glass vials and topped with an additional 15 mL of distilled water. Vials were frozen at −50° C. before being freeze dried for approximately 48 hours. After 48 hours, the samples had not completely lyophilized and the vials were returned to the desiccators and freeze dried for a further 72 hours. The material analyzed by XRPD was found to still contain Pattern 2 peaks.

In other embodiments, the lyophilization of the CHP hydrate of the present disclosure shows that Pattern 2 is more stable than Pattern 1 and remains after amorphization at least about 10% to about 40% pure.

L. Solubility Screen

33×10 mg samples of CHP Pattern 1 (anhydrous form) were lyophilized in 2 mL vials and 100 μL different solvent systems were added to each vial. Between each addition, the mixture was checked for dissolution and if no dissolution was observed, the mixture was heated to ca. 40° C. and checked again. After 300 μL of solvent had been added, 100 μL aliquots were added. This procedure was continued until dissolution was observed or until 1 mL of solvent had been added. If no dissolution occurred, the solids were isolated by filtration and an XRPD was collected. If dissolution occurred, the solvent was allowed to evaporate and an XRPD was collected on any solid remaining.

FIG. 43 provides the approximate solubility of Pattern 1 in various solvents and FIG. 44 provides the solvent solubility results of Pattern 1 based on volume of solvent added. As shown in FIGS. 43 and 44, high solubility was observed in ethanol, methanol, N,N-dimethyl acetamide, water, DMSO, trifluoroethanol, 1-propanol, and the methanol/water mixtures. Samples were left uncapped to allow evaporation, and observed solids were analyzed by XRPD.

As shown in FIG. 45, XRPD analysis identified 2 unique patterns in addition to pattern 1 (the crystalline form) from the kinetic solubility screening, although pattern 3 only appeared as a mixture with pattern 2. Acetone, dichloromethane (DCM), ethyl formate, and MtBE produced pattern 2 (the hydrate form). A mixture of the crystalline and hydrate forms were observed in ethanol. Chlorobenzene produced a mixture of patterns 2 and 3, and THF returned mainly amorphous material with some pattern 2 peaks. A colorless gel was seen in methanol and was not analyzed by XRPD. The solvent system produced crystals during evaporation and was identified as a potential THF solvate.

As shown in FIG. 45, 9 out of the 30 solvent systems listed produced insufficient solid for XRPD analysis. Sixteen of the solvents returned Pattern 2, Pattern 1 was observed in 1-propanol, a mixture of Patterns 1 and 2 was seen in ethanol, a mixture of Patterns 2 and 3 was produced in chlorobenzene, and mainly amorphous material with some Pattern 2 peaks was produced in TIHF.

FIG. 46 illustrates the primary polymorph screening solvents.

In other embodiments, the CHP hydrate of the present disclosure can be produced from kinetic crystallization (2-6 hours) from 1-propanol, 2-propanol, methanol/water mixture, acetone, acetonitrile, ethyl acetate, ethyl formate, heptane, isopropyl acetate, methyl ethyl ketone (MEK), methyl isobutyl ketone, itromethane, toluene, and trifluoroethanol.

M. Primary Polymorph Screen

To twenty-four (24) vials containing 40 mg of anhydrous CHP different solvent was added in 100 μL aliquots until a thin slurry was observed. The vials were then temperature cycled between an ambient temperature and 40° C. in 4 hour cycles over 72 hours. All remaining solids were isolated by centrifugation and analyzed by XRPD.

FIG. 46 shows the solvents used for the kinetic (2-6 hours) polymorph screening and FIG. 50 shows the primary polymorph screen temperature cycling of Pattern 1.

The results show that when water is present in the sample, Pattern 2 predominates. Pattern 1 is only formed if there is insufficient water present in the sample, either from the sample itself, the solvent system or allowed to adsorb it from the atmosphere. These results are summarized in the Tables 24 and 25.

Example 2—Process of Making CHP Hydrate

This study was conducted to (1) evaluate the transferred process for converting pattern 1 (anhydrate, C16081735-D) to pattern 2 (hydrate, PATTERN 2); (2) evaluate a demonstration run at around 100 gram scale by using non-GMP CHP Pattern 1 (anhydrate) stored at designated manufacturer; (3) manufacture about 400 g of PATTERN 2 under Current Good Manufacturing Practice regulations (cGMP) conditions; and (4) evaluate the drying condition to ensure get the desired pattern 2 (hydrate, PATTERN 2).

The specifications were set as follows: HPLC purity: ≥98.0%; Impurity profiles: H-His-OH≤1.0%, each other individual ≤1.0%; Chiral purity: ≥98.0%; Chiral impurities: Report each ≥0.1% impurities; DL, LD, LL Optical isomers ≤1.0%, etc.

A reproducible process was developed for the manufacture of pattern 2 (Cyclo (L-His-L-Pro) dipeptide hydrate) by dissolving the pattern 1 (anhydrate) in EtOH/$H_2O$=9/1 (V/V) and precipitation the pattern 2 (hydrate) by MtBE addition. The process had been successfully implemented on a 370 g scale. Ultimately, a total of 288 g of pattern 2 (CHP hydrate) with 99.9% HPLC purity and 100.0% chiral purity was produced under cGMP conditions.

A. Introduction and Synthetic Scheme

A process for converting pattern 1 (anhydrate) to pattern 2 (hydrate, pattern 2) was evaluated. Two crystallization procedures were provided, one was dissolving anhydrate solid in water and precipitation by acetone addition (see synthetic scheme 1); the other is dissolving anhydrate solid in EtOH/water=9/1 and precipitation by MtBE addition (see synthetic scheme 2). The quality and yield of two procedures and fixed on scheme 2 for optimization work were evaluated.

Finally, the optimized process (see Scheme 3) was successfully executed to produce 288 g of pattern 2 (CHP hydrate). The campaign production followed Scheme 3.

Scheme 1: The first synthetic route to Pattern 2 (CHP Hydrate)

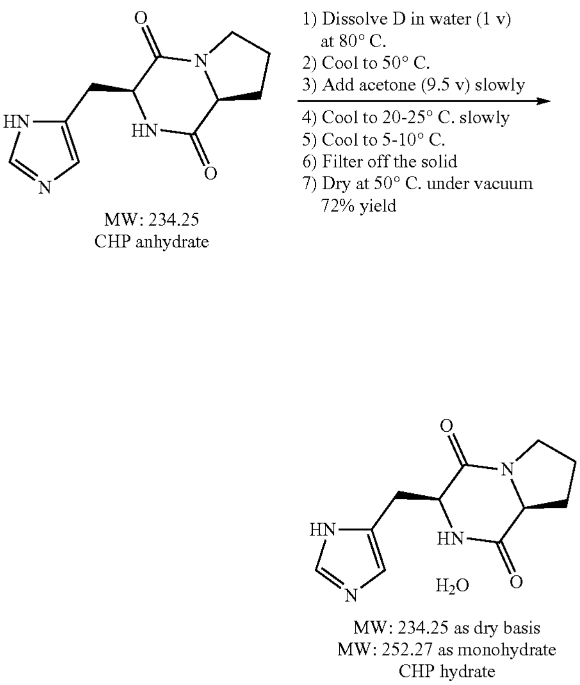

Scheme 2: The second synthetic route to Pattern 2 (CHP Hydrate)

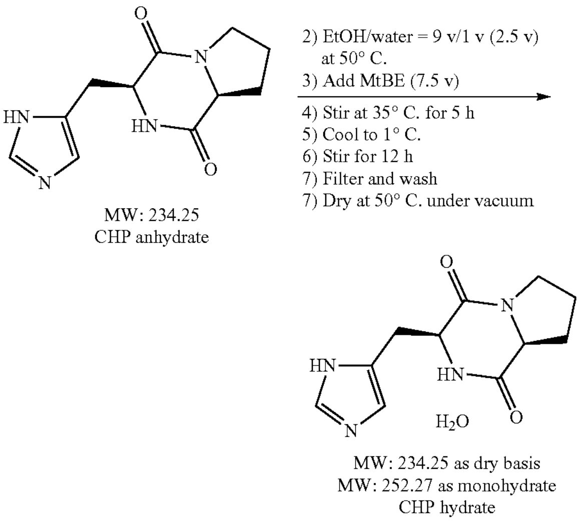

Scheme 3: The Optimized synthetic route to Pattern 2 (CHP Hydrate) for cGMP production

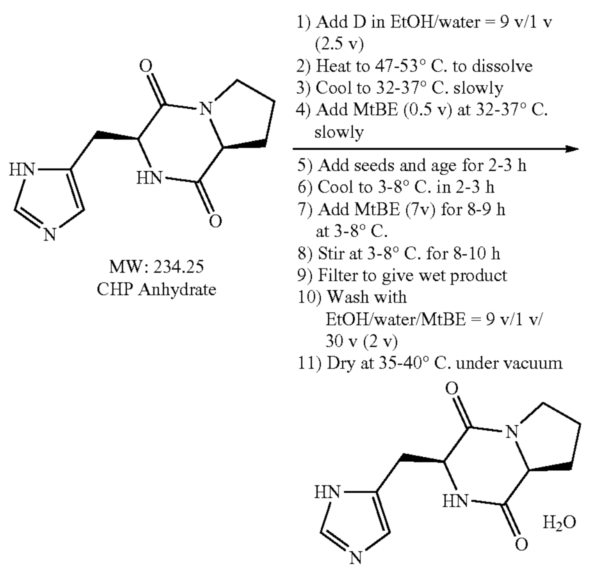

MW: 234.25
CHP Anhydrate

MW: 234.25 as dry basis
MW: 252.27 as monohydrate
CHP hydrate

Both procedures (scheme 1 and 2) were evaluated and afforded product as a hydrate with target pattern 2. The chemical stability under both conditions was studied and pattern 2 was stable at 50° C. for 20 h. However, the water/acetone procedure utilized very small amount of water (1V) as good solvent and was tough to select suitable reactor with so small minimum stirring volume. Furthermore, the water/acetone procedure gave only about 70% isolated yield. The EtOH/$H_2O$/MtBE procedure was chosen for optimization work with approx. 90% isolated yield. Following the optimized crystallization procedure, a 370 g scale cGMP batch was successfully executed in kilo-lab.

B. Summary

For the preparation of pattern 2, the two crystallization procedures with water/acetone and EtOH/$H_2O$/MtBE were evaluated, and both afforded product as a hydrate with target pattern 2. The chemical stability under both conditions was studied and the product was stable at 50° C. for 20 h. Considering water/acetone procedure gave only about 70% isolated yield, the EtOH/$H_2O$/MtBE procedure was chosen for optimization work. The temperature and rate of MtBE addition were studied, and the procedure to add MtBE at 5° C. by relatively slow rate was finalized to avoid having significant amount of solid attached to the wall of the vessel. Following the optimized crystallization procedure, one demo run on 100 g scale was conducted and the crystallization successfully afforded 96.44 g of product as pattern 2 with approx. 90% isolated yield. Based on the drying stability study, the hydrate product was stable at below 40° C. in lab oven under −0.09 MPa.

C. Evaluation of the Crystallization Procedure with Water/Acetone Condition

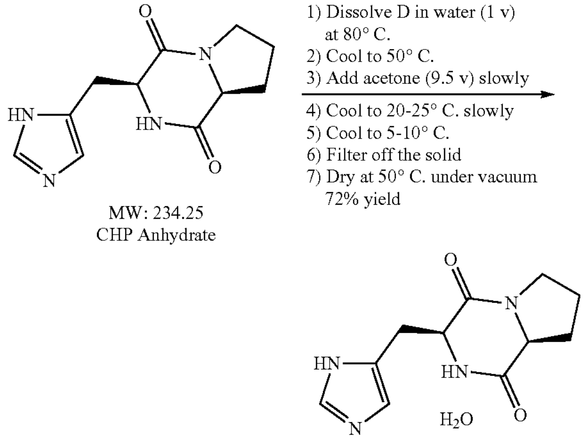

MW: 234.25
CHP Anhydrate

MW: 234.25 as dry basis
MW: 252.27 as monohydrate
CHP hydrate

Two trials were carried out to evaluate the RFP crystallization procedure with water/acetone condition (Table 2). No crystallization was observed without seed in experiment PS03027-2, and solid precipitated after seed addition. Seed was added in experiment PS03027-4, and crystallization went smoothly. XRPD indicated target pattern 2 was obtained. The loss product in water/acetone system was relatively high (about 20%), which was consistent with the yield in RFP (72%).

TABLE 2

Results for preparation of CHP hydrate

| | Starting Materials | | Observation | | CHP hydrate | |
|---|---|---|---|---|---|---|
| Lot/Batch# | CHP Anhydrate | Solvent | Observation | Wt | XRPD | Loss in ML |
| PS03027-2 | 2 g Lot#: PS00726-55-D-P | Water/acetone | No crystallization without seed Solid precipitated with seed | 1.15 g | Pattern 2 | n/a |
| PS03027-4 | 5 g Lot#: PS00726-55-D-P | Water/acetone | Solid precipitated after seeding | 3.65 g | Pattern 2 | 20% |

Note:
Seed was prepared by re-slurry pattern 1 in 1 vol water at RT

D. Evaluation the Alternative Crystallization Procedure with EtOH/Water/MTBE

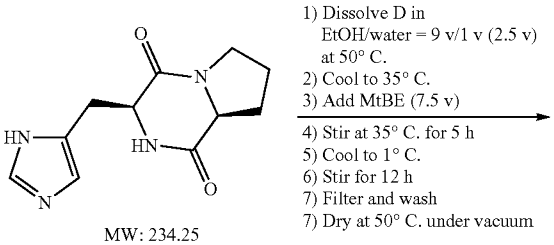

MW: 234.25
CHP Anhydrate

-continued

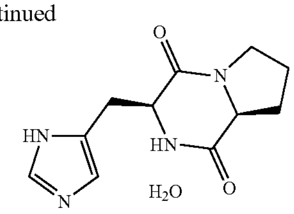

MW: 234.25 as dry basis
MW: 252.27 as monohydrate
CHP hydrate

One lot on 5 g scale was performed to evaluate the alternative EtOH/water/MTBE crystallization condition, and the crystals nucleated during the MtBE addition and XRPD indicated target Pattern 2 was obtained. The loss in the mother liquor was relatively lower (8%) than water/acetone condition (Table 3).

TABLE 3

Results for Preparation of CHP Hydrate

| | Starting Materials | | Observation | CHP hydrate (PATTERN 2) | | | |
|---|---|---|---|---|---|---|---|
| Lot/Batch# | CHP Anhydrate | Solvent | Observation | Wt | XRPD | Residual solvent | Loss |
| PS03027-5 | 5 g Lot#: PS00726-55-D-P | EtOH/water/MtBE | Spontaneous nucleation during MtBE addition | n/a | Pattern 2 | EtOH:0.01%; MtBE:0.01% | 8% |

E. Study Chemical Stability in Water/Acetone and EtOH/Water/MtBE

Solution state chemical stability of the compound was studied in different solvent systems at different temperatures (Table 4). The solution was held at 50° C. and 80° C., and purity of the solution was tracked. The compound was generally stable for at least 20 hours.

TABLE 4

Chemical stability in water/acetone and EtOH/water/MtBE

| Experiment No. | Solvent | Concentration | Input | T/° C. | Purity (a %) 0 h | 2 h | 20 h | Observation |
|---|---|---|---|---|---|---|---|---|
| PS03027-8-H-1 | $H_2O$ | 10 mg/ml | PS00726-55-D-P | 80 | 99.82% | 99.77% | 99.82% | No change |
| PS03027-8-H-2 | $EtOH:H_2O$ = 9:1(v/v) | 10 mg/ml | Purity:99.7% | 50 | 99.76% | 99.86% | 99.69% | No change |
| PS03027-8-H-3 | $H_2O$:Acetone = 0.5:9.5(v/v) | 10 mg/ml | | 50 | 99.77% | 99.72% | 99.73% | No change |
| PS03027-8-H-4 | ($EtOH:H_2O$ = 9:1): MTBE = 1:3(v/v) | 10 mg/ml | | 50 | 99.82% | 99.77% | 99.82% | No change |

F. Study Solubility of CUP Hydrate (Pattern 2)

The solubility of CHIP hydrate in water/acetone and EtOH/water/MtBE was studied and was found to be sensitive to solvent ratio and temperature under both conditions (Tables 5 and 6). The yield in EtOH/water/MtBE crystallization was 90% or higher.

TABLE 5

Solubility of Pattern 2 in water/acetone

| Experiment No. | Input | Solvent Water/ acetone (v/v) | T/° C. | Solubility (mg/ml) |
|---|---|---|---|---|
| PS03029-4-H-1 | CHP | 0/10 | 50 | 14 |
| PS03029-4-H-2 | hydrate | 0.5/9.5 | | 49 |
| PS03029-4-H-3 | (pattern 2) | 1/9 | | 159 |
| PS03029-4-H-4 | | 2/8 | | >200 |
| PS03029-4-H-5 | | 4/6 | | >200 |
| PS03029-4-H-6 | | 6/4 | | >200 |
| PS03029-4-H-7 | | 8/2 | | >200 |
| PS03029-4-H-8 | | 9/1 | | >200 |
| PS03029-4-H-14 | | 0/10 | 5 | 17 |
| PS03029-4-H-15 | | 0.5/9.5 | | 19 |
| PS03029-4-H-16 | | 1/9 | | 48 |
| PS03029-4-H-17 | | 2/8 | | 110 |
| PS03029-4-H-18 | | 4/6 | | 179 |
| PS03029-4-H-19 | | 6/4 | | 206 |
| PS03029-4-H-20 | | 8/2 | | >200 |
| PS03029-4-H-21 | | 9/1 | | 215 |

TABLE 6

Solubility of pattern 2 in EtOH/water/MtBE

| Experiment No. | Input | Solvent (EtOH/water = 9/1)/MtBE (v/v) | T/° C. | Solubility (mg/ml) |
|---|---|---|---|---|
| PS03029-4-H-9 | CHP | 3/0 | 50 | >200 |
| PS03029-4-H-10 | hydrate | 3/1 | | >200 |
| PS03029-4-H-11 | (pattern 2) | 3/3 | | 101 |
| PS03029-4-H-12 | | 3/6 | | 24 |
| PS03029-4-H-13 | | 3/9 | | 17 |
| PS03029-4-H-22 | | 3/0 | 5 | 121 |
| PS03029-4-H-23 | | 3/1 | | 59 |
| PS03029-4-H-24 | | 3/3 | | 30 |
| PS03029-4-H-25 | | 3/6 | | 6 |
| PS03029-4-H-26 | | 3/9 | | 6 |

Note:
1) the lot PS03027-2-H was used as pattern 2 material.

G. Process Optimization of EtOH/Water/MtBE Condition

In order to further understand the crystallization in EtOH/water/MtBE, three experiments were carried out, in which MtBE was added at 50° C., 35° C., and 5° C., respectively. As shown in Table 7, three experiments delivered the desired crystalline form, and residual solvents were low.

TABLE 7

Process optimization in EtOH/water/MtBE (5 g scale)

| | Starting Materials | | Condition | CHP hydrate (pattern 2) | | | |
|---|---|---|---|---|---|---|---|
| | | | | | | Residual | Loss |
| Lot/Batch# | CHP Anhydrate | Solvent | | Wt | XRPD | solvent | yield |
| PS03027-9 | 5 g Lot# PS00726-55-D-P | EtOH/ water/MtBE | MtBE addition at 50° C. | 4.35 g | Pattern 2 | EtOH:0.01%; MTBE:0.02% | 5% |
| PS03027-11 | 5 g Lot# PS00726-55-D-P | EtOH/ water/MtBE | MtBE addition at 35° C. | 4.49 g | Pattern 2 | EtOH:0.01% MTBE:0.01% | Not measured |
| PS03027-10 | 5 g Lot# PS00726-55-D-P | EtOH/ water/MtBE | MtBE addition at 5° C. | 4.89 g | Pattern 2 | EtOH:0.02%; MTBE:0.02% | 5% |

In order to verify the procedure at larger scale, three 15 g scale experiments were carried out, as shown in Table 8. During experiments PS03027-13 and PS03027-14 (in which MtBE was added at 50° C. and 35° C.), an encrustation issue was observed. Significant amount of solid attached on the wall of the vessel especially during MtBE addition. In order to avoid this issue, in experiment PS0027-15, MtBE was added at 5° C. and the addition was extended to 8 h (4 h in pervious experiments). It was found that the crust on the wall was much less. It was therefore concluded that MtBE should be added at 5° C. at relatively slow rate.

TABLE 8

Process optimization in EtOH/water/MtBE (15 g scale)

| Lot/Batch# | Starting Materials: CHP Anhydrate | Starting Materials: Solvent | Condition | CHP hydrate (pattern 2): Wt | CHP hydrate (pattern 2): XRPD | CHP hydrate (pattern 2): Residual solvent | CHP hydrate (pattern 2): Loss yield |
|---|---|---|---|---|---|---|---|
| PS03027-13 | 15 g Lot# PS00726-55-D-P | EtOH/water/MtBE | MtBE addition at 50° C. | 7.42 g | Pattern 2 | MTBE:0.02% EtOH:0.03% | Not measured |
| PS03027-14 | 15 g Lot# PS00726-55-D-P | EtOH/water/MtBE | MtBE addition at 35° C. | 11.93 g | Pattern 2 | MTBE:0.01% EtOH:0.04% | 6% |
| PS03027-15 | 15 g Lot# PS00726-55-D-P | EtOH/water/MtBE | MtBE addition at 5° C. with slower rate | 14.44 g | Pattern 2 | MTBE:0.01% EtOH:0.04% | 7% |

H. Stress Test of Fast Addition of MtBE

As shown in Table 9, a stress test was carried out for the procedure, in which MtBE addition was carried out at relatively fast rate. XR-PD of the solid during the experiment was tracked, and the data indicated that pattern 2 was observed all along the crystallization.

TABLE 9

Stress test of fast addition of MtBE

| Lot/Batch# | Starting Materials: CHP Anhydrate | Starting Materials: Solvent | Condition | CHP hydrate (pattern 2): Wt | CHP hydrate (pattern 2): XRPD | CHP hydrate (pattern 2): Residual solvent | CHP hydrate (pattern 2): Loss yield |
|---|---|---|---|---|---|---|---|
| PS03027-17 | 5 g Lot# PS00726-55-D-P | EtOH/water/MtBE | MtBE addition at 5° C. with faster rate | 4.58 g | Pattern 2 | MTBE:0.00% ETOH:0.02% | 3% |

L. Study Form Stability in EtOH/Water/MtBE

In order to study form stability in EtOH/water/MtBE, competitive repining experiments were carried out at 50° C., 35° C., and 5° C. respectively, by adding 100 mg of anhydrous Pattern 1 solid and 100 mg of Pattern 2 solid. As shown in Table 10, mixed forms of pattern 1 and pattern 2 convert to pattern 2 quickly under different conditions.

TABLE 10

Competitive slurry of Pattern 1 and Pattern 2 in EtOH/water/MtBE

| Experiment NO. | Solvent(v/v) | T/° C. | XRPD tracking: 0 h | XRPD tracking: 2 h | XRPD tracking: 6 d | XRPD tracking: 7 d |
|---|---|---|---|---|---|---|
| PS03027-16-H-1 | ($EtOH:H_2O$ = 9:1):MTBE = 3:0 | 50 | Pattern 2 | n/a | n/a | n/a |
| PS03027-16-H-2 | ($EtOH:H_2O$ = 9:1):MTBE = 2.5:0.5 | | Pattern 2 | Pattern 2 | Pattern 2 | n/a |

TABLE 10-continued

Competitive slurry of Pattern 1 and Pattern 2 in EtOH/water/MtBE

| Experiment NO. | Solvent(v/v) | T/° C. | XRPD tracking 0 h | 2 h | 6 d | 7 d |
|---|---|---|---|---|---|---|
| PS03027-16-H-3 | ($EtOH:H_2O$ = 9:1):MTBE = 1:2 | | Pattern 2 | Pattern 2 | n/a | n/a |
| PS03027-16-H-4 | ($EtOH:H_2O$ = 9:1):MTBE = 1:3 | | Pattern 2 | Pattern 2 | Pattern 2 | Pattern 2 |
| PS03027-16-H-5 | ($EtOH:H_2O$ = 9:1):MTBE = 3:0 | 35 | Pattern 2 | Pattern 2 | Pattern 2 | Pattern 2 |
| PS03027-16-H-6 | ($EtOH:H_2O$ = 9:1):MTBE = 2.5:0.5 | | Pattern 2 | Pattern 2 | Pattern 2 | Pattern 2 |
| PS03027-16-H-7 | ($EtOH:H_2O$ = 9:1):MTBE = 1:2 | | Pattern 2 | Pattern 2 | n/a | n/a |
| PS03027-16-H-8 | ($EtOH:H_2O$ = 9:1):MTBE = 1:3 | | Pattern 2 | Pattern 2 | Pattern 2 | Pattern 2 |
| PS03027-16-H-9 | ($EtOH:H_2O$ = 9:1):MTBE = 3:0 | 5 | Pattern 2 | Pattern 2 | Pattern 2 | Pattern 2 |
| PS03027-16-H-10 | ($EtOH:H_2O$ = 9:1):MTBE = 2.5:0.5 | | Pattern 2 | Pattern 2 | Pattern 2 | Pattern 2 |
| PS03027-16-H-11 | ($EtOH:H_2O$ = 9:1):MTBE = 1:2 | | Pattern 2 | Pattern 2 | Pattern 2 | Pattern 2 |
| PS03027-16-H-12 | ($EtOH:H_2O$ = 9:1):MTBE = 1:3 | | Pattern 2 | Pattern 2 | Pattern 2 | Pattern 2 |

Note:
input materials: 100 mg of anhydrous solid (Pattern 1, Lot# PS00726-55-D) was added together with 100 mg of pattern 2 solid (Lot# PS03027-5/9/10/11-H).

J. Study Dry Stability at 35° C., 40° C., 50° C. and 65° C.

Drying stability was carried out at 35° C., 40° C., 50° C., and 65° C. respectively. As shown in Table 11, Pattern 2 is stable up to 40° C. for at least 4 days.

TABLE 11

Dry stability at 35° C., 40° C., 50° C. and 65° C.

| Experiment No. | Input/form | T/° C. | 1 d XRPD | 2 d XRPD | 3 d XRPD | 4 d XRPD |
|---|---|---|---|---|---|---|
| PS03027-15-H-35 | PS03027-15-H/ Pattern 2 | 35° C. | Pattern 2 | NT | NT | Pattern 2 |
| PS03027-21-H-40 | PS03027-21-H/ Pattern 2 | 40° C. | Pattern 2 | Pattern 2 | Pattern 2 | Pattern 2 |
| PS03027-15-H-50 | PS03027-15-H/ Pattern 2 | 50° C. | Pattern 2 | Pattern 2 | NT | Pattern 1 |
| PS03027-15-H-65 | | 65° C. | Pattern 2 | Pattern 1 | NT | NT |

K. Study the Slurry Procedure to Convert Worse Crystalline Back to Pattern 2

Because over-dryness (KF=5.4%, theoretical 7.4%) led to less crystallinity for the cGMP batch of Pattern 2 (PATTERN 218001) even when drying at 35-40° C. for 10 h. In order to convert the poor crystalline pattern 2 solid to desired pattern 2, two re-slurry experiments were carried out. 2 g of PATTERN 218001-STEP5.7 was re-slurried in 8 vol EtOH/water/MtBE=9 v/lv/30 v at RT and 5° C., and was found to convert to pattern 2 in only 30 minutes. The solid was isolated and dried for 14 h, and the form did not change during this period. The loss based on the mother liquor concentration was around 5% (whereas the total loss was expected to be 10% including the loss in the flask wall and operation). One advantage is that this procedure results in all the solid converting to pattern 2, although about 10% product may be lost.

L. General Route from Pattern 1 to Pattern 2

1. Charge EtOH (1.75-1.79×; 2.25V) into R1 under $N_2$
2. Charge purified water (0.245-0.255×; 0.25V) into R1 under $N_2$
3. Stir R1 for 5-10 min to give a mixed solution EtOH/water=9:1 (v/v).
4. Transfer the solution from R1 to a drum
5. Charge pattern 1 (1.0 eq, 1.0×) into R1.
6. Charge the EtOH/water mixture from Step 4 (1.61-1.63×, 2.0V) into R1 under $N_2$
7. Adjust R1 to 47-53° C. under $N_2$.
8. Stir R1 at 47-53° C. for 10-60 min under $N_2$. Polish filter the solution from R1 to R2. The jacket of R2 was pre-heated to 50-55° C.
9. Charge the EtOH/water mixture from Step 4 (0.39-0.41×; 0.5V) into R1 under $N_2$
10. Stir R1 for 5-30 min under $N_2$
11. Polish filter the solution from R1 into R2

12. Adjust R2 to 47-53° C. and stir for 10-60 min under $N_2$. Confirm complete dissolution by project leader.
13. Adjust R2 to 32-37° C. under $N_2$.
14. Add MtBE (0.36-0.38×; 0.5V) at 32-37° C. into R2 slowly under $N_2$.
15. Charge pattern 2 seed crystal (0.015-0.025×) into R2 at 32-37° C.
16. Stir R2 at 32-37° C. for 2-3 h under $N_2$.
17. Adjust R2 to 3-8° C. in 2-3 h under $N_2$.
18. Take a sample and filter, send the cake for XRPD analysis: XRPD (consistent as PS03027-15-H). Criteria: If the results meet the specification, do Step 20; otherwise, consult project leader.
19. Charge MtBE (5.1-5.3×; 7V) into R2 over 8 h at 3-8° C. under $N_2$.
20. Stir R2 at 3-8° C. for 8-10 h under $N_2$.
21. Take a sample and filter, send the cake for XRPD analysis: XRPD (consistent as PS03027-15-H); send the filtrate for residual Pattern 2 analysis: Residual H in the supernatant liquor (≤1.5% w/w).
    Criteria: If the results meet the specification, do Step 25; otherwise, do Step 23.
22. Stir R2 at 3-8° C. for 4-10 h under $N_2$.
23. Take a sample and filter, send the cake for XRPD analysis: XRPD (consistent as PS03027-15-H); send the filtrate for residual H analysis: Residual H in the supernatant liquor (≤1.5% w/w). Criteria: If the results meet the specification, do Step 25.
24. Filter the suspension at 3-8° C. under $N_2$.
25. Charge EtOH (0.355×), purified water (0.05×) and MtBE (1.11×) into a clean drum.
26. Stir the material in STEP 26 to give a clear mixture solution.
27. Transfer the STEP 27 solution (1.5-1.6×) into R2 to rinse R2.
28. Cool R2 to 3-8° C.
29. Wash the wet cake with the R2 rinsing solution at 3-8° C.
30. Check the quality of wet product:
    XRPD (consistent as PS03027-15-H); HPLC ≥98.0% area; H-His-OH≤1.0% area
    Each other individuals 1.0% area; Report each impurities≥0.05% area with RRT
    Note: Do Step 32 in parallel.
    Criteria: If the results meet the specification, do Step 33.
31. Check the residue pattern 2 in the mother liquid. Report the residual amount of pattern 2 (%, report).
32. Dry at 35-40° C. under vacuum for 10-12 h. Recommend to lay a water bath in the oven to avoid over-drying.
33. Check the residual solvent:
    EtOH (≤5000 ppm); MtBE (≤5000 ppm); Water content (report)
    Check the polymorph of dry product: XRPD (consistent as PS03027-15-H)
    Criteria: If the results meet the specification, do Step37; otherwise, do Step 35.
34. Dry at 35-40° C. under vacuum for 5-8 h. Recommend to lay a water bath in the oven to avoid over-drying.
35. Check the residual solvent:
    EtOH (≤5000 ppm); MtBE (≤5000 ppm); Water content (report)
    Check the polymorph of dry product: XRPD (consistent as PS03027-15-H)
    Criteria: If the results meet the specification, do Step37.
36. Fill the dry product into drums and sieve.
37. Take samples for release analysis.

M. Full Characterization

The HPLC purity, $^1$HNMR, TGA, DSC and XRPD spectra are showed in Table 12.

TABLE 12

Characterization of Pattern 2

| Compound ID | Structure | Characterization data $^1$H-NMR | HPLC purity | TGA | XRPD | DSC |
|---|---|---|---|---|---|---|
| PATTERN 2 | 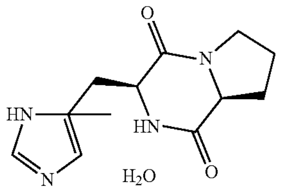 | Conform | 99.9% | Onset 170 Outset 172 | Pattern 2 | Two peaks 104.29° C. 172.17° C. |

Example 3—Crystallization Process Development of CHP Hydrate

This research focused on crystallization development of CHP Hydrate (pattern 2). After initial characterization of a batch of CHP Hydrate, solubility studies, small-scale crystallization assessments, metastable zone width measurements and scale-up crystallizations were carried out. The aim of the work program was to establish crystallization conditions that would allow for successful production of CHP Hydrate pattern 2, which could be effectively scaled up for manufacturing.

Solubility assessments carried out on CHP pattern 1 indicated high solubility in all solvent mixture that contained water with the exception of ethanol:water:MtBE blends with the highest percentage of MtBE. Particularly high solubility was observed from water (≥200 mg/mL) and acetone:water blends (≥200 in water:acetone [90:10]). The material was observed to be poorly soluble in acetone, acetonitrile and THF (≤10 mg/mL).

Two-point solubility indicated that out of the two solvent systems assessed, ethanol:water:MtBE allowed for slightly better yields, but there was a risk of Pattern 1 formation. Acetone:water allowed for pattern 2 exclusively but at the expense of yield.

In one embodiment, the following process is provided to make CHP Hydrate:

- Add approximately 20 g of CHP pattern 1 into a jacketed reactor vessel, pre-heated to 50° C.
- Add 50 mL of ethanol:water (90:10 v/v %) solvent mixture to the vessel, to achieve a starting concentration of 400 mg/mL.
- Stir at 300 rpm using an overhead stirrer.
- When complete dissolution is achieved, add 25 mL of MtBE (dropwise) to the vessel.
- On completion of MtBE addition, seed the experiment with 2 wt. % (400 mg) ground crystalline pattern 2 CHP.
- Continue stirring at 50° C. for 20 minutes.
- Add a further 5 mL of MtBE (dropwise) to the vessel.
- Add 70 mL of MtBE at a rate of 20 mL/hour.
- When the addition is complete, cool from 30° C. to 29° C. at 0.1° C./min.
- Continue stirring at 29° C. for 8 hours.
- Cool from 29° C. to 5° C. at a rate of 0.25° C./min.
- Add 190 mL of MtBE at a rate of 20 mL/hour.
- Continue stirring at 5° C. for 12 hours
- Isolate the solid by filtration, and wash filter cake with 40 mL of ethanol:water:MtBE (9 vol:1 vol 30 vol).
- Dry solid under vacuum at 40° C. for 1 hour.

An estimation of mixing performance at the laboratory scale was carried out, with the plant scale geometries then modelled to estimate mixing parameters that would allow a successful transfer of the process. Transferring this procedure to the 10 kg scale may be carried out with the following procedure:

- Add approximately 10 kg of CHP pattern 1 into a jacketed reactor vessel, pre-heated to 50° C.
- Add 25 L of ethanol:water (90:10 v/v %) solvent mixture to the vessel, to achieve a starting concentration of 400 mg/mL.
- Stir at 48 rpm.
- When complete dissolution is achieved, add 12.5 L of MtBE to the vessel.
- On completion of MtBE addition, seed the experiment with 2 wt. % (200 g) ground crystalline pattern 2 CHP.
- Continue stirring at 50° C. for 20 minutes.
- Add a further 2.5 L of MtBE (dropwise) to the vessel.
- Add 35 L of MtBE at a rate of 10 L/hour.
- When the addition is complete, cool from 30° C. to 29° C. at 0.1° C./min.
- Continue stirring at 29° C. for 8 hours.
- Cool from 29° C. to 5° C. at a rate of 0.25° C./min.
- Add 95 L of MtBE at a rate of 10 L/hour.
- Continue stirring at 5° C. for 12 hours
- Isolate the solid by filtration, and wash filter cake with 20 L of ethanol:water:MtBE (9 vol:1 vol:30 vol).
- Dry solid under vacuum at 40° C.

Use of 48 RPM is recommended as this allows the power dissipation in the plant scale vessel to be more comparable to the power dissipation of the laboratory scale vessel. The power dissipation at plant is estimated to be 0.067 W/kg, whereas at the laboratory scale this is estimated to be 0.064 W/kg. The model used to estimate these parameters also estimates that the particles are probably suspended.

Alternatively, the agitator at plant can be operated at 55 RPM. This has been estimated by the mixing model to be the NJS, the just suspended mixing speed, where the particles will be suspended in the vessel. This adds confidence that mixing will be effective, however there is a risk that the particles will experience a much higher power dissipation of 0.101 W/kg.

It is to be understood, however, that one or more of the steps described above to obtain CHP Hydrate may be omitted or the order of the steps may be varied.

B. Methods of Analysis

1. X-Ray Powder Diffraction (XRPD)

XRPD analysis was carried out on a PANalytical X'pert pro, scanning the samples between 3 and 35° 2θ. The material was gently ground to release any agglomerates and loaded onto a multi-well plate with Mylar polymer film to support the sample. The multi-well plate was then placed into the diffractometer and analyzed using Cu K radiation ($\alpha 1\lambda$=1.54060 Å; $\alpha 2$=1.54443 Å; β=1.39225 Å; $\alpha 1$: $\alpha 2$ ratio=0.5) running in transmission mode (step size 0.0130° 2θ) using 40 kV/40 mA generator settings.

2. Polarized Light Microscopy (PLM)

The presence of birefringence, and particle size and morphology was assessed using an Olympus BX50 polarising microscope, equipped with a Motic camera and image capture software (Motic Images Plus 2.0). All images were recorded using the 20× objective, unless otherwise stated.

3. Thermogravimetric Analysis (TGA)

Approximately 5 mg of material was weighed into an open aluminum pan and loaded into a simultaneous thermogravimetric/differential thermal analyzer (TG/DTA) and held at room temperature. The sample was then heated at a rate of 10° C./min from 20° C. to 350° C. during which time the change in sample weight was recorded along with any differential thermal events (DTA). Nitrogen was used as the purge gas, at a flow rate of 300 $cm^3$/min.

4. Nuclear Magnetic Resonance (NMR)

NMR experiments were performed on a Bruker AVIIIHD spectrometer equipped with a DCH cryoprobe operating at 500.12 MHz for protons. Experiments were performed in deuterated dimethyl sulfoxide and each sample was prepared to ca. 10 mM concentration.

5. Focused Beam Reflectance Measurements (FBRM)

Focused beam reflectance measurements were carried out using a Mettler Toledo D600 probe. For each crystallization, the probe was placed into the reaction vessel at the start of the crystallization and the nucleation and crystal growth were monitored. The chord length distributions and various count statistics were monitored throughout, using the following settings:

Electronic Discrimination Range Fine

Scan Speed 2 $ms^{-1}$

Sample Time 10 s

6. Crystal 16

The Crystal16 instrument uses percentage transmittance of light through a solution (or slurry) in a clear vial, to create a turbidity profile of the solution (or slurry), as a function of time and temperature. The profile obtained was used to determine cloud (nucleation temperature) and clear (dissolution temperature) points.

7. High Performance Liquid Chromatography-Ultraviolet Detection (HPLC-UV)

HPLC analysis was carried out with the following equipment parameters:

- Instrument: Dionex Ultimate 3000
- Column: LC/168 X-Bridge Phenyl Column (150 mm×4.6 mm×3.5 μm)
- Column Temperature: 30° C.
- Autosampler Temperature: 5° C.
- UV wavelength: 220 nm
- Injection Volume: 5 μL
- Flow Rate: 1 ml/min
- Mobile Phase A: 10 mM Ammonium acetate
- Mobile Phase B: Acetonitrile
- Diluent: 0.1% TFA in water
- Gradient program:

| Time (minutes) | Solvent B [%] |
|---|---|
| 0.01 | 0 |
| 10.3 | 30 |
| 15 | 95 |
| 15.1 | 0 |
| 25 | 0 |

C. Experimental

1. Initial Characterization of CHP Pattern 1

The CHP Pattern 1, was characterized by XRPD, $^{1}H$-, HSCQ- & $^{13}C$-NMR and HPLC following the procedures detailed in section B.

2. Approximate Solubility of CHP Pattern 1 (Anhydrous)

The approximate solubility of CHP in 37 selected solvent systems (Table 13) was estimated by solvent addition technique. The following procedure was used:

- Approximately 20 mg of CHP Pattern 1 was weighed out into each of 37vials.
- Each solvent/solvent mixture was added to the appropriate vial in 5 volume aliquots (100 μL) until dissolution was observed or a maximum of 2 mL solvent was added.
- In between additions, the sample was heated to 40° C. to check for dissolution at elevated temperature.
- If 2 mL of solvent was added without dissolution of the material, solubility was calculated to be below 10 mg/mL.
- After solvent addition, all 37 vials were placed in a fridge to crash cool between 2-8° C. for ca. 18 hours.
- Any solids present were isolated by centrifuge filtration and analyzed by XRPD (where material amount allowed).
- Where no solids were produced, vials were uncapped and left to evaporate at ambient temperature.
- Any solids present were analyzed by XRPD (where material amount allowed).

TABLE 13

Approximate Solubility Solvent List

| Number | Solvent | ICH Class |
|---|---|---|
| 1 | Water | N/A |
| 2 | Acetone | 3 |
| 3 | Acetonitrile | 2 |
| 4 | THF | 2 |
| 5 | water:acetone (10:90) | 3 |
| 6 | water:acetone (20:80) | 3 |
| 7 | water:acetone (30:70) | 3 |
| 8 | water:acetone (40:60) | 3 |
| 9 | water:acetone (50:50) | 3 |
| 10 | water:acetone (60:40) | 3 |
| 11 | water:acetone (70:30) | 3 |
| 12 | water:acetone (80:20) | 3 |
| 13 | water:acetone (90:10) | 3 |
| 14 | water:acetonitrile (10:90) | 2 |
| 15 | water:acetonitrile (20:80) | 2 |
| 16 | water:acetonitrile (30:70) | 2 |
| 17 | water:acetonitrile (40:60) | 2 |
| 18 | water:acetonitrile (50:50) | 2 |
| 19 | water:acetonitrile (60:40) | 2 |
| 20 | water:acetonitrile (70:30) | 2 |
| 21 | water:acetonitrile (80:20) | 2 |
| 22 | water:acetonitrile (90:10) | 2 |
| 23 | water:THF (10:90) | 2 |
| 24 | water:THF (20:80) | 2 |
| 25 | water:THF (30:70) | 2 |
| 26 | water:THF (40:60) | 2 |
| 27 | water:THF (50:50) | 2 |
| 28 | water:THF (60:40) | 2 |
| 29 | water:THF (70:30) | 2 |
| 30 | water:THF (80:20) | 2 |
| 31 | water:THF (90:10) | 2 |
| 32 | ethanol:water (90:10):tBME [10:90] | 3 |
| 33 | ethanol:water (90:10):tBME [30:70] | 3 |
| 34 | ethanol:water (90:10):tBME [50:50] | 3 |
| 35 | ethanol:water (90:10):tBME [70:30] | 3 |
| 36 | ethanol:water (90:10):tBME [90:10] | 3 |
| 37 | ethanol:water (90:10) | 3 |

3. Two-Point Solubility

Two-point solubility studies were carried out at 5° C. and 50° C. in 11 solvent mixtures using the following procedure:

- 1 mL of a selected solvent mixture was added to 1.5 mL screw top glass vial containing a pre-weighed mass of CHP Pattern 1 to produce a slurry. Initial mass selected for each solvent system was based on the findings of the approximate solubility as detailed in Section 2. Solvent blends are shown in Table 14.
- Vials were held in a thermostatically controlled reaction block set to either 5° C. or 50° C. and agitation provided via a magnetic stirrer plate.
- Where complete dissolution was observed after 1 hour, more CHP Pattern 1 solid was added to the experiments to form slurries.
- When mobile slurries were formed in all the vials, the experiments were allowed to stir at the required temperature for ca. 18 hours. Final masses of CHP pattern 2 required are shown in Table 14.
- After ca. 18 hours, stirring was stopped and the supernatants were filtered using 0.45 μm PVDF needle filters and syringes.
- The concentration of the supernatants were analyzed by HPLC.
- The remaining slurries in the vials were each transferred into 0.22 μm nylon filter centrifuge tubes and the solids were isolated by centrifugation.

The recovered solid (where amounts allowed) was analyzed by XRPD and HPLC for purity.

TABLE 14

Final CHP Masses for Two-point Solubility

| Solvent | Mass Added (mg) 5° C. | 50° C. |
|---|---|---|
| water:acetone (40:60) | 211 | 655 |
| water:acetone (80:20) | 383 | 725 |
| water:acetone (90:10) | 365 | 681 |
| water:acetone (20:80) | 100 | 340 |
| water:acetone (10:90) | 100 | 210 |
| water:acetone (5:95) | 250 | 250 |
| ethanol:water (90:10):tBME [20:80] | 60 | 60 |
| ethanol:water (90:10):tBME [25:75] | 60 | 60 |
| ethanol:water (90:10):tBME [30:70] | 60 | 60 |
| ethanol:water (90:10):tBME [40:60] | 100 | 126 |
| ethanol:water (90:10) | 250 | 475 |

4. Small-Scale Crystallizations

Small scale crystallization trials were carried out on the received CHP (Pattern 1). The aim of these trials was to investigate the most suitable solvent systems, temperatures and concentrations for further crystallization studies. This was carried out using two different solvent systems: acetone: water and ethanol:water:MtBE.

Crystallization Set A: Acetone:Water

- Approximately 500 mg of the received CHP (Pattern 1) was weighed out into 4×20 mL scintillation vials.
- To each vial, the appropriate volume of acetone:water (80:20 v/v %) was added to dissolve the sample. See Table 15 for solvent volumes used.
- Stirrer bars were added to each vial, and the experiments were stirred at 50° C.
- After 1 hour at 50° C., acetone was added dropwise to 2 of the four vials (vials 1 and 3).
- The experiments were left to stir at 50° C. for ca. 1 hr.
- After 1 hour, the vials were cooled to 5° C. at a rate of 0.25° C./min.
- Once at 5° C., acetone was added dropwise to the remaining 2 vials (vials 2 and 4).
- The experiments were left to stir at 5° C. for approximately 18 hours.
- After 18 hours at 5° C., the resulting slurries were then filtered using a 47 mm Buchner funnel and Whatman Grade1 filter paper (diameter=42.5 mm; pore size=11 μm).
- The solids were transferred into pre-weighed vials and analyzed by XRPD, PLM, and HPLC for chemical purity.
- Filtered mother liquors were submitted for HPLC concentration analysis.
- The experiments are summarized in Table 15.

Crystallization Set B: Ethanol:Water:MtBE

- Approximately 500 mg of the received CHP (Pattern 1) was weighed out into 5×20 mL scintillation vials.
- To each vial, 2 mL of ethanol:water (90:10 v/v %) was added to dissolve the sample.
- Stirrer bars were added to each vial, and the experiments were stirred at 50° C.
- After 1 hour at 50° C., MtBE was added dropwise to 3 of the five vials (vials 1, 3 and 5).
- The experiments were left to stir at 50° C. for ca. 1 hr.
- After 1 hour at 50° C., the slurry present in vial 1 was filtered using a 47 mm Buchner funnel and Whatman Grade1 filter paper (diameter=42.5 mm; pore size=11 μm).
- Experiment filtered at 50° C. as previous results indicated a potential risk of pattern 1 formation post cool, at this percentage of MtBE (80%).
- Remaining vials were cooled to 5° C. at a rate of 0.25° C./min.
- Once at 5° C., MtBE was added dropwise to the remaining 2 vials (vials 2 and 4).
- The experiments were left to stir at 5° C. for approximately 18 hours.
- After 18 hours at 5° C., the resulting slurries were then filtered using a 47 mm Buchner funnel and Whatman Grade1 filter paper (diameter=42.5 mm; pore size=11 μm).
- All solids were transferred into pre-weighed vials and analysed by XRPD, PLM, and HPLC for chemical purity.
- Filtered mother liquors were submitted for HPLC concentration analysis.
- The experiments are summarized in Table 15.

TABLE 15

Small-scale Crystallizations-Solvent Summary

| Solvent System | Anti-solvent Addition Temperature | Starting Volume (acetone:water 80/20) | Acetone Added |
|---|---|---|---|
| 1-acetone:water (95.5) | 50° C. | 2 mL | 6 mL |
| 2-acetone:water (95:5) | 5° C. | 2 mL | 6 mL |
| 3-acetone:water (95:5) | 50° C. | 1.65 mL | 4.95 mL |
| 4-acetone:water (95:5) | 5° C. | 1.65 mL | 4.95 mL |
| **Solvent System** | **Anti-solvent Addition Temperature** | **Starting Volume (acetone:water 90/10)** | **tBME added** |
| 1-ethanol:water (90:10) tBME (20:80) | 50° C. | 2 mL | 8 mL |
| 2-ethanol:water (90:10) tBME (30:70) | 5° C. | 2 mL | 4.7 mL |
| 3-ethanol:water (90:10) tBME (30:70) | 50° C. | 2 mL | 4.7 mL |
| 4-ethanol:water (90:10) tBME (40:60) | 5° C. | 2 mL | 3 mL |
| 5-ethanol:water (90:10) tBME (40:60) | 50° C. | 2 mL | 3 mL |

5. Metastable Zone Width (MSZW) Measurements

MSZW measurements were carried out on the received CHP (Pattern 1) by investigating two parameters—cooling and anti-solvent addition.

Cooling Method

Determination of MSZW through cooling was completed using a Crystal16. The procedure used is outlined below:

- A known amount of CHP (Pattern 1) was weighed into screw cap vials.
- Into each vial, 1 mL of the appropriate solvent system was added to form slurries. Stirrer bars were placed in each vial.
- The solvent systems and mass of CHP used in each experiment is summarized in Table 16. The vials were placed in the sample holder of a Crystal16 instrument, and the required temperature program was started. Temperature profile can be seen in Table 17A.
- The turbidity of the system was monitored throughout and allowed for the determination of the clear and cloud points.

TABLE 16

| Experimental Details for Cooling MSZW Determination | | |
|---|---|---|
| Solvent | Mass of CHP (mg) | Input Material |
| ethanol:water (90:10) | 2 | Pattern 2 |
| ethanol:water (90:10) tBME (20:80) | | Pattern 2 |
| ethanol:water (90:10) tBME (40:60) | | Pattern 2 |
| ethanol:water (90:10) tBME (80:20) | | Pattern 2 |
| ethanol:water (90:10) | 25 | Pattern 2 |
| ethanol:water (90:10) tBME (20:80) | | Pattern 2 |
| ethanol:water (90:10) tBME (40:60) | | Pattern 2 |
| ethanol:water (90:10) tBME (80:20) | | Pattern 2 |
| ethanol:water (90:10) | 100 | Pattern 2 |
| ethanol:water (90:10) tBME (20:80) | | Pattern 2 |
| ethanol:water (90:10) tBME (40:60) | | Pattern 2 |
| ethanol:water (90:10) tBME (80:20) | | Pattern 2 |
| ethanol:water (90:10) | 325 | Pattern 1 |
| ethanol:water (90:10) tBME (90:10) | | Pattern 1 |
| ethanol:water (90:10) tBME (80:20) | | Pattern 1 |
| ethanol:water (90:10) tBME (70:30) | | Pattern 1 |
| ethanol:water (90:10) tBME (40:60) | | Pattern 1 |
| ethanol:water (90:10) | 425 | Pattern 2 |
| ethanol:water (90:10) tBME (20:80) | | Pattern 2 |
| ethanol:water (90:10) tBME (40:60) | | Pattern 2 |
| ethanol:water (90:10) tBME (80:20) | | Pattern 2 |

TABLE 17A

| Temperature Profile for Cooling MSZW Determination | |
|---|---|
| 1. Stir at: | 700 rpm |
| 2. Hold at: | 25° C. for 10 minutes |
| 3. Heat to: | 70° C. at 0.5° C./min |
| 4. Hold at: | 70° C. for 1 hour |
| 5. Cool to: | 5° C. at 0.25° C./min |
| 6. Hold at: | 5° C. for 1 hour |
| 7. Heat to: | 70° C. at 0.25° C./min |
| 8. Hold at: | 70° C. for 1 hour |
| 9. Cool to: | 5° C. at 0.25° C./min |
| 10. Hold at: | 5° C. for 1 hour |
| 11. Heat to: | 70° C. at 0.25° C./min |
| 12. Hold at: | 70° C. for 1 hour |
| 13. Stir at: | 700 rpm |
| 14. Hold at: | 20° C. |

a. Anti-Solvent Addition Method

Determination of the MSZW relative to anti-solvent addition was completed using ethanol:water:MtBE. The following procedure was used:

- Approximately 20 g of the received CHP pattern 1 was transferred into a 250 mL j acketed vessel, which had been pre-heated to 50° C.
- 50 mL of ethanol:water (90:10 v/v %) solvent mixture was added to the vessel, to achieve a starting concentration of 400 mg/mL.
- The experiment was stirred at 50° C., at ca. 300 rpm using an overhead stirrer.
- An FBRM probe was inserted into the vessel to monitor and record the nucleation and particle counts.
- When complete dissolution was achieved (approximately 40 minutes), 75 mL of MtBE was added via peristaltic pump at a rate of 10 mL/hour.
- At the completion of MtBE addition, the experiment was cooled to 5° C. at 0.25° C./min and held at 5° C. overnight.
- After 9 hours at 5° C., the solid was isolated by vacuum filtration using 83 mm Buchner funnel and Whatman Grade 1 filter paper (diameter=70 mm; pore size=11 μm).
- A sample of the filter cake was taken and analyzed by XRPD.

- The remaining cake was dried under vacuum at 35° C. for 1 hour.
- The concentration of the filtered mother liquor was determined by HPLC.

6. Crystallization Development

Crystallization scale up experiments were carried out in ethanol:water:MtBE. Various experimental conditions such as cooling rate, anti-solvent addition rate and temperature, seeding load and temperature, and anti-solvent ratio were assessed. The following protocols were considered:

a. Crystallization 1

For Crystallization 1, the solution was seeded with 2 wt. % seed crystals. Seeding and MtBE addition was carried out at 35° C. The slurry was cooled to 5° C. at a rate of 0.25° C./min. The following procedure was used:

- Approximately 20 g of the received CHP pattern 1 was transferred into a jacketed vessel, which had been pre-heated to 50° C.
- 50 mL of ethanol:water (90:10 v/v %) solvent mixture was added to the vessel to achieve a starting concentration of 400 mg/mL.
- The experiment was stirred at 50° C., at ca. 300 rpm using an overhead stirrer.
- An FBRM probe was inserted into the vessel to monitor and record the nucleation and particle counts.
- When complete dissolution was achieved (approximately 30 minutes), the experiment was cooled to 35° C. at a rate of 0.25° C./min, and 10 mL of MtBE was added via peristaltic pump at a rate of 10 mL/hour.
- At the completion of MtBE addition, the experiment was seeded with 400 mg of CHP pattern 2;
- System was monitored for ca. 2 hours at 35° C.
- The experiment was then cooled to 5° C. at 0.25° C./min, and 140 mL of MtBE was added via peristaltic pump at a rate of 10 mL/hour (14 hours) to give a final solvent ratio of 25:75 v/v %.
- The solid was isolated by vacuum filtration using 83 mm Buchner funnel and Whatman Grade1 filter paper (diameter=70 mm; pore size=11 μm).
- The filter cake was washed with 40 mL of ethanol:water: MtBE (9 vol:1 vol:30 vol) after which it was dried under vacuum at 40° C. for 1 hour.
- The dried solid was analyzed by XRPD, TG/DTA, PLM, and HPLC;
- The concentration of the filtered mother liquor was determined by HPLC.

b. Crystallization 2

For Crystallization 2, the solution was seeded with 2 wt. % seed crystals. Seeding and MtBE addition was carried out at 50° C. The slurry was cooled to 5° C. at a rate of 0.25° C./min. The following procedure was used:

Approximately 20 g of received CHP pattern 1 was weighed, and transferred into a jacketed vessel, which had been pre-heated to 50° C.

- 50 mL of ethanol:water (90:10 v/v %) solvent mixture was added to the vessel, to achieve a starting concentration of 400 mg/mL.
- The experiment was stirred at 50° C., at ca. 300 rpm using an overhead stirrer.
- An FBRM probe was inserted into the vessel to monitor and record the nucleation and particle counts.
- When complete dissolution was achieved (approximately 20 minutes), the experiment was held at 50° C. and 10 mL of MtBE was added via a syringe pump at a rate of 10 mL/hour;
- At the completion of MtBE addition, the experiment was seeded with 400 mg of CHP pattern 2;

System was monitored for ca. 2 hours at 50° C.;

140 mL of MtBE was added via peristaltic pump at a rate of 20 mL/hour to give a final solvent ratio of 25:75 v/v %.

The experiment was then cooled to 5° C. at 0.25° C./min and held at 5° C. for ca. 9 hours;

After 9 hours at 5° C., the solid was isolated by vacuum filtration using 88 mm Buchner funnel and Whatman Grade1 filter paper (diameter=70 mm; pore size=11 μm).

The filter cake was washed with 40 mL of ethanol:water: MtBE (9 vol:1 vol 30 vol) after which it was dried under vacuum at 40° C. for 1 hour.

The dried solid was analysed by XRPD, TG/DTA, PLM, and HPLC for purity;

The concentration of the filtered mother liquor was determined by HPLC.

c. Crystallization 3

For Crystallization 3, the solution was seeded with 2 wt. % seed crystals. Seeding and MtBE addition was carried out at 35° C. The slurry was cooled to 5° C. at a rate of 0.25° C./min. The following procedure was used:

Approximately 20 g of received CHP pattern 1 was weighed, and transferred into a jacketed vessel, which had been pre-heated to 50° C.

50 mL of ethanol:water (90:10 v/v %) solvent mixture was added to the vessel, to achieve a starting concentration of 400 mg/mL.

The experiment was stirred at 50° C., at ca. 300 rpm using an overhead stirrer.

An FBRM probe was inserted into the vessel to monitor and record the nucleation and particle counts.

When complete dissolution was achieved (approximately 20 minutes), the experiment was cooled to 5° C. at a rate of 0.25° C./min ° C.;

Nucleation was observed once the system reached 23° C.;

System was heated to 50° C. to re-dissolve the material. Once dissolution was observed, system was cooled to 25° C. at a rate of 0.25° C./min ° C.

Nucleation was observed once the system reached 25° C.;

System was heated to 50° C. to re-dissolve the material. Once dissolution was observed, system was cooled to 35° C. and the experiment was seeded with 400 mg of CHP pattern 2;

140 mL of MtBE was added via peristaltic pump at a rate of 20 mL/hour to give a final solvent ratio of 26:74 v/v %;

The experiment was then cooled to 5° C. at 0.25° C./min and held at 5° C. for ca. 9 hours;

The solid was isolated by vacuum filtration using 88 mm Buchner funnel and Whatman Grade1 filter paper (diameter=70 mm; pore size=11 μm).

The filter cake was washed with 40 mL of ethanol:water: MtBE (9 vol:1 vol 30 vol) after which it was dried under vacuum at 40° C. for 1 hour.

The dried solid was analyzed by XRPD, TG/DTA, PLM, and HPLC for purity.

The concentration of the filtered mother liquor was determined by HPLC.

d. Crystallization 4

For Crystallization 4, the solution was seeded with 2 wt. % seed crystals. Seeding and MtBE addition was carried out at 50° C. The slurry was cooled to 5° C. at a rate of 0.1° C./min. The following procedure was used:

Approximately 20 g of the CHP pattern 2 (material returned from Crystallization 1 and 3) was weighed, and transferred into a jacketed vessel, which had been pre-heated to 50° C.

50 mL of ethanol:water (90:10 v/v %) solvent mixture was added to the vessel, to achieve a starting concentration of 400 mg/mL.

The experiment was stirred at 50° C., at ca. 300 rpm using an overhead stirrer.

An FBRM probe was inserted into the vessel to monitor and record the nucleation and particle counts.

When complete dissolution was achieved (approximately 20 minutes), the experiment was held at 50° C. and 20 mL of MtBE was added via a syringe pump at a rate of20 mL/hour;

At the completion of MtBE addition, the experiment was seeded with 400 mg of CHP pattern 2;

System was monitored for ca. 2 hours at 50° C.;

140 mL of MtBE was added via peristaltic pump at a rate of 20 mL/hour to give a final solvent ratio of 24:76 v/v %.

The experiment was then cooled to 5° C. at 0.1° C./min;

System was held at 5° C. overnight;

After 8 hours at 5° C., the solid was isolated by vacuum filtration using 88 mm Buchner funnel and Whatman Grade1 filter paper (diameter=70 mm; pore size=11 μm).

The filter cake was washed with 40 mL of ethanol:water: MtBE (9 vol:1 vol 30 vol) after which it was dried under vacuum at 40° C. for 1 hour.

The dried solid was analyzed by XRPD, TG/DTA, PLM, and HPLC for purity;

The concentration of the filtered mother liquor was determined by HPLC.

e. Crystallization 5

For Crystallization 5, the solution was seeded with 2 wt. % ground seed crystals. Seeding and MtBE addition was carried out at 50° C. The slurry was cooled to 5° C. at a rate of 0.1° C./min. The following procedure was used:

Approximately 20 g of the CHP pattern 1 and 2 blend (pattern 1 from received CS/352/18 and pattern 2 from crystallization 4) was weighed, and transferred into a jacketed vessel, which had been pre-heated to 50° C.

50 mL of ethanol:water (90:10 v/v %) solvent mixture was added to the vessel, to achieve a starting concentration of 400 mg/mL.

The experiment was stirred at 50° C., at ca. 300 rpm using an overhead stirrer.

An FBRM probe was inserted into the vessel to monitor and record the nucleation and particle counts.

When complete dissolution was achieved (approximately 20 minutes), the experiment was held at 50° C. and 25 mL of MtBE was added dropwise using a syringe;

At the completion of MtBE addition, the experiment was seeded with 400 mg of CHP pattern 2 which had been ground using a pestle and mortar.

System was monitored for ca. 75 minutes at 50° C.;

140 mL of MtBE was added via peristaltic pump at a rate of 20 mL/hour to give a final solvent ratio of 23:77 v/v %.

The experiment was then cooled to 5° C. at 0.1° C./min;

System was held at 5° C. overnight;

After 9 hours at 5° C., the solid was isolated by vacuum filtration using 88 mm Buchner funnel and Whatman Grade1 filter paper (diameter=70 mm; pore size=11 μm).

The filter cake was washed with 40 mL of ethanol:water: MtBE (9 vol:1 vol 30 vol) after which it was dried under vacuum at 40° C. for 1 hour.

The dried solid was analyzed by XRPD, TG/DTA, PLM, and HPLC for purity;

The concentration of the filtered mother liquor was determined by HPLC.

f. Crystallization 6

For Crystallization 6, the solution was seeded with 2 wt. % ground seed crystals. Seeding was carried out at 50° C. and stage wise MtBE addition was used. The slurry was cooled to 29° C. at a rate of 0.1° C./min and held at this temperature for 8 hours. The slurry was then cooled to 5° C. at a rate of 0.25° C./min. The following procedure was used:

Approximately 20 g of the CHP pattern 1 and 2 blend (pattern 1 from received CS/352/18 and pattern 2 from crystallization 5) was weighed, and transferred into a jacketed vessel, which had been pre-heated to 50° C.

50 mL of ethanol:water (90:10 v/v %) solvent mixture was added to the vessel, to achieve a starting concentration of 400 mg/mL.

The experiment was stirred at 50° C., at ca. 300 rpm using an overhead stirrer.

An FBRM probe was inserted into the vessel to monitor and record the nucleation and particle counts.

When complete dissolution was achieved (approximately 20 minutes), the experiment was held at 50° C. and 25 mL of MtBE was added dropwise using a syringe;

At the completion of MtBE addition, the experiment was seeded with 400 mg of CHP pattern 2 which had been ground using a pestle and mortar;

System was monitored for ca. 10 minutes at 50° C.;

Seeds did not persist. An additional 5 mL of MtBE was added dropwise to the vessel using a syringe.

70 mL of MtBE was added via peristaltic pump at a rate of 20 mL/hour;

The experiment was then cooled to 29° C. at 0.1° C./min;

System was held at 29° C. for 8 hours.

After 8 hours at 29° C. the system was cooled to 5° C. at a rate of 0.25° C./min.

Once the system had reached 5° C., second step MtBE addition was started. 190 mL was added at a rate of 20 mL/hour. Final solvent ratio of 15:85 v/v %.

System was held at 5° C. for approximately 12 hours.

The solid was then isolated by vacuum filtration using 88 mm Buchner funnel and Whatman Grade1 filter paper (diameter=70 mm; pore size=11 μm).

The filter cake was washed with 40 mL of ethanol:water: MtBE (9 vol:1 vol 30 vol) after which it was dried under vacuum at 40° C. for 1 hour.

The dried solid was analyzed by XRPD, TG/DTA, PLM, and HPLC for purity and chiral HPLC.

The concentration of the filtered mother liquor was determined by HPLC.

g. Crystallization 7

For Crystallization 7, the solution was seeded with 2 wt. % ground seed crystals. Seeding was carried out at 50° C. and stage wise MtBE addition was used. The slurry was cooled to 5° C. at a rate of 0.1° C./min. The following procedure was used:

Approximately 20 g of the CHP pattern 1 and 2 blend (pattern 1 from received CS/352/18 and pattern 2 from crystallization 6) was weighed, and transferred into a jacketed vessel, which had been pre-heated to 50° C.

50 mL of ethanol:water (90:10 v/v %) solvent mixture was added to the vessel, to achieve a starting concentration of 400 mg/mL.

The experiment was stirred at 50° C., at ca. 300 rpm using an overhead stirrer.

An FBRM probe was inserted into the vessel to monitor and record the nucleation and particle counts.

When complete dissolution was achieved (approximately 20 minutes), the experiment was held at 50° C. and 27.5 mL of MtBE was added manually (dropwise) using a syringe;

At the completion of MtBE addition, the experiment was seeded with 400 mg of CHP pattern 2 which had been ground using a pestle and mortar;

System was monitored for ca. 10 minutes at 50° C.;

70 mL of MtBE was added via peristaltic pump at a rate of 20 mL/hour;

The experiment was then cooled to 5° C. at 0.1° C./min;

System was held at 5° C. overnight.

After approximately 9 hours at 5° C., second step MtBE addition was started. 190 mL was added at a rate of 20 mL/hour. Final solvent ratio of 15:85 v/v %.

The solid was isolated by vacuum filtration using 88 mm Buchner funnel and Whatman Grade1 filter paper (diameter=70 mm; pore size=11 μm).

The filter cake was washed with 40 mL of ethanol:water: MtBE (9 vol:1 vol 30 vol) after which it was dried under vacuum at 40° C. for 1 hour.

The dried solid was analyzed by XRPD, TG/DTA, PLM, and HPLC for purity;

The concentration of the filtered mother liquor was determined by HPLC.

h. Crystallization 8

For Crystallization 8, the solution was seeded with 5 wt. % ground seed crystals. Seeding was carried out at 50° C. and stage wise MtBE addition was used. The slurry was cooled to 5° C. at a rate of 0.1° C./min. The following procedure was used:

Approximately 20 g of the CHP pattern 1 and 2 blend (pattern 1 from received CS/352/18 and pattern 2 from crystallization 7) was weighed, and transferred into a jacketed vessel, which had been pre-heated to 50° C.

50 mL of ethanol:water (90:10 v/v %) solvent mixture was added to the vessel, to achieve a starting concentration of 400 mg/mL.

The experiment was stirred at 50° C., at ca. 300 rpm using an overhead stirrer.

An FBRM probe was inserted into the vessel to monitor and record the nucleation and particle counts.

When complete dissolution was achieved (approximately 20 minutes), the experiment was held at 50° C. and 27.5 mL of MtBE was added manually (dropwise) using a syringe;

At the completion of MtBE addition, the experiment was seeded with 1 g of CHP pattern 2 which had been ground using a pestle and mortar;

System was monitored for ca. 10 minutes at 50° C.;

70 mL of MtBE was added via peristaltic pump at a rate of 20 mL/hour;

The experiment was then cooled to 5° C. at 0.1° C./min;

System was held at 5° C. overnight.

After approximately 9 hours at 5° C., second step MtBE addition was started. 190 mL was added at a rate of 20 mL/hour. Final solvent ratio of 15:85 v/v %.

The solid was isolated by vacuum filtration using 88 mm Buchner funnel and Whatman Grade1 filter paper (diameter=70 mm; pore size=11 μm).

The filter cake was washed with 40 mL of ethanol:water: MtBE (9 vol:1 vol 30 vol) after which it was dried under vacuum at 40° C. for 1 hour.

The dried solid was analyzed by XRPD, TG/DTA, PLM, and HPLC for purity;

The concentration of the filtered mother liquor was determined by HPLC.

i. Crystallization 9

For Crystallization 9, the solution was seeded with 5 wt. % ground seed crystals. Seeding was carried out at 50° C. and stage wise MtBE addition was used. The slurry was cooled to 30° C. at a rate of 0.1° C./min and held at this temperature for 8 hours. The slurry was then cooled to 5° C. at a rate of 0.1° C./min. The following procedure was used:

Approximately 20 g of the CHP pattern 1 and 2 blend (pattern 1 from received CS/352/18 and pattern 2 from crystallization 8) was weighed, and transferred into a jacketed vessel, which had been pre-heated to 50° C.

50 mL of ethanol:water (90:10 v/v %) solvent mixture was added to the vessel, to achieve a starting concentration of 400 mg/mL.

The experiment was stirred at 50° C., at ca. 300 rpm using an overhead stirrer.

An FBRM probe was inserted into the vessel to monitor and record the nucleation and particle counts.

When complete dissolution was achieved (approximately 20 minutes), the experiment was held at 50° C. and 27.5 mL of MtBE was added manually (dropwise) using a syringe;

At the completion of MtBE addition, the experiment was seeded with 1 g of CHP pattern 2 which had been ground using a pestle and mortar;

System was monitored for ca. 10 minutes at 50° C.;

70 mL of MtBE was added via peristaltic pump at a rate of 15 mL/hour;

The experiment was then cooled to 30° C. at 0.1° C./min;

System was held at 30° C. for 8 hours.

After 8 hours at 30° C., system resumed cooling to 5° C. at a rate of 0.1° C./min.

Second step MtBE addition was started. 190 mL was added at a rate of 20 mL/hour. Final solvent ratio of 15:85 v/v %.

System was held at 5° C. overnight.

After ca. 10 hours at 5° C., the solid was isolated by vacuum filtration using Buchner funnel and Whatman Grade1 filter paper (diameter=70 mm; pore size=11 μm).

The filter cake was washed with 40 mL of ethanol:water: MtBE (9 vol:1 vol:30 vol) after which it was dried under vacuum at 40° C. for 1 hour.

The dried solid was analyzed by XRPD, TG/DTA, PLM, and HPLC for purity;

The concentration of the filtered mother liquor was determined by HPLC.

j. Crystallization 10

Crystallization 10 utilized the same procedure as crystallization 6. Due to vessel size, the parameters were scaled down to 70% of the original experiment. A new batch of received CHP (Pattern 1) was also used in this experiment (CS/802/18).

The solution was seeded with 2 wt. % ground seed crystals. Seeding was carried out at 50° C. and stage wise MtBE addition was used. The slurry was cooled to 29° C. at a rate of 0.1° C./min and held at this temperature for 8 hours. The slurry was then cooled to 5° C. at a rate of 0.25° C./min. The following procedure was used:

Approximately 14 g of received CHP pattern 1 was weighed, and transferred into a jacketed vessel, which had been pre-heated to 50° C.

35 mL of ethanol:water (90:10 v/v %) solvent mixture was added to the vessel, to achieve a starting concentration of 400 mg/mL.

The experiment was stirred at 50° C., at ca. 300 rpm using an overhead stirrer.

An FBRM probe was inserted into the vessel to monitor and record the nucleation and particle counts.

When complete dissolution was achieved (approximately 20 minutes), the experiment was held at 50° C. and 17.5 mL of MtBE was added dropwise using a syringe;

At the completion of MtBE addition, the experiment was seeded with 280 mg of CHP pattern 2 which had been ground using a pestle and mortar;

System was monitored for ca. 10 minutes at 50° C.;

Seeds did not persist. An additional 3.5 mL of MtBE was added dropwise to the vessel using a syringe.

50 mL of MtBE was added via peristaltic pump at a rate of 20 mL/hour;

The experiment was then cooled to 29° C. at 0.1° C./min;

System was held at 29° C. for 8 hours.

After 8 hours at 29° C. the system was cooled to 5° C. at a rate of 0.25° C./min.

Once the system had reached 5° C., second step MtBE addition was started. 134 mL was added at a rate of 20 mL/hour. Final solvent ratio of 15:85 v/v %.

System was held at 5° C. for approximately 12 hours.

The solid was then isolated by vacuum filtration using 88 mm Buchner funnel and Whatman Grade1 filter paper (diameter=70 mm; pore size=11 μm).

The filter cake was washed with 28 mL of ethanol:water: MtBE (9 vol:1 vol 30 vol) after which it was dried under vacuum at 40° C. for 1 hour.

The dried solid was analyzed by XRPD, TG/DTA, PLM, chiral HPLC and HPLC for purity.

The concentration of the filtered mother liquor was determined by HPLC.

Example 4—Purity Determination

The purity of CHP and CHP-hydrate was measured using HPLC. The chromatographic parameters of the HPLC Method for purity measurement for CHP and CHP-Hydrate are summarized in Table 17B.

TABLE 17B

Chromatographic Parameters of the HPLC Method for Purity Measurement for CHP and CHP-Hydrate

| | | | |
|---|---|---|---|
| Column | XBridge Phenyl column (150 mm* 4.6 mm* 3.5 μm, PN: 186003335) | | |
| Wavelength | 220 nm | | |
| Column Oven Temp. | 30° C. | | |
| Flow Rate | 1.0 mL/min | | |
| Injection Volume | 5 μL | | |
| Mobile Phases | A: 10 mM $NH_4OAc$ in water (w/v)<br>B: Purified ACN | | |
| Gradient Program | Time (min) | A % | B % |
| | 0.01 | 100 | 0 |
| | 10.3 | 70 | 30 |
| | 15.0 | 5 | 95 |
| | 15.1 | 100 | 0 |
| | 25.0 | 100 | 0 |
| Auto-sampler Temp. | 5° C. | | |
| Run Time | 25 min | | |
| Needle Wash Solvent | Purified ACN | | |
| Diluent | 0.1% TFA in water (v/v) | | |

Preparation of Standard solution for assay determination (0.8 mg/mL CHIP Anhydrous or 0.85 mg/mL CHIP Hydrate): weigh approximately 40 mg of C16081735-D reference standard and transfer to a 50 mL volumetric flask. Dilute to volume with diluent and mix well (sonicate to dissolve if necessary). Label it as STD-1. Prepare a second Standard solution for use as a Standard Check. Label it as STD-2.

Preparation of Sample Solution for assay determination (0.85 mg/mL CHIP Hydrate): weigh approximately 42.5 mg of CHIP Hydrate sample into a 50 mL volumetric flask. Dilute to volume with diluent and mix well.

Figure 52:
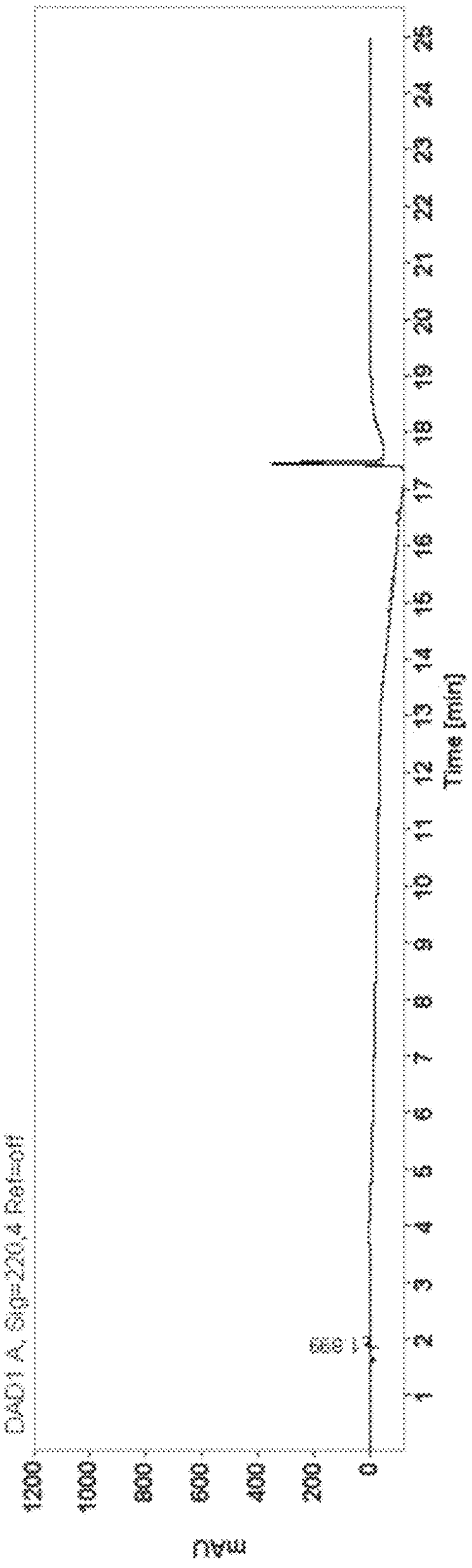
FIG. 52 is the representative blank chromatogram.
Figure 53:
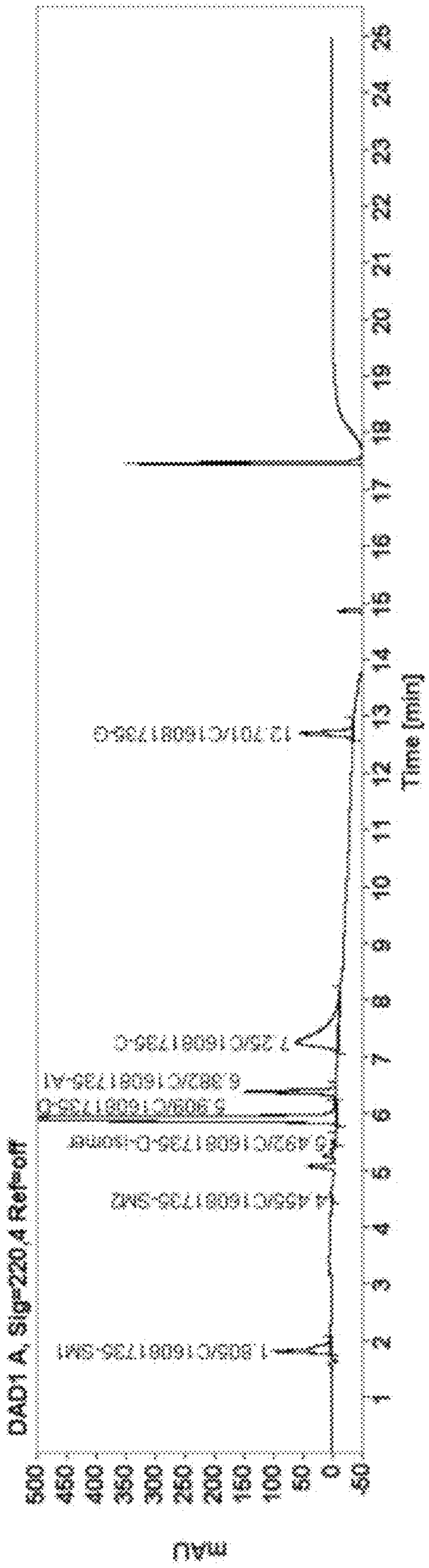
FIG. 53 is the representative resolution solution chromatogram.

The representative blank chromatogram and the representative resolution solution chromatogram are shown in FIGS. 52 and 53, respectively.

Example 5—Stability Comparison for CHP Hydrate

A. Chemical Stability Comparison Between CHP Anhydrate and CHP Hydrate Pattern 2

CHP anhydrate (Pattern 1) and hydrate (Pattern 2) compounds were manufactured under GMP conditions. A stability study for the CHP anhydrate compound was conducted under ccelerated conditions (40±5° C./75±5% RH) for six months and room temperature conditions (25±5° C./60±5% RH) for 12 months. A further stability study for the CHP hydrate compound was conducted under accelerated conditions (40±5° C./75±5% RH) for 6 months (Table 18).

TABLE 18

Stability Study for CHP Anhydrate and Hydrate Pattern 2

| | Initial | 1 Month | | 3 Month | | 6 Month | | 12 Month | |
|---|---|---|---|---|---|---|---|---|---|
| | 25° C. | 25° C. | 40° C. | 25° C. | 40° C. | 25° C. | 40° C. | 25° C. | 40° C. |
| CHP anhydrate compound | T[1] | NS[2] | T[1] | T[1] | T[1] | T[1] | T[1] | T[1] | NS[2] |
| CHP hydrate compound pattern 2 | T[1] | NS[2] | T[1] | T[1] | T[1] | S[3] | S[3] | S[3] | NS[2] |

[1]T = Tested
[2]NS = Not Scheduled
[3]S = Scheduled

Long term storage conditions for CHP anhydrate compound require careful handling because CHP is hygroscopic. CHP anhydrate had absorbed moisture during the stability study, growing of new impurities and a decrease of CHP anhydrate was observed due to the degradation of CHP (Table 19). The stability data of CHP hydrate pattern 2 is shown in Table 20.

TABLE 19

Impurities growing in CHP anhydrate (pattern 1) at accelerated conditions CHP anhydrate (pattern 1) at 40° C./75% RH

| | 0M | 1M | 3M | 6M |
|---|---|---|---|---|
| Growth of total Impurities | 0% | 0% | 0.27% | 0.53% |

TABLE 20

Impurities growing in CHP hydrate (pattern 2) at accelerated conditions CHP hydrate (pattern 2) at 40° C./75% RH

| | 0M | 1M | 3M | 6M |
|---|---|---|---|---|
| Growth of total Impurities | 0% | 0% | 0.00% | 0.05% |

CHP anhydrate absorbed moisture until the water content in the CHP reached 7%. Thus, CHP anhydrate has a tendency to absorb moisture. Degradation of CHP anhydrate was also observed. In contrast, there was no significant quality changes in the stable pattern 2 hydrate form during the stability study under accelerated conditions for 6 months.

Figure 54:
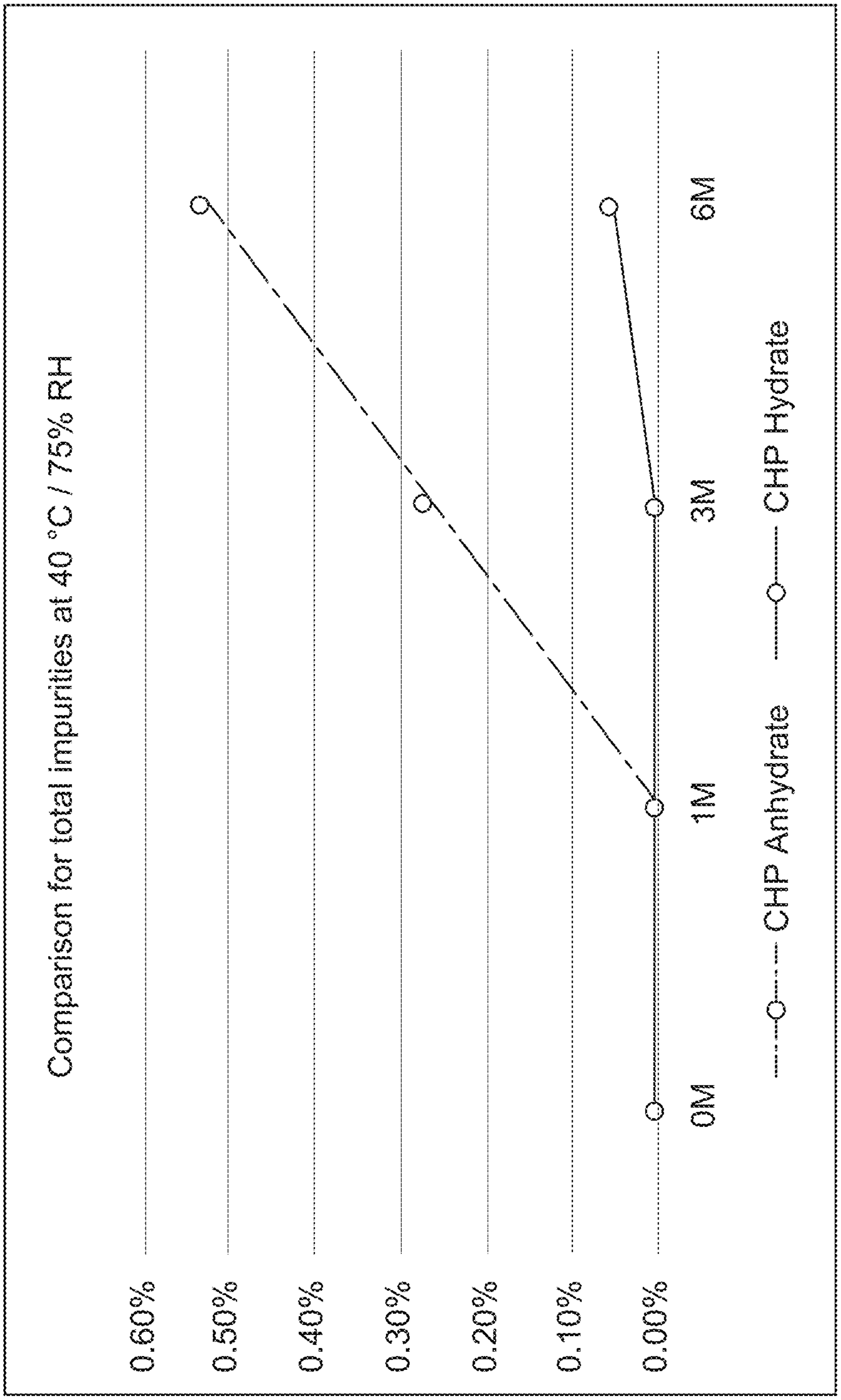
FIG. 54 is a comparison of the total impurities between CHP anhydrate (Pattern 1) and CHP hydrate (pattern 2).

A comparison of the total impurities between CHP anhydrate and CHP hydrate (pattern 2) is shown in FIG. 54.

Example 6—Polymorph Screen on CHP Hydrate

A polymorphism study was performed on CHP with the aim of identifying any novel polymorphs with improved solid-state properties. Within this study, CHP pattern 2 was identified as a stable form for development which is a stoichiometric mono hydrate. The study entailed initial analysis of the received CHP anhydrate (Pattern 1, Batch: 1058707), a solvent solubility screen in 30 solvent systems, and a primary polymorph screen employing the use of 24 solvent systems and four process relevant conditions (cycling, cooling, anti-solvent addition and evaporation). This was followed by a secondary screen scale-up of CHP pattern 2, including stability assessments of 1 week and a pH solubility assessment.

The material, as received, was found to be crystalline by XRPD and consisted of birefringent particles with no defined morphology. Thermally, pattern 1 was found to exhibit three small mass losses at the onset of heating before a sample melt was noted at 170° C. DVS analysis showed that a form change occurred and suggested that the material produced, post-DVS, was a hydrated form of the input material. A TG/DTA of the solid post-DVS supported this, with the TG/DTA thermogram matching the thermal data of pattern 2 material analyzed during the secondary polymorph screen.

High solubility was observed in ethanol and methanol with the approximate solubilities estimated between $100 \geq x \geq 50$ mg/mL. Using information gathered from the solubility screen, a primary polymorph screen was conducted using predominately amorphous input material, prepared from the received CHP (Pattern 1). One new polymorph, pure pattern 1, in addition to patterns 1 and 2 were observed in the primary screen.

Based on the results from the primary polymorph screen, pattern 2 was scaled-up for further analysis. Thermally, pattern 2 material was found to lose 0.9 equivalents water from the start of the TG/DTA experiment before a re-crystallization occurred at approx. 120° C. This was followed by a melt at 170° C. The temperature of the melt was found to be the same as that of pattern 1 which suggested that the sample dehydrated and re-crystalized to pattern 1 on heating. Although the re-crystallization event was not visible in the DSC trace, evidence of pattern 2 to pattern 1 re-crystallization was apparent by hostage PLM microscopy. Short term 1-week stability studies on pattern 2 CHP, indicated good chemical stability under the conditions assessed but XRPD analysis showed that pattern 2 input material converted to pattern 1 after 7 days storage at 80° C. in closed vials. Sample stored at ambient and 40° C./75% RH remained as pattern 2.

Longer term 8-week stability studies on pattern 2 CHP, indicated good physical stability at 40° C./75% RH. XRPD analysis confirmed that pattern 2 prevailed throughout the duration of the 8-week assessment.

Pure pattern 1 was initially observed during VT/VH-XRPD characterization of pattern 2. The diffractogram produced at 80° C./0% RH showed a peak profile that was similar to pattern 1 material, with some missing peaks, most notably at 17° 2Θ. Further comparison with the initial pattern 2 diffractogram revealed the missing peaks were present in the pattern 2 diffractogram. This suggested that the received material (assigned as pattern 1) was a mixture of pure pattern 1 and pattern 2. Scale-up of pure pattern 1 was not successful by heating to 50° C. or 80° C. but was achieved by fast evaporation in ethanol/dichloromethane, as the ethanol/DCM mixture dissolves the material in addition to azeotroping the water, promoting the formation of anhydrous pattern 1.

Eight (8)-week stability studies on pure pattern 1 CHP, indicated poor physical stability at 40° C./75% RH. XRPD analysis confirmed that pure pattern 1 converted to pattern 2 to after 14 days.

Both pattern 1 and pattern 2 material remained chirally pure throughout the duration of the stability assessment. Although the study was continued on the original samples, the material undergoing stability testing from the 2-week timepoint was pattern 2 rather than pattern 1, due to the poor stability of pure pattern 1 at this temperature and humidity.

Short term 1-day stability testing of Pure pattern 1 CHP showed that the material converted to pattern 2 after 2 hours at 40° C./75% RH.

Based on the observations described within this document highlighting pattern 2 as the most stable form, a crystallization development work program is recommended with the view to provide a reliable, scalable procedure to prepare pattern 2 material.

A. Materials

The following materials were analyzed.

Batch/Lot/Sample ID: Cyclo (-His-Pro) Batch: 1058707
SFS ID: CS/298/18/1 and CS/298/18/2
Amount Received: 10 g
Appearance: Off white solid B. Methods of Analysis 1. X-Ray Powder Diffraction (XRPD)

XRPD analysis was carried out on a PANalytical X'pert pro, scanning the samples between 3 and 35° 2θ. The material was gently ground to release any agglomerates and loaded onto a multi-well plate with Kapton or Mylar polymer film to support the sample. The multi-well plate was then placed into the diffractometer and analyzed using Cu K radiation ($\alpha 1 \lambda$=1.54060 Å; $\alpha 2$=1.54443 Å; $\beta$=1.39225 Å; $\alpha 1$: $\alpha 2$ ratio=0.5) running in transmission mode (step size 0.0130° 2θ) using 40 kV/40 mA generator settings.

2. Polarized Light Microscopy (PLM)

The presence of crystallinity (birefringence) was determined using an Olympus BX50 polarizing microscope, equipped with a Motic camera and image capture software (Motic Images Plus 2.0). All images were recorded using the 20× objective, unless otherwise stated.

3. Hot Stage Light Microscopy

Thermal events were monitored visually using a calibrated Linkam THM600 hotstage with connected controller unit coupled to an Olympus BX50 polarizing microscope equipped with a Motic camera and image capture software (Motic Images Plus 2.0). Approximately 0.5 mg of material was placed onto a microscope coverslip and heated at a rate of 10° C./min with images taken at routine intervals to document any thermal transitions. All images were recorded using the 10× objective, unless otherwise stated.

4. Thermogravimetric Analysis (TGA)

Approximately, 5 mg of material was weighed into an open aluminum pan and loaded into a simultaneous thermogravimetric/differential thermal analyzer (TG/DTA) and held at room temperature. The sample was then heated at a rate of 10° C./min from 20° C. to 300° C. during which time the change in sample weight was recorded along with any differential thermal events (DTA). Nitrogen was used as the purge gas, at a flow rate of 300 cm3/min.

5. Differential Scanning Calorimetry (DSC)

Approximately, 5 mg of material was weighed into an aluminum DSC pan and sealed non-hermetically with a pierced aluminum lid. The sample pan was then loaded into a Seiko DSC6200 (equipped with a cooler) cooled and held at 20° C. Once a stable heat-flow response was obtained, the sample and reference were heated to 250° C. at a scan rate of 10° C./min and the resulting heat flow response monitored. Nitrogen was used as the purge gas, at a flow rate of 50 cm3/min.

6. Infrared Spectroscopy (IR)

Infrared spectroscopy was carried out on a Bruker ALPHA P spectrometer. Sufficient material was placed onto the center of the plate of the spectrometer and the spectra were obtained using the following parameters:

Resolution: 4 $cm^{-1}$
Background Scan Time: 16 scans
Sample Scan Time: 16 scans Data Collection: 4000 to 400 $cm^{-1}$
Result Spectrum: Transmittance
Software: OPUS version 6

7. Nuclear Magnetic Resonance (NMR)

NMR experiments were performed on a Bruker AVIIIHD spectrometer equipped with a DCH cryoprobe operating at 500.12 MHz for protons. Experiments were performed in deuterated DMSO and each sample was prepared to ca. 10 mM concentration.

8. Dynamic Vapor Sorption (DVS)

Approximately, 10-20 mg of sample was placed into a mesh vapor sorption balance pan and loaded into a DVS Intrinsic dynamic vapor sorption balance by Surface Measurement Systems. The sample was subjected to a ramping profile from 40-90% relative humidity (RH) at 10% increments, maintaining the sample at each step until a stable weight had been achieved (dm/dt 0.004%, minimum step length 30 minutes, maximum step length 500 minutes) at 25° C. After completion of the sorption cycle, the sample was dried using the same procedure to 0% RH and then a second sorption cycle back to 40% RH. Two cycles were performed. The weight change during the sorption/desorption cycles were plotted, allowing for the hygroscopic nature of the sample to be determined. XRPD analysis was then carried out on any solid retained.

9. Variable Temperature Dynamic Vapour Sorption (VT-DVS)

Approximately, 10-20 mg of sample was placed into a mesh vapor sorption balance pan and loaded into a DVS Advantage dynamic vapor sorption balance by Surface Measurement Systems. The sample was subjected to a ramping profile from 40-90% relative humidity (RH) at 10% increments, maintaining the sample at each step until a stable weight had been achieved (dm/dt 0.004%, minimum step length 30 minutes, maximum step length 500 minutes) at 40° C. After completion of the sorption cycle, the sample was dried using the same procedure to 0% RH and then a second sorption cycle back to 40% RH. The weight change during the sorption/desorption cycles were plotted, allowing for the hygroscopic nature of the sample to be determined. The experiment was repeated at 50° C. and finally at 60° C. XRPD analysis was then carried out on any solid retained.

10. Variable Temperature and Humidity X-Ray Powder Diffraction (VT-/VH-XRPD)

VT-/VH-XRPD analysis was carried out on a Philips X'Pert ProMultipurpose diffractometer equipped with a temperature and humidity chamber. The samples were scanned between 4 and 35.99° 2θ using Cu K radiation ($\alpha 1\lambda$=1.54060 Å; $\alpha 2$=1.54443 Å; β=1.39225 Å; $\alpha 1$:$\alpha 2$ ratio=0.5) running in Bragg-Brentano geometry (step size 0.008° 2θ) using 40 kV/40 mA generator settings. Measurements were performed at each step of the humidity profile below:

Program: 40% RH/ambient temperature—initial scan
- 0% RH/ambient temperature—initial scan, 1-hour hold, scan
- 0% RH/80° C.—initial scan, 20-minute hold, scan
- 0% RH/80° C.—initial scan, 80-minute hold, scan 11. High Performance Liquid Chromatography-Ultraviolet Detection (HPLC-UV)

Instrument: Dionex Ultimate 3000
Column: LC/168 X-Bridge Phenyl Column (150 mm×4.6 mm×3.5 µm)
Column Temperature: 30° C.
Autosampler Temperature: 5° C.
UV wavelength: 220 nm
Injection Volume: 5 µL
Flow Rate: 1 ml/min
Mobile Phase A: 10 mM Ammonium acetate
Mobile Phase B: Acetonitrile
Diluent: 0.1% TFA in water
Gradient program:

| Time (minutes) | Solvent B [%] |
|---|---|
| 0.01 | 0 |
| 10.3 | 30 |
| 15 | 95 |
| 15.1 | 0 |
| 25 | 0 |

12. Liquid Chromatography-Mass Spectroscopy (LC-MS)

Instrument: Dionex Ultimate 3000
Column: ACE Excel 3 Super C18, 75×4.6 mm
Column Temperature: 30° C.
Injection Volume: 10 µL
Flow Rate: 1.0 mL/min
Mobile Phase A: 0.1% Formic Acid in De-ionized water
Mobile Phase B: 0.1% Formic Acid in Acetonitrile
Diluent: Acetonitrile
Needle Wash: Acetonitrile, Vial position #100
PDA Range: 190-400 nm
Gradient program:

| Time (minutes) | Solvent B [%] |
|---|---|
| 0.00 | 5 |
| 12.00 | 95 |
| 15.00 | 95 |
| 15.10 | 5 |
| 20.00 | 5 |

13. Chiral HPLC

Column: Daicel IC (5.0 um, 250*4.6 mm)
Column Temperature: 30° C.
Injection Volume: 5 µL
Flow Rate: 1.0 mL/min
Mobile Phase A: 0.01% DEA in n-Hexane
Mobile Phase B: EtOH:MeOH=2:8 (v/v)
Diluent: Acetonitrile
PDA Range: 220 nm
Gradient program:

| Time (min) | A % | B % |
|---|---|---|
| 0.01 | 70 | 30 |
| 28.0 | 70 | 30 |

C. Experimental

1. Initial Characterization

On receipt of the supplied Cyclo(His-Pro), herein referred to as CHP, initial characterization was performed using XRPD, PLM, TG/DTA, DSC, DVS (with post-XRPD analysis), 1H and HSQC NMR, HPLC (for purity and UV Spectrum), pKa, and LC-MS, employing the techniques and methods outlined in Section B.

2. Sample Preparation for Solvent Solubility Screen

Lyophilization in Water

Material was prepared by lyophilization for the solvent solubility screen as follows:

To the received CHP (Pattern 1) (330 mg) 3.3 mL of distilled water was added, yielding a clear, colorless solution;

This solution was equally divided between 33. 2 mL glass vials (containing approx. 100 μL in each vial and 10 mg of solid);

The vials were frozen at −50° C. in preparation for freeze drying;

Once frozen, the samples were placed in a desiccator attached to the freeze dryer and dried for approx. 18 hours. After this time, a sample was taken and analyzed by XRPD to confirm the amorphous nature of the batch.

Repeat Lyophilization in Water

Repeat lyophilization was carried out as follows:

Each 10 mg sample (prepared as per Section 5.2.1) was re-dissolved in 200 μL of distilled water.

The vials were frozen at −50° C. in preparation for freeze drying;

Once frozen, the samples were placed in a desiccator attached to the freeze dryer and dried for approx. 72 hours. After this time, a sample was taken and analyzed by XRPD to confirm the amorphous nature of the batch.

3. Solvent Solubility Screen

To a known mass of CHP lyophile (10 mg, from Section 5.2.2), 100 μL of the appropriate solvent was added and if solid remained the vial was gently heated to ~40° C. to aid dissolution. Solvent addition continued until the material fully dissolved or 2 mL had been added (<5 mg/mL). The samples were uncapped and allowed to evaporate at ambient. The solvents used in the solubility screen can be found in Table 21.

4. Sample Preparation for Primary Polymorph Screen a. Lyophilization in Water

Material was prepared by lyophilization for the primary polymorph screen as follows:

To the received CHP (1.04) 13 mL of distilled water was added, yielding a clear, colorless solution;

This solution was equally divided between 26, 2 mL glass vials (containing approx. 500 μL in each vial and 40 mg of solid);

The vials were frozen at −50° C. in preparation for freeze drying;

Once frozen, the samples were placed in a desiccator attached to the freeze dryer and dried for approx. 48 hours. After this time, a sample was taken and analyzed by XRPD to confirm the amorphous nature of the batch.

b. Repeat Lyophilization in Water

A second lyophilization attempt was carried out as follows:

To each 40 mg sample (prepared as per Section a) 1.5 mL of distilled water was added to re-dissolve the material;

The vials were frozen at −50° C. in preparation for freeze drying;

Once frozen, the samples were placed in a desiccator attached to the freeze dryer and dried for approx. 72 hours. After this time, a sample was taken and analyzed by XRPD to confirm the amorphous nature of the batch.

TABLE 21

Solvent Solubility Screen Solvent List

| Number | Solvent | ICH Class |
|---|---|---|
| 1 | 1-Butanol | 3 |
| 2 | 2-Butanol | 3 |
| 3 | 1-Propanol | 3 |
| 4 | 2-Propanol | 3 |
| 5 | 40% Methanol:60% Water (% v/v) (calc. aw 0.8) | 2 |
| 6 | 95% Methanol:5% Water (% v/v) (calc. aw 0.2) | 2 |
| 7 | Acetone | 3 |
| 8 | Acetonitrile | 2 |
| 9 | Dichloromethane | 2 |
| 10 | Ethanol | 3 |
| 11 | Ethyl Acetate | 3 |
| 12 | Ethyl Formate | 3 |
| 13 | Heptane | 3 |
| 14 | Isopropyl Acetate | 3 |
| 15 | Methanol | 2 |
| 16 | Methylethyl Ketone | 3 |
| 17 | Methylisobutyl Ketone | 3 |
| 18 | N,N$^1$-Dimethylacetamide | 2 |
| 19 | Nitromethane | 2 |
| 20 | tert-Butylmethyl Ether | 3 |
| 21 | THF | 2 |
| 22 | Toluene | 2 |
| 23 | Water | N/A |
| 24 | Triflouroethanol | Not Classified |
| 25 | Benzyl Alcohol | 2 |
| 26 | Chloroform | 2 |
| 27 | Chlorobenzene | 2 |
| 28 | 1,4-Dioxane | 2 |
| 29 | 2-Methoxyethonal | 2 |
| 30 | Dimethylsulfoxide | 3 |

C. Repeat Lyophilization in Water (2)

A third lyophilization attempt was carried out as follows:

To each 40 mg sample (prepared as per Section b) 1 mL of distilled water was added to re-dissolve the material;

Solutions were then pipetted into 26, 20 mL glass vials and topped up with an additional 15 mL of distilled water;

The vials were frozen at −50° C. in preparation for freeze drying;

Once frozen, the samples were placed in a desiccator attached to the freeze dryer and dried for approx. 120 hours. After this time, a sample was taken and analyzed by XRPD to confirm the amorphous nature of the batch.

5. Primary Polymorph Screen

Primary polymorph screening of CHP was conducted as follows:

24 vials containing ca. 40 mg of CHP from Section b were used in this experiment;

The material was suspended in the appropriate solvent/solvent mixture and temperature cycled between ambient and 40° C. in 4 hours cycles over 72 hours. Solvents used can be found in Table 22;

The resulting solids were isolated by filtration by centrifugation and analyzed by XRPD. Any new forms were analyzed by TG/DTA;

Filtered, saturated solutions were then divided into three vials and used for subsequent polymorph screening experiments as below:

a. Evaporation

Saturated solutions of CHP were transferred to 2 mL vials; these vials were then uncapped and allowed to evaporate at ambient temperature to recover material. All recovered material was characterized by XRPD.

b. Crash Cool

Saturated solutions of CHP were stored at 2-8° C. for 96 h. At this time any material recovered was analyzed by XRPD and the vials were moved and stored at −20° C. for 72 hours. After this time any material recovered was analyzed by XRPD.

c. Anti-Solvent Addition at Ambient

Up to 2 mL of anti-solvent (heptane or MtBE) was added dropwise to saturated solutions of CHP. The samples were left capped, at ambient temperature, for 72 hours. Any resulting solid was analyzed by XRPD.

TABLE 22

Primary Polymorph Screen Solvent List

| Number | Solvent | ICH Class |
|---|---|---|
| 1 | 1-Propanol | 3 |
| 2 | 2-Propanol | 3 |
| 3 | 95% Methanol:5% Water (% v/v) | 2 |
| 4 | 50% Methanol:50% TBME (% v/v) | 2 |
| 5 | 10% Methanol:90% TBME | 2 |
| 6 | Acetone | 3 |
| 7 | Acetonitrile | 2 |
| 8 | Dichloromethane | 2 |
| 9 | Ethanol | 3 |
| 10 | 50% Ethanol/50% TBME (% v/v) | 3 |
| 11 | 10% Ethanol/90% TBME | 3 |
| 12 | Ethyl Acetate | 3 |
| 13 | Ethyl Formate | 3 |
| 14 | Heptane | 3 |
| 15 | Isopropyl Acetate | 3 |
| 16 | Methylethyl Ketone | 3 |
| 17 | Methylisobutyl Ketone | 3 |
| 18 | Nitromethane | 2 |
| 19 | tert-Butylmethyl Ether | 3 |
| 20 | Toluene | 2 |
| 21 | Trifluoroethanol | Not Classified |
| 22 | Chlorobenzene | 2 |
| 23 | THF | 2 |
| 24 | Methanol | 2 |

6. Secondary Polymorph Screen a. Scale-Up of Pattern 2

CHP pattern 2 was scaled up with procedures outlined as follows:

5 g of received CHP (pattern 1) was slurried in 6 mL of 90:10 ethanol/water mixture;

Resulting slurry was placed on a stirrer and agitated for ca. 24 hours;

After 24 hours the sample was removed from the shaker and the solid analyzed by XRPD;

The solid was characterized as per P-SFS1482-00 Section 2.4 a. Scale-Up of Pure Pattern 1 i. 80° C. Heating of Pattern 2

Ca. 2.2 g of pattern 2 material (prepared as per Section 5.6.1) was placed inside a vacuum oven set to 50° C.;

After 1 hour, a sample was taken and analyzed by XRPD;

Vial was returned to the vacuum oven and the temperature increased to 60° C.;

After 30 minutes, a sample was taken and analyzed by XRPD;

Vial was returned to the vacuum oven and the temperature increased to 80° C.;

After 18 hours at 80° C., a sample was taken and analyzed by XRPD;

ii. Fast Rotary Evaporation in Ethanol/DCM 1 g of received CHP pattern 1 was weighed in to a round bottom flask and dissolved in 40 mL of ethanol;

Once the solid had dissolved, 2 mL of dichloromethane was pipetted into the flask;

The flask was then attached to a rotary evaporator and fast evaporated at ambient temperature under vacuum;

A pale beige solid was recovered an analyzed by XRPD.

7. pH Solubility Assessment

CHP patterns 1 and 2 were prepared for pH solubility assessment as follows:

100 mg of CHP pattern 1 and pattern 2 were each weighed out into 4, 5 mL screw top glass vials;

100 μL of a selected buffer, pre-heated to 37° C., was added to each vial;

Samples were heated to 37° C. in an incubator shaker for ca. 10 minutes after each volume of buffer and checked for sample dissolution.

C. Results

1. Initial Characterization

Initial characterization of CHP (CS/298/18) indicated the following:

The material was crystalline by XRPD (FIG. 1). The XRPD pattern of the supplied CHP was denoted pattern 1.

Figure 12:
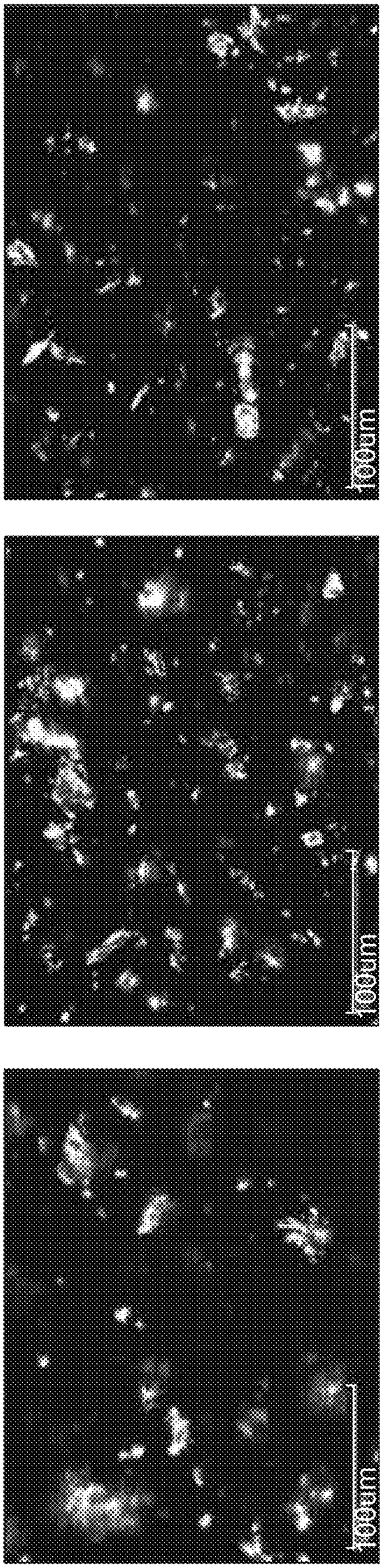
FIG. 12 illustrates the polarized light microscopy analysis of the received CHP (mostly Pattern 1).

PLM analysis found the material to be birefringent with no clear morphology. Polarized and non-polarized images can be seen in FIGS. 12 and 11, respectively.

TG analysis showed that from the onset of heating there was a series of small mass losses (0.6%, 0.2% and 0.3%) until approx. 280° C. where sample degradation was observed. DTA identified one sharp endothermic event with an onset of 170° C. and a peak at 172° C. This is most likely a sample melt. The TG/DTA thermogram can be seen in FIG. 14.

FIG. 16 shows the first heat cycle of the DSC analysis. A small broad endothermic event was noted at 75° C. and a peak at 85° C. A second endothermic event was observed at 169° C. with a peak at 171° C. This was consistent with the melt seen in the TG/DT. No significant thermal events were observed in the cool cycle (FIG. 17) A very small endodermic event, most likely a weak glass transition, was noted at 75° C.-80° C. during the second heat cycle (FIG. 18).

The DVS isotherm plot in FIG. 23 showed a +6.3% change in mass from 60% RH to 90% RH indicating a clear form change. After the change in form, the material appeared slightly hygroscopic with a maximum uptake of 0.8 wt. % between 0 and 90% RH (FIG. 24). The DVS kinetic plot can be seen in FIG. 25. XRPD analysis confirmed that the pattern 1 input material re-crystallized to pattern 2 (initially seen in the solvent solubility screen, detailed in Section 3) after exposure to the DVS humidity conditions. The XRPD diffractograms can be seen in FIG. 26. Comparison of the pattern 1 and pattern 2 diffractograms show a number of the pattern 2 peaks were also present in the received pattern 1. This suggested that the received pattern 1 was a potential mixture. This was investigated further by carrying out VT/VH-XRPD on pattern 2 material (as per Section B.1).

TG/DTA analysis was carried out on the solid recovered post-DVS for Pattern 2. The thermogram can be seen in FIG. 27. TG analysis showed an initial weight loss of 6.8% (0.95 equiv. water) followed by sample degradation at 280° C. The DT trace identified an endothermic event associated with the initial weight loss. This was followed by an exothermic event, most likely a recrystallization of the material, before a second endotherm (sample melt) was observed at 168° C.

$^1$H-NMR (FIG. 35) and HSQC-NMR (FIG. 38) of the received CHP was consistent with the supplied structure. The imidazole CH signal was not observed, probably due to slow relaxation Analysis of received material gave a pKa value of 6.38 (FIG. 10).

Figure 55:
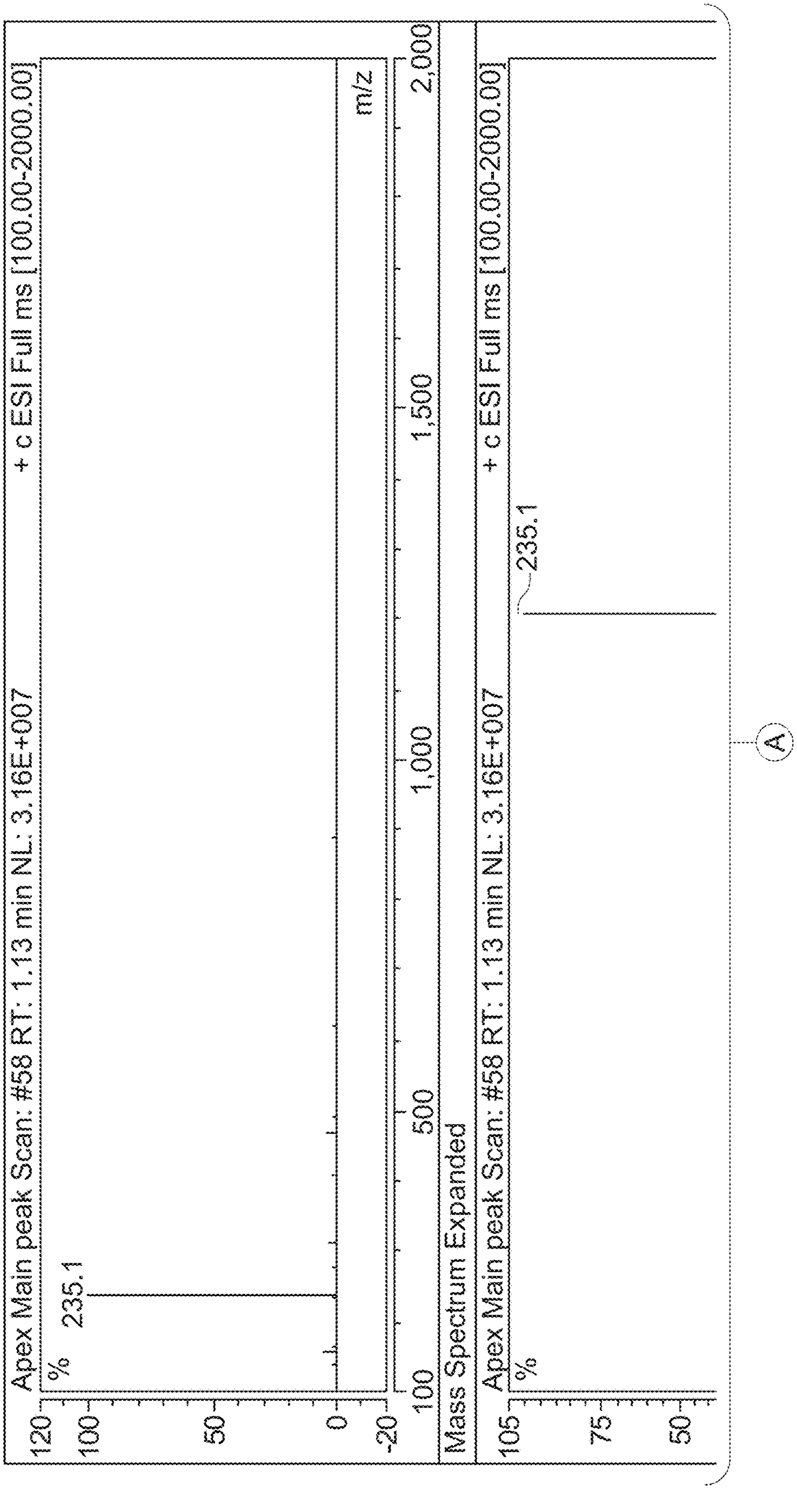
FIG. 55 is the LC-MS spectrum of Pattern 1 and Pattern 2 that confirmed the expected m/z of 235.1, corresponding to $[C_{11}H_{14}N_4O_2]H^+$. Both patterns give the same LC-MS as once dissolved in solvent (water) because there will be no “solid form” or polymorph in solvent. LC-MS measures the solubilized CHP, not solid form.
Figure 55:
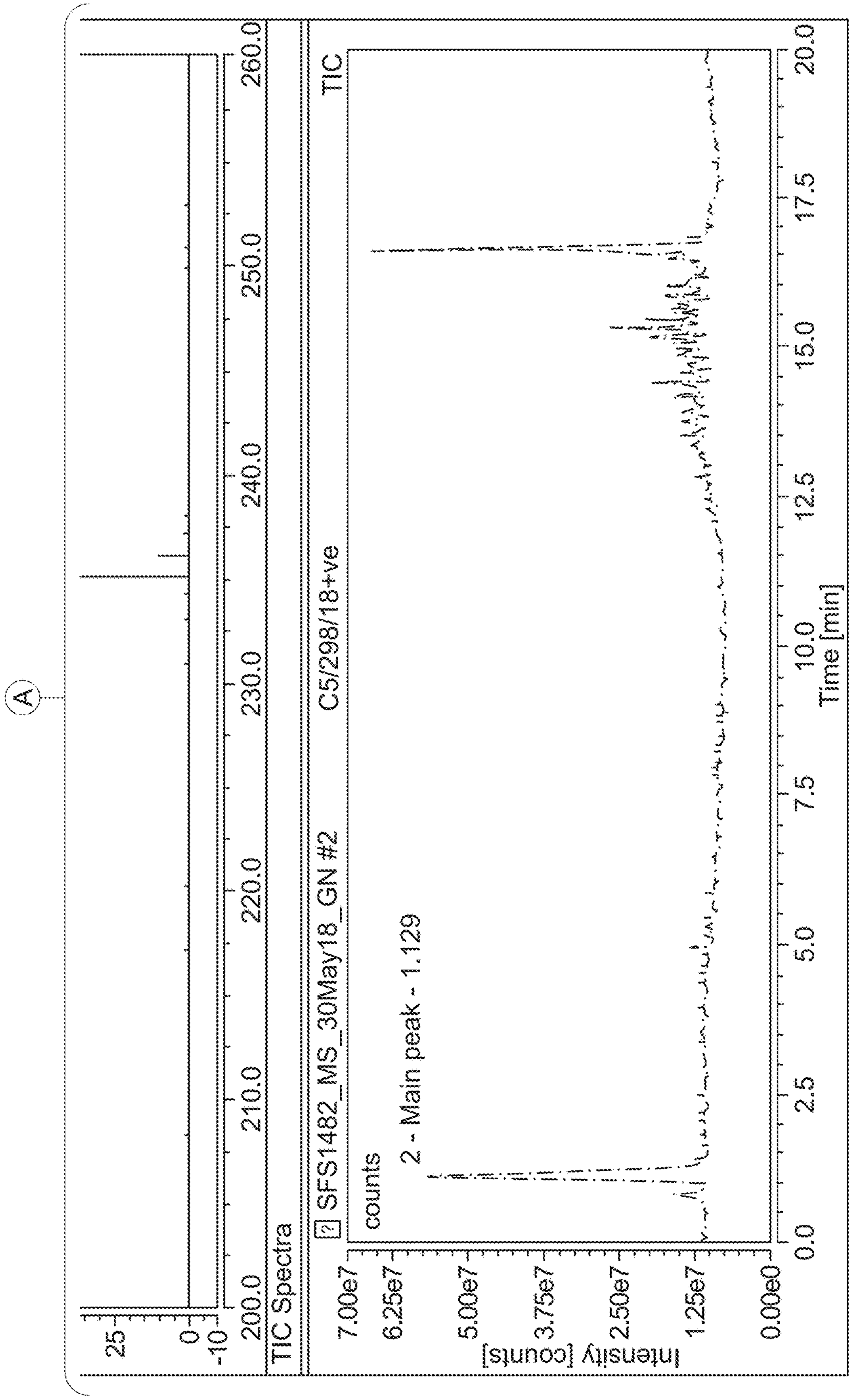

LC-MS spectrum of CHP pattern 1 confirmed the expected m/z of 235.1, corresponding to $[C_{11}H_{14}N_4O_2]H^+$ (FIG. 55).

Figure 56:
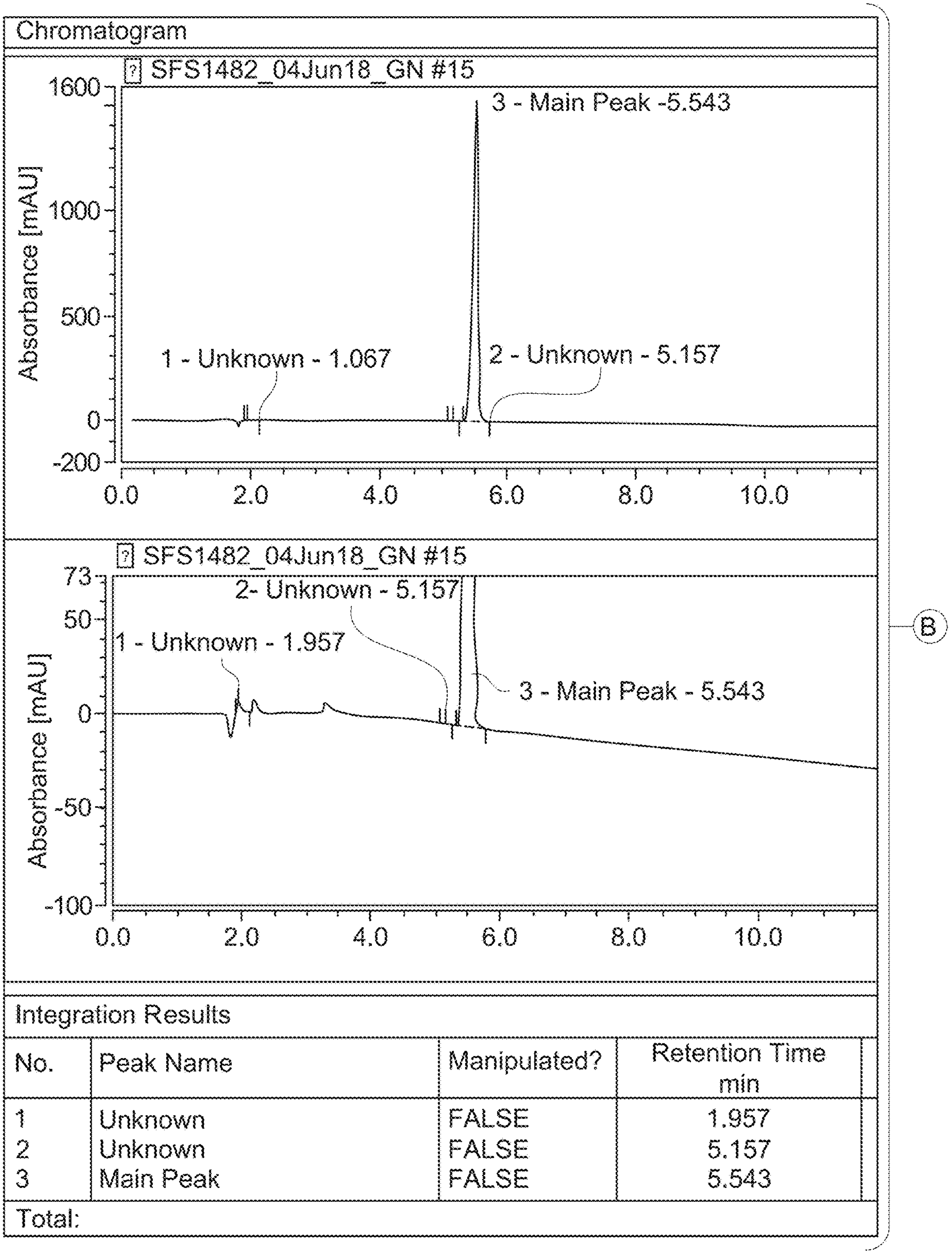
FIG. 56 is the HPLC-UV chromatogram of the received CHP. It shows that the received CHP was 99.5% pure.
Figure 56:
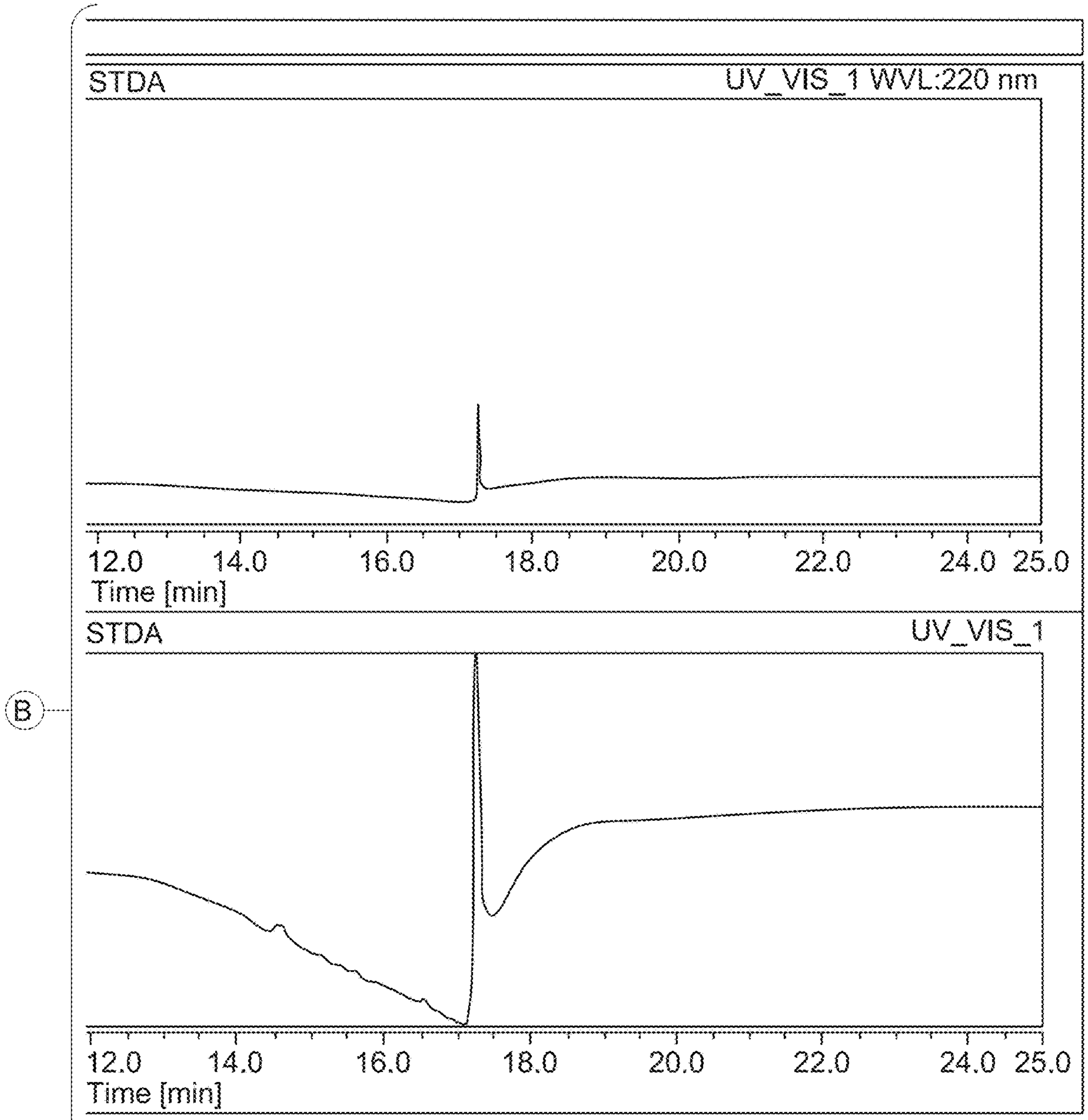

Received CHP was 99.5% pure when analyzed by HPLC-UV. Associated chromatogram is in FIG. 56.

2. Sample Preparation for Solvent Solubility Screen a. Lyophilisation in Water

Analysis of the solid from lyophilization in water indicated that the material was still crystalline. The 2Θ diffractogram of the amorphous material is presented in FIG. 40.

b. Repeat Lyophilisation in Water

Analysis of repeat lyophilised solids from water indicated the material was predominately.

3. Solvent Solubility Screen

As outlined above, the solubility of the CHP lyophile was assessed in 30 selected solvents/solvent mixtures. From the results in Table 23, the material showed low solubility in most of solvent/solvent mixtures used in this study. High solubility was observed in ethanol and methanol with the approximate solubilities estimated between 100≥x≥50 mg/mL. The material was also observed to be soluble in water, DMSO, DMA, trifluoroethanol and both methanol/water mixtures.

Figure 57:
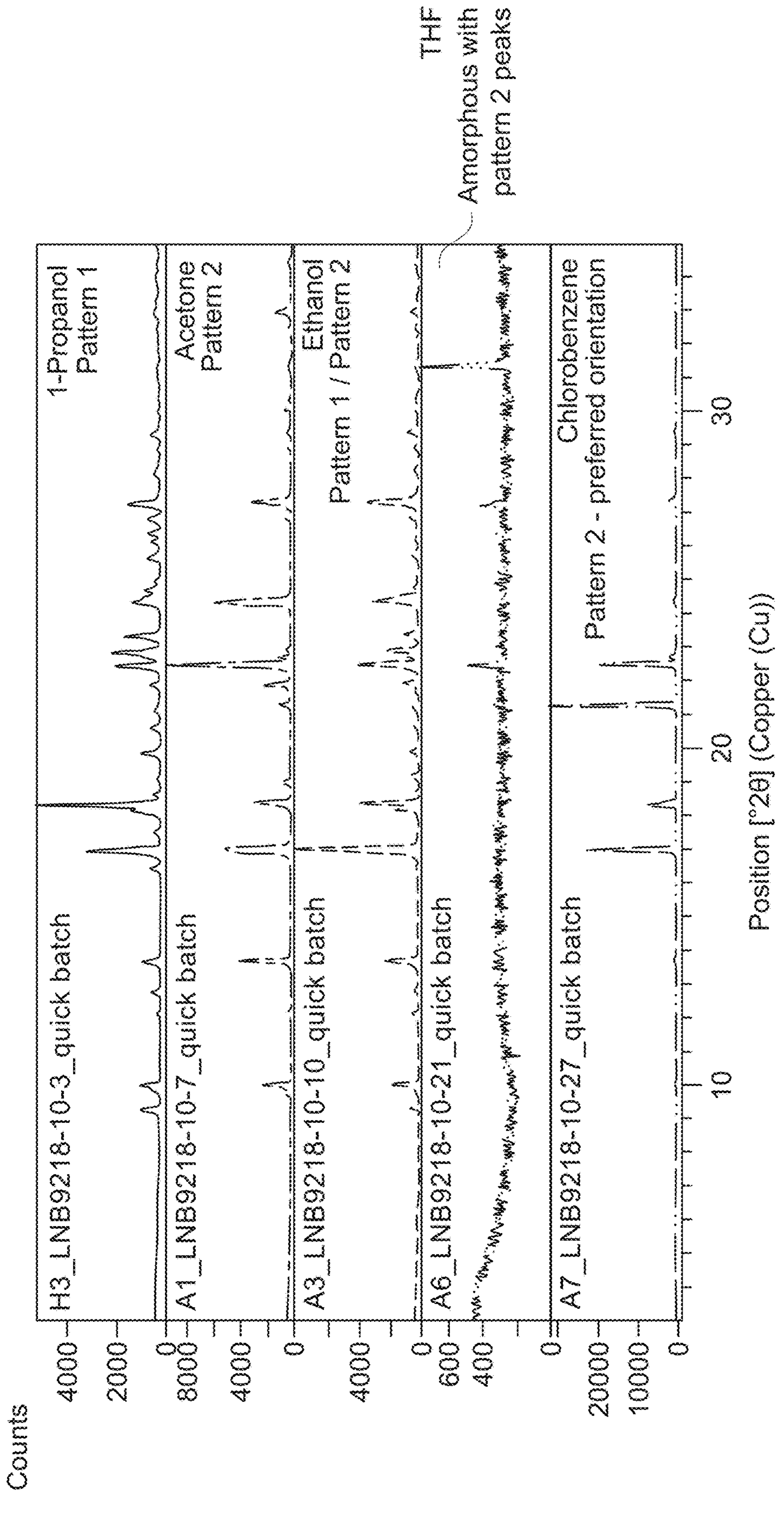
FIG. 57 is an example XRPD diffractograms for solids recovered from solvent solubility screen.
Figure 58:
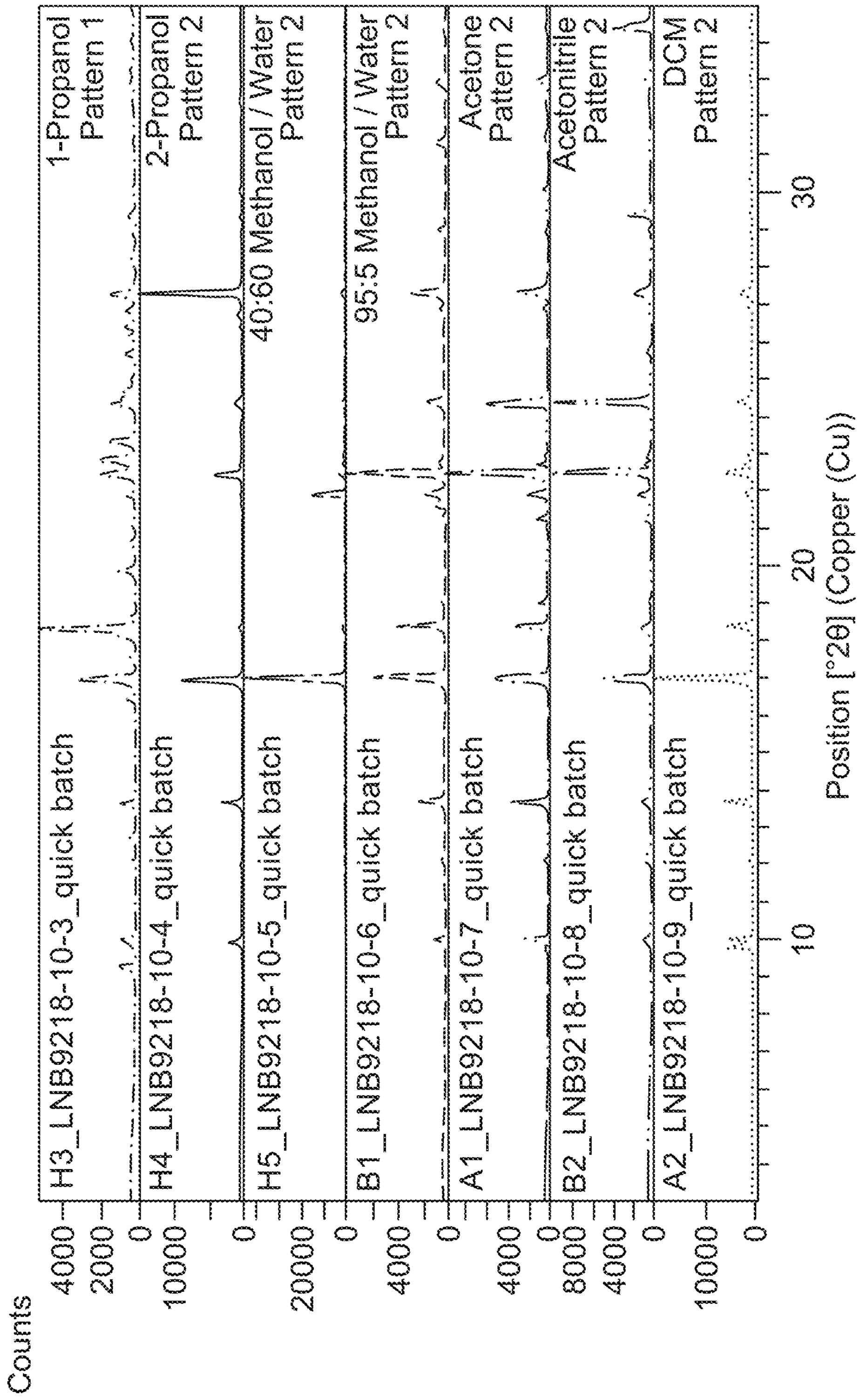
FIGS. 58-60 are the XRPD diffractograms for solids recovered from temperature cycling.
Figure 59:
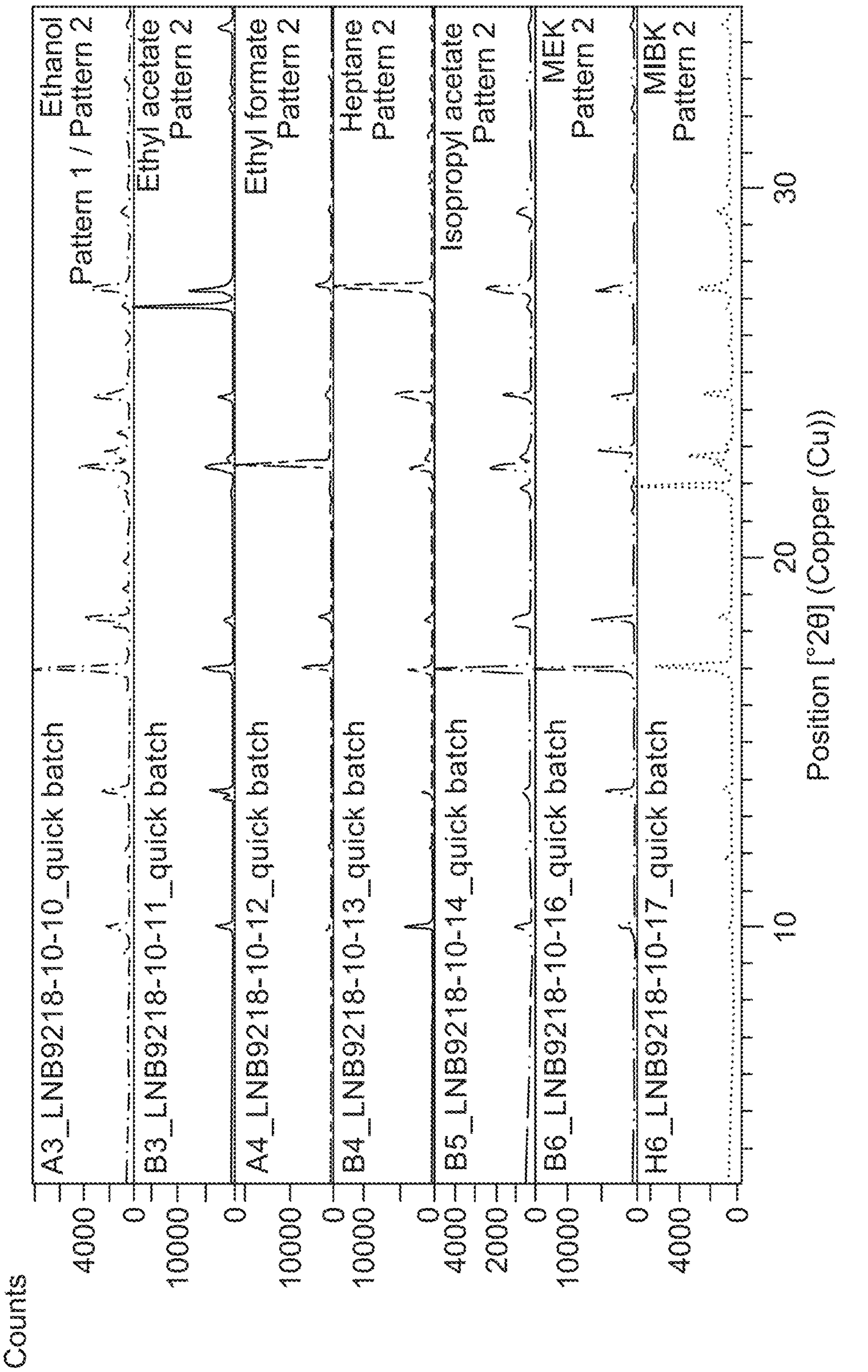
Figure 60:
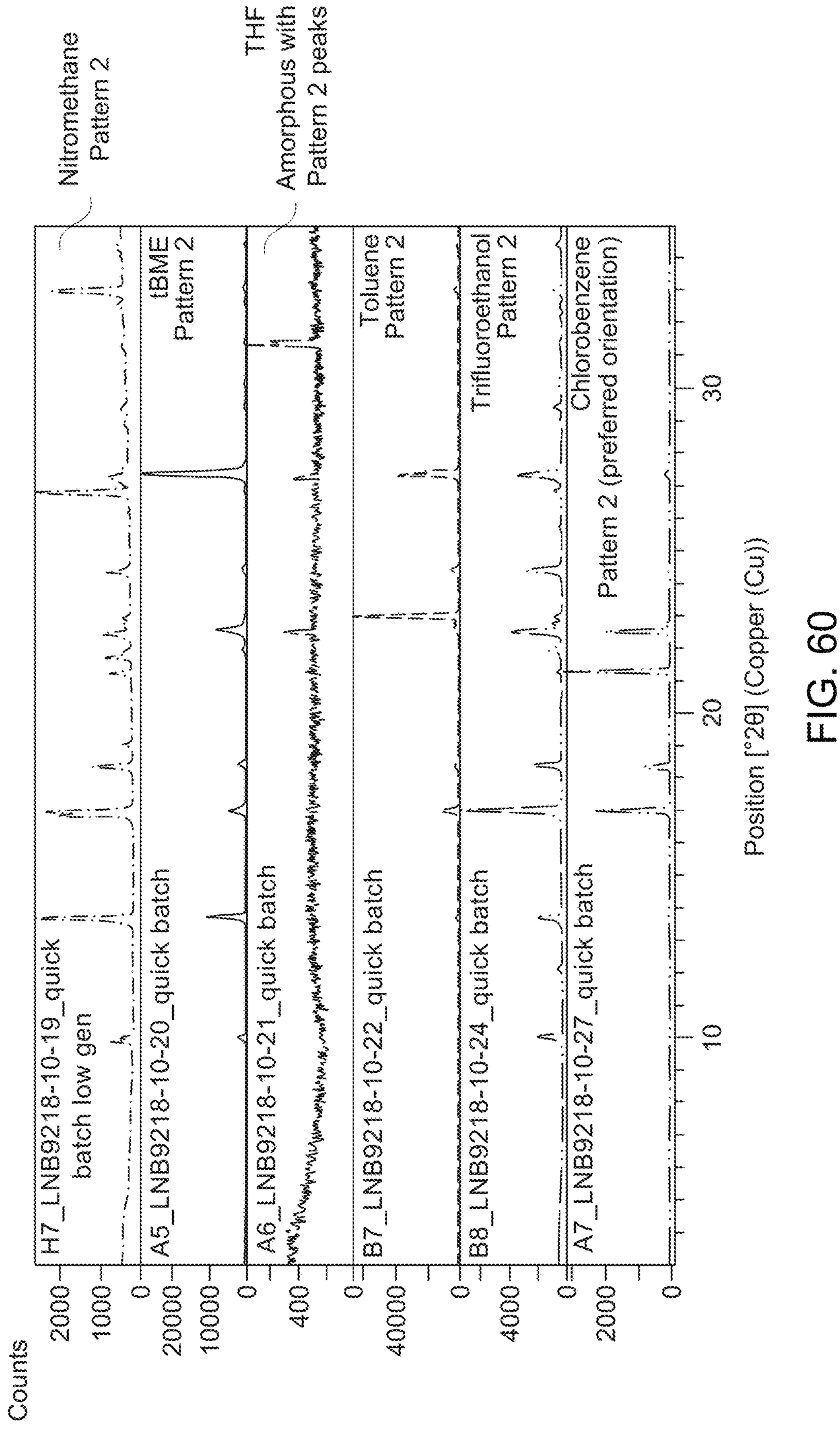

Results from the XRPD analysis of the recovered solids from the solvent solubility are in Table 24. Example XRPD diffractograms for each of the patterns produced can be seen in FIG. 57. Remaining diffractograms are included in FIG. 58-FIG. 60.

TABLE 23

CHP Lyophile Solvent Solubility Results

| | Solvent | Approximate Solubility (mg/mL) |
|---|---|---|
| 1 | 1-Butanol | ≥5 |
| 2 | 2-Butanol | ≥5 |
| 3 | 1-Propanol | 14.3 ≥ x ≥ 12.5 |
| 4 | 2-Propanol | 5.6 ≥ x ≥ 5.3 |
| 5 | 40% Methanol:60% Water (% v/v) (calc. aw 0.8) | 20 ≥ x ≥ 16.7 |
| 6 | 95% Methanol:5% Water (% v/v) (calc. aw 0.2) | 33.3 ≥ x ≥ 25 |
| 7 | Acetone | ≤5 |
| 8 | Acetonitrile | ≤5 |
| 9 | Dichloromethane | ≤5 |
| 10 | Ethanol | 100 ≥ x ≥ 50 |
| 11 | Ethyl Acetate | ≤5 |
| 12 | Ethyl Formate | ≤5 |
| 13 | Heptane | ≤5 |
| 14 | Isopropyl Acetate | ≤5 |
| 15 | Methanol | 100 ≥ x ≥ 50 |
| 16 | Methylethyl Ketone | ≤5 |
| 17 | Methylisobutyl Ketone | ≤5 |
| 18 | N,N$^1$-Dimethylacetamide | 33.3 ≥ x ≥ 25 |
| 19 | Nitromethane | ≤5 |
| 20 | tert-Butylmethyl Ether | ≤5 |
| 21 | THF | ≤5 |

TABLE 24

XRPD Pattern Summary Table from Solvent Solubility Screen

| | Solvent | XRPD Results |
|---|---|---|
| 1 | 1-Butanol | N/A-no solid produced |
| 2 | 2-Butanol | N/A-no solid produced |
| 3 | 1-Propanol | Pattern 1 |
| 4 | 2-Propanol | Pattern 2 |
| 5 | 40% Methanol:60% Water (% v/v) (calc. aw 0.8) | Pattern 2 |
| 6 | 95% Methanol:5% Water (% v/v) (calc. aw 0.2) | Pattern 2 |
| 7 | Acetone | Pattern 2 |
| 8 | Acetonitrile | Pattern 2 |
| 9 | Dichloromethane | Pattern 2 |
| 10 | Ethanol | Pattern 1 Pattern 2 |
| 11 | Ethyl Acetate | Pattern 2 |
| 12 | Ethyl Formate | Pattern 2 |
| 13 | Heptane | Pattern 2 |
| 14 | Isopropyl Acetate | Pattern 2 |
| 15 | Methanol | N/A-colourless gel |
| 16 | Methylethyl Ketone | Pattern 2 |
| 17 | Methylisobutyl Ketone | Pattern 2 |
| 18 | N,N$^1$-Dimethylacetamide | N/A-no solid produced |
| 19 | Nitromethane | Pattern 2 |
| 20 | tert-Butylmethyl Ether | Pattern 2 |
| 21 | THF | Amorphous with pattern 2 peaks |

4. Sample Preparation for Primary Polymorph Screen a. Lyophilization in Water

Figure 61:
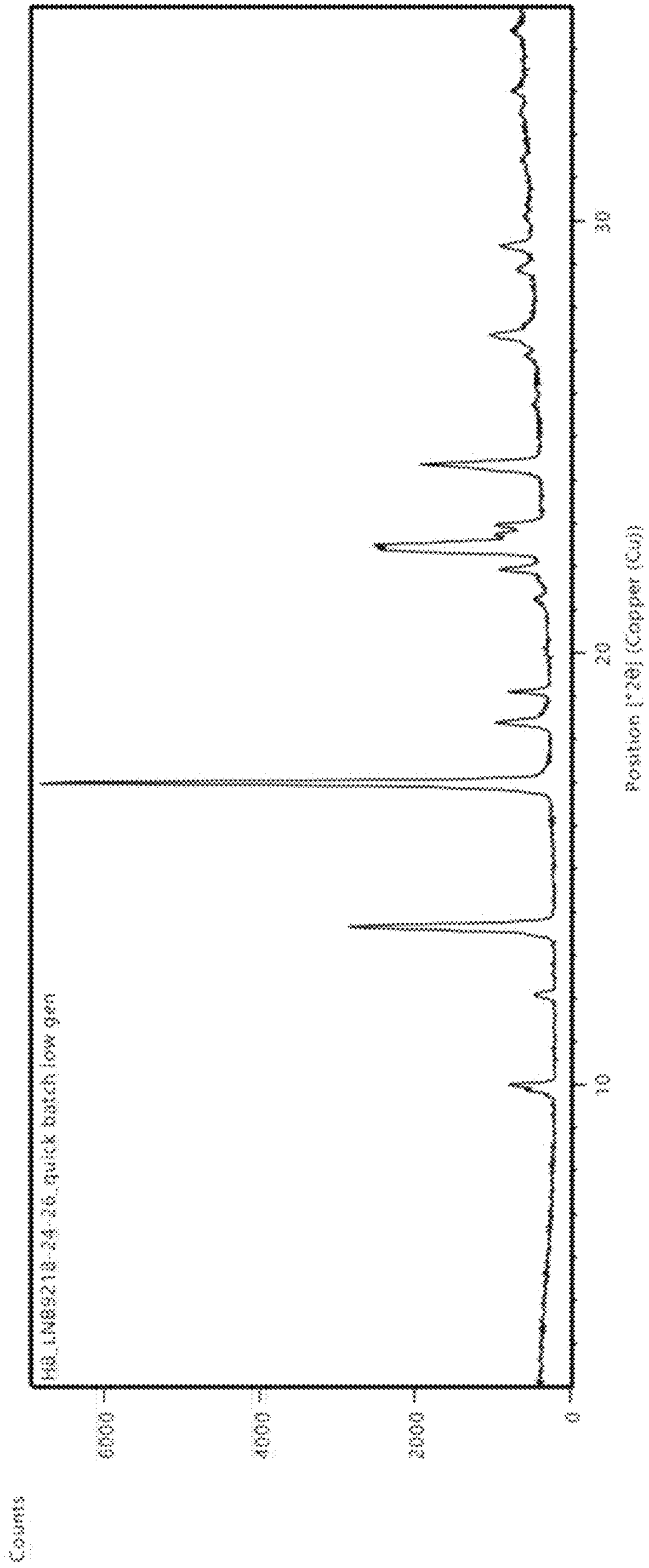
FIG. 61 is the XRPD diffractogram pattern of pattern 2.

Analysis of lyophilized solids from water indicated that the samples were still crystalline. Diffractogram pattern was identified as pattern 2 (FIG. 61).

b. Repeat Lyophilization in Water

Figure 62:
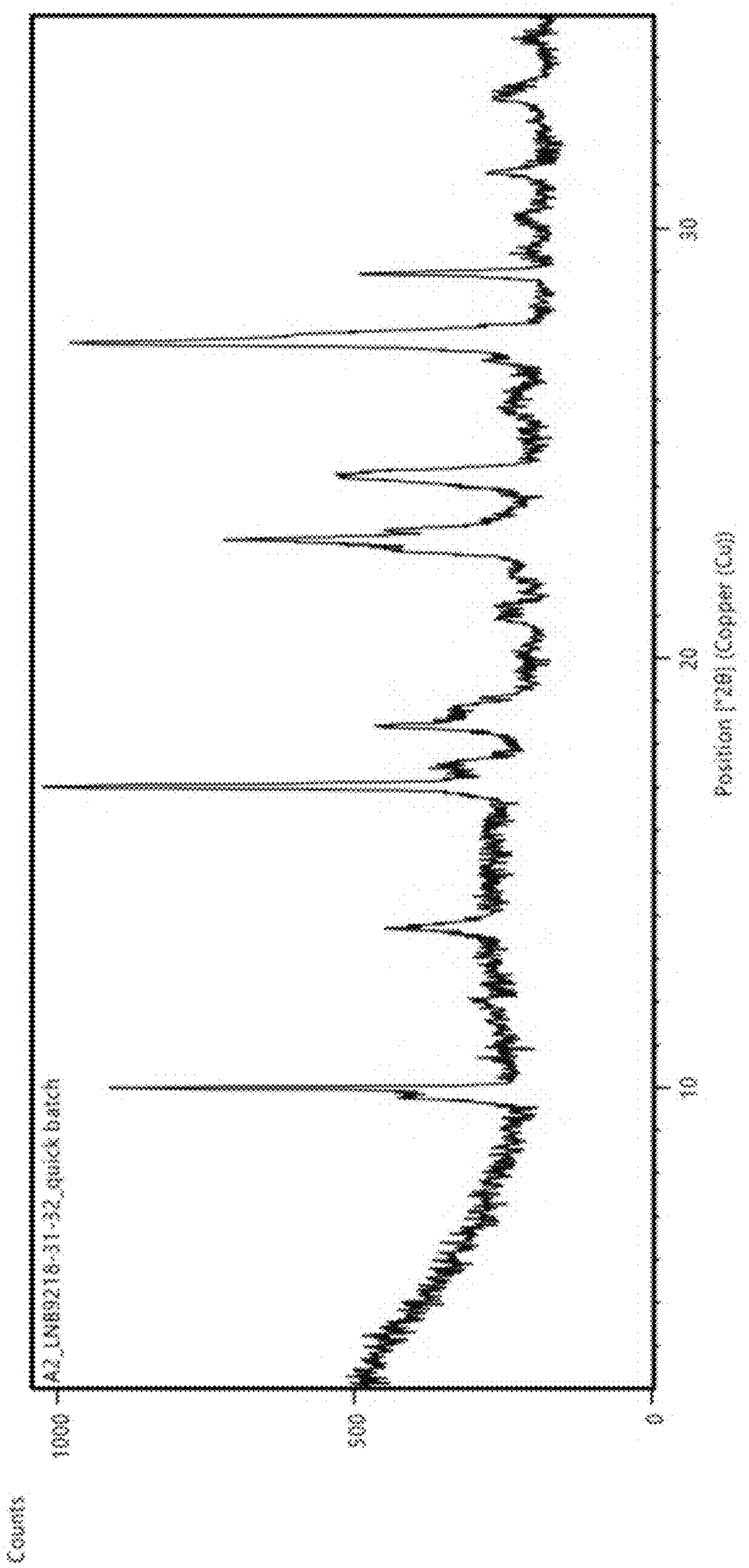
FIG. 62 is the XRPD diffractogram obtained from repeat lyophilization of CHP in water.

FIG. 62 shows the diffractogram obtained from repeat lyophilisation of CHP in water. XRPD analysis confirmed that the material was less crystalline that the previous sample shown in FIG. 61, but still contained pattern 2 peaks.

c. Repeat Lyophilization in Water (2)

Figure 63:
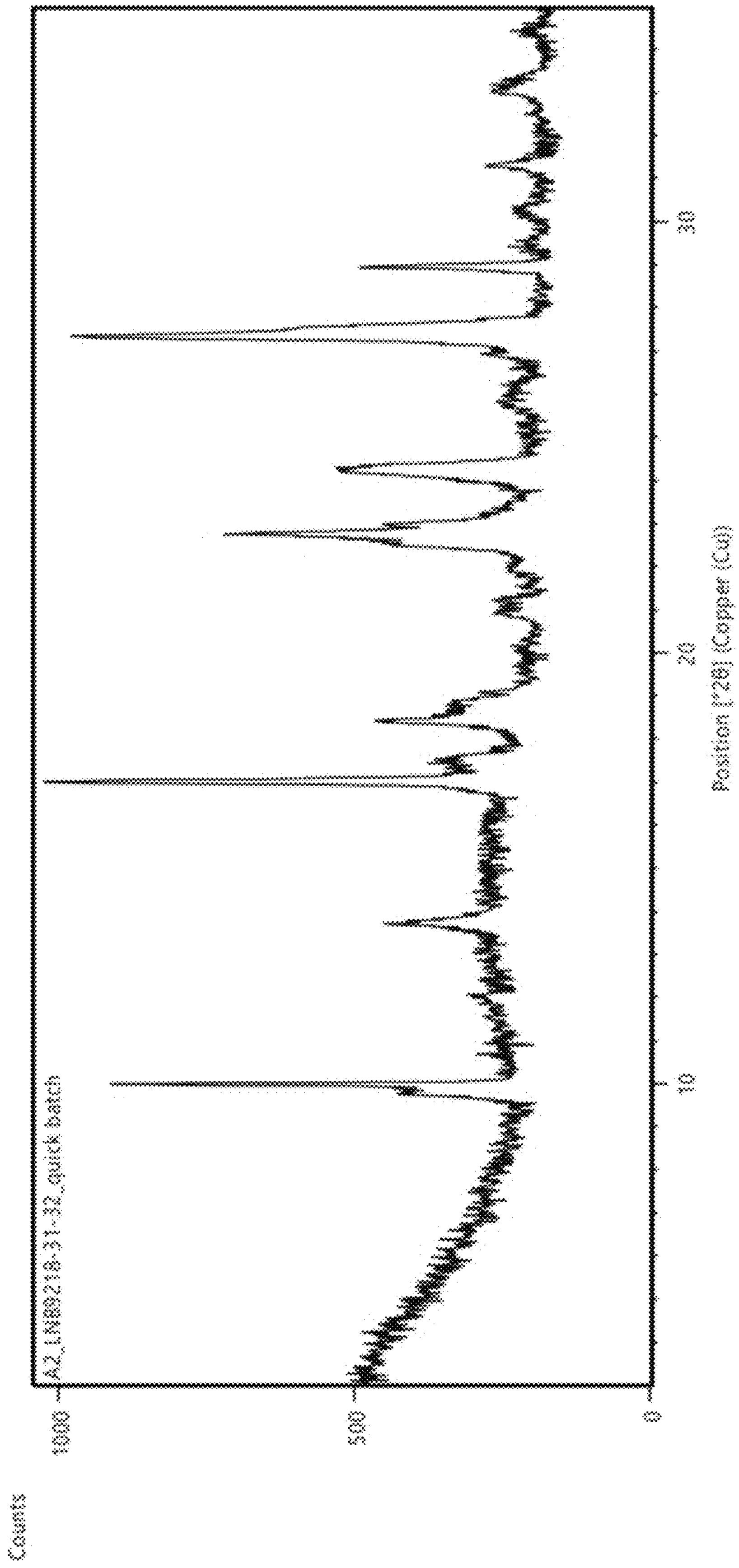
FIG. 63 is the XRPD diffractogram obtained from the third lyophilization attempt of CHP in water.

FIG. 63 shows the diffractogram obtained from the third lyophilization attempt of CHP in water. XRPD analysis confirmed that the material was less crystalline that the sample shown in FIG. 61, but the pattern 2 peaks from FIG. 62 remained.

5. Primary Polymorph Screen

As outlined above, the propensity of CHP to exhibit polymorphism was assessed in 24 selected solvents/solvent mixtures.

a. Temperature Cycling

Figure 64:
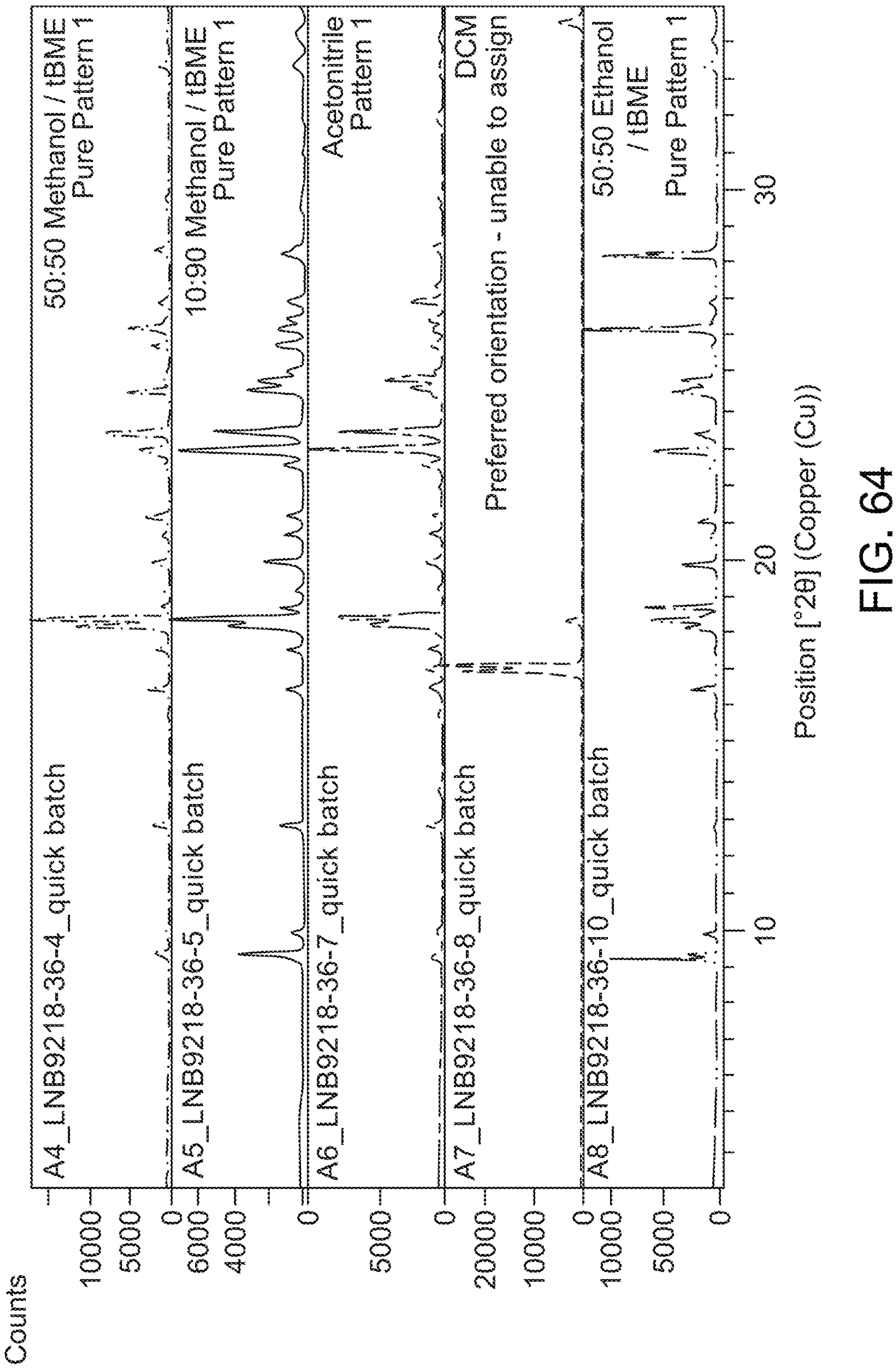
FIGS. 64-66 are the diffractograms associated with the temperature cycling experiments from the primary polymorph screen.
Figure 65:
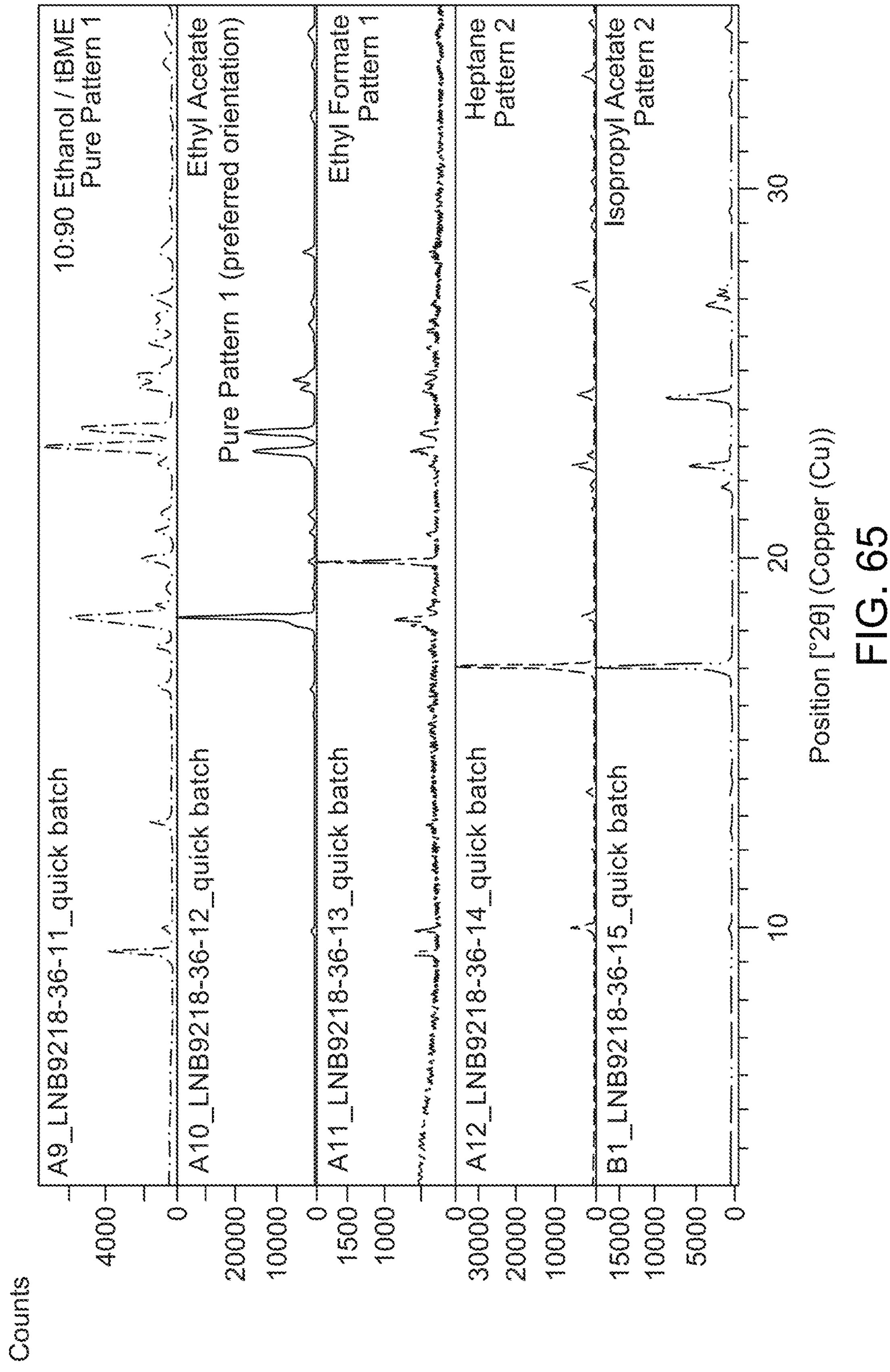
Figure 66:
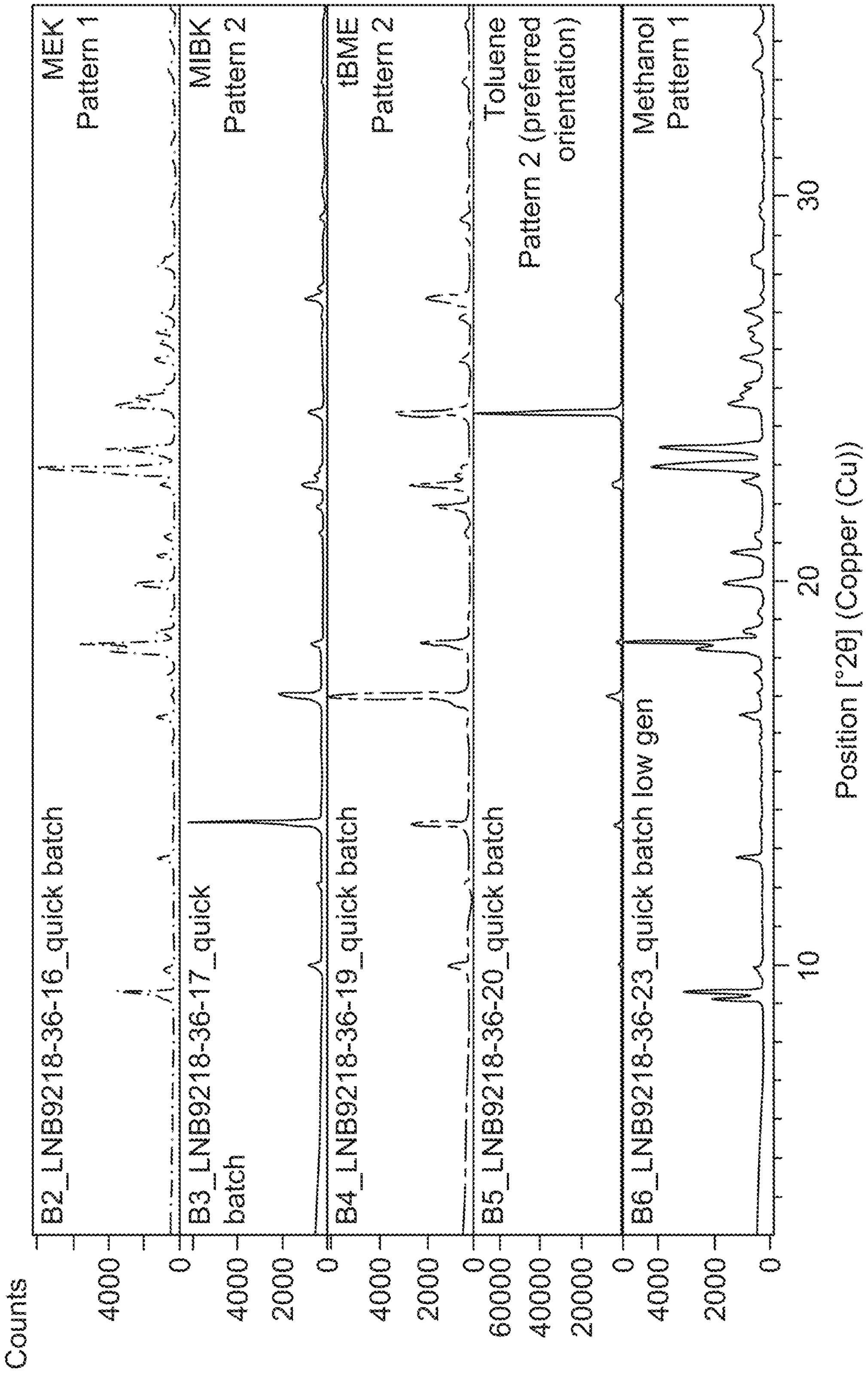

The results of the temperature cycling experiments from the primary polymorph screen are presented in Table 25. The associated diffractograms are presented in FIGS. 64-66.

CHP pure pattern 1 was recovered 50:50 methanol/MtBE, 10:90 methanol/MtBE, both ethanol/MtBE mixtures and from ethyl acetate, although some preferred orientation was evident in this sample.

Pattern 1 was returned from ethyl formate, acetonitrile, MEK and THF.

5 solvent systems produced pattern 2; heptane, isopropyl acetate, MIBK, MtBE, and toluene.

Preferred orientation in the solid produced from DCM meant that a pattern could not be assigned.

Solid was noted from chlorobenzene but was produced in insufficient quantity, therefore XRPD analysis could not be carried out.

An oil was produced in methanol.

Remaining solvent systems produced solutions, therefore no XRPD analysis could be performed.

TABLE 25

| Primary Polymorph Screen Temperature Cycling | |
|---|---|
| Solvent | Pattern |
| 1-Propanol | N/A-solution |
| 2-Propanol | N/A-solution |
| 95% Methanol:5% Water (% v/v) | N/A-solution |
| 50% Methanol:50% TBME (% v/v) | Pure Pattern 1 |
| 10% Methanol:90% TBME | Pure Pattern 1 |
| Acetone | N/A-solution |
| Acetonitrile | Pattern 1 |
| Dichloromethane | Preferred orientation-unable to assign |
| Ethanol | N/A-solution |
| 50% Ethanol/50% TBME (% v/v) | Pure Pattern 1 |
| 10% Ethanol/90% TBME | Pure Pattern 1 |
| Ethyl Acetate | Pure Pattern 1 (preferred orientation) |
| Ethyl Formate | Pattern 1-poorly crystalline |
| Heptane | Pattern 2 |
| Isopropyl Acetate | Pattern 2 |
| Methylethyl Ketone | Pattern 1 |
| Methylisobutyl Ketone | Pattern 2 |
| Nitromethane | N/A-solution |
| tert-Butylmethyl Ether | Pattern 2 |
| Toluene | Pattern 2 (preferred orientation) |
| Trifluoroethanol | N/A-solution |
| Chlorobenzene | N/A-insufficient solid |
| THF | Pattern 1 |
| Methanol | N/A-oil |

b. Evaporation

Figure 67:
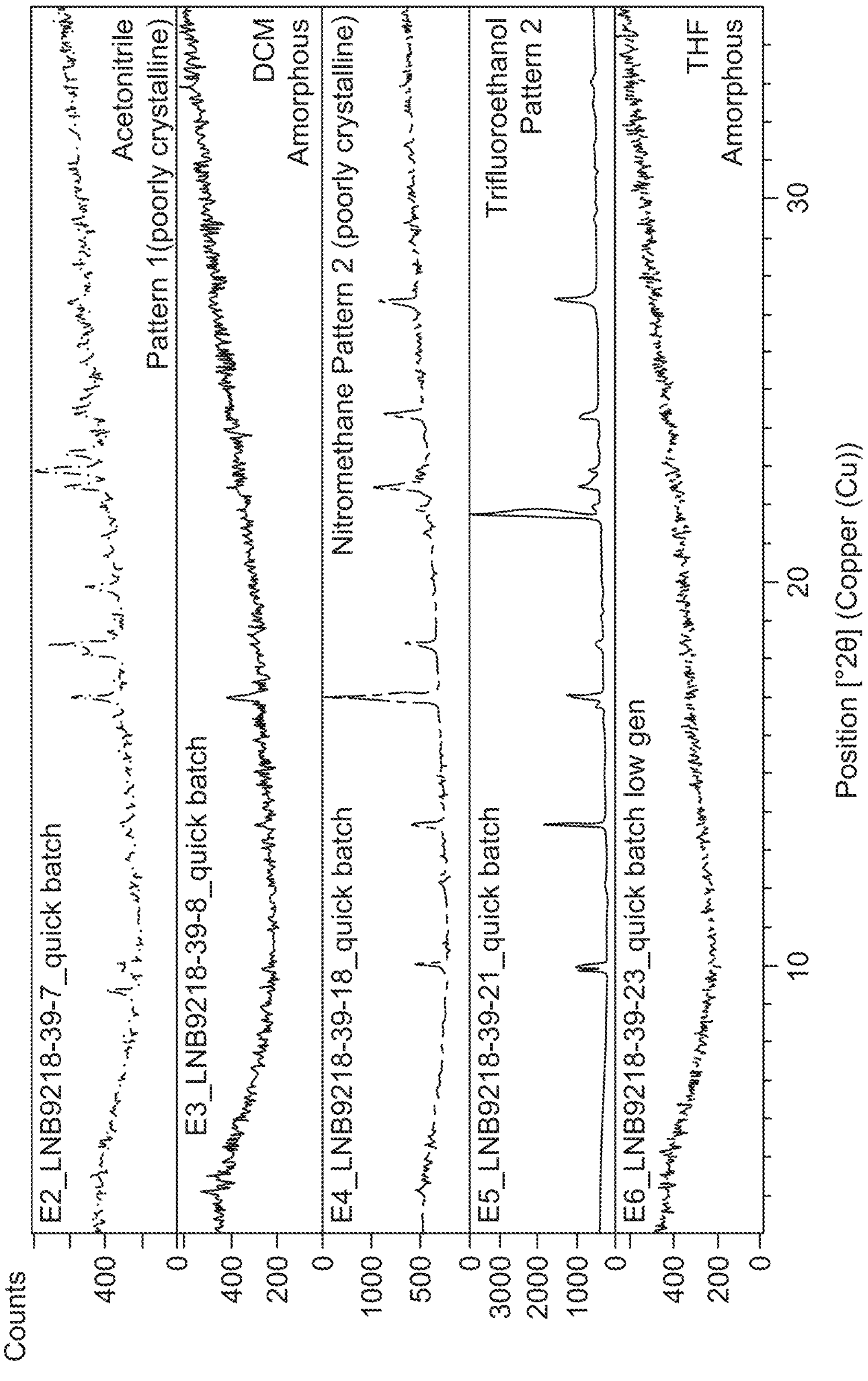
FIG. 67 is the diffractogram associated with the evaporation experiments from the primary polymorph screen.

The results of the evaporation experiments from the primary polymorph screen are presented in Table 26 and FIG. 113. The associated diffractograms are presented in FIG. 67.

- Poorly crystalline pattern 1 was returned from acetonitrile.
- Pattern 2 was produced twice, once from Trifluoroethanol and also from nitromethane.
- Amorphous material was identified from DCM and THF.
- Solid was noted from 10:90 ethanol/MtBE, 50:50 ethanol/MtBE, MIBK and ethanol but was produced in insufficient quantity, therefore XRPD analysis could not be carried out.
- The majority of solvent systems produced a colorless film on the vial wall which could not be analyzed by XRPD.

TABLE 26

| Primary Polymorph Screen Evaporations | |
|---|---|
| Solvent | Pattern |
| 1-Propanol | N/A-colourless film on vial wall |
| 2-Propanol | N/A-colourless film on vial wall |
| 95% Methanol:5% Water (% v/v) | N/A-colourless film on vial wall |
| 50% Methanol:50% TBME (% v/v) | N/A-no solution after temp cycling |
| 10% Methanol/90% TBME | N/A-insufficient solid |
| Acetone | N/A-oily residue on vial wall |
| Acetonitrile | Pattern 1 (poorly crystalline) |
| Dichloromethane | amorphous |
| Ethanol | N/A-insufficient solid |
| 50% Ethanol/50% TBME (% v/v) | N/A-insufficient solid |
| 10% Ethanol/90% TBME | N/A-colourless film on vial wall |
| Ethyl Acetate | N/A-colourless film on vial wall |
| Ethyl Formate | N/A-colourless film on vial wall |
| Heptane | N/A-colourless film on vial wall |
| Isopropyl Acetate | N/A-colourless film on vial wall |
| Methylethyl Ketone | N/A-colourless film on vial wall |
| Methylisobutyl Ketone | N/A-insufficient solid |
| Nitromethane | Pattern 2 (poorly crystalline) |
| tert-Butylmethyl Ether | N/A-colourless film on vial wall |
| Toluene | N/A-colourless film on vial wall |
| Trifluoroethanol | Pattern 2 |
| Chlorobenzene | N/A-colourless film on vial wall |
| THF | amorphous |
| Methanol | N/A-oil produced after temp cycle |

c. Crash Cool

Table 27 shows the results obtained from crash cooling at both 2-8° C. and −20° C. from the primary polymorph screen.

- Crash cool experiments were not performed in 50:50 methanol/MtBE and methanol due to insufficient mother liquor production from temperature cycling.
- The remaining experiments produced solutions only, therefore no XRPD analysis could be performed.

TABLE 27

| Primary Polymorph Screen Crash Cool | | |
|---|---|---|
| Solvent | Pattern (2-8° C.) | Pattern (−20° C.) |
| 1-Propanol | solution | solution |
| 2-Propanol | solution | solution |
| 95% Methanol:5% Water (% v/v) | solution | solution |
| 50% Methanol:50% TBME (% v/v) | N/A-no solution after temp cycle | N/A-no solution after temp cycle |
| 10% Methanol/90% TBME | solution | solution |
| Acetone | solution | solution |
| Acetonitrile | solution | solution |
| Dichloromethane | solution | solution |
| Ethanol | solution | solution |
| 50% Ethanol/50% TBME (% v/v) | solution | solution |
| 10% Ethanol/90% TBME | solution | solution |
| Ethyl Acetate | solution | solution |
| Ethyl Formate | solution | solution |
| Heptane | solution | solution |
| Isopropyl Acetate | solution | solution |
| Methylethyl Ketone | solution | solution |
| Methylisobutyl Ketone | solution | solution |
| Nitromethane | solution | solution |
| tert-Butylmethyl Ether | solution | solution |
| Toluene | solution | solution |
| Trifluoroethanol | solution | solution |
| Chlorobenzene | solution | solution |
| THF | solution | solution |
| Methanol | N/A-oil produced after temp cycle | N/A-oil produced after temp cycle |

d. Anti-Solvent Addition

Figure 68:
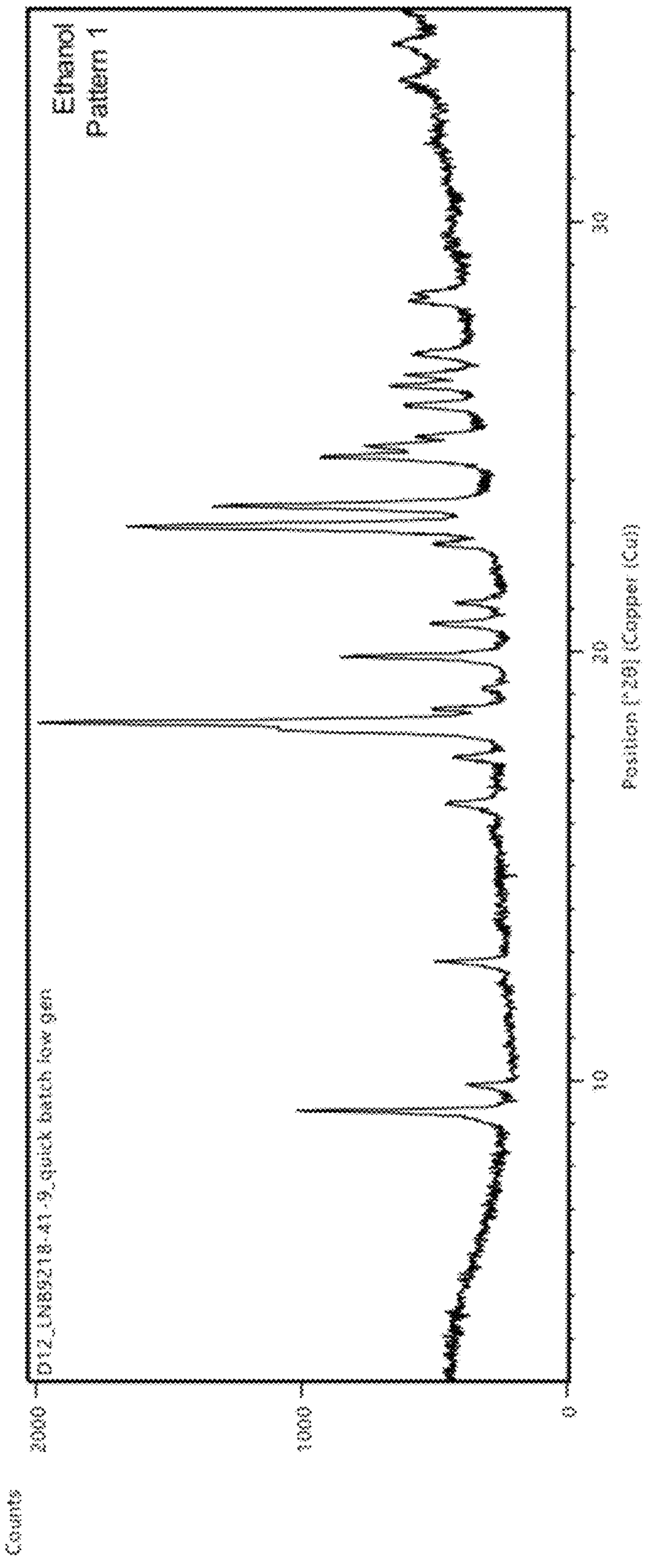
FIG. 68 is the diffractogram associated with the anti-solvent addition from the primary polymorph screen.

Table 28 shows the results obtained from anti-solvent addition from the primary polymorph screen. The associated diffractogram is presented in FIG. 68.

- Insufficient solids were produced in acetone, DCM, and 50:50 ethanol/MtBE
- Pattern 1 (from ethanol) was the only pattern observed in the anti-solvent addition experiments.
- No anti-solvent experiments were performed 50:50 methanol/MtBE and methanol due to insufficient mother liquor production from temperature cycling.

TABLE 28

| Primary Polymorph Screen Anti-Solvent Addition | | |
|---|---|---|
| Solvent | Anti-Solvent | Pattern |
| 1-Propanol | tBME | N/A-solution |
| 2-Propanol | tBME | N/A-solution |
| 95% Methanol:5% Water (% v/v) | tBME | N/A-solution |
| 50% Methanol:50% TBME (% v/v) | N/A | N/A-no solution after temp cycle |
| 10% Methanol/90% TBME | tBME | N/A-solution |
| Acetone | tBME | N/A-insufficient solid |
| Acetonitrile | tBME | N/A-solution |
| Dichloromethane | tBME | N/A-insufficient solid |
| Ethanol | tBME | Pattern 1 |
| 50% Ethanol/50% TBME (% v/v) | tBME | N/A-insufficient solid |
| 10% Ethanol/90% TBME | tBME | N/A-solution |
| Ethyl Acetate | tBME | N/A-solution |
| Ethyl Formate | acetone | N/A-solution |
| Heptane | tBME | N/A-solution |
| Isopropyl Acetate | tBME | N/A-solution |
| Methylethyl Ketone | tBME | N/A-solution |
| Methylisobutyl Ketone | tBME | N/A-solution |
| Nitromethane | tBME | N/A-solution |
| tert-Butylmethyl Ether | heptane | N/A-solution |
| Toluene | tBME | N/A-solution |
| Trifluoroethanol | tBME | N/A-solution |
| Chlorobenzene | tBME | N/A-solution |
| THF | tBME | N/A-solution |
| Methanol | N/A | N/A-oil produced after temp cycle |

2. Primary Polymorph Screen Summary

FIG. 114 present a summary of the results from the primary polymorph screen.

The primary polymorph screen identified 1 new form of CHP, assigned as pure pattern 1 and was produced after temperature cycling. Pattern 1 and 2 were also reproduced in multiple solvent systems from temperature cycling. Crash cooling experiments at both 2-8° C. and −20° C. returned clear solutions only. The majority of solvent systems returned clear solutions in anti-solvent addition experiments but pattern 1 was seen from ethanol after addition of MtBE 3. Secondary Polymorph Screen Scale-Up of Pattern 2

Figure 69:
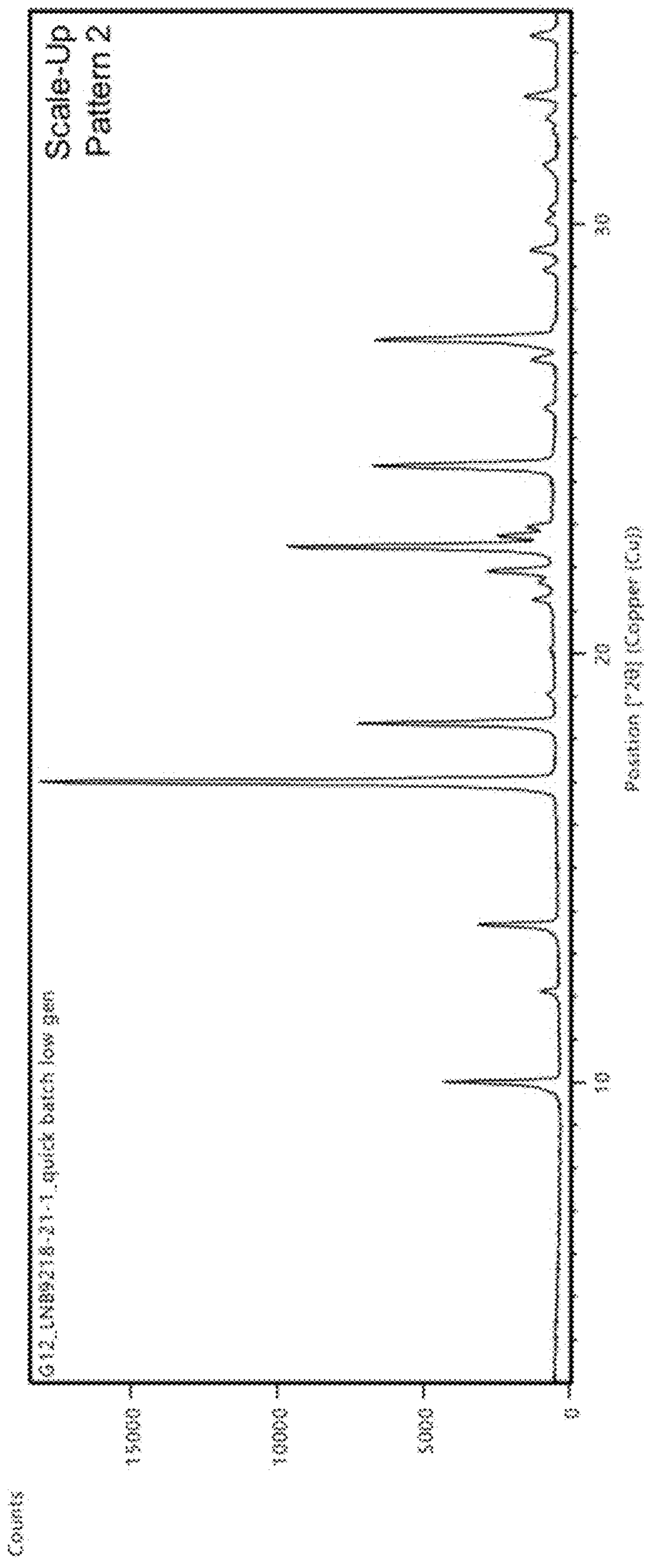
FIG. 69 is the XRPD results of pattern 2 scale-up.

FIG. 69 shows the XRPD results of pattern 2 scale-up. XRPD diffractogram confirmed pattern 2 formation.

Scale-Up of Pure Pattern 1

80° C. heating of Pattern 2

Figure 70:
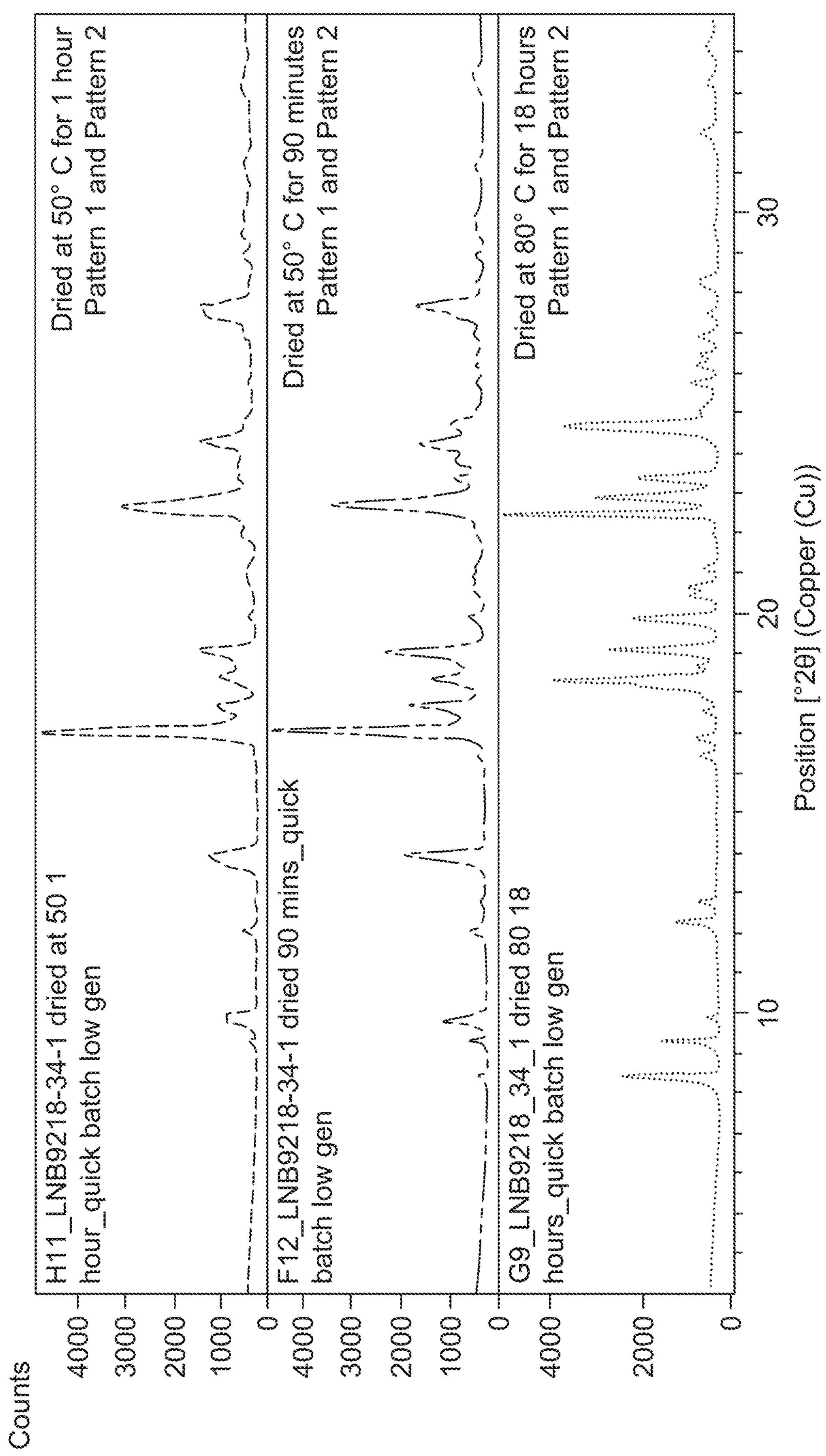
FIG. 70 is the XRPD diffractogram of the material obtained when Pattern 2 material was heated to 80° C.

Pure pattern 1 was not successfully produced in this experiment. A mixture of pattern 1 and pattern 2 was returned at both 50° C. and 80° C. A previously unseen peak at 8° 2 Θ appeared after the sample was held at 50° C. for 90 minutes. This peak increased in intensity after 18 hours at 80° C. Associated diffractograms can be seen in FIG. 70.

Fast Rotary Evaporation in Ethanol/DCM

Figure 71:
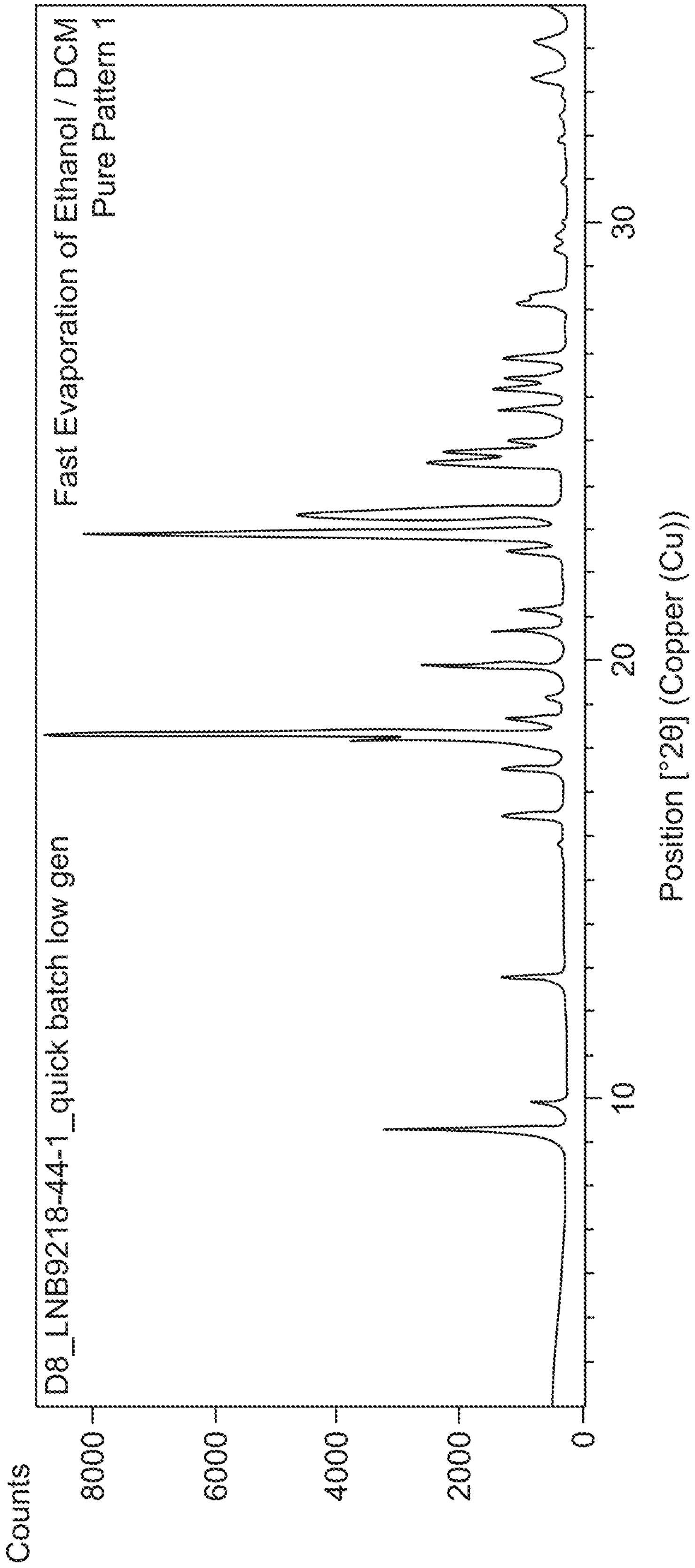
FIG. 71 is the XRPD diffractogram of the recovered solids of the fast rotary evaporation in ethanol/DCM experiment.

Analysis of the recovered solids from the fast evaporation of ethanol/DCM indicated that the material was pure pattern 1 by XRPD. The diffractogram is in FIG. 71.

Characterization of Pattern 2

Figure 72:
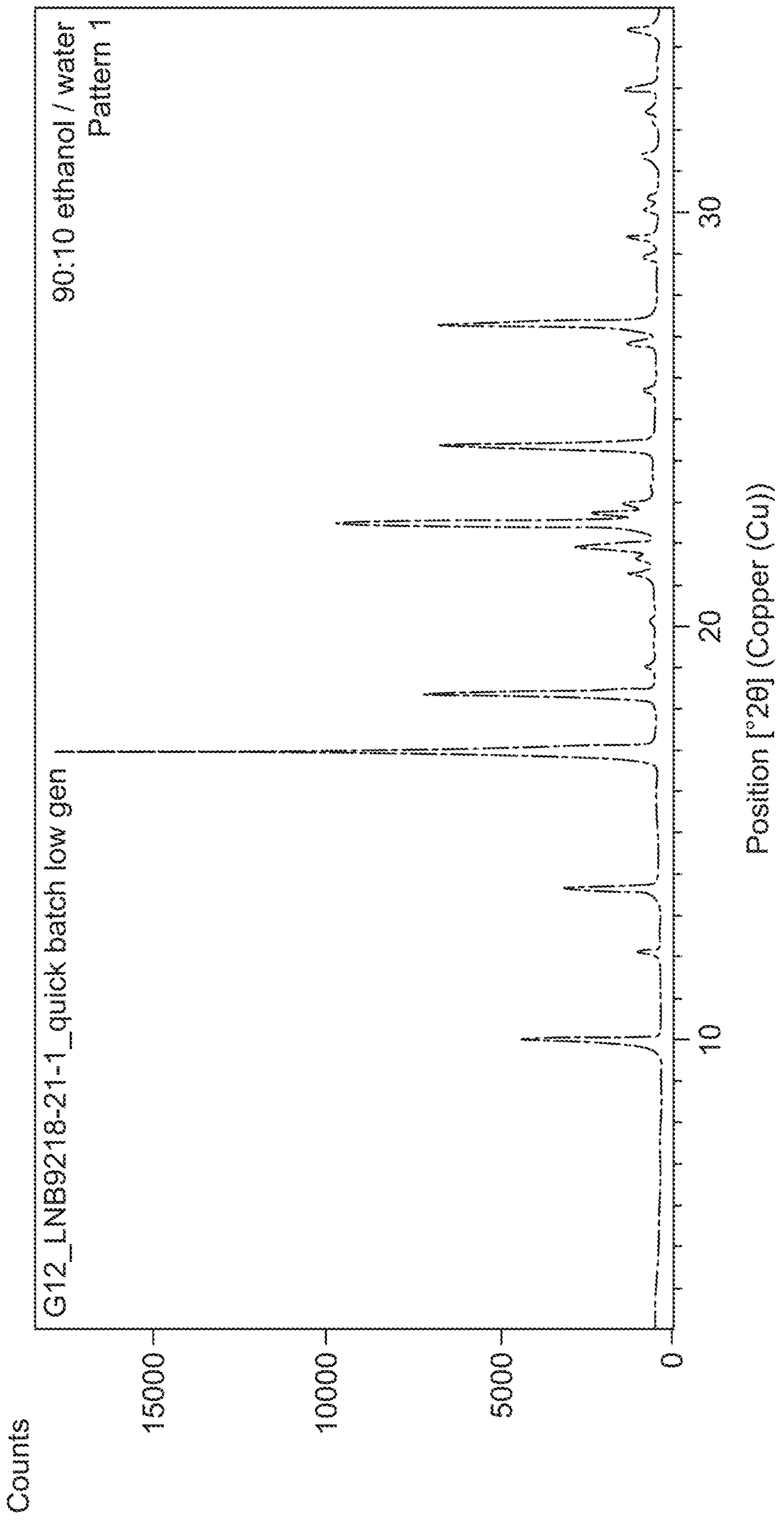
FIG. 72 is the XRPD diffractogram of the primary polymorph screen of Pattern 2.

Analysis of CHP pattern 2 from 90:10 ethanol/water yielded the following results:

The material was crystalline by XRPD and matched that of the pattern 2 diffractograms obtained in the primary polymorph screen (FIG. 72).

Figure 73:
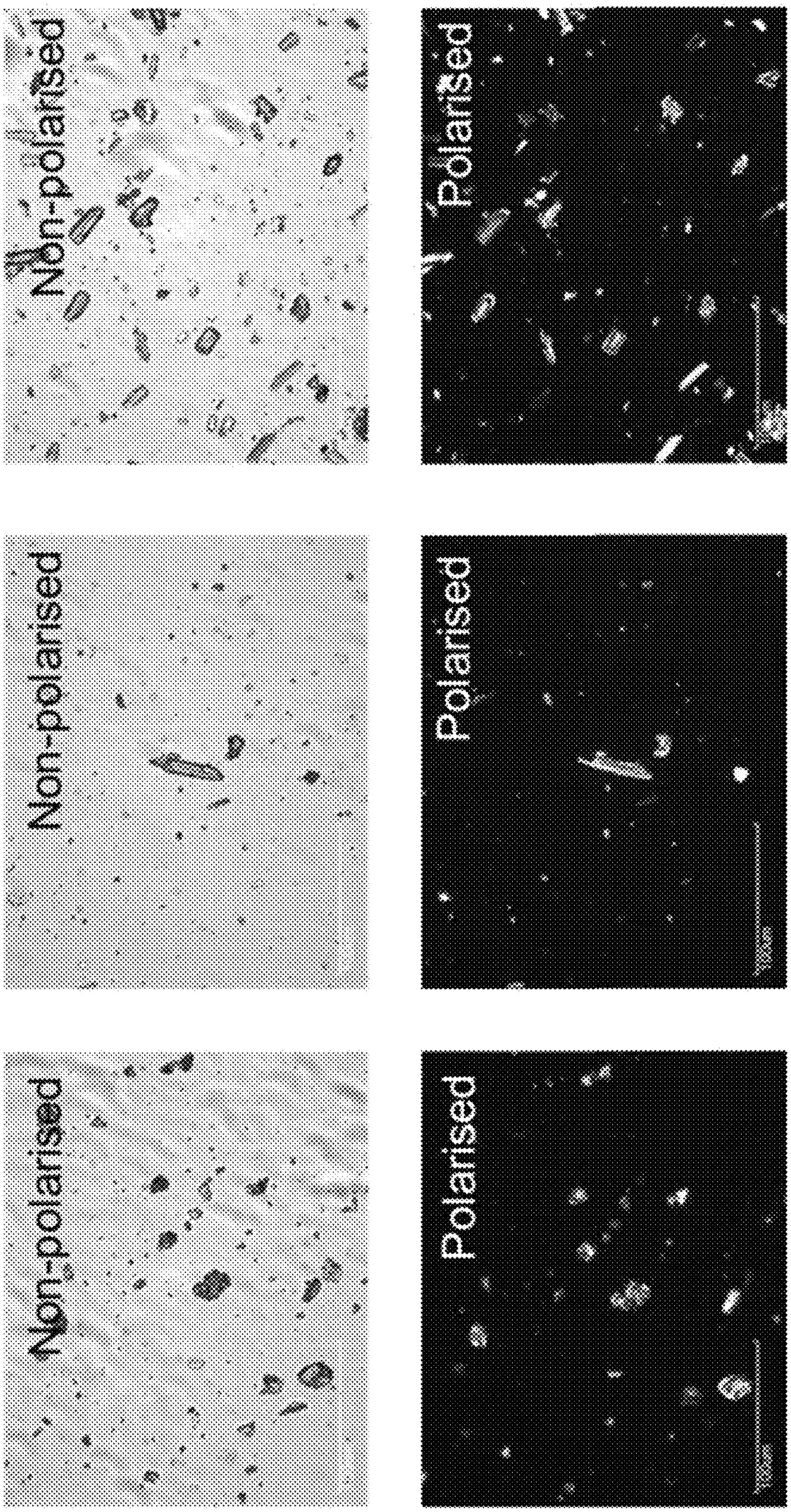
FIG. 73 is the images in polarized and non-polarized light of Pattern 2.

PLM images were also taken of CHP pattern 2 and the material was found to be birefringent with a fragmented, rod-like morphology. Images in polarized and non-polarized light can be seen in FIG. 73.

Figure 74:
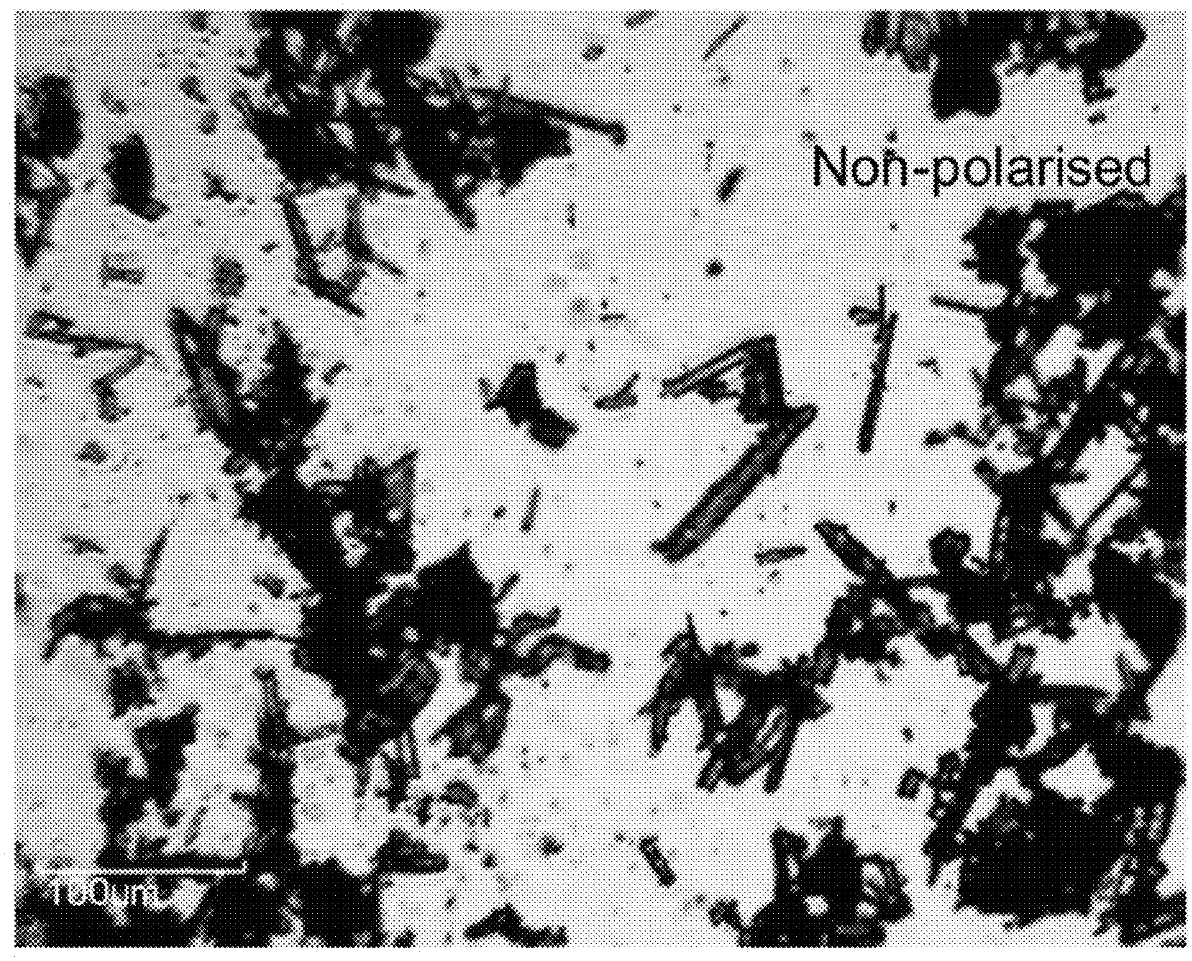
FIG. 74 is the hot stage microscopy of CHP pattern 2.
Figure 75:
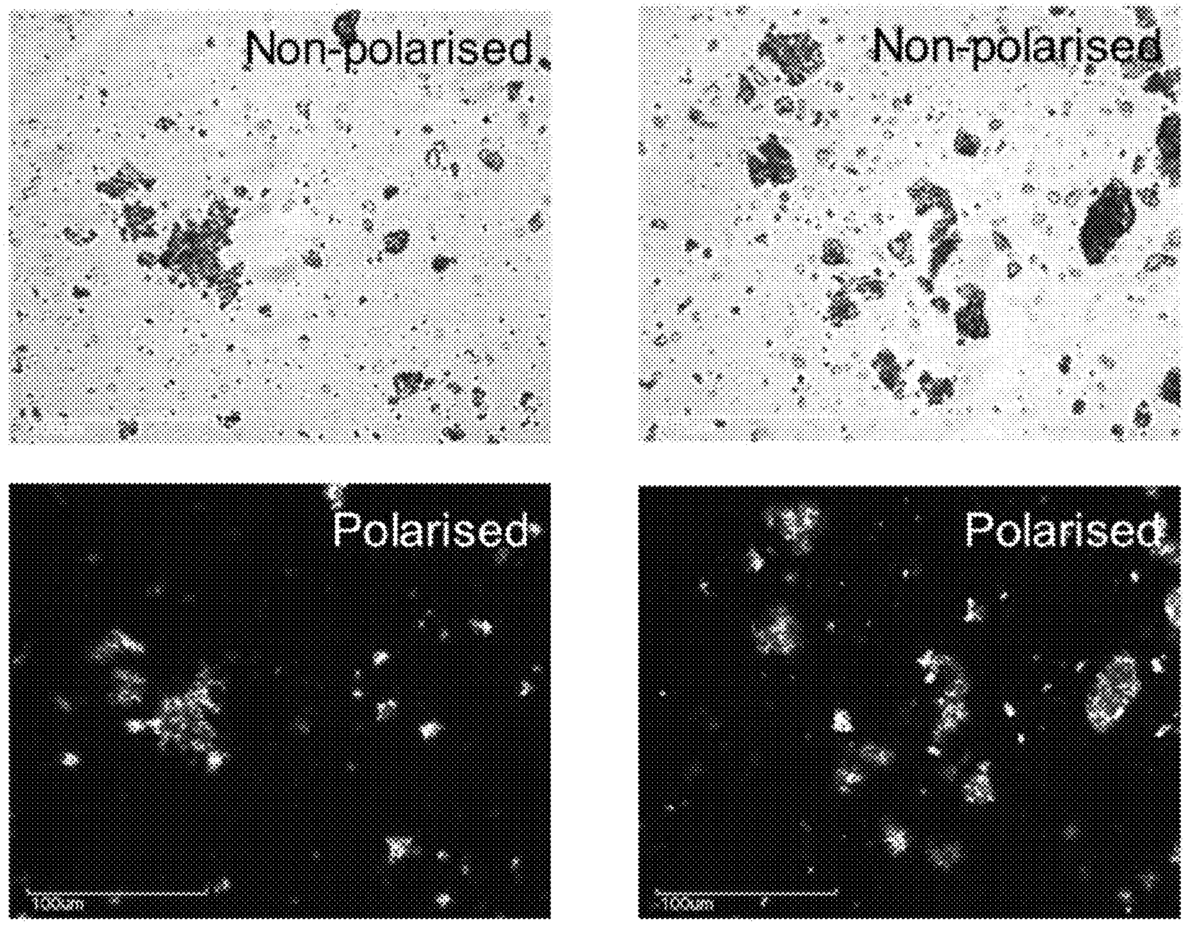
FIG. 75 is the polarized and non-polarized images of the material post-hot stage.

Hot stage microscopy was also performed on CHP pattern 2. Initial image identified a rod-like morphology (FIG. 74). This was consistent with the images from PLM analysis in FIG. 69. The material was observed to start melting at 95° C. and had fully melted at 101° C. A re-crystallization was observed to occur at 115° C. PLM images taken post-hot stage show that the material morphology was no longer clearly defined but the sample was still birefringent. Polarized and non-polarized images of the material post-hot stage can be seen in FIG. 75.

Figure 76:
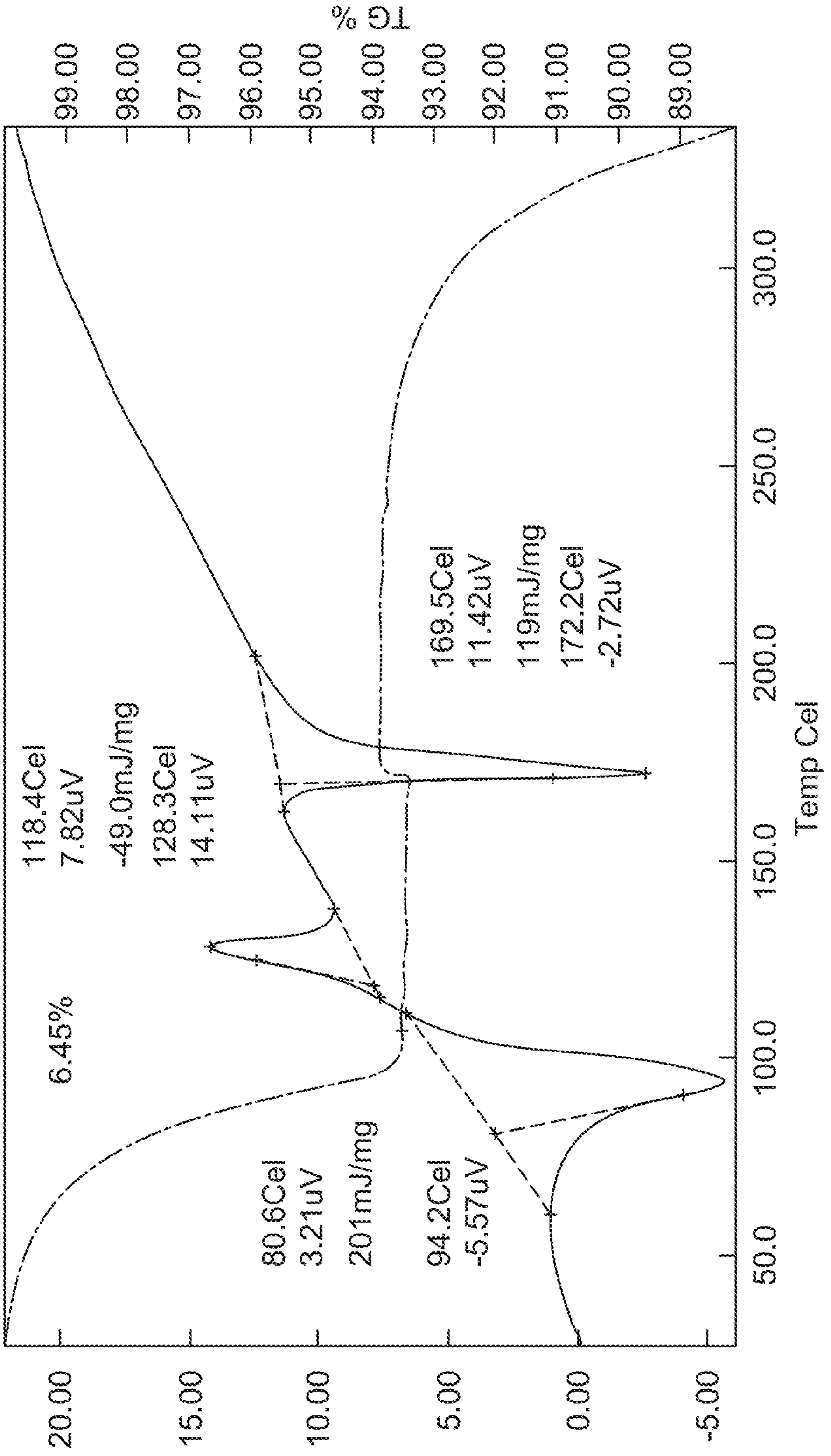
FIG. 76 is the TG/DTA—TG analysis of Pattern 2.

TG/DTA—TG analysis showed an initial weight loss of 6.5% followed by sample degradation at 280° C. (0.9 equivalents of water). The DT trace identified an endothermic event associated with the initial weight loss. This was followed by an exothermic event, most likely a re-crystallization of the material, before a second endotherm (sample melt) was observed at 170° C. (FIG. 76).

Figure 77:
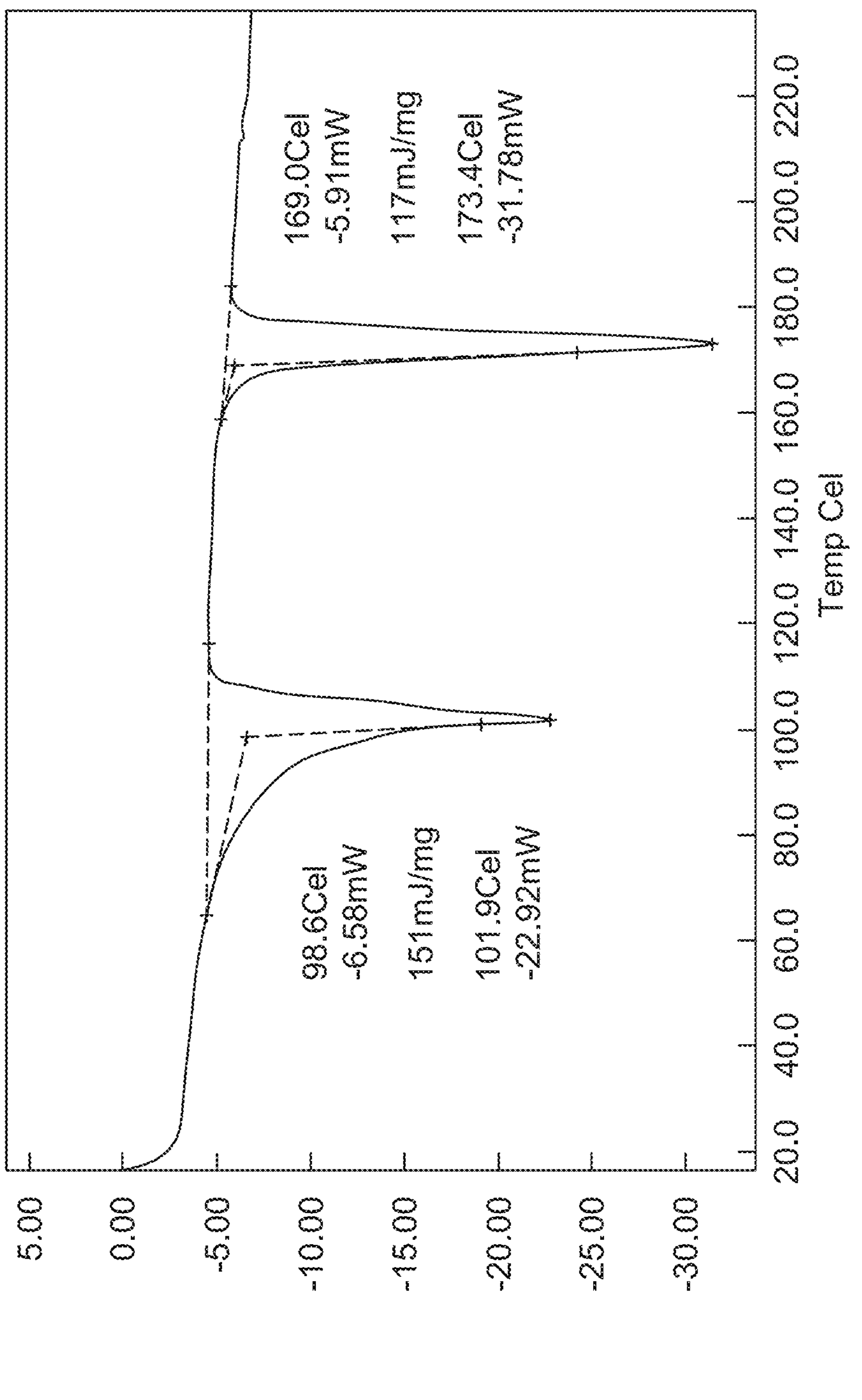
FIG. 77 is the initial heat cycle of the DSC identified an endothermic event with an onset of 99° C. and a peak at 102° C.
Figure 78:
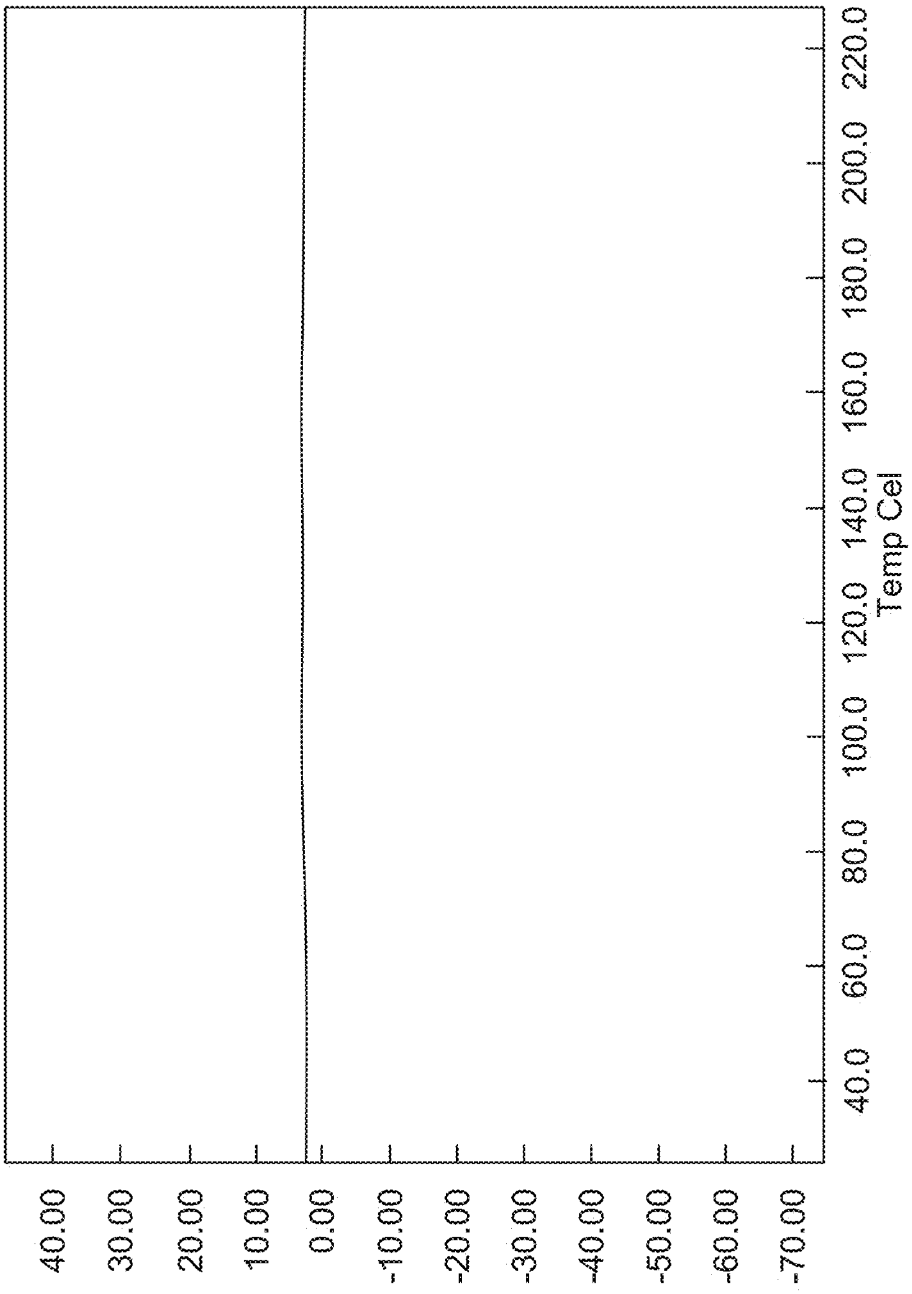
FIG. 78 is the cooling cycle of the DSC.
Figure 79:
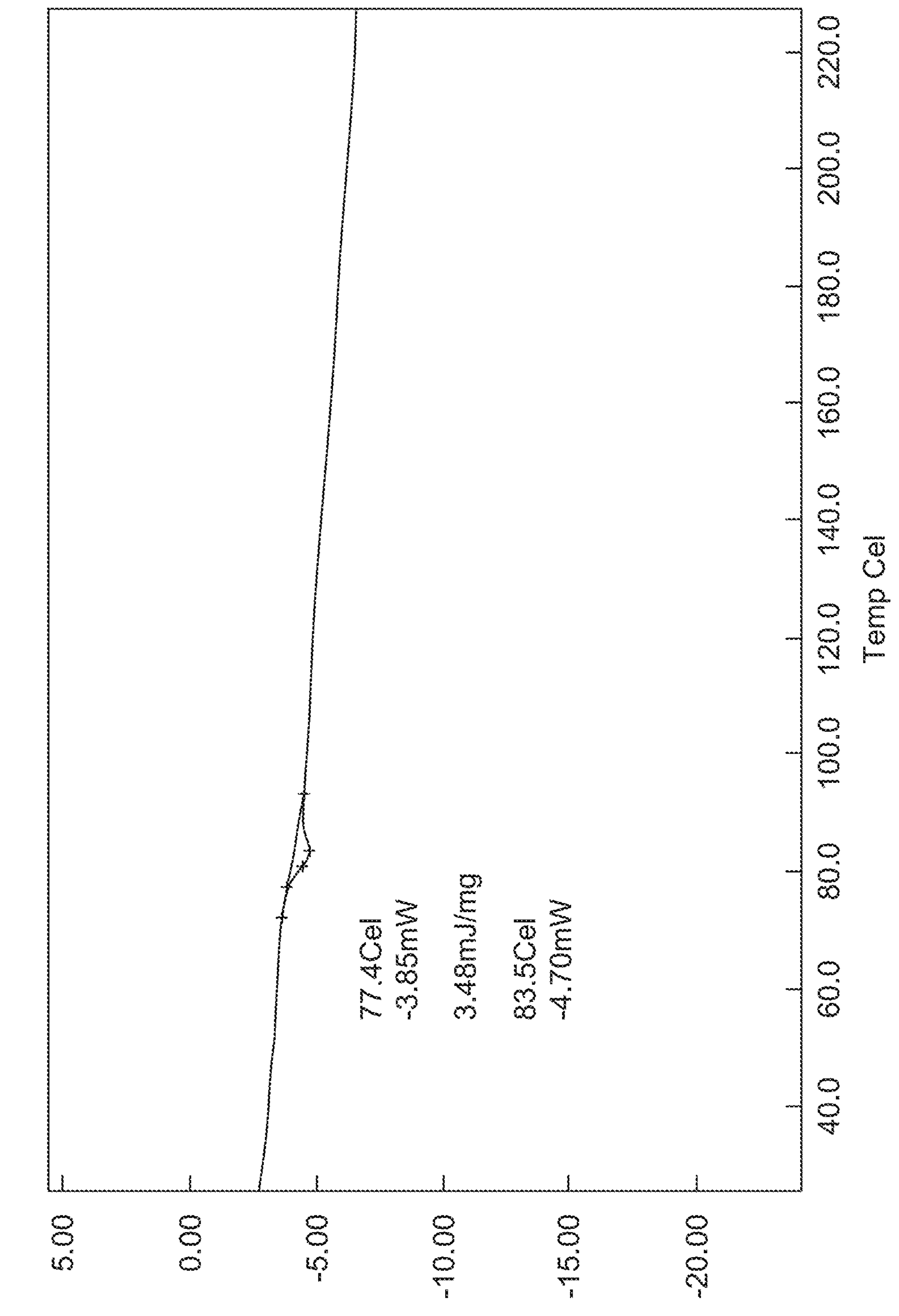
FIG. 79 is the second heating cycle of the DSC.

The initial heat cycle of the DSC identified an endothermic event with an onset of 99° C. and a peak at 102° C. (FIG. 77). This was consistent with the endotherm data observed in the TGA, although the re-crystallization event seen in the TGA was not present in the DSC. No thermal events were observed in the cool cycle (FIG. 78). The second heat cycle identified a possible glass transition at 75° C. (FIG. 79).

Figure 80:
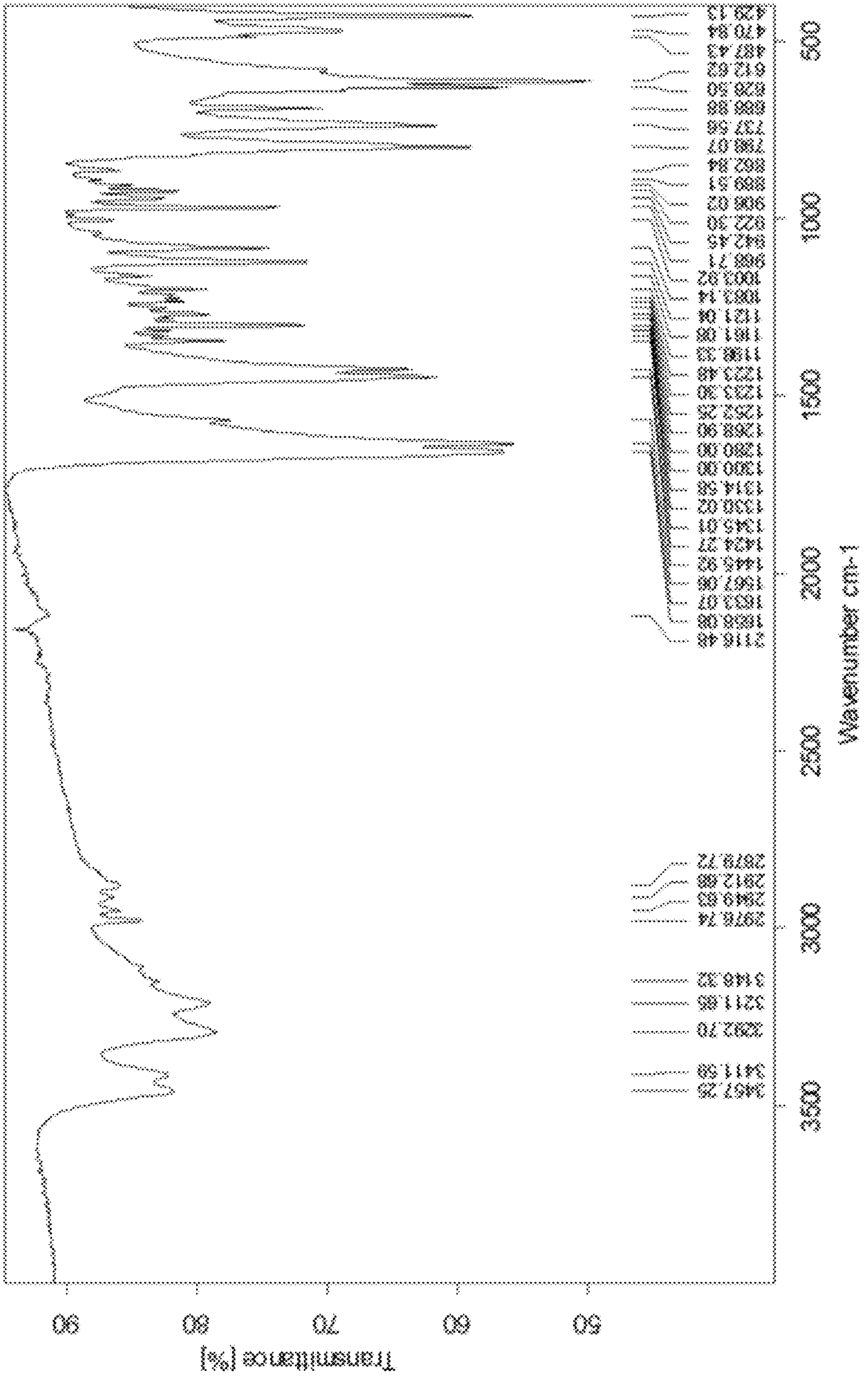
FIG. 80 is the FT-IR spectra of CHP pattern 2.

FIG. 80 displays the FT-IR spectra of CHP pattern 2. A peak table can be found in Table 29.

Figure 81:
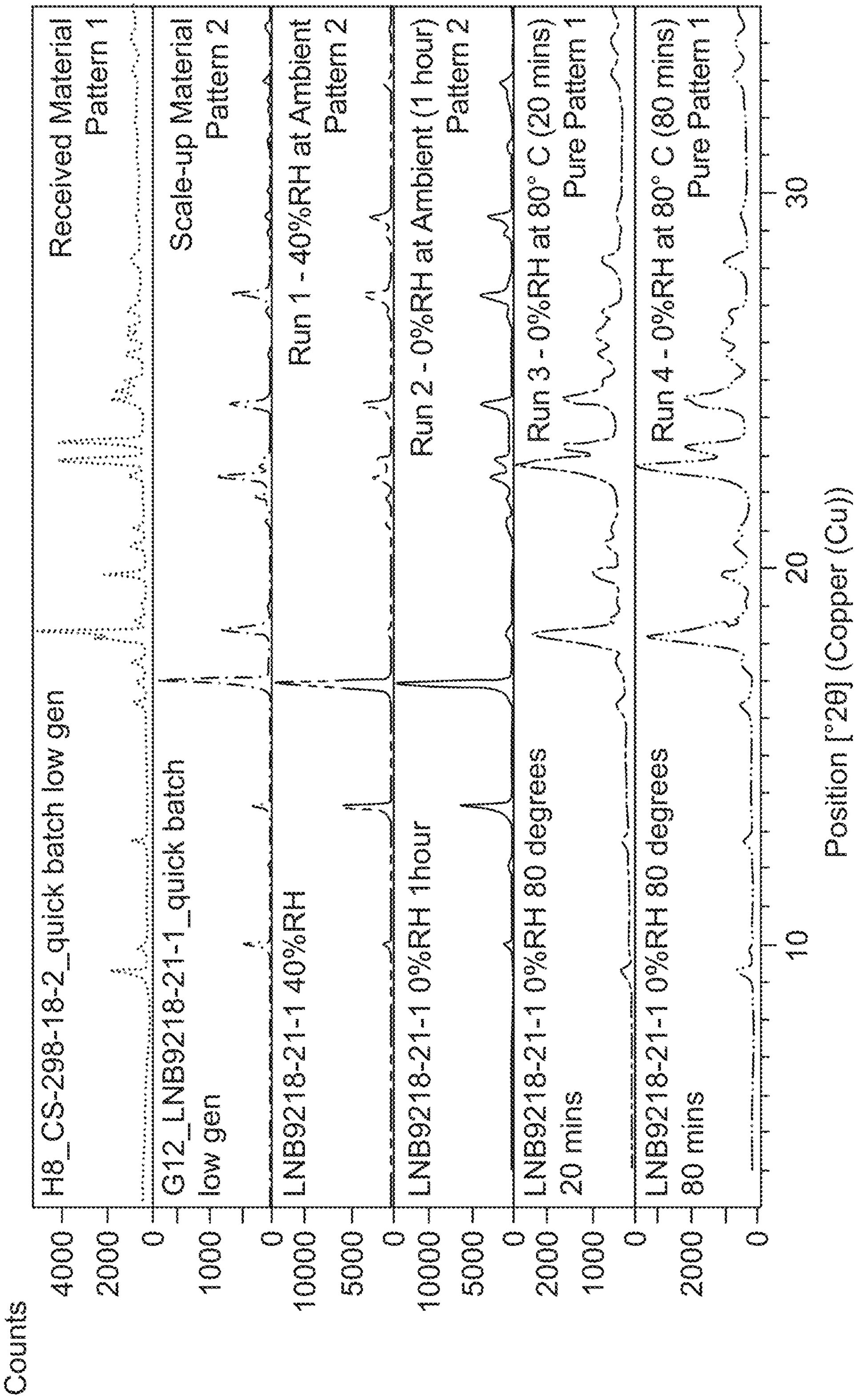
FIG. 81 is the diffractogram associated with the VT-/VH-XRPD analysis.

VT-/VH-XRPD analysis: Pattern 2 input material remained when the humidity was lowered to 0% at ambient temperature. As the temperature was increased to 80° C., the material changed form which was assigned as pure pattern 1. Pure pattern 1 remained when held at 80° C. for 80 minutes. Table 30 shows the humidity, temperature and pattern identity at each step. Associated diffractogram can be seen in FIG. 81.

Figure 82:
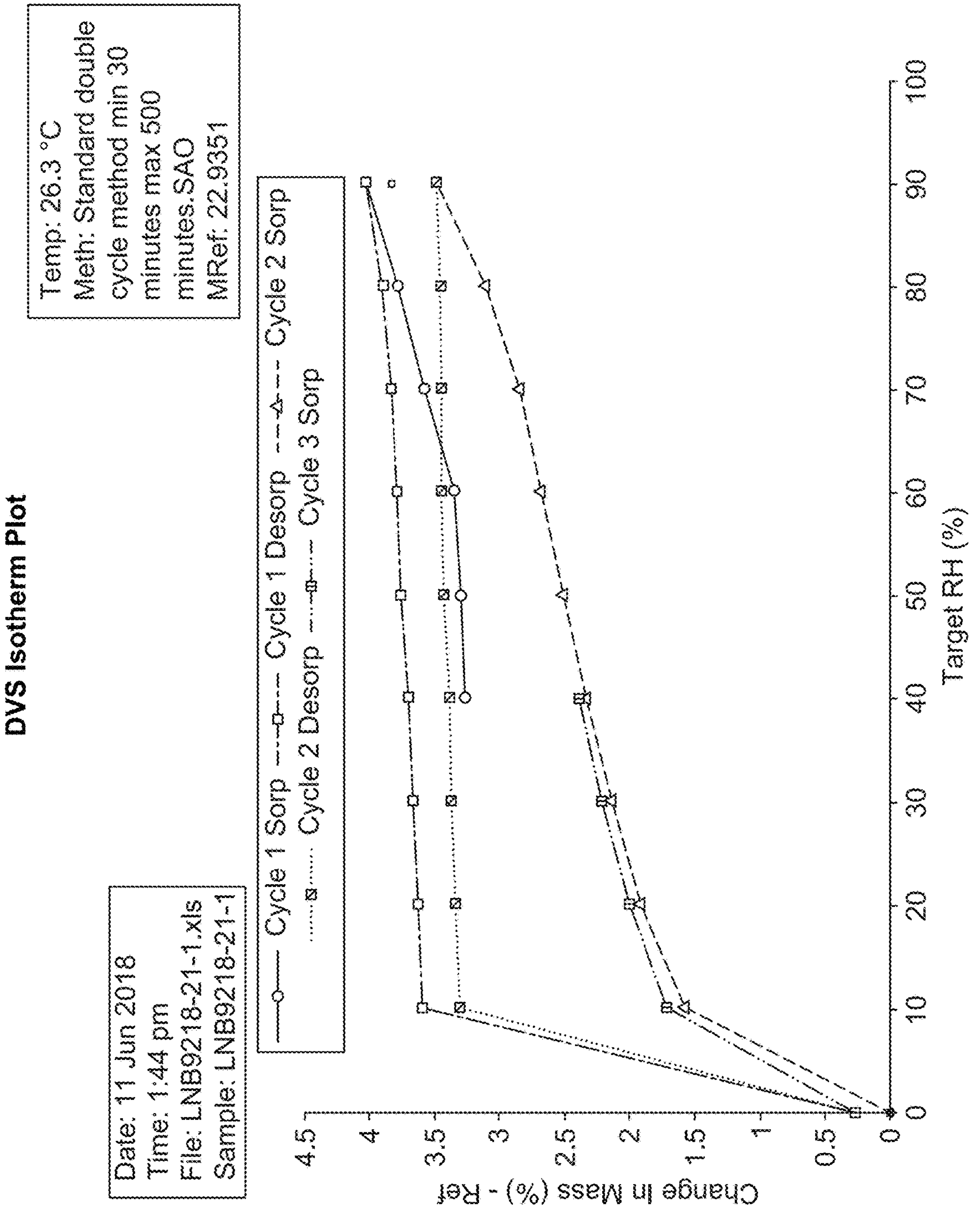
FIG. 82 is the DVS isotherm plot of CHP pattern 2.
Figure 83:
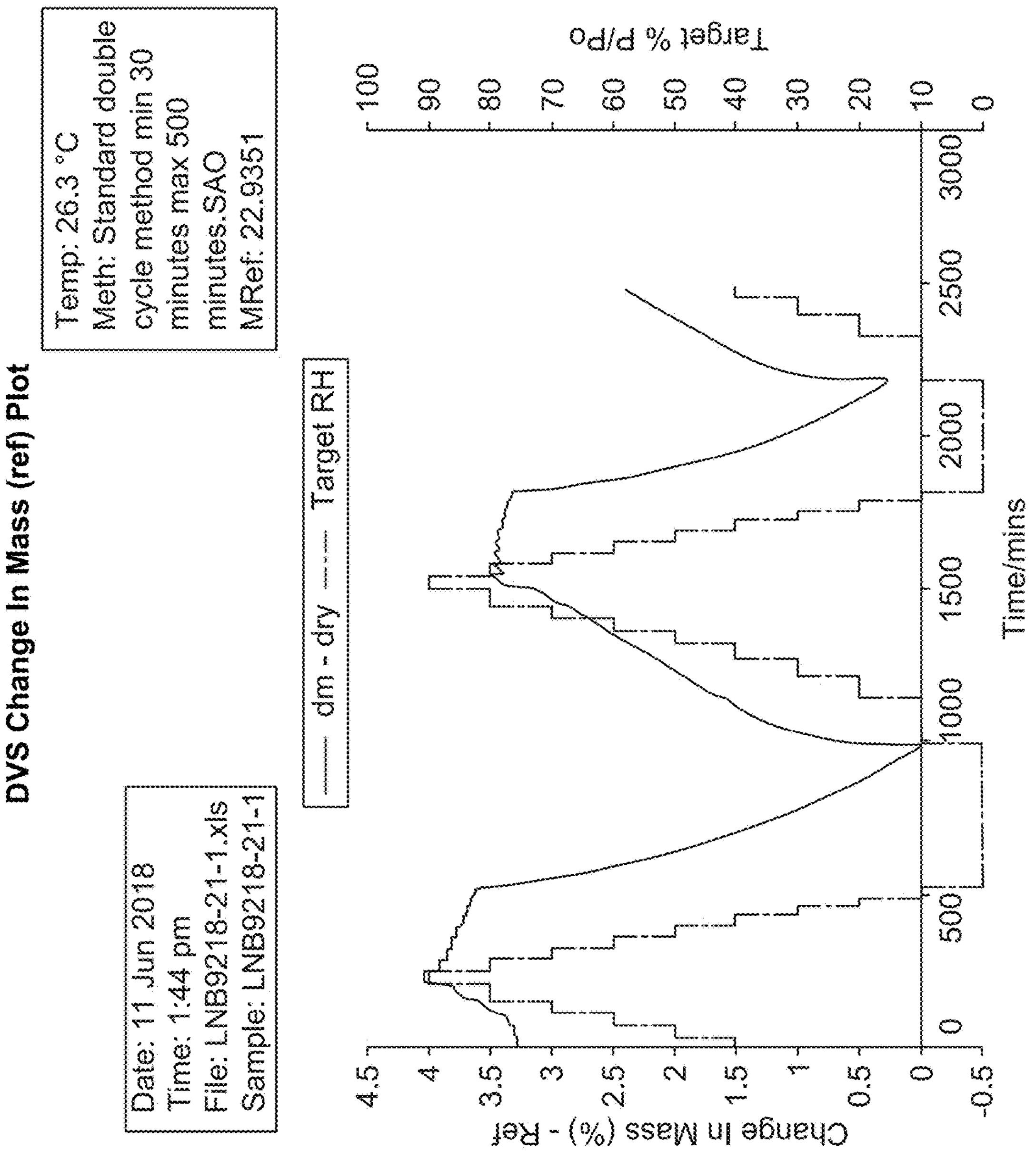
FIG. 83 is the DVS kinetic plot of CHP pattern 2.
Figure 84:
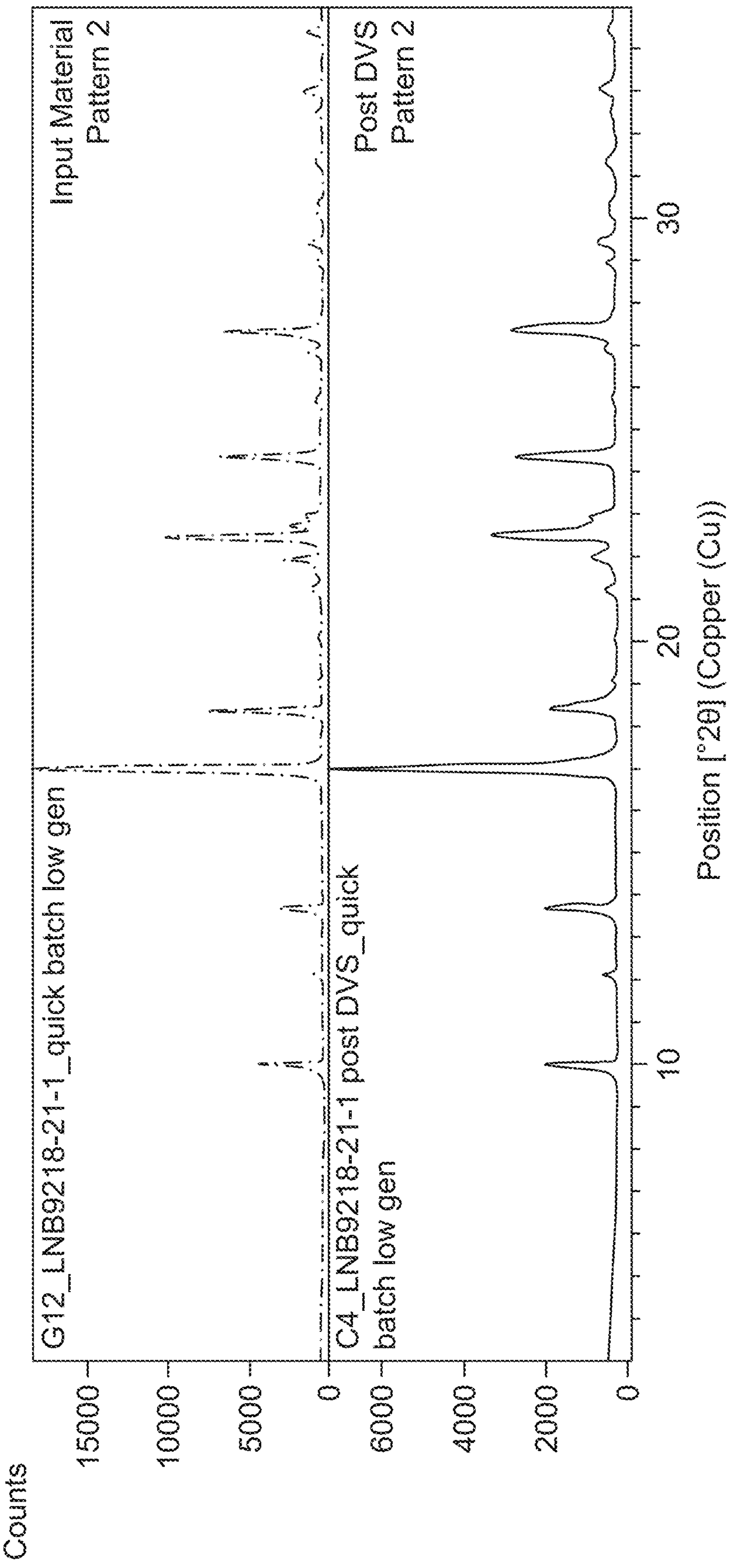
FIG. 84 illustrates the comparison XRPD diffractograms.

DVS analysis of CHP pattern 2 showed that the material did not change form from 40% RH to 90% RH or from 90% RH to 10% RH but loses 3.5 wt. % (0.5 equiv. water) below 10% RH. Rehydration was noted to occur from 0 to 90% RH. This can be seen in the DVS isotherm plot in FIG. 82. FIG. 83 shows the DVS kinetic plot. XRPD analysis post-DVS showed no change in form at 40% RH. Comparison XRPD diffractograms can be seen in FIG. 84. The non-stoichiometric water loss observed in this experiment was thought to be attributed to the ambient temperature (ca 25° C.), with the kinetics of the dehydration being too slow, and thus the instrument moving to the next stage before complete. To investigate this further, variable temperature DVS experiments were carried out, detailed below.

Figure 85:
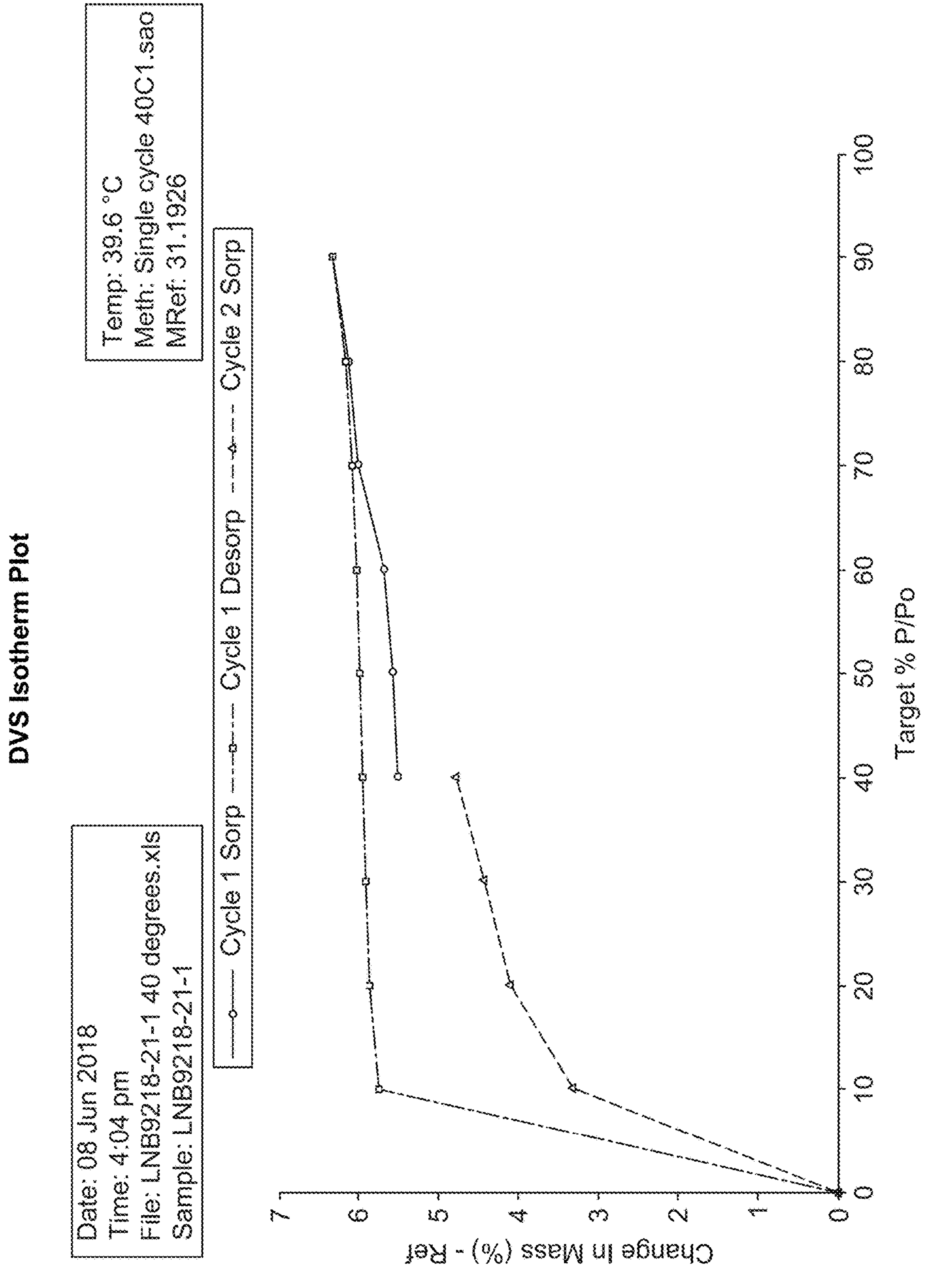
FIG. 85 is the DVS isotherm plot of Pattern 2 at 40° C.
Figure 86:
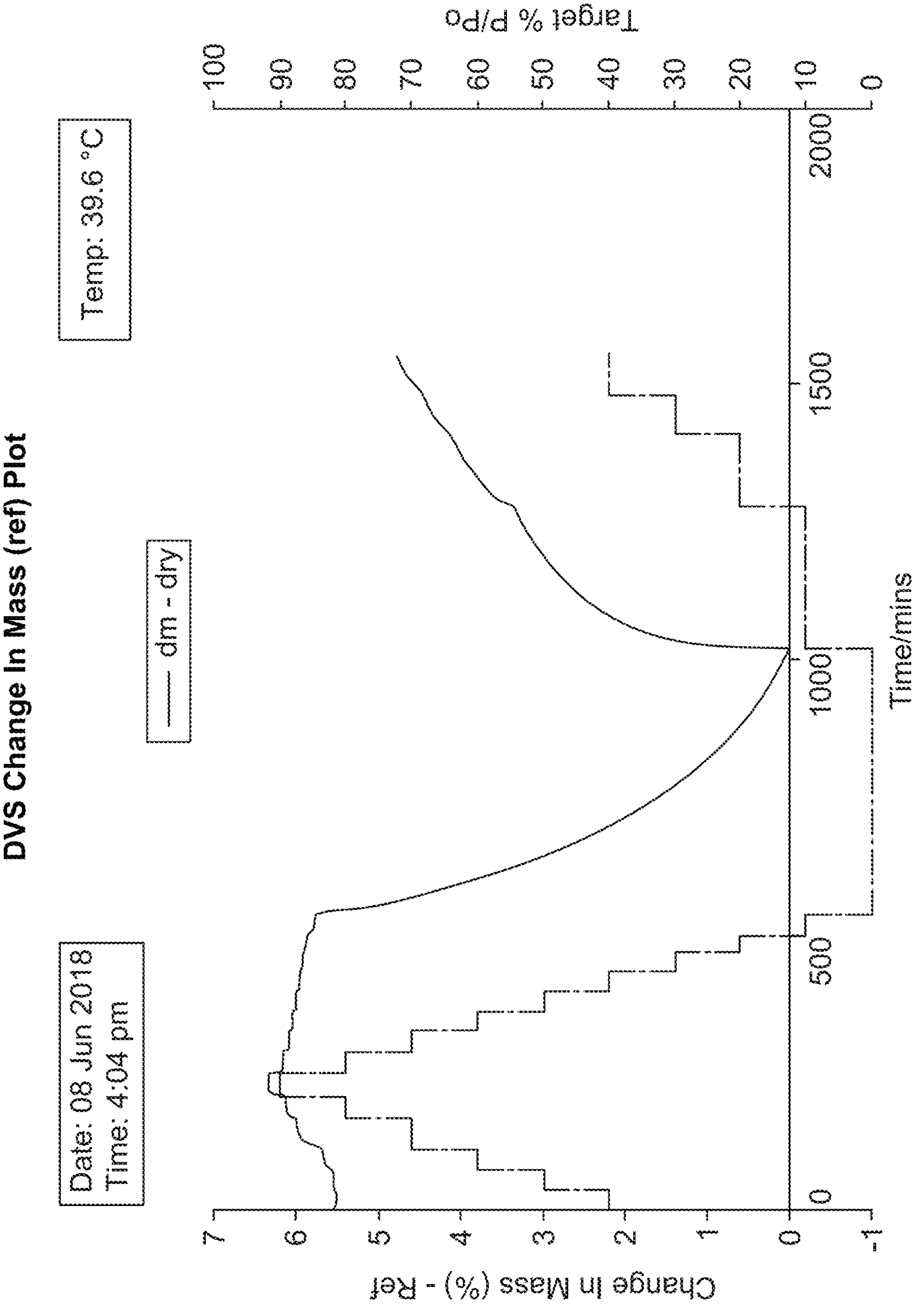
FIG. 86 is the kinetic plot of Pattern 2 at 40° C.
Figure 87:
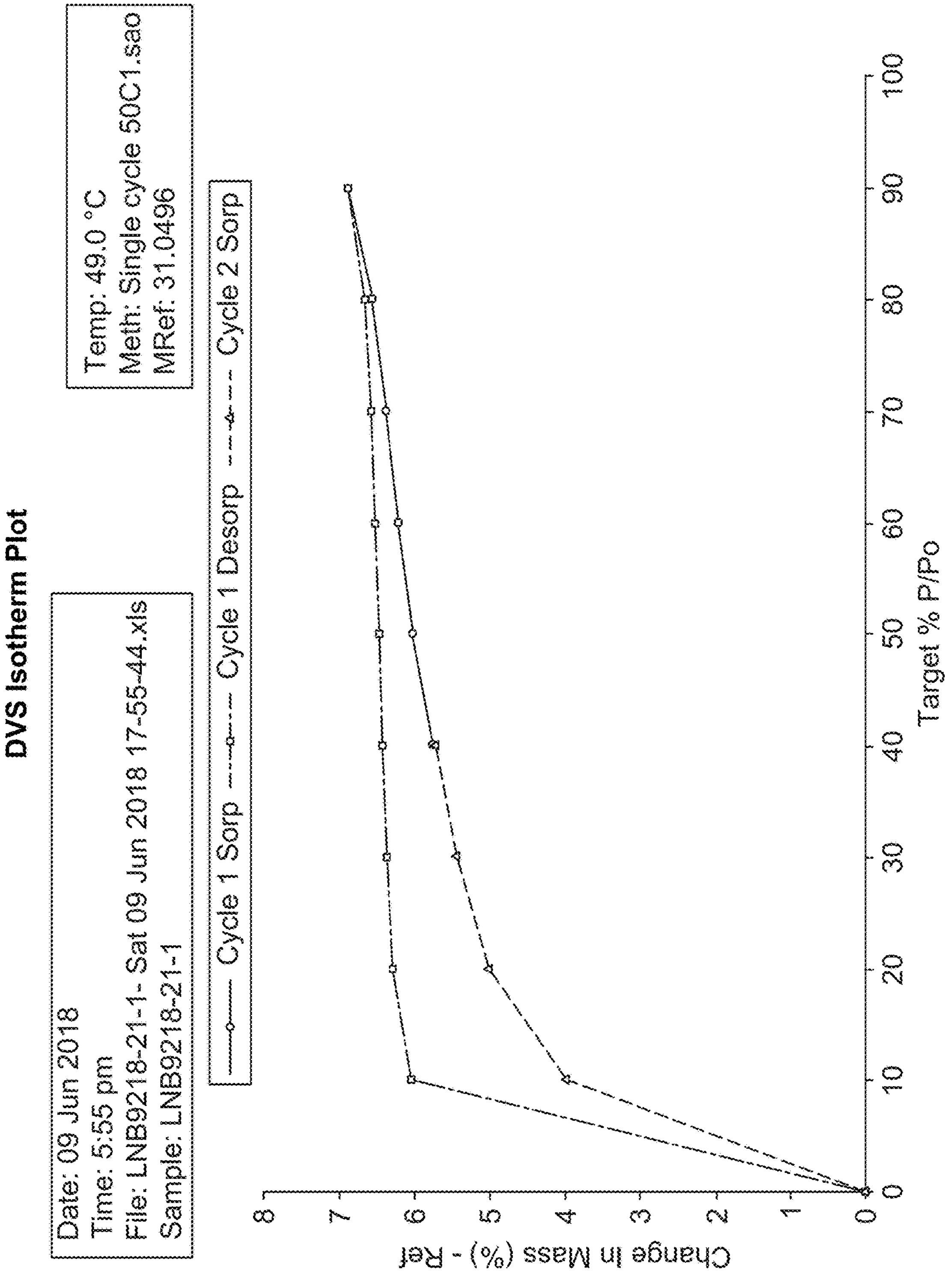
FIG. 87 is the isotherm plot of Pattern 2 at 50° C.
Figure 88:
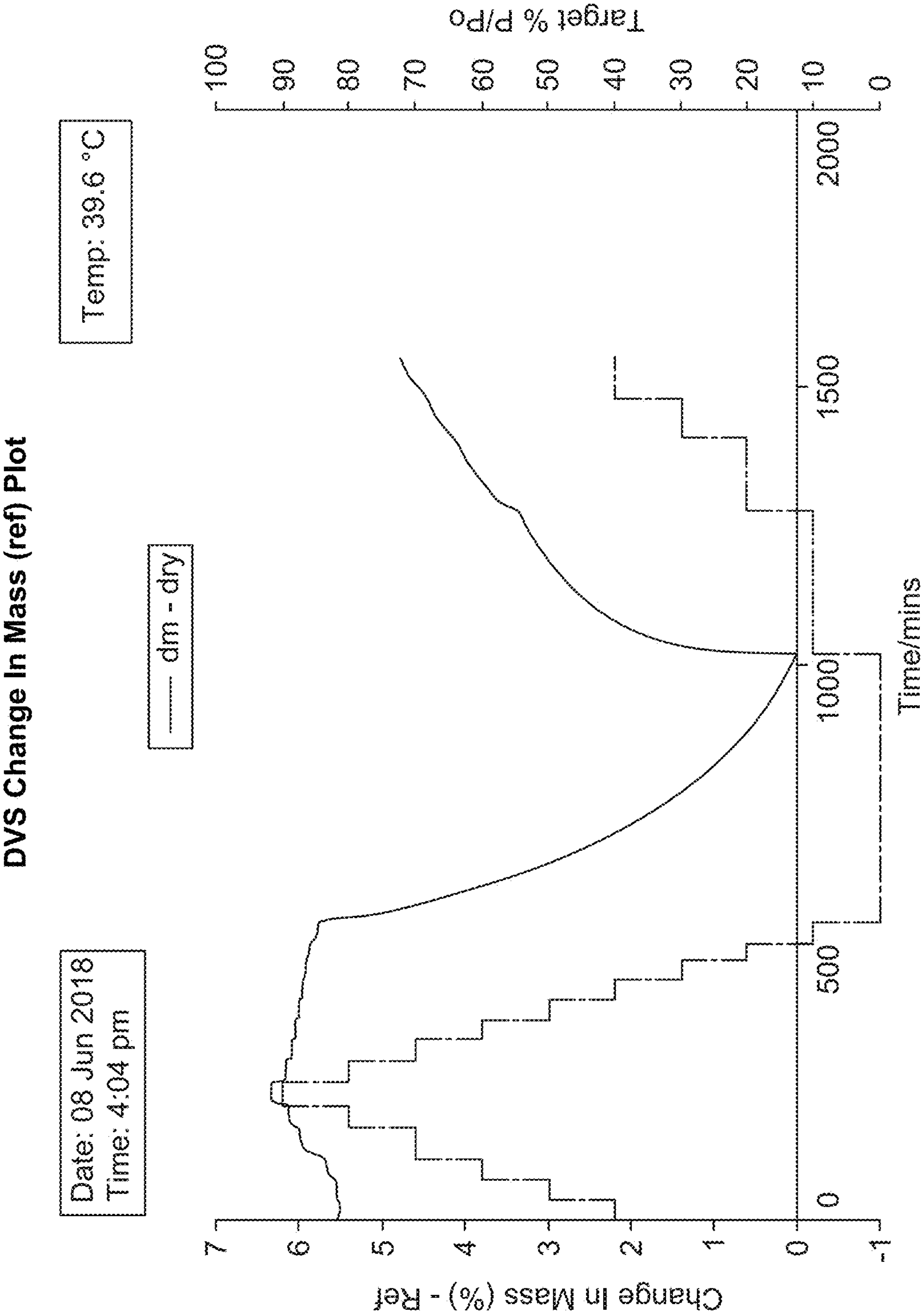
FIG. 88 is the kinetic plot of Pattern 2 at 40° C.
Figure 89:
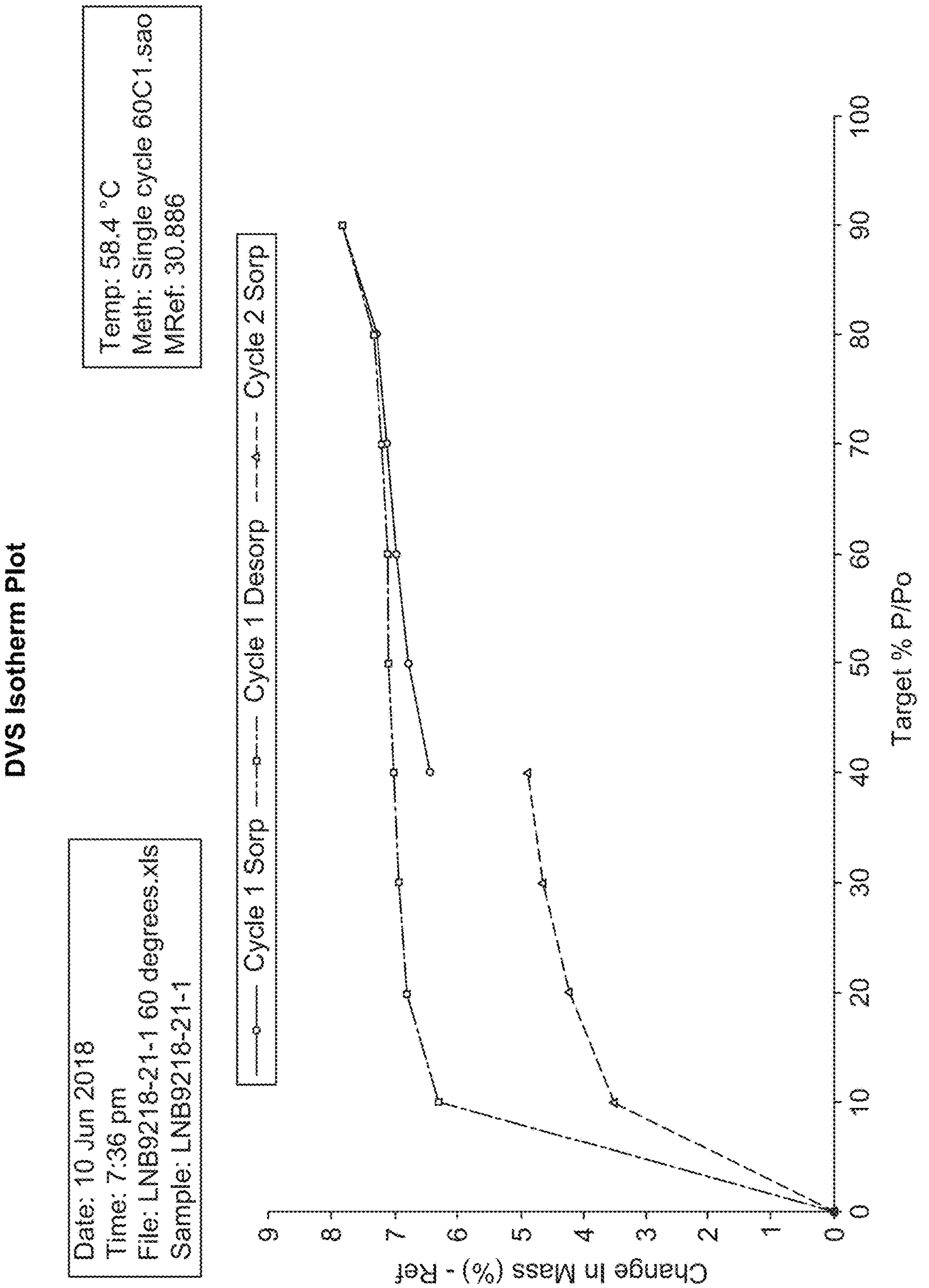
FIG. 89 is the isotherm plot of Pattern 2 at 60° C.
Figure 90:
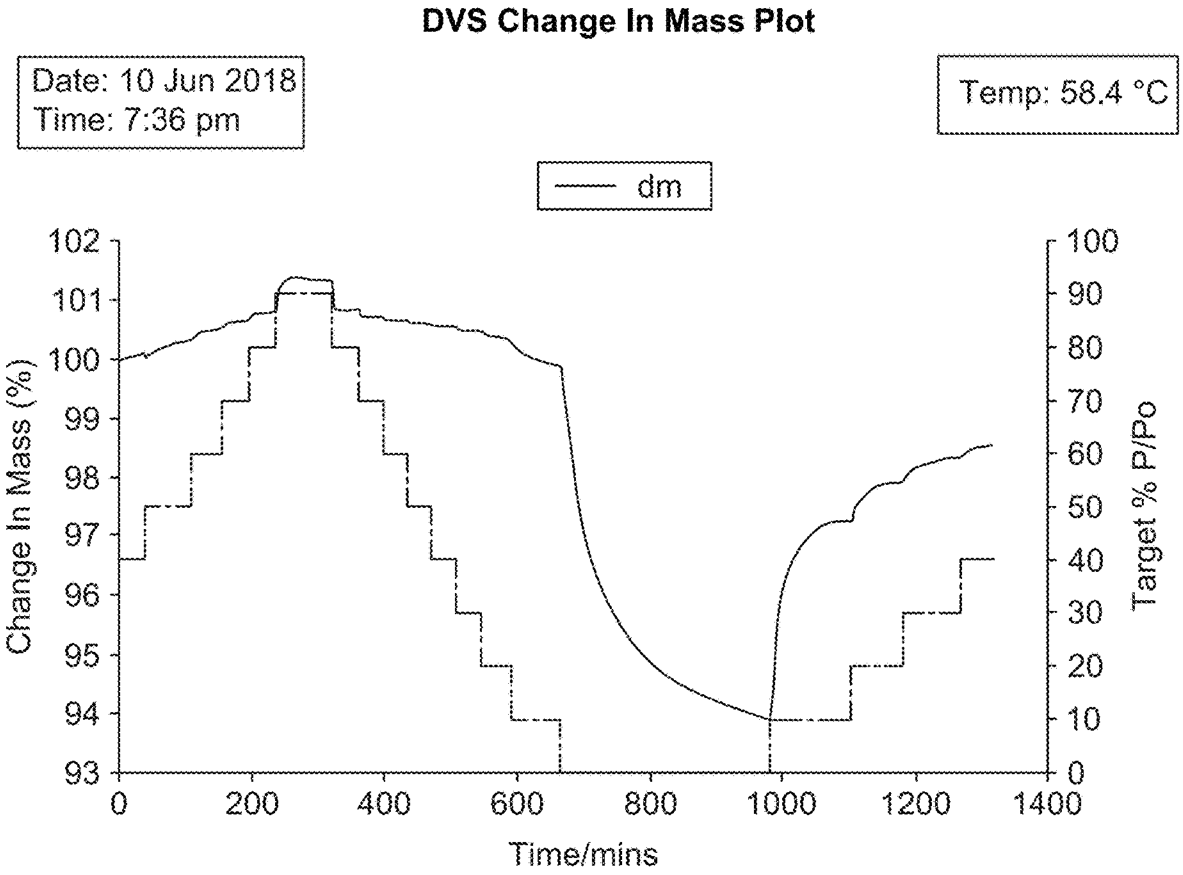
FIG. 90 is the kinetic plot of Pattern 2 at 60° C.
Figure 91:
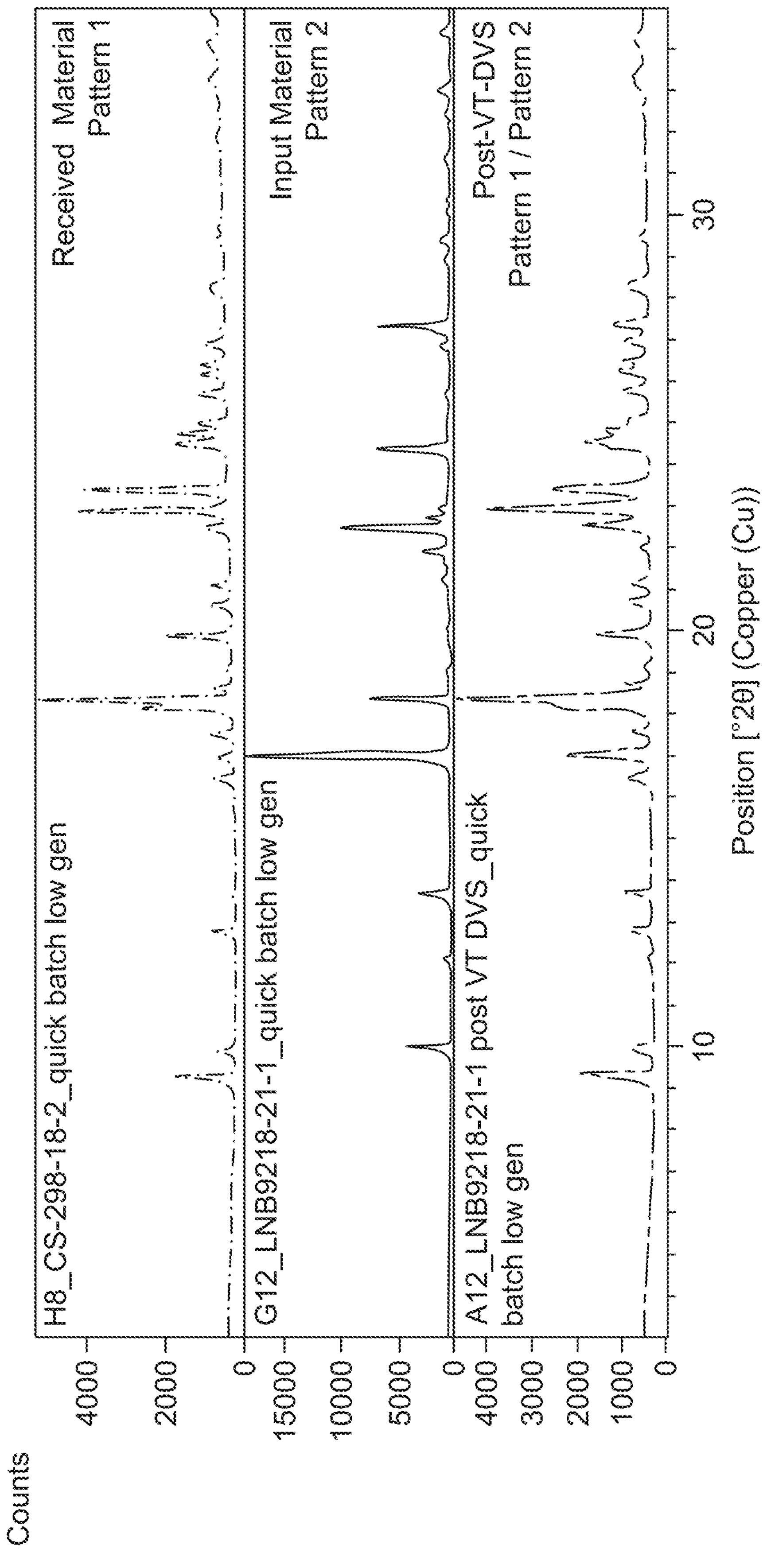
FIG. 91 illustrates the comparison XRPD diffractograms.

VT-DVS analysis at 40° C. showed that the material started dehydrating below 10% RH, losing approximately 5.8 wt. % from 10 to 0% RH (0.8 equiv. water). The material subsequently rehydrates from 0 to 40% RH. The DVS isotherm plot can be seen in FIG. 85 and the kinetic plot in FIG. 86. DVS analysis at 50° C. showed that the material started dehydrating below 20% RH, losing approx. 6.1 wt. % (0.8 equiv. water). The material then rehydrates from 0 to 40% RH. FIG. 87 shows the 50° C. isotherm plot and FIG. 88 shows the kinetic plot. VT-DVS at 60° C. showed that the material started dehydrating below 20% RH, losing approx. 7 wt. % or 1.0 equiv. water. The material was noted to rehydrate between 0 to 40% RH. The 60° C. isotherm plot can be seen in FIG. 89. The kinetic plot can be seen in FIG. 90. XRPD analysis on the recovered solid showed that post-DVS, the material was a mixture of pattern 1 and pattern 2. Comparison XRPD diffractograms can be seen in FIG. 91.

HPLC purity of CHP pattern 2 was found to be 99.5%.

TABLE 29

FT-IR Peak Table of CHP Pattern 2 From Ethanol/Water

| Wavenumber | Transmittance (%) | Wavenumber | Transmittance (%) |
|---|---|---|---|
| 3457.2 | 81.8 | 1233.3 | 80.9 |
| 3411.6 | 82.2 | 1223.5 | 81.4 |
| 3292.7 | 78.6 | 1198.3 | 79.2 |
| 3211.7 | 79.1 | 1161.1 | 83.6 |
| 3148.3 | 82.9 | 1121.0 | 71.5 |
| 2976.7 | 84.3 | 1083.1 | 74.5 |
| 2949.6 | 85.8 | 1003.9 | 86.4 |
| 2912.7 | 86.4 | 968.7 | 73.7 |
| 2879.7 | 86.0 | 942.5 | 82.4 |
| 2116.5 | 91.3 | 922.3 | 81.4 |
| 1658.1 | 56.5 | 906.0 | 84.9 |
| 1633.1 | 55.6 | 889.5 | 87.3 |
| 1567.1 | 77.5 | 862.8 | 85.8 |
| 1445.9 | 61.6 | 798.1 | 58.9 |
| 1424.3 | 63.4 | 737.6 | 61.6 |
| 1345.0 | 77.9 | 688.9 | 70.4 |
| 1330.0 | 82.3 | 628.5 | 56.0 |
| 1314.6 | 82.0 | 612.6 | 49.5 |
| 1300.0 | 71.8 | 487.4 | 75.4 |
| 1280.0 | 81.8 | 470.8 | 68.9 |
| 1268.0 | 79.0 | 429.1 | 59.9 |
| 1252.2 | 82.3 | | |

TABLE 30

VT/VH-XRPD Results of CHP Pattern 2

| Run | % RH | Temperature | Identity |
|---|---|---|---|
| 1 | 40 | Ambient | Pattern 2 |
| 2 | 0 | | Pattern 2 |
| 3 | 0 | 80° C. | Pattern 1 |
| 4 | 0 | | Pattern 1 |

4. pH Solubility Assessment pH solubility assessments for both CHP pattern 1 and pattern 2 found that dissolution occurred after the addition of 3 volumes of buffer at all pH values tested (pH 1, 4, 6.8 and 7.2). Solubility of pattern 1 and pattern 2 was estimated to be 500≥x≥333.3 mg/mL. A summary of the results is displayed in Table 31.

Figure 92:
FIG. 92 illustrates images of the Pattern 1 samples post dissolution.
Figure 93:
FIG. 93 illustrates images of the Pattern 2 samples post dissolution.

Images of the samples post dissolution can be seen in FIG. 92 for pattern 1 material and FIG. 93 for pattern 2.

TABLE 31 pH Solubility Results Summary Table

| CHP Pattern | pH | μL for Dissolution at 37° C. | Approximate Solubility (mg/mL) |
|---|---|---|---|
| 1 | 1 | 300 | 500 ≥ x ≥ 333.3 mg/mL |
| 1 | 4 | 300 | 500 ≥ x ≥ 333.3 mg/mL |
| 1 | 6.8 | 300 | 500 ≥ x ≥ 333.3 mg/mL |
| 1 | 7.2 | 300 | 500 ≥ x ≥ 333.3 mg/mL |
| 2 | 1 | 300 | 500 ≥ x ≥ 333.3 mg/mL |
| 2 | 4 | 300 | 500 ≥ x ≥ 333.3 mg/mL |
| 2 | 6.8 | 300 | 500 ≥ x ≥ 333.3 mg/mL |
| 2 | 7.2 | 300 | 500 ≥ x ≥ 333.3 mg/mL |

5. Stability Studies

1-Week Stability Assessment

Figure 94:
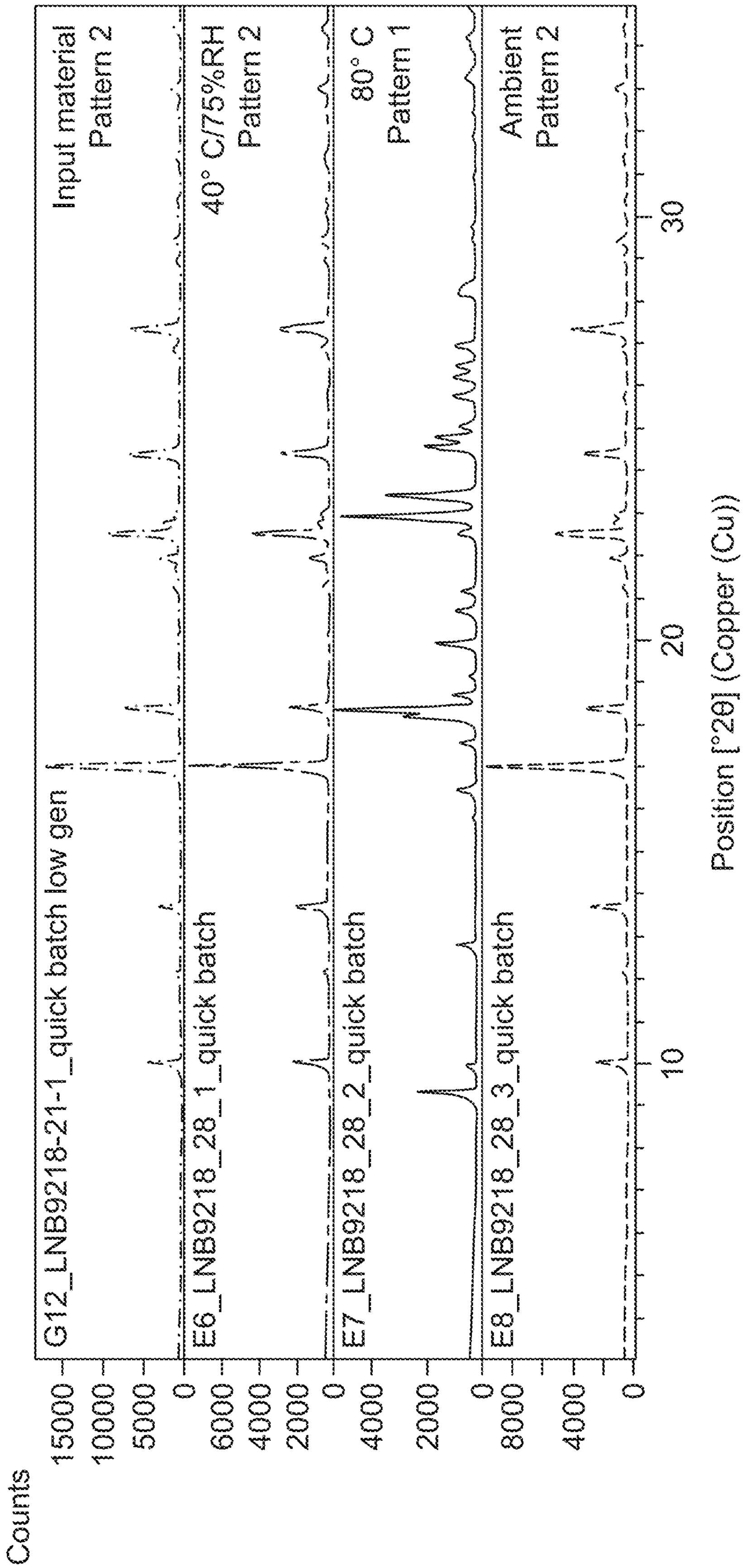
FIG. 94 is the XRPD 2Θ diffractograms for samples tested at 40° C./75% RH, 80° C. and ambient light.

XR-PD 2Θ diffractograms for samples tested at 40° C./75% RH, 80° C. and ambient light are shown in FIG. 94. No change in form was observed for samples stored at 40° C./75% RH or in ambient light. Pattern 2 material was found to convert to pattern 1 after 7 days at 80° C. as expected based on previous thermal, DVS and VT/VH XRPD experiments.

Figure 95:
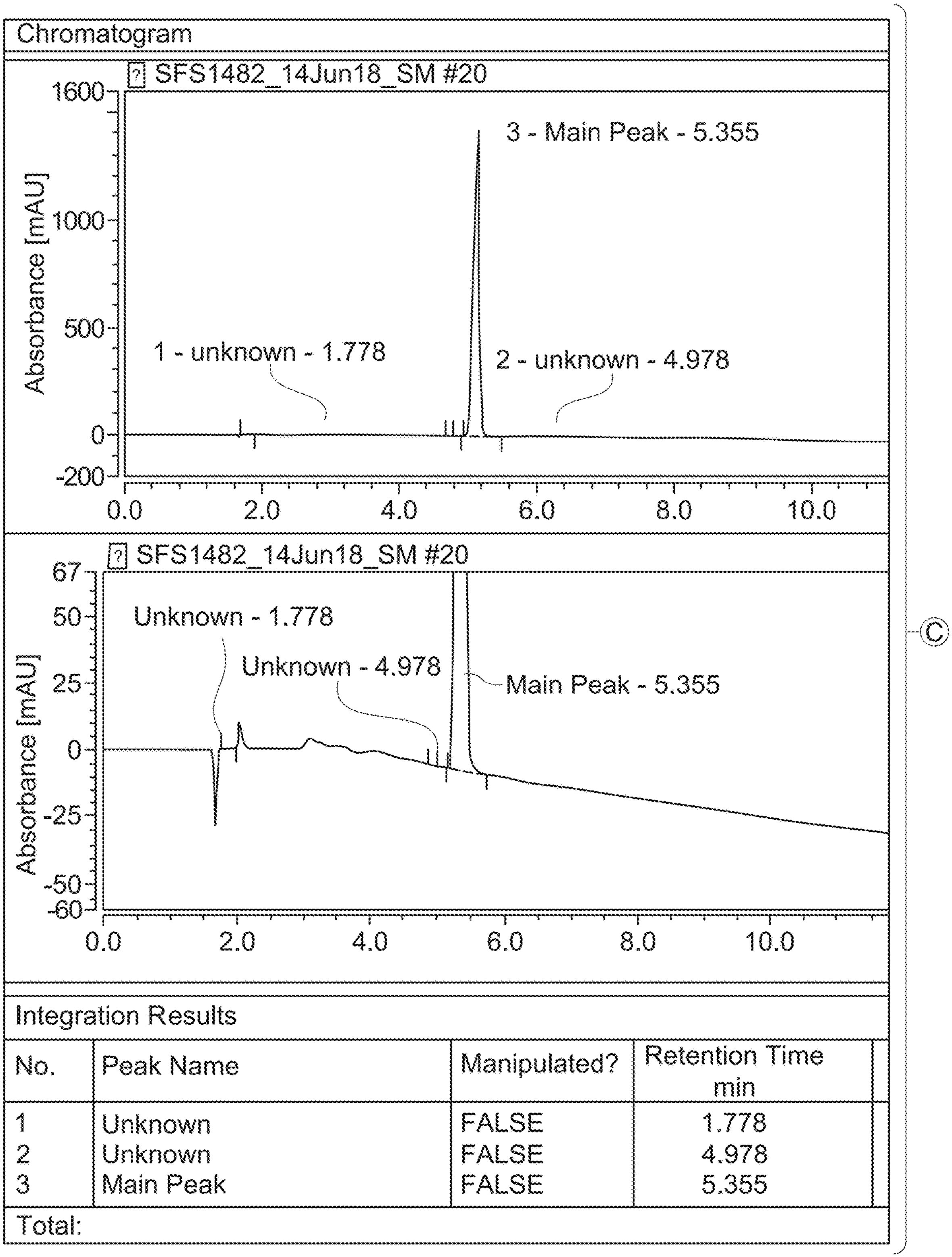
FIG. 95 is one of the HPLC chromatograms for stability samples. It is 1 week stability at 40° C./75% RH.
Figure 95:
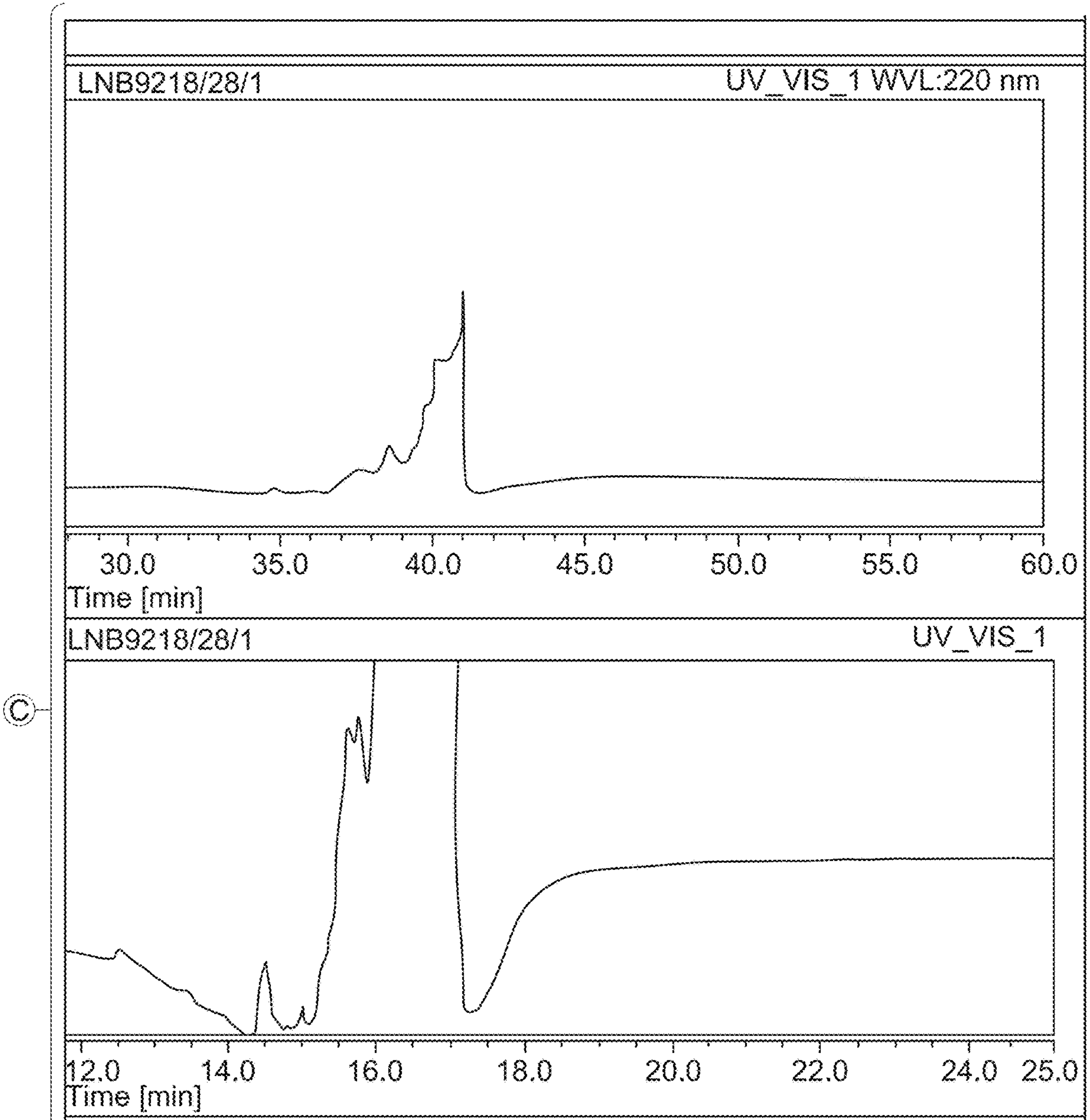
Figure 96:
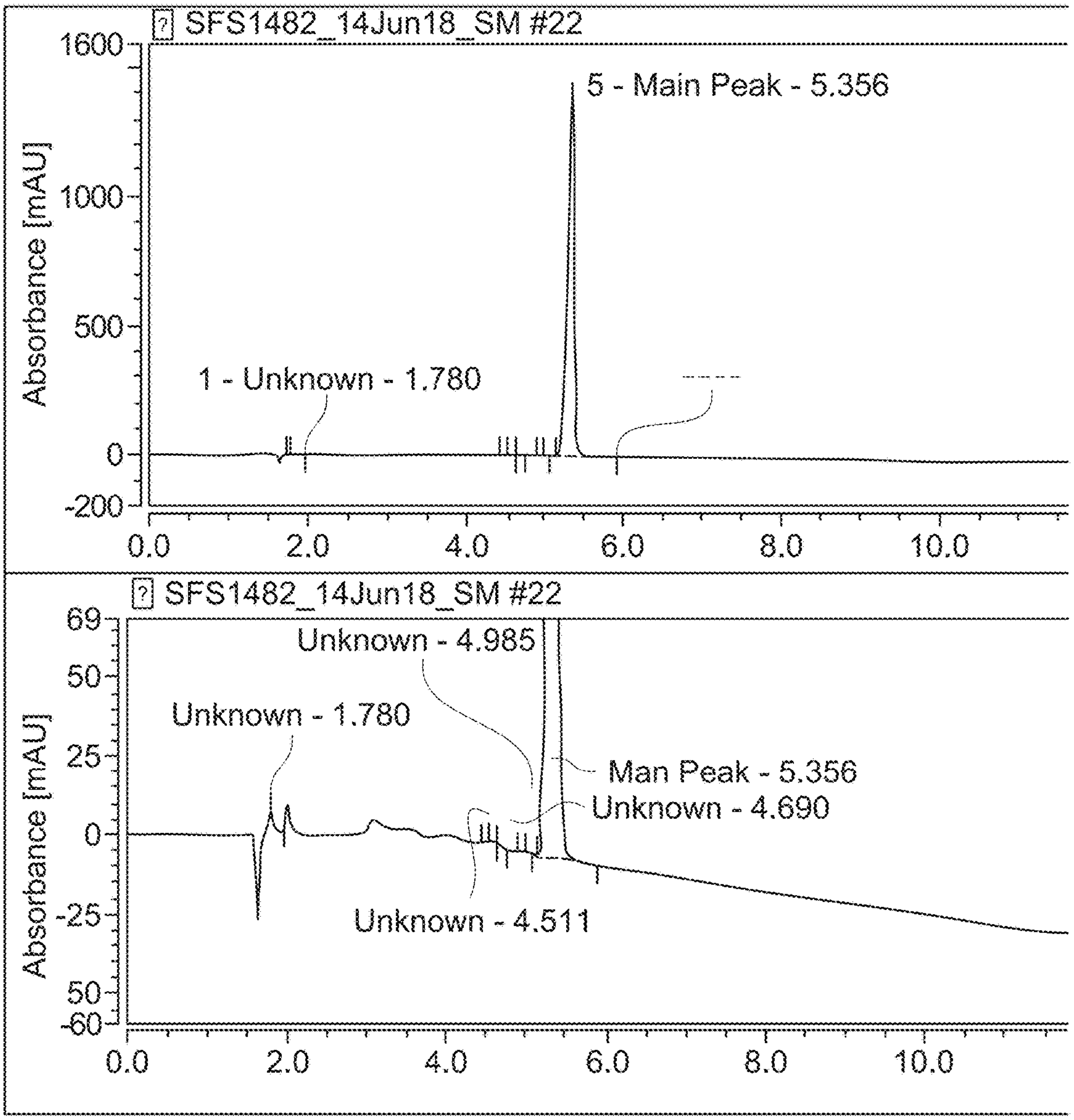
FIG. 96 is one of the HPLC chromatograms for stability samples. It is 1 week stability at 80° C.
Figure 96:
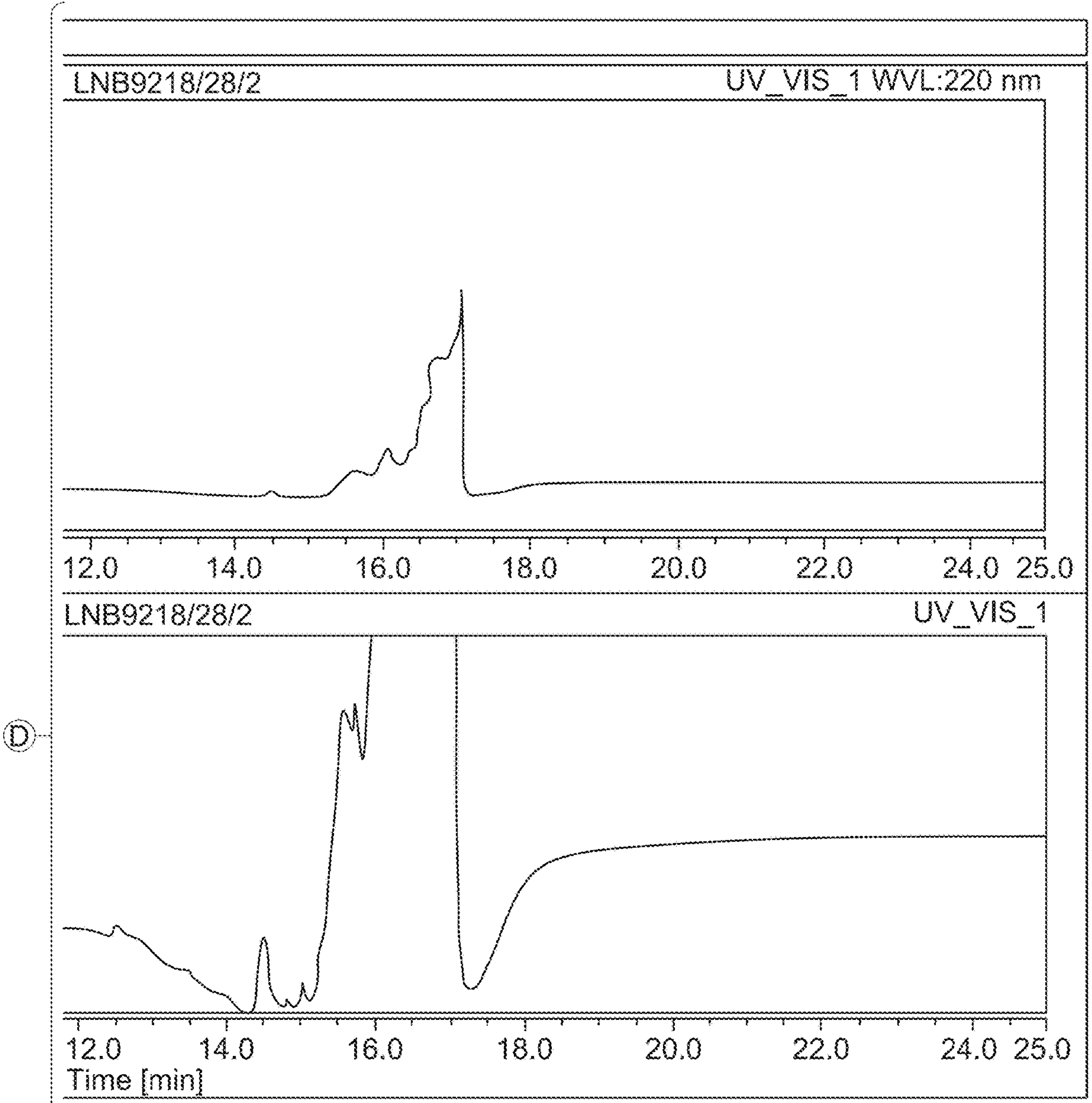
Figure 97:
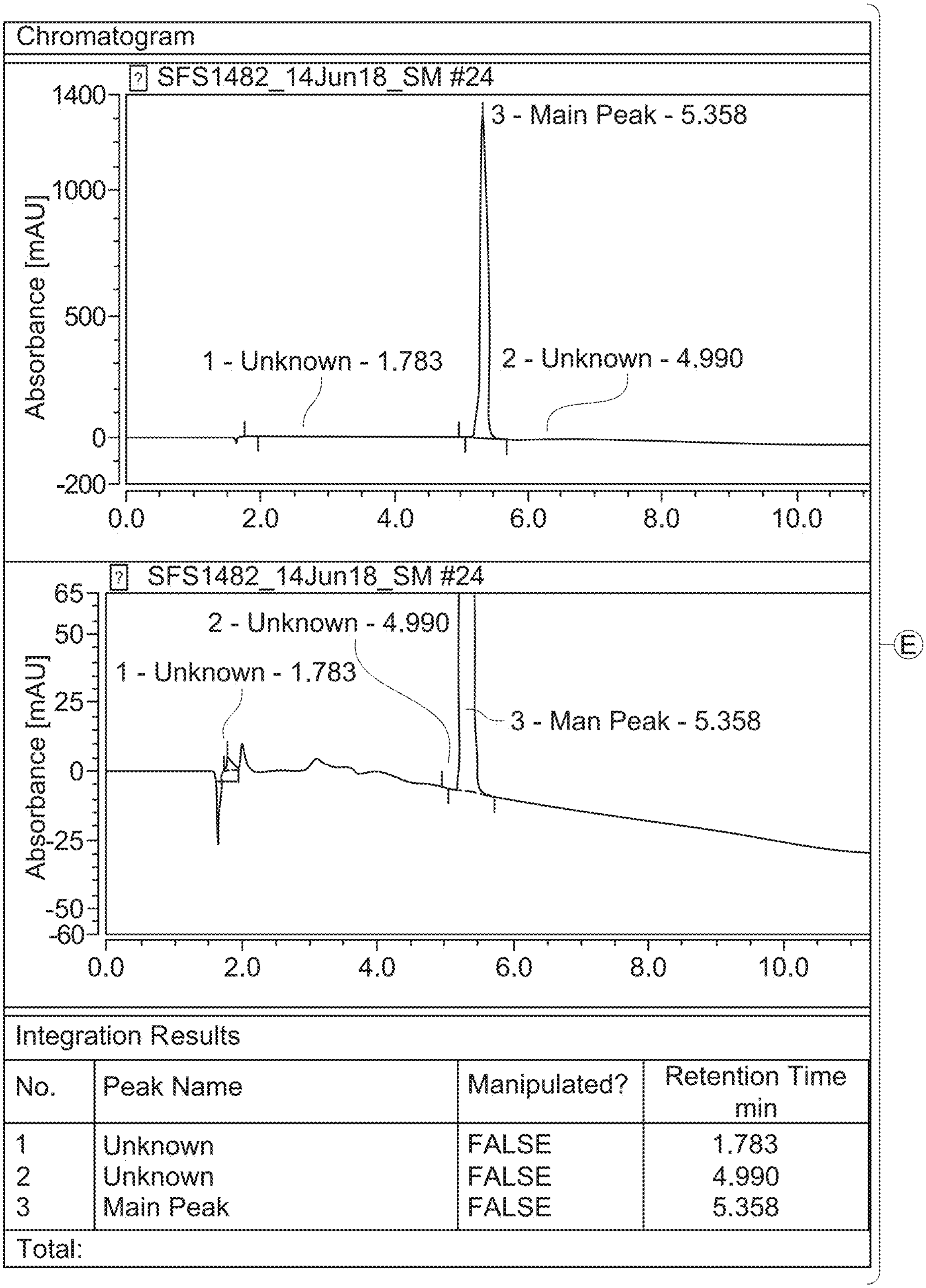
FIG. 97 is one of the HPLC chromatograms for stability samples. It is 1 week stability at ambient temperature.
Figure 97:
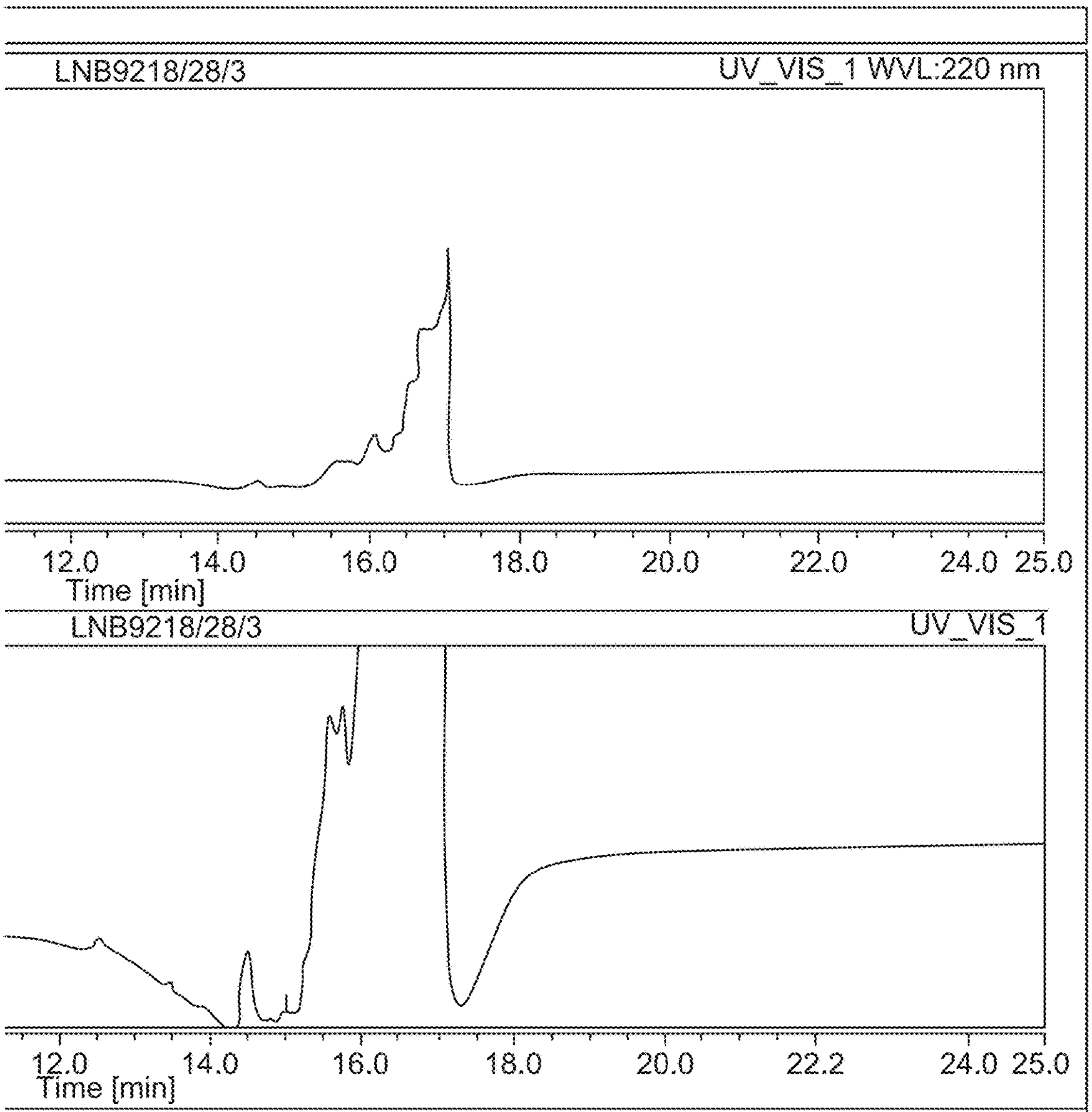

HPLC purity results for CHIP pattern 2 are presented in Table 32. There was no drop in purity after 7 days of storage in all conditions. HPLC chromatograms for stability samples are shown in FIGS. 95-97.

TABLE 32

1 Week Stability Purity Results of CHP Pattern 2

| Purity of starting material (%) | Condition | Purity after 1 week (%) |
|---|---|---|
| 99.5 | 40° C./75% RH | 99.5 |
| | 80° C. | 99.4 |
| | Ambient | 99.5 |

8-Week Stability Assessment

Two-Week Timepoint

Figure 98:
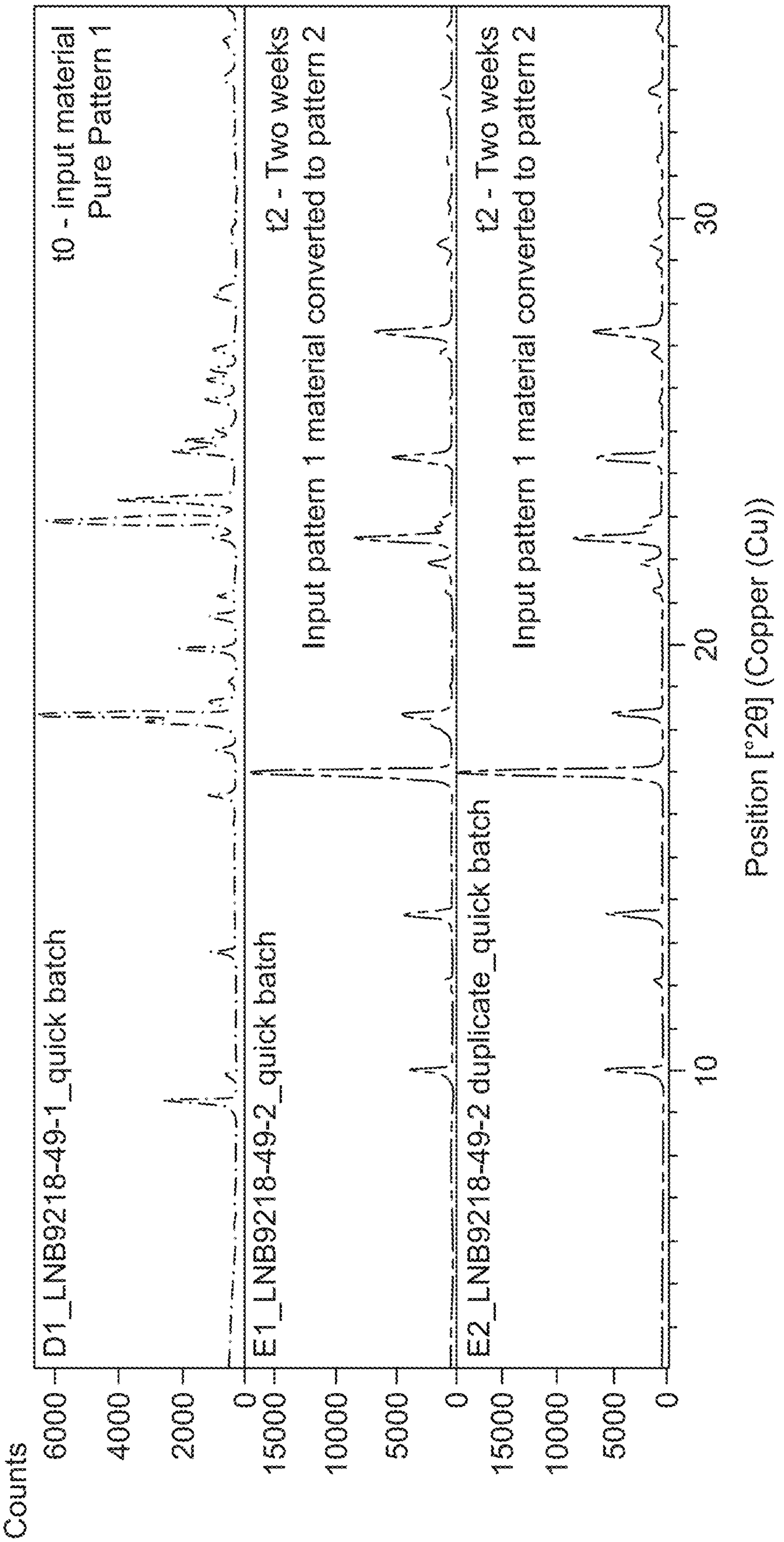
FIG. 98 is the XRPD 2Θ diffractogram for two-week timepoints for pure pattern 1.
Figure 99:
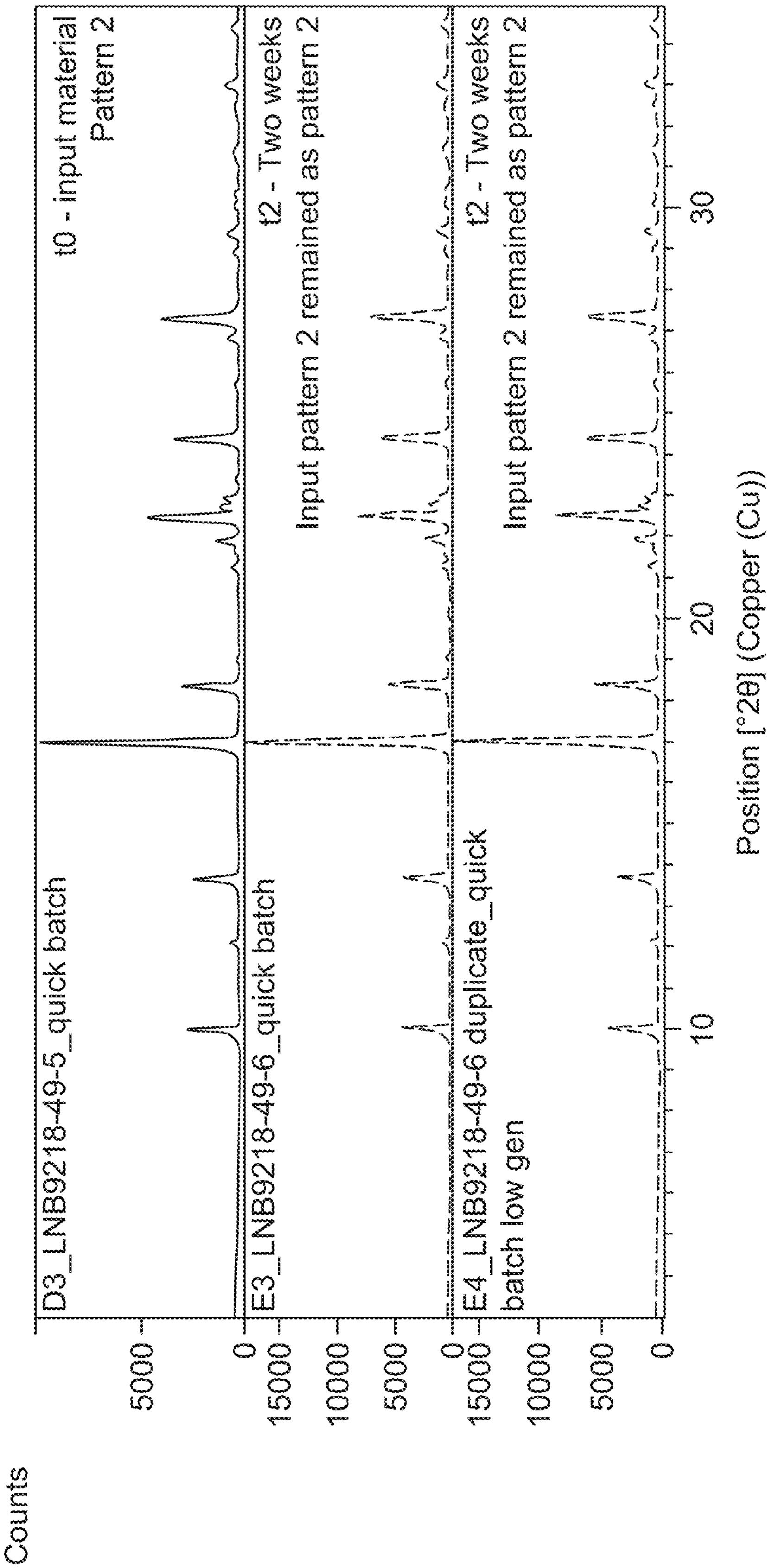
FIG. 99 is the XRPD 2Θ diffractogram for two-week timepoints for Pattern 2.

XRPD 2Θ diffractograms for two-week timepoints are shown in FIG. 98 for pure pattern 1 and FIG. 99 for Pattern 2. Results show that pure pattern 1 converted to pattern 2 after 14 days at 40° C./75% RH. There was no change in form observed for CHP pattern 2 after 14 days.

Four-Week Timepoint

Figure 100:
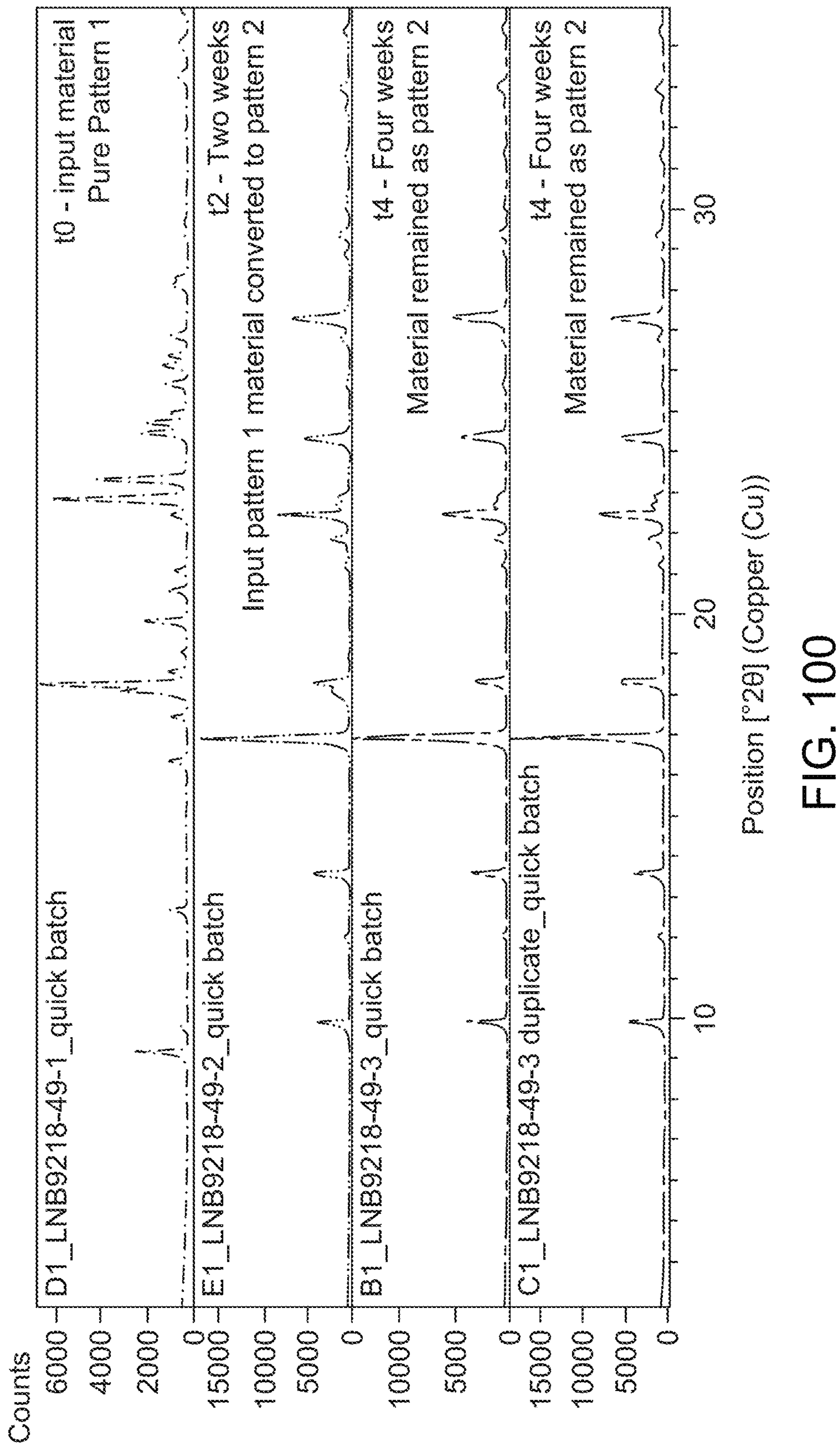
FIG. 100 is the XRPD 2Θ diffractogram for four-week timepoints for pure pattern 1.
Figure 101:
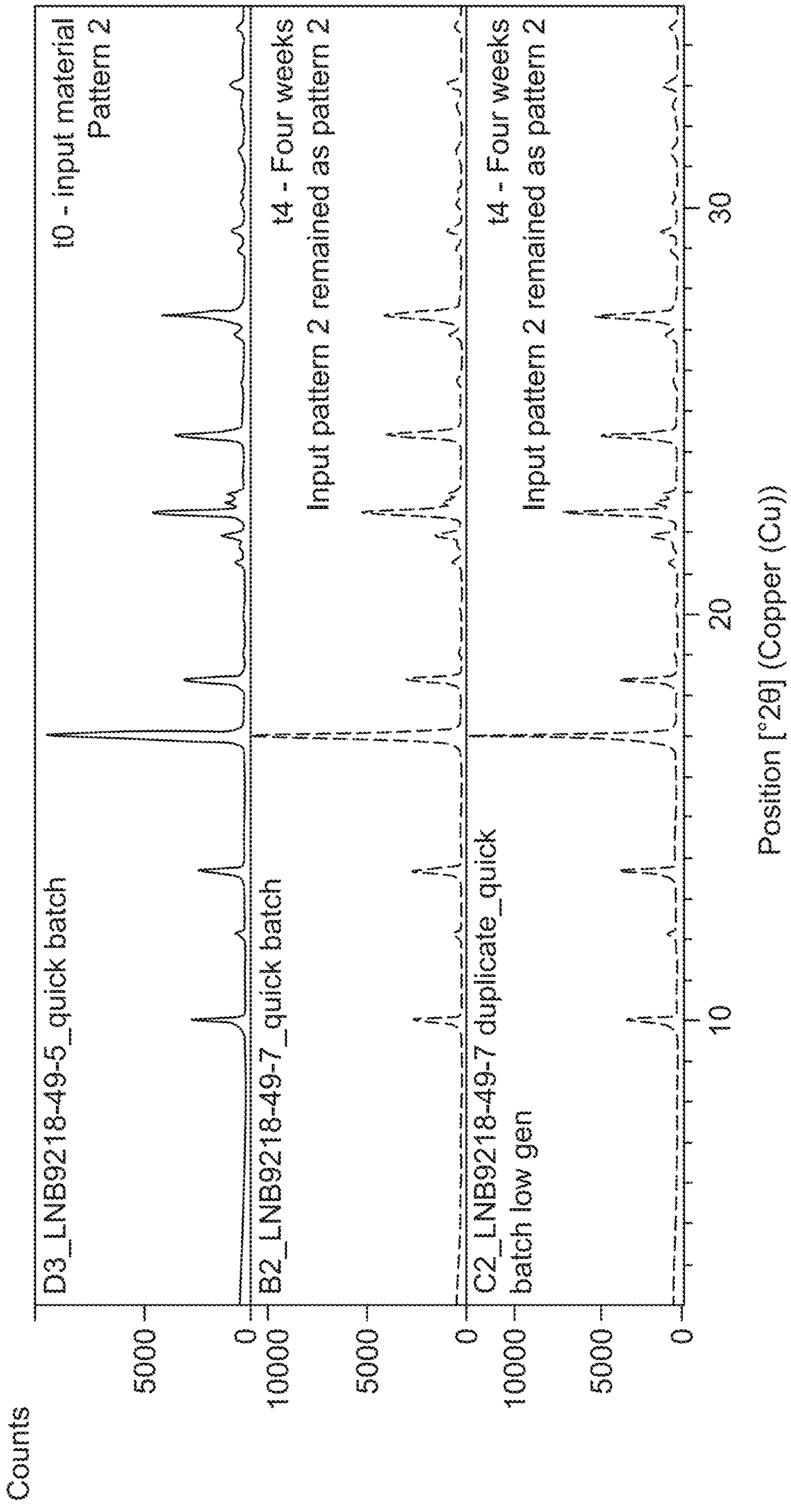
FIG. 101 is the XRPD 2Θ diffractogram for four-week timepoints for Pattern 2.

XRPD 2Θ diffractograms for four-week timepoints are shown in FIG. 100 for pure pattern 1 and FIG. 101 for Pattern 2. Results show that the pure pattern 1 material that had previously converted to pattern 2 after two weeks, remained as pattern 2 after 4 weeks at 40° C./75% RH. There was no change in form observed for CHP pattern 2 after 4 weeks.

Eight-Week Timepoint

Figure 102:
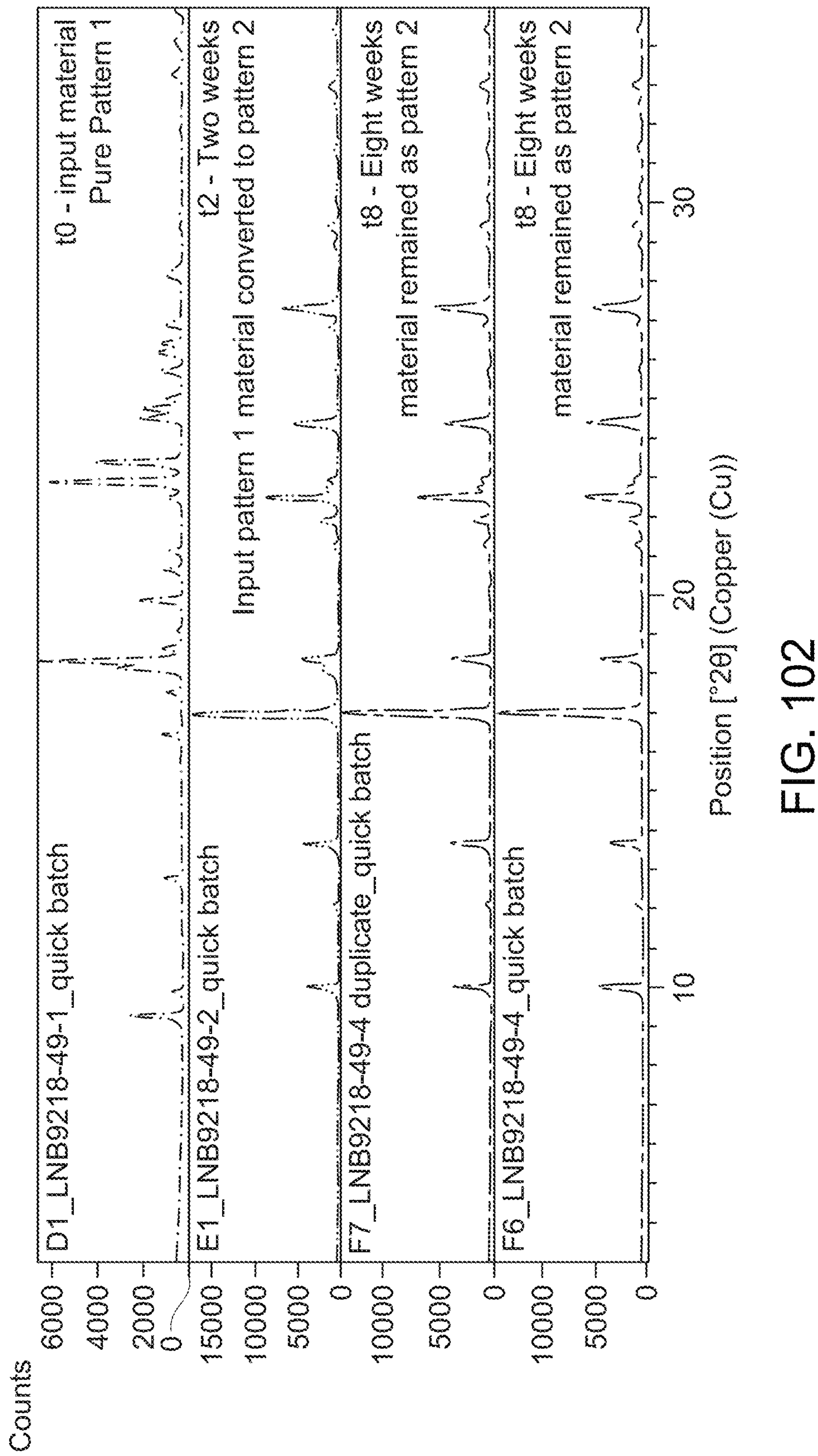
FIG. 102 is the XRPD 2Θ diffractogram for eight-week timepoints for pure pattern 1.
Figure 103:
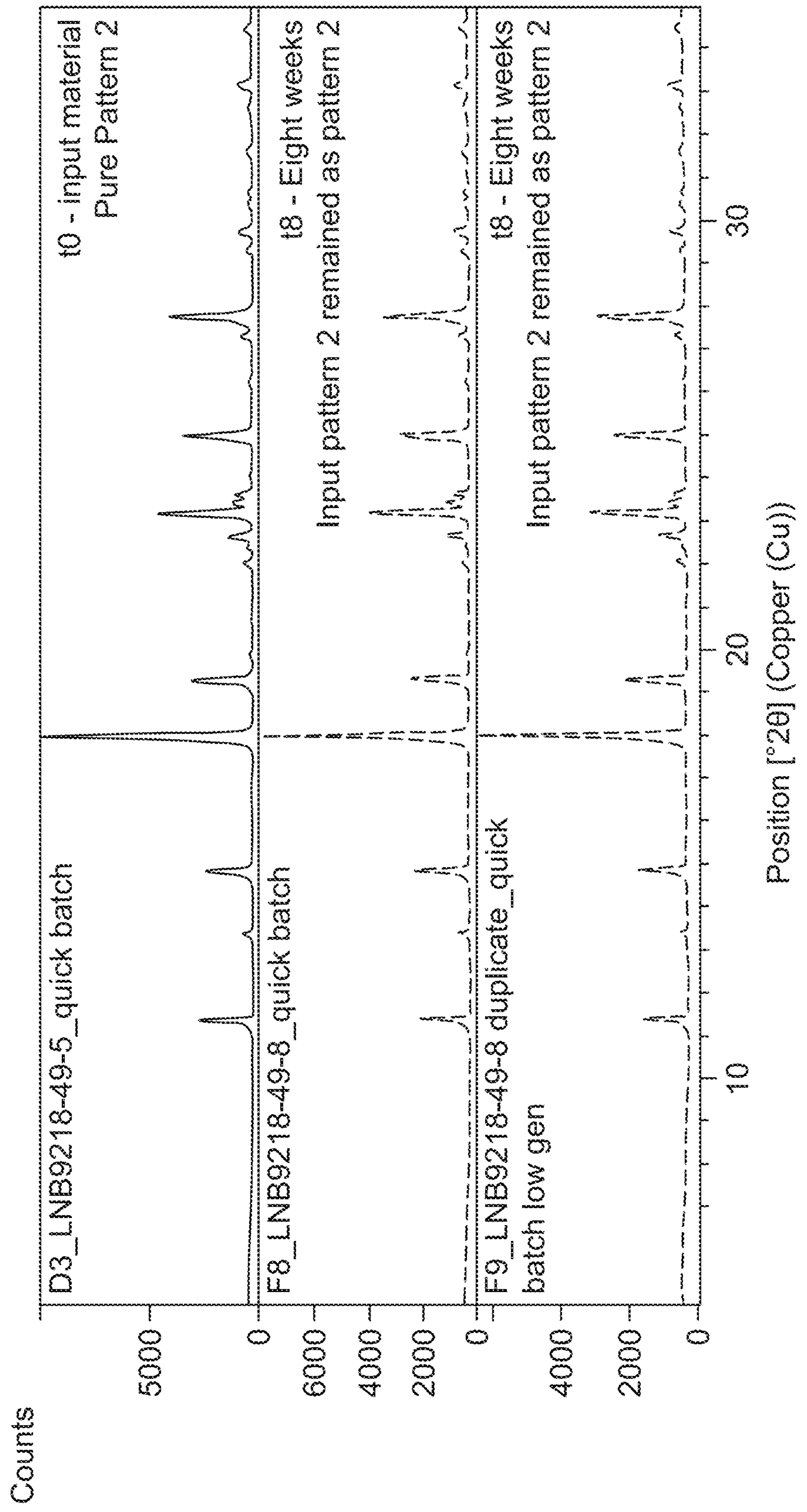
FIG. 103 is the XRPD 2Θ diffractogram for eight-week timepoints for Pattern 2.
Figure 104:
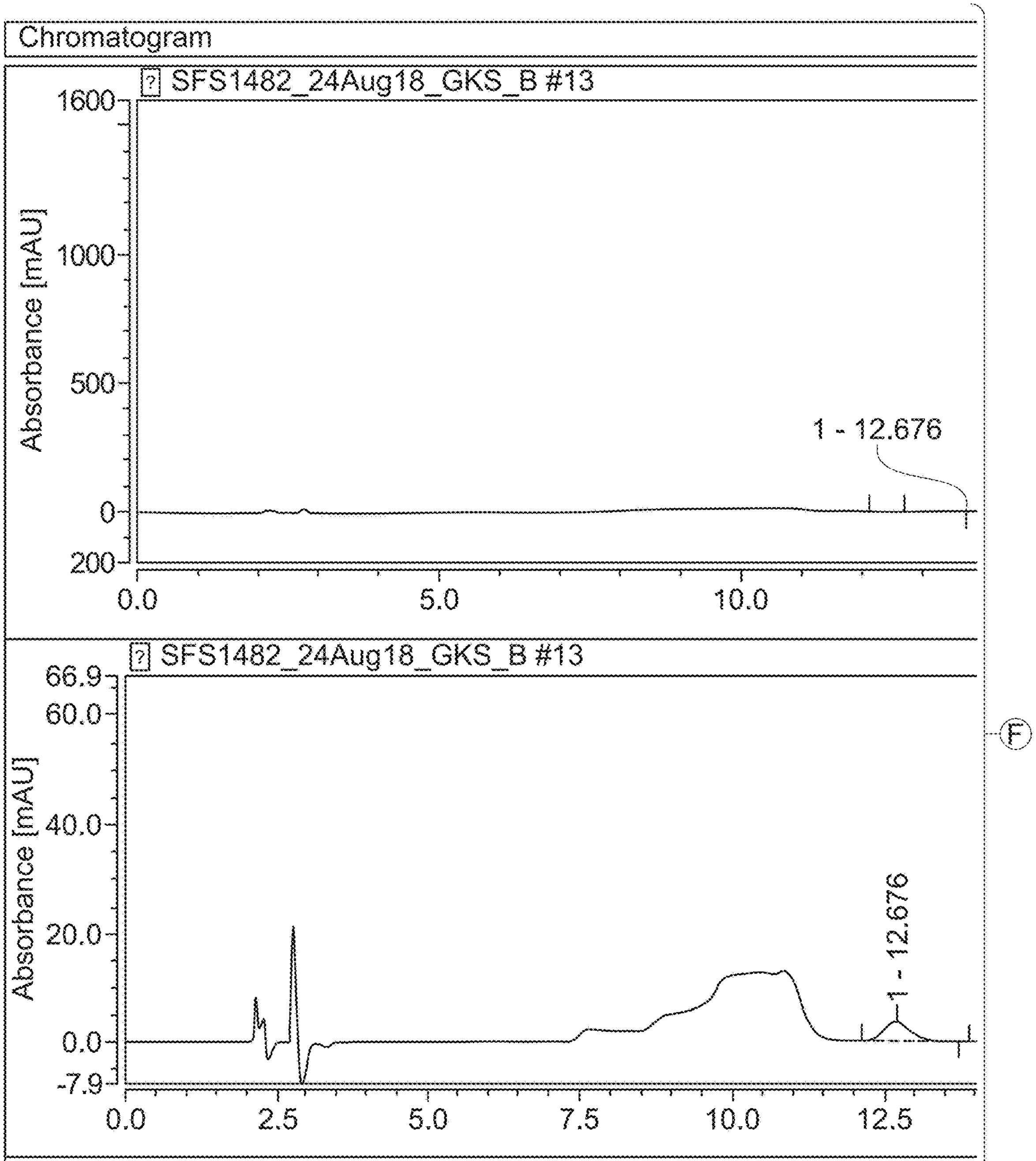
FIG. 104 is the HPLC chromatogram of pure Pattern 1—initial time point.
Figure 104:
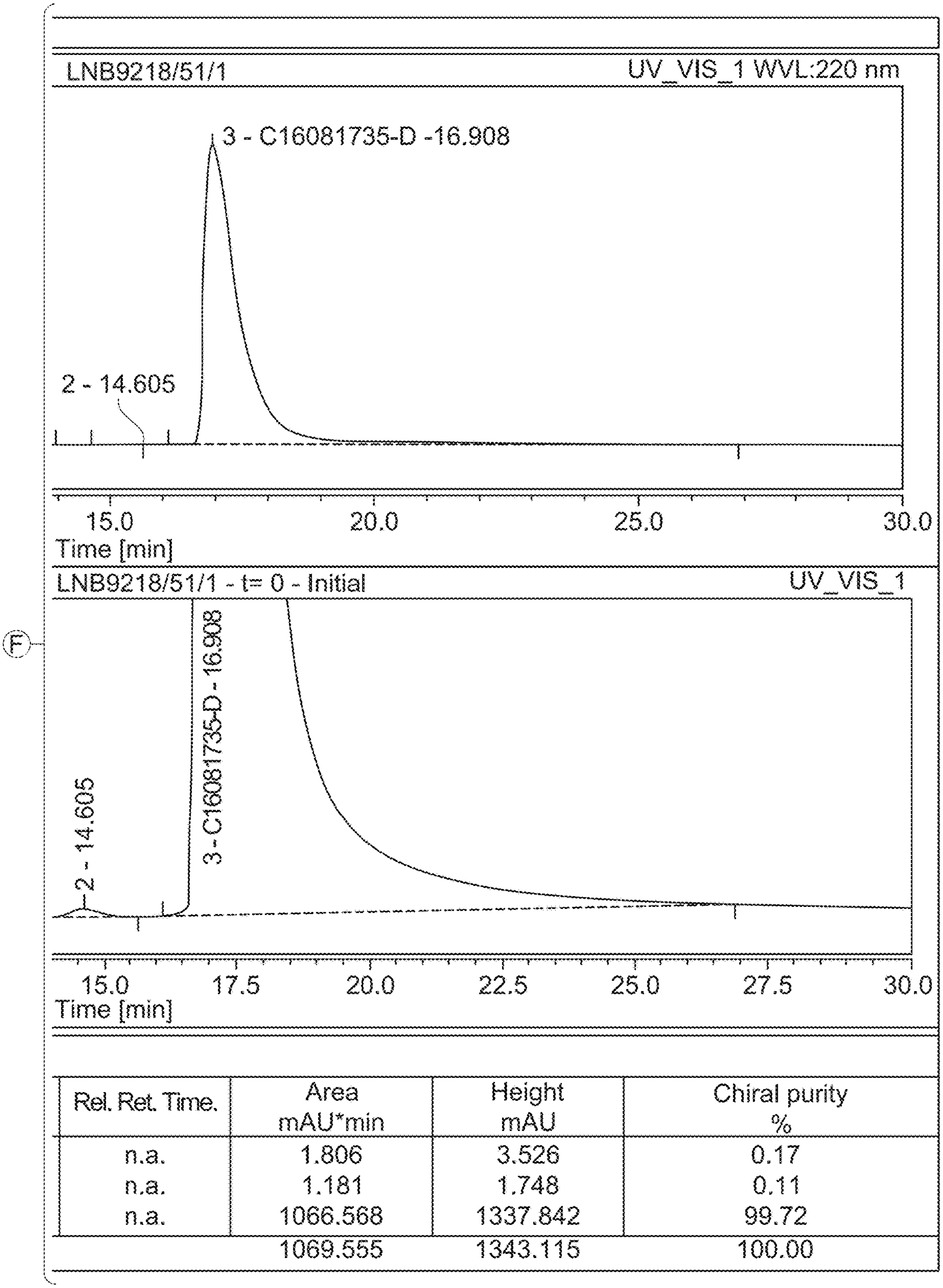
Figure 105:
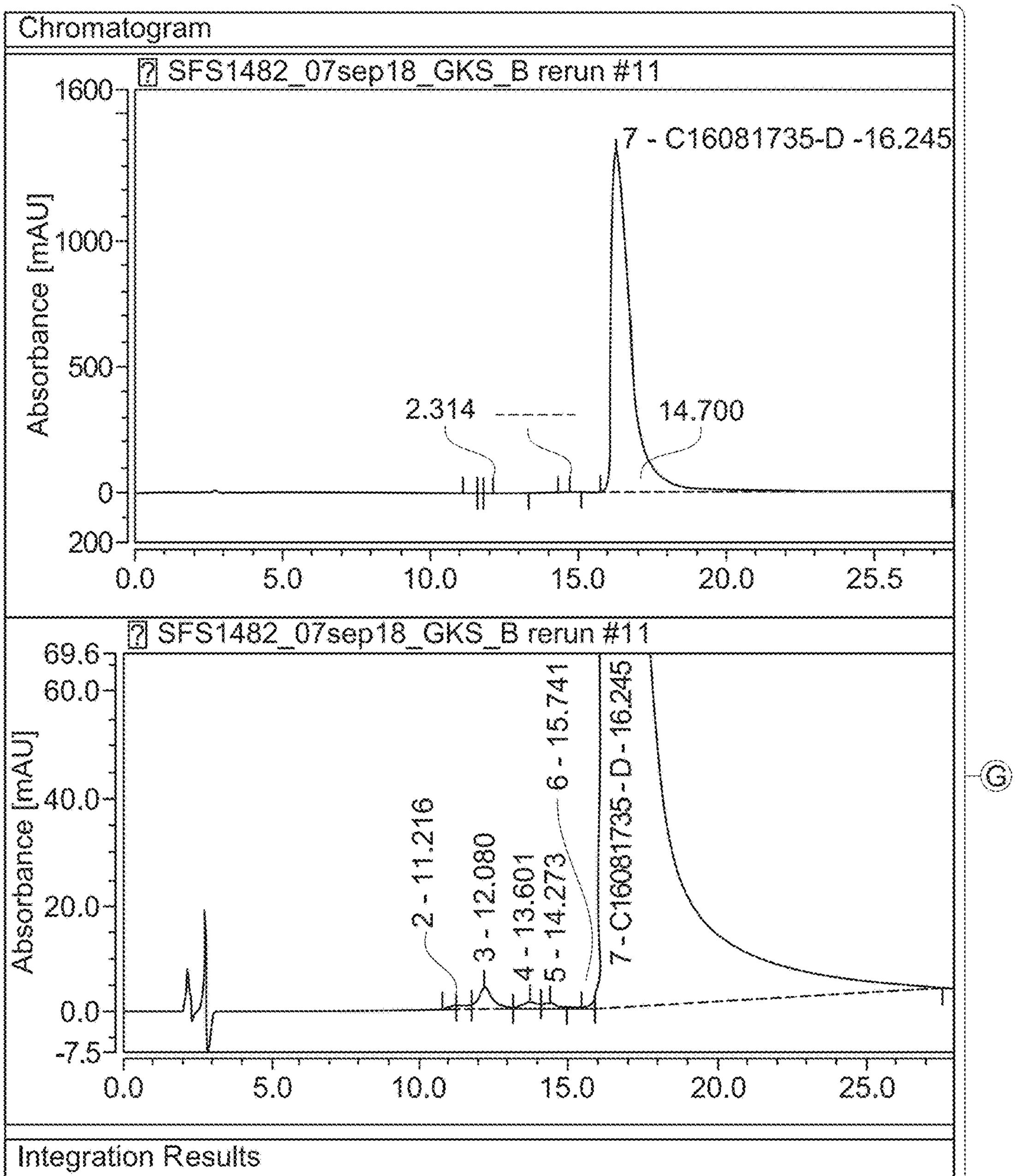
FIG. 105 is the HPLC chromatogram of pure Pattern 1-2 week.
Figure 105:
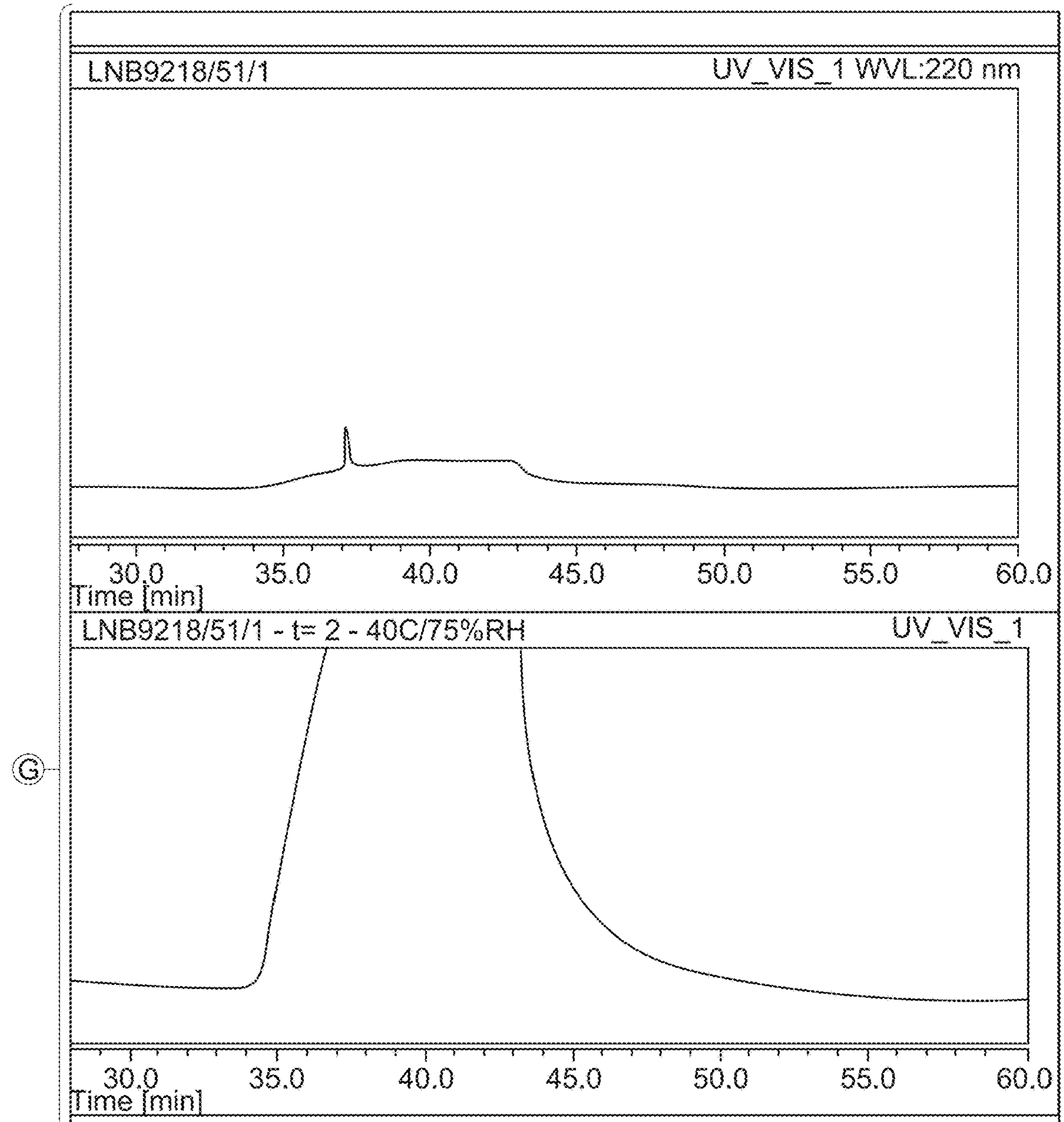
Figure 106:
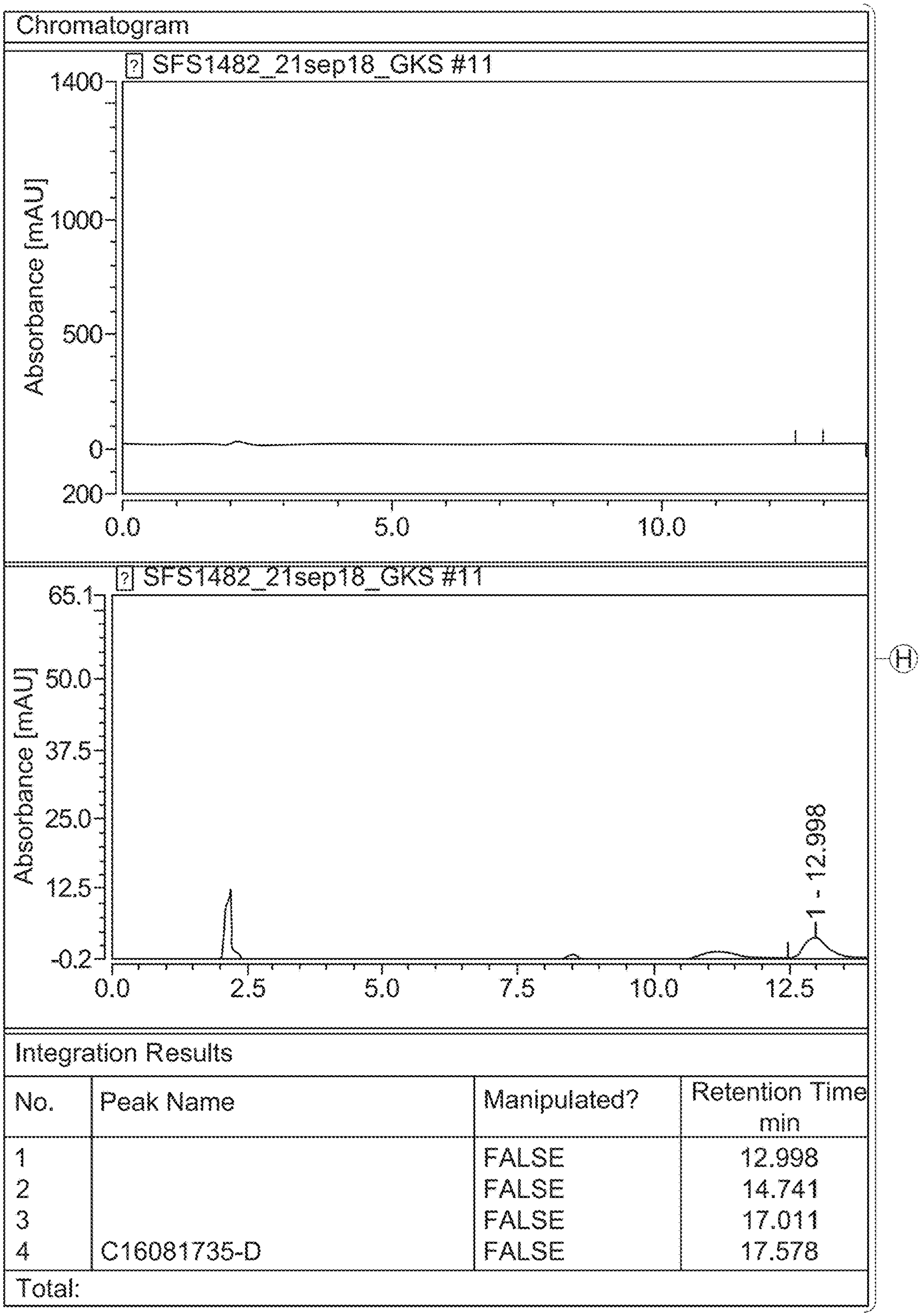
FIG. 106 is the HPLC chromatogram of pure Pattern 1-4 week.
Figure 106:
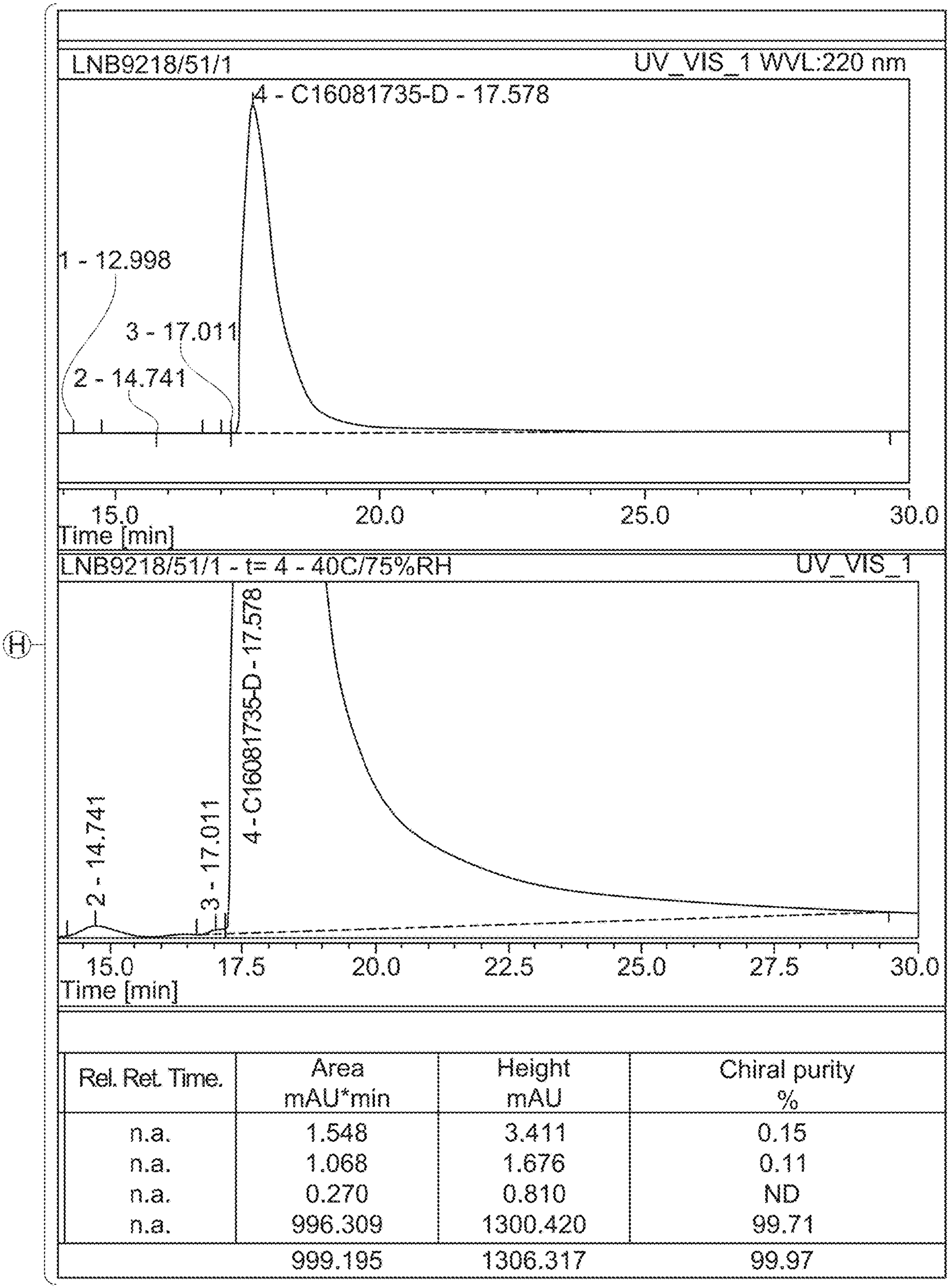
Figure 107:
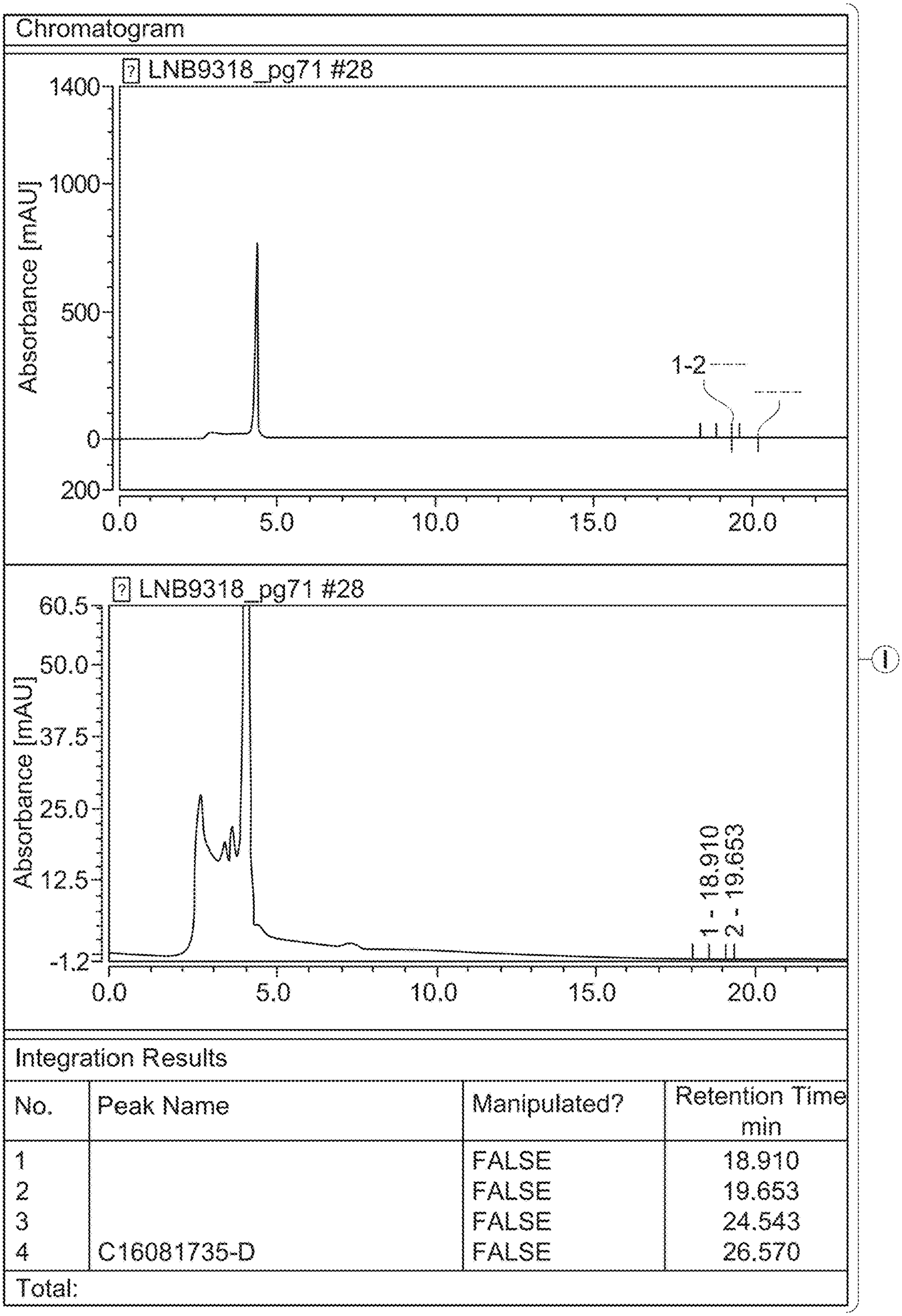
FIG. 107 is the HPLC chromatogram of pure Pattern 1-8 week.
Figure 107:
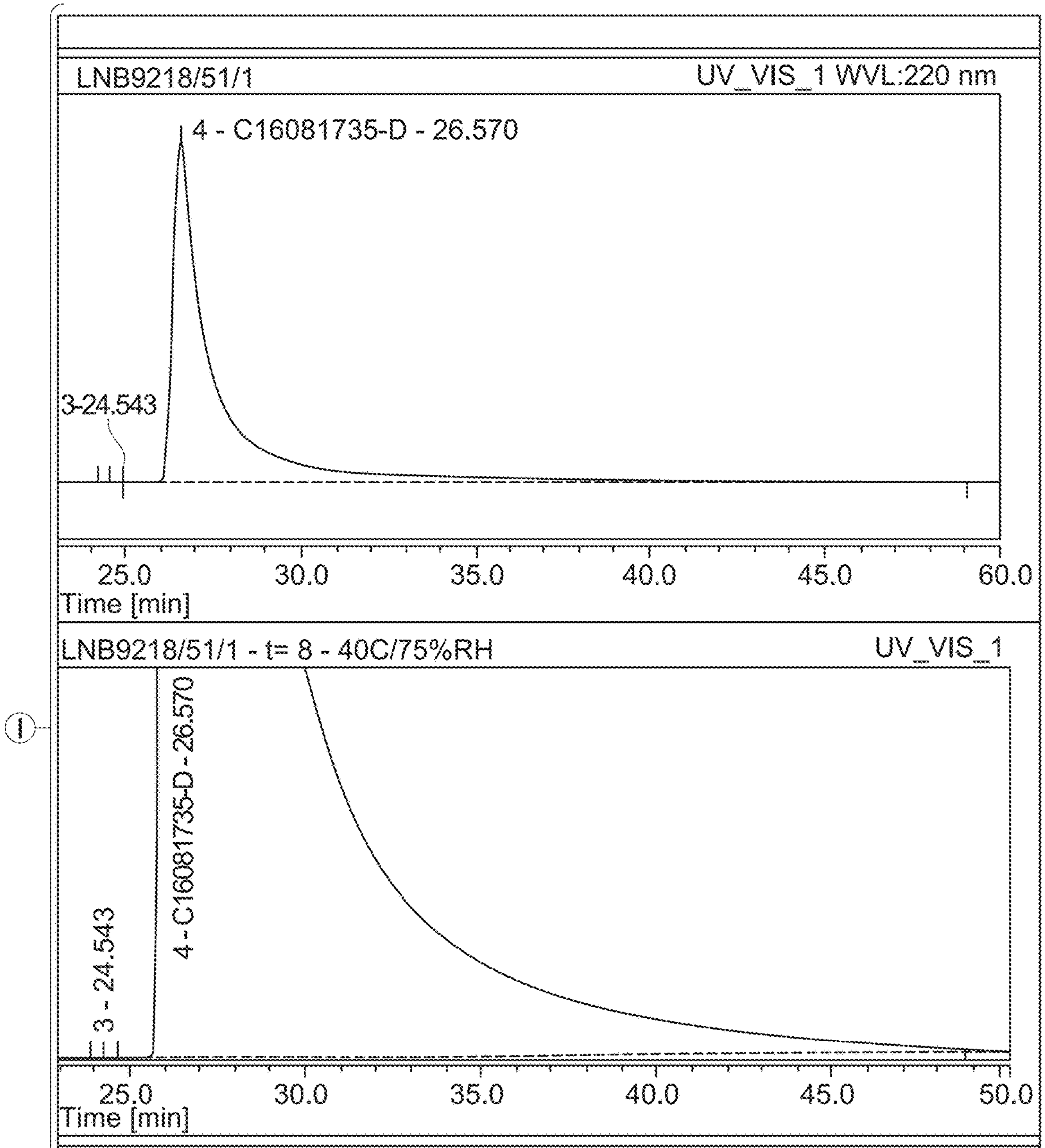
Figure 108:
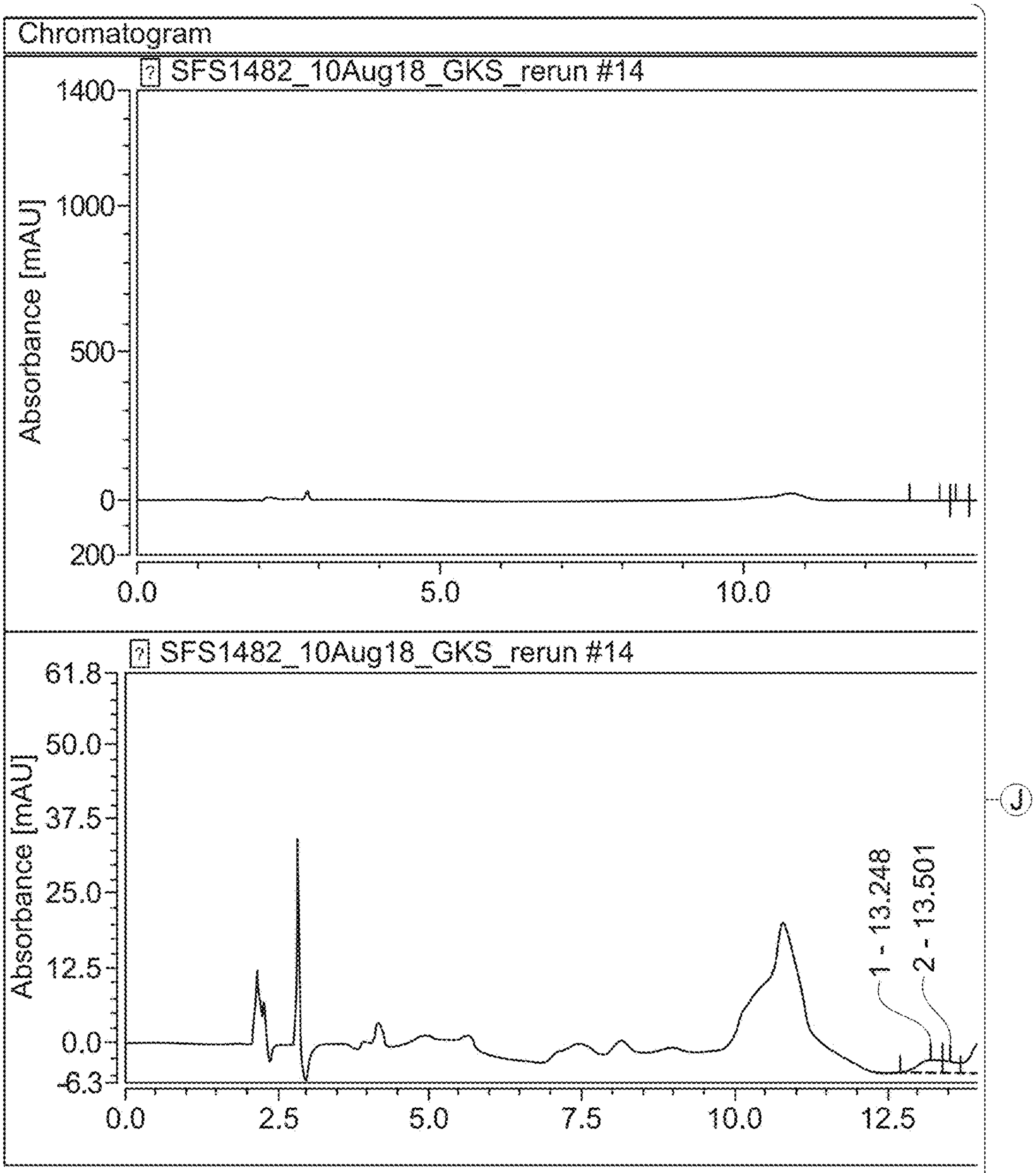
FIG. 108 is the HPLC chromatogram of pure Pattern 2—initial time point.
Figure 108:
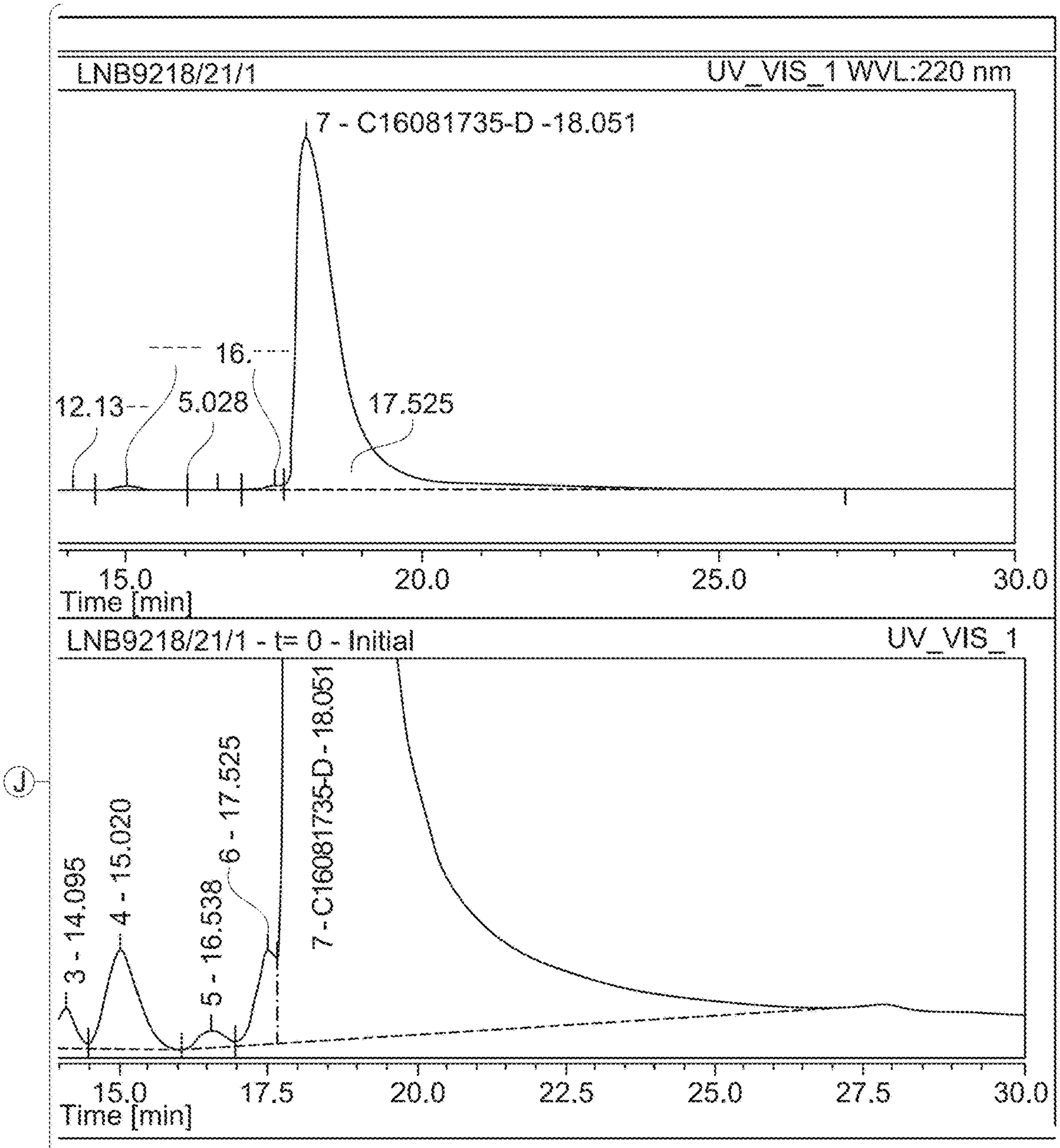
Figure 109:
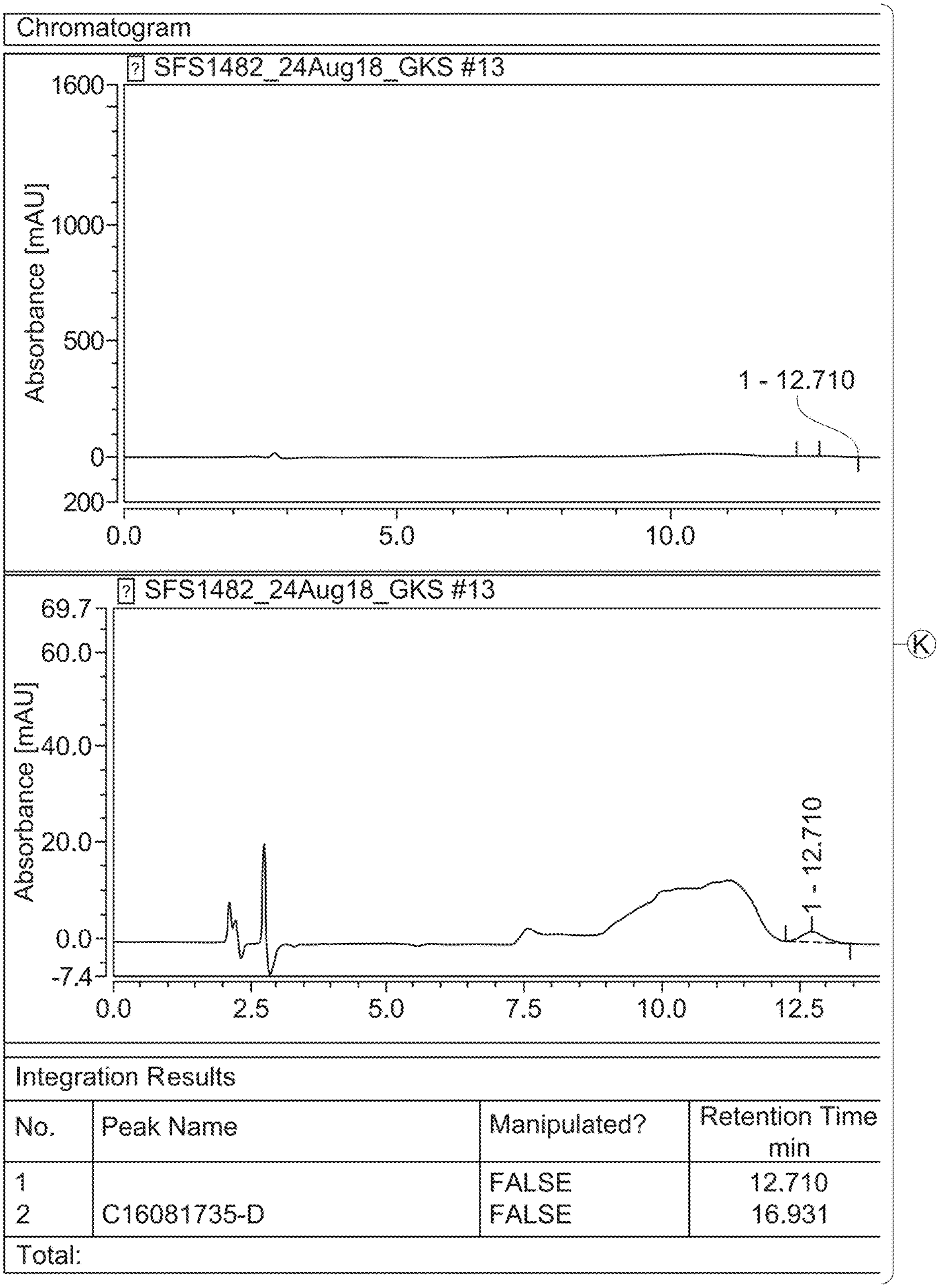
FIG. 109 is the HPLC chromatogram of pure Pattern 2-2 week.
Figure 109:
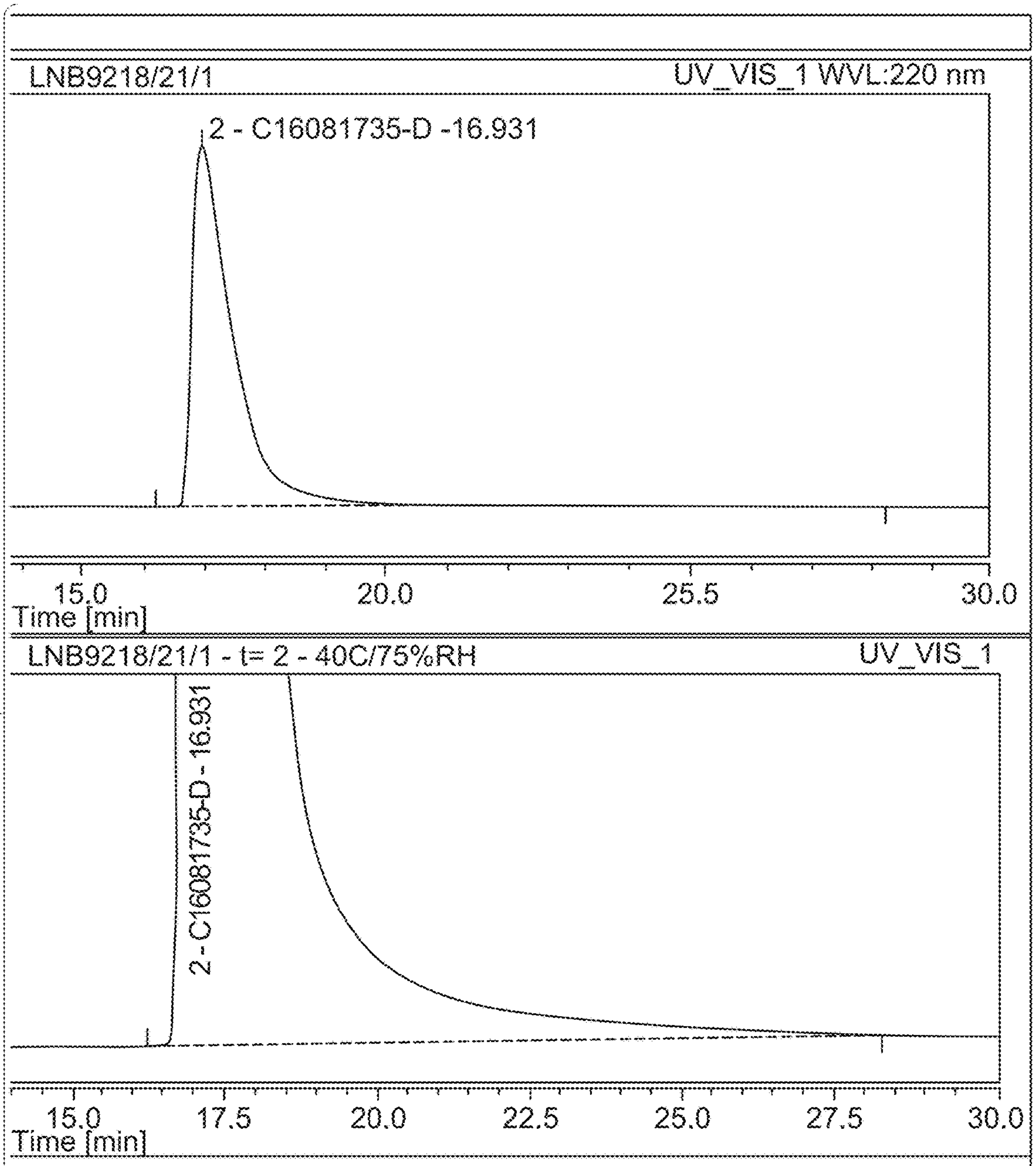
Figure 110:
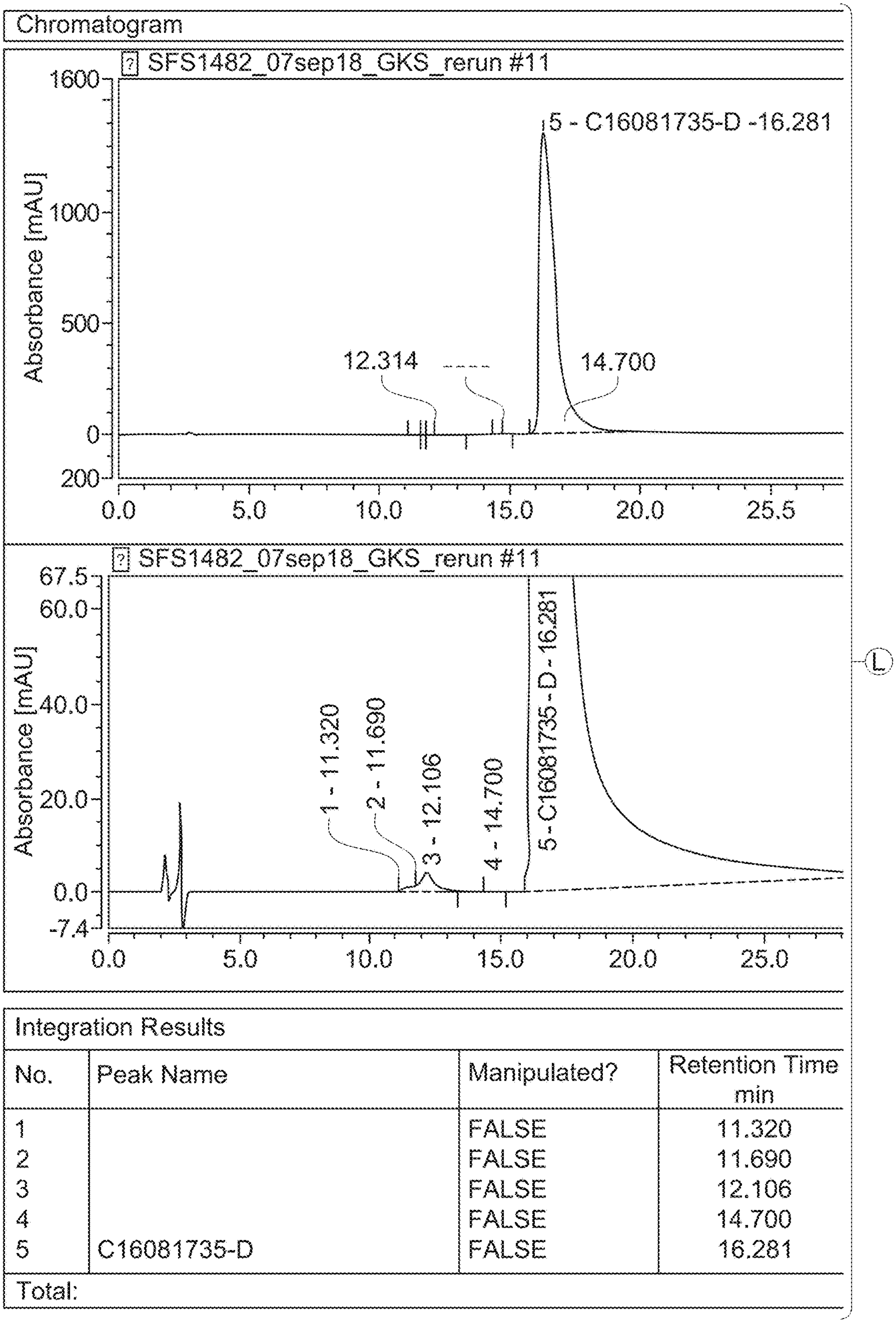
FIG. 110 is the HPLC chromatogram of pure Pattern 2-4 week.
Figure 110:
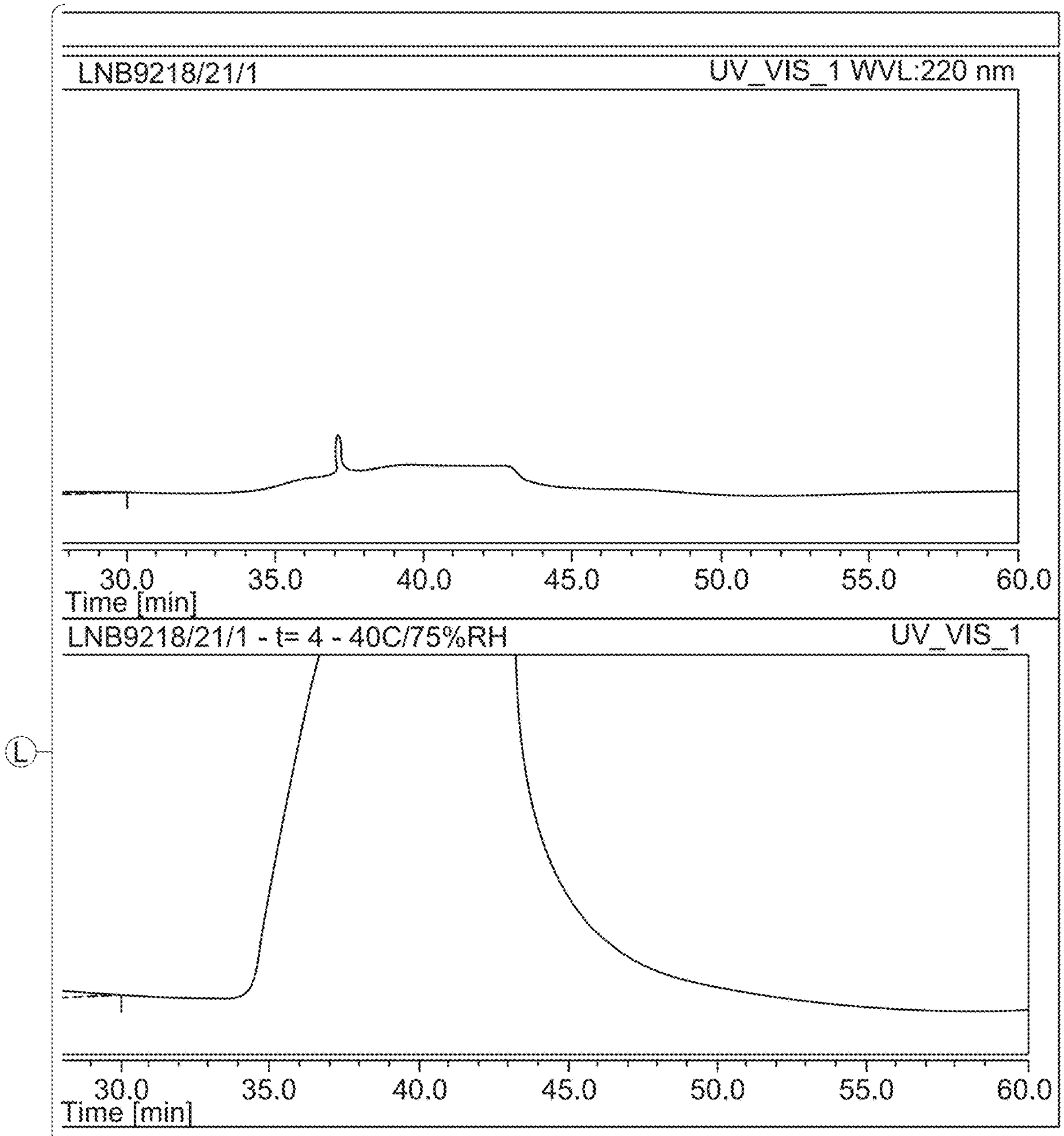

XRPD 2Θ diffractograms for eight-week timepoints are shown in FIG. 102 for pure pattern 1 and FIG. 103 for Pattern 2. Results show that the pure pattern 1 material that had previously converted to pattern 2 after two weeks, remained as pattern 2 after 8 weeks at 40° C./75% RH. There was no change in form observed for CHP pattern 2 after 8 weeks.

Appearance Testing

Table 33 and FIG. 115 show the appearance testing results of the 8-week stability study. Appearance of pure pattern 1 and pattern 2 remained consistent throughout the duration of the experiment.

TABLE 33

8-Week Stability Appearance Results Summary

| Input Pattern | Timepoint | Appearance |
|---|---|---|
| Pure Pattern 1 | Initial | Faint beige |
| Pure Pattern 1 | 2-week | Faint beige |
| Pure Pattern 1 | 4-week | Faint beige |
| Pure Pattern 1 | 8-week | Faint beige |
| Pattern 2 | Initial | White |
| Pattern 2 | 2-week | White |
| Pattern 2 | 4-week | White |
| Pattern 2 | 8-week | White |

Chiral HPLC

HPLC analysis confirmed that both pure pattern 1 and pattern 2 input samples were of high chiral purity. There was no change in chiral purity throughout the duration of the stability assessment. A results summary can be seen in Table 34. HPLC chromatograms are available in FIG. 104-FIG. 110.

TABLE 34

Chiral HPLC Results Summary

| Input Pattern | Timpoint | Chiral Purity (%) |
|---|---|---|
| Pure Pattern 1 | Initial | >99.9 |
| | 2-week | 99.9 |
| | 4-week | 99.9 |
| | 8-week | 99.9 |
| Pattern 2 | Initial | 99.9 |
| | 2-week | >99.9 |
| | 4-week | 99.9 |

1 Day Stability Assessment

Figure 111:
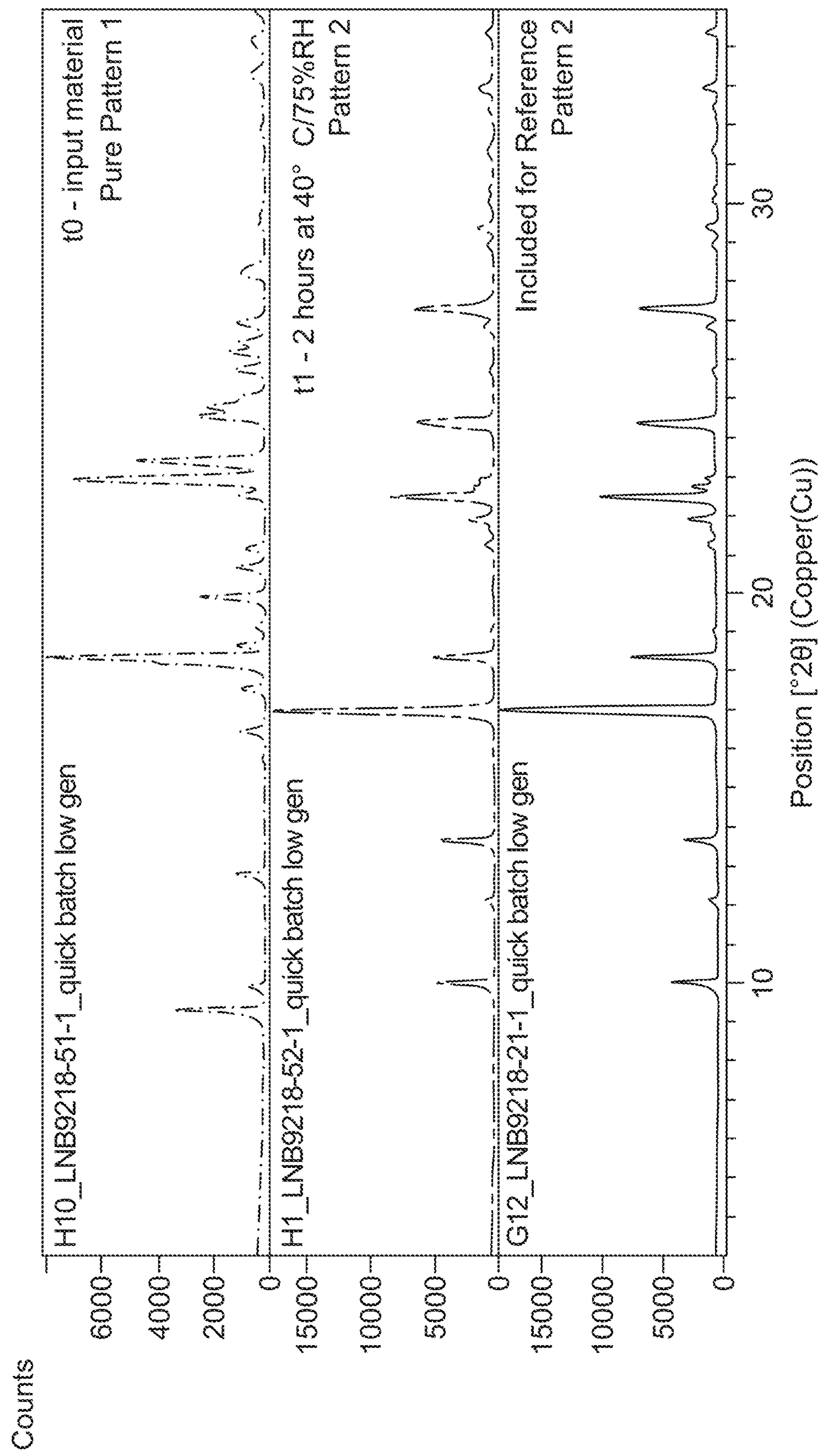
FIG. 111 is the XRPD results from storage at 40° C./75% RH.

XRPD results from storage at 40° C./75% RH are shown in FIG. 111. Pure pattern 1 was found to convert to pattern 2 after 2 hours at 40° C./75% RH. Original experiment included further timepoints at 4, 6 and 8 hours but as the material converted to pattern 2 after the first timepoint, the experiment was stopped after 2 hours.

Results Summary

1. Initial Characterization

The supplied material, CHP, was found to be crystalline by XRPD and birefringent with no clearly defined morphology by PLM. The material had several mass losses of 0.6, 0.2 and 0.3% by TG/DTA and was found to degrade when heated to 280° C. A melt was also observed at 170° C. DSC resulted in a small endothermic event at 75° C. which was due to solvent (water) loss. A second endothermic event was observed at 169° C. with a peak at 171° C. This was consistent with the melt seen in the TG/DT. No significant thermal events were observed in the cool cycle, but a weak glass transition was noted at 75° C. during the second heat cycle.

The DVS data showed a +6.3% change in mass from 60% RH to 90% RH indicating clear re-crystallization event. Post re-crystallization, the material appeared slightly hygroscopic with a maximum uptake of 0.8 wt. % between 0 and 90% RH. Post-DVS XRPD analysis confirmed a change in form. The diffractogram pattern produced post-DVS was assigned as Pattern 2 and was identified as a hydrated form of pattern 1. Post-DVS TG/DTA showed that the pattern 2 input material dehydrated on heating and lost 6.8 wt. % (0.95 equiv. water). This was followed by a re-crystallization, before the sample melted at 168° C. The temperature of this melt was consistent with the pattern 1 melt. The consistency of the melting point between the two samples implies that pattern 2 is a monohydrate and loses ca. 1 equiv. of water on heating before re-crystallizing to pattern 1.

NMR data was consistent with the supplied structure and showed no solvent content.

2. Solvent Solubility

Received CHP (Pattern 1) showed low solubility in most of solvent/solvent mixtures used in this study. High solubility was observed in methanol and ethanol with the approximate solubilities estimated between 100≥x≥50 mg/mL. The material was also observed to be soluble in water, DMSO, DMA, trifluoroethanol and both methanol/water mixtures. Pattern 2 was the only new crystalline form identified during this experiment (in addition to received pattern 1). Pattern 2 was returned from 17 solvent systems and Pattern 1 was seen only oncefrom 1-propanol. A mixture of pattern 1 and pattern 2 was noted from ethanol. THF returned amorphous material with some pattern 2 peaks.

3. Primary Polymorph Screen

The primary polymorph screen identified 1 new form of CHP, assigned as pure pattern 1 and was produced after temperature cycling. Pattern 1 and 2 were also reproduced in multiple solvent systems from temperature cycling. Crash cooling experiments at both 2-8° C. and −20° C. returned clear solutions only. The majority of solvent systems returned clear solutions in anti-solvent addition experiments but pattern 1 was seen from ethanol after addition of MtBE.

4. Secondary Polymorph Screen

The secondary polymorph screen saw the successful scale up of CHP pattern 2 from ethanol/water. Analysis of the material yielded the following results:

The material was crystalline by XRPD and matched that of the pattern 2 diffractograms obtained in the primary polymorph screen.

PLM images were also taken of CHP pattern 2 and the material was found to be birefringent with a fragmented, rod-like morphology.

Initial image taken at the beginning of the hot-stage microscopy experiment identified a rod-like morphology which was consistent with the pattern 2 PLM images. The material was observed to start melting at 95° C. and had fully melted at 101° C. A re-crystallization was observed to occur at 115° C. PLM images taken post-hot stage show that the material morphology was no longer clearly defined but the sample was still birefringent.

TG/DTA—TG analysis showed an initial weight loss of 6.5% followed by sample degradation at 280° C. The DT trace identified an endothermic event associated with the initial weight loss. This was followed by an exothermic event, most likely a re-crystallization of the material, before a second endotherm (sample melt) was observed at 170° C.

The initial heat cycle of the DSC identified an endothermic event with an onset of 99° C. and a peak at 102° C. This was consistent with the endotherm data observed in the TGA, although the re-crystallization event seen in the TGA was not present in the DSC. No thermal events were observed in the cool cycle, but a small glass transition was observed at 75° C. in the second heat cycle.

VT-/VH-XRPD analysis: Pattern 2 input material remained when the humidity was lowered to 0% at ambient temperature. As the temperature was increased to 80° C., the material changed form which was assigned as pure pattern 1. Pure pattern 1 remained when held at 80° C. for 80 minutes.

DVS analysis of CHP pattern 2 showed that the material did not change form from 40% RH to 90% RH or from 90% RH to 10% RH but lost 3.5 wt. % (0.5 equiv. water) below 10% RH. Rehydration was noted to occur from 0 to 90% RH. XRPD analysis post-DVS showed no change in form at 40% RH.

VT-DVS—Sample dehydrated below 10% RH at 40° C. and below 20% RH at 50 and 60° C. The material lost a higher percentage of water at each temperature increase but rehydrated from 0 to 40% RH in each experiment. A mixture of pattern 1 and 2 was seen by XRPD, post-VT-DVS.

HPLC purity of CHP pattern 2 was found to be 99.5%.

Pure pattern 1 was not successfully re-produced at heating to 80° C., with a mixture of pattern 1 and 2 being confirmed by XRPD. XRPD also identified a previously unseen peak at 8° 2 Θ once the sample was held at 50° C. for 90 minutes. This peak increased in intensity after 18 hours at 80° C. This peak was not seen in any other diffractogram produced in this study.

Successful re-preparation of pure pattern 1 was achieved by fast evaporation in ethanol/DCM.

5. 1-Week Stability Studies 1-week stability studies showed that pattern 2 displayed good chemical stability under the conditions assessed (40° C./75% RH, 80° C. and ambient light). No change in purity was observed for any sample after 7 days.

The elevated temperature of 80° C. resulted in a dehydration from pattern 2 to pattern 1 after 1 week but the material did remain as pattern 2 when stored at 40° C./75% RH and in ambient light.

6. 8-Week Stability Studies 8-week stability studies showed that pure pattern 1 material displayed poor physical stability at 40° C./75% RH, with the material converting to the hydrated pattern 2 after the first (two week) timepoint. Although the study was continued on the original samples, the material undergoing stability testing from the 2-week timepoint was pattern 2 rather than pattern 1, due to the poor stability of pure pattern 1 at this temperature and humidity. No change in appearance was noted at any of the timepoints tested, despite the change in form identified by XRPD.

Conversely, pattern 2 showed good physical stability with no change in form observed for the duration of the 8-week stability assessment. The appearance of the pattern 2 material did not change at any point through the experiment. Both pure pattern 1 and pattern 2 were found to be of high chiral purity at the beginning of the 8-week assessment and this remained high in all samples through the experiment duration.

7. 1-Day Stability Study 1-day stability assessment confirmed that pure pattern 1 material readily converts to pattern 2 in high humidity conditions. XRPD analysis confirmed that the form change occurred after only 2 hours at 40° C./75% RH.

8. pH Solubility Assessment pH solubility assessments for both CHP pattern 1 and pattern 2 found that dissolution occurred after the addition of 3 volumes of buffer at all pH values tested (pH 1, 4, 6.8 and 7.2). Solubility of pattern 1 and pattern 2 was estimated to be $500 \geq x \geq 333.3$ mg/mL.

e. Conclusion

Longer term 8-week stability studies on pattern 2 CHP, indicated good physical stability at 40° C./75% RH. XRPD analysis confirmed that pattern 2 prevailed throughout the duration of the 8-week assessment. Eight (8)-week stability studies on pure pattern 1 CHP, indicated poor physical stability at 40° C./75% RH. Pattern 2 is the most suitable form of CHP for further development.

Example 7—Stability Study

Purpose: To store and generate stability data for the Drug Substance, GMP mode.

Packaging: Sample at each individual time point was packaged into double Antistatic LDPE bags both secured with cable ties. The sample packed for the same storage condition were stored together within a fiber drum, and closed with metal lid. All packages were prepared in the same fashion and labeled. Details about the package material description is provided in Table 35.

TABLE 35

Package Material Description

| Item | Manufacturer | Batch No | Size |
|---|---|---|---|
| Antistatic LDPE Bag | Beyers Plastics N.V. | 18031413 | Length*Wide*Thickness cm = 22*10*0.0125 |
| Fiber Drum | VWR International | VWR Catalog #: 16465-149 | Inner Length × I.D. = 19.1 × 7.9– cm |

Note:
The antistatic LDPE bag was provided by STA, it will be cut into small one and heat sealed before used for stability study.

Time zero will be the day samples are placed on station. Initial testing results were from the release testing as long as samples are put on station within 30 days of the release test date, otherwise, initial was repeated. Stability protocol provided in Table 36.

TABLE 36

Stability protocol

| Storage Condition | Initial* | 1M | 3M | 6M | 12M | 24M | 36M | 48M | Reserve Bags | Total Bags |
|---|---|---|---|---|---|---|---|---|---|---|
| 25 ± 2° C./ 60 ± 5% RH | XY | — | X | X | XY | XY | XY | XY | 3 | 9 |
| 40 ± 2° C./ 75 ± 5% RH | | X | X | XY | — | — | — | — | 2 | 5 |

Test Items:

X = Pull the sample and test for Appearance, Assay and Impurities by HPLC, Chiral and Water Content.

Y = Pull the sample and test for XRPD

"—" = Not scheduled

Study Requirements: Total 22.5 g sample (Total 21 g sample if initial test is not needed):

1.5 g for initial test if needed;

21 g sample will be divided into 14 parts, 1.5 g for each parts, sample for each part should be weighed into double Antistatic LDPE bags both secured with cable ties. The stability samples for each storage condition are stored together within a fiber drum, closed with metal lid, and then stored at 25±2° C./60+5% RH (9 bags) and 40±2° C./75±5% RH (5 bags), respectively.

Sampling Time:

Samples stored not more than 6 months were pulled on schedule date or within 2 business days after the scheduled date. Samples stored more than 6 months were pulled within +2 business days of the scheduled date.

Sample Storage and Test Period Limitation:

Stability samples stored for one month to one year, and greater than one year were analyzed and completed within 10 and 20 business days after the samples pulled out from stability chamber, respectively. If time zero testing was performed, it was analyzed within 10 business days after study initiation.

Detailed information about the stability of Pattern 2 is provided in Table 37 and Table 38.

TABLE 37

6 Month stability result at 25° C./60% RH

| | | | |
|---|---|---|---|
| Project No.: | NMP-20180620 | Stability Protocol No.: | ST-C180726100-H-01, Revision 00 |
| Stability Sample/ Batch No.: | C180726100-H Batch No.: C180726100-H18001 | Specification: | ASU-SP-C180726100-H-01, Revision 00 |
| | | Stability Study Conditions: | 25∀2° C./60∀5% RH; 40∀2° C./75∀5% RH |
| Stability Start Date: | 28 Sep. 2018 | Report No.: | RP-C180726100-H-03, Revised 00 |

| Testing Items | Analytical Method | Acceptance Criteria | Initial*[1] | 40∀2EC/75∀5% RH 3M | 6M |
|---|---|---|---|---|---|
| Appearance | GM-036-AT | White to off-white powder | Off-white powder | Off-white powder | Off-white powder |
| Assay by HPLC* | AM-C180726100-H-01 | NLT 95.0% | 103.4% | 103.3% | 103.4% |
| Impurities, HPLC* | | H-His-OH#1.0%<br>Individual unspecified impurity#1.0%<br>Report each impurity∃0.05% by RRT or ID if known | 0.07%<br>Each other individual <0.05% | 0.08%<br>Each other individual <0.05% | 0.08%<br>Each other individual <0.05% |
| Chiral, HPLC* | AM-C180726100-H-03 | Chiral purity: NLT 98.0%<br>Chiral impurities: DL, LD, DD Optical isomers#1.0%<br>Report each∃0.1% impurities | 100.0%<br>(D, L):N.D<br>(L, D):N.D<br>(D, D):N.D | 100.0%<br>(D, L):N.D<br>(L, D):N.D<br>(D, D):N.D | 100.0%<br>(D, L):N.D<br>(L, D):N.D<br>(D, D):N.D |
| Water content (KF) | GM-016-KFT (Solvent: MeOH Titration reagent: Hydranal Composite 5, Sample weigh: 0.1 g) | Report result | 7.4% | 7.1% | 7.2% |
| XRPD* | GM-017-XRPD | Conform to reference standard of Pattern 2 (Bath No.: PS03027-15-H) | Conform to reference standard of Pattern 2 (Bath No.: PS03027-15-H) | Not applicable | Conform to reference standard of Pattern 2 (Bath No.: PS03027-15-H) |

*Note:

The reference standard (Batch No.: PS03027-15-H) was used for XRPD analysis. The reference standard (Batch No.: 1056491) was used for other chemical, respectively.

*[1]Note:

The data of initial was referred to the release COA of C180726100-H.

TABLE 38

6 Month stability result at 40° C./75% RH.

| | | | |
|---|---|---|---|
| Project No.: | NMP-20180620 | Stability Protocol No.: | ST-C180726100-H-01, Revision 00 |
| Stability Sample/ Batch No.: | C180726100-H Batch No.: C180726100-H18001 | Specification: | ASU-SP-C180726100-H-01, Revision 00 |
| | | Stability Study Conditions: | 25 ± 2° C./60 ± 5% HR; 40 ± 2° C./ 75 ± 5% RH |
| Stability Start Date: | 28 Sep. 2018 | Report No.: | RP-C180726100-H-03, Revision 00 |

| Testing Items | Analytical Method | Acceptance Criteria | Initial*[1] |
|---|---|---|---|
| Appearance | GM-036-AT | White to off-white powder | Off-white powder |
| Assay by HPLC* | AM-C180726100-H-01 | NLT 95.0% | 103.4% |
| Impurities, HPLC* | | H-His-OH ≤ 1.0% Individual unspecified impurity ≤ 1.0% Report each impurity ≥ 0.05% by RRT or ID if known | 0.07% Each other individual < 0.03% |
| Chiral, HPLC* | AM-C180726100-H-03 | Chiral purity: NLT 98.0% Chiral impurities: DL, LD, DD Optical isomers ≤ 1.0% Report each ≥ 0.1% impurities | 100.0% (D, L):N, D (L, D):N, D (D, D):N, D |
| Water content (KF) | GM-016-KFT (Solvent: MeOH Titration reagent: Hydranal Composite 5, Sample weigh: 0.1 g) | Report result | 7.4% |
| XRPD* | GM-017-XRPD | Conform to reference standard of Pattern 2 (Bath No.: PS03027-15-H) | Conform to reference standard of Pattern 2 (Bath No.: PS03027-15-H) |

| | 40 ± 2° C./75 ± 5% RH | | |
|---|---|---|---|
| Testing Items | 1M | 3M | 6M |
| Appearance | Off-white powder | Off-white powder | Off-white powder |
| Assay by HPLC* | 103.2% | 103.3% | 102.4% |
| Impurities, HPLC* | 0.08% Each other individual < 0.05% | 0.07% Each other individual < 0.05% | 0.06% C16081735-D-isomer: 0.05% |
| Chiral, HPLC* | 100.0% (D, L):N, D (L, D):N, D (D, D):N, D | 100.0% (D, L):N, D (L, D):N, D (D, D):N, D | 99.9% (D, L):N, D (L, D):0.5% (D, D):N, D |
| Water content (KF) | 7.2% | 7.2% | 7.2% |
| XRPD* | Not applicable | Not applicable | Conform to reference standard of Pattern 2 (Bath No.: PS03027-15-H) |

Figure 112:
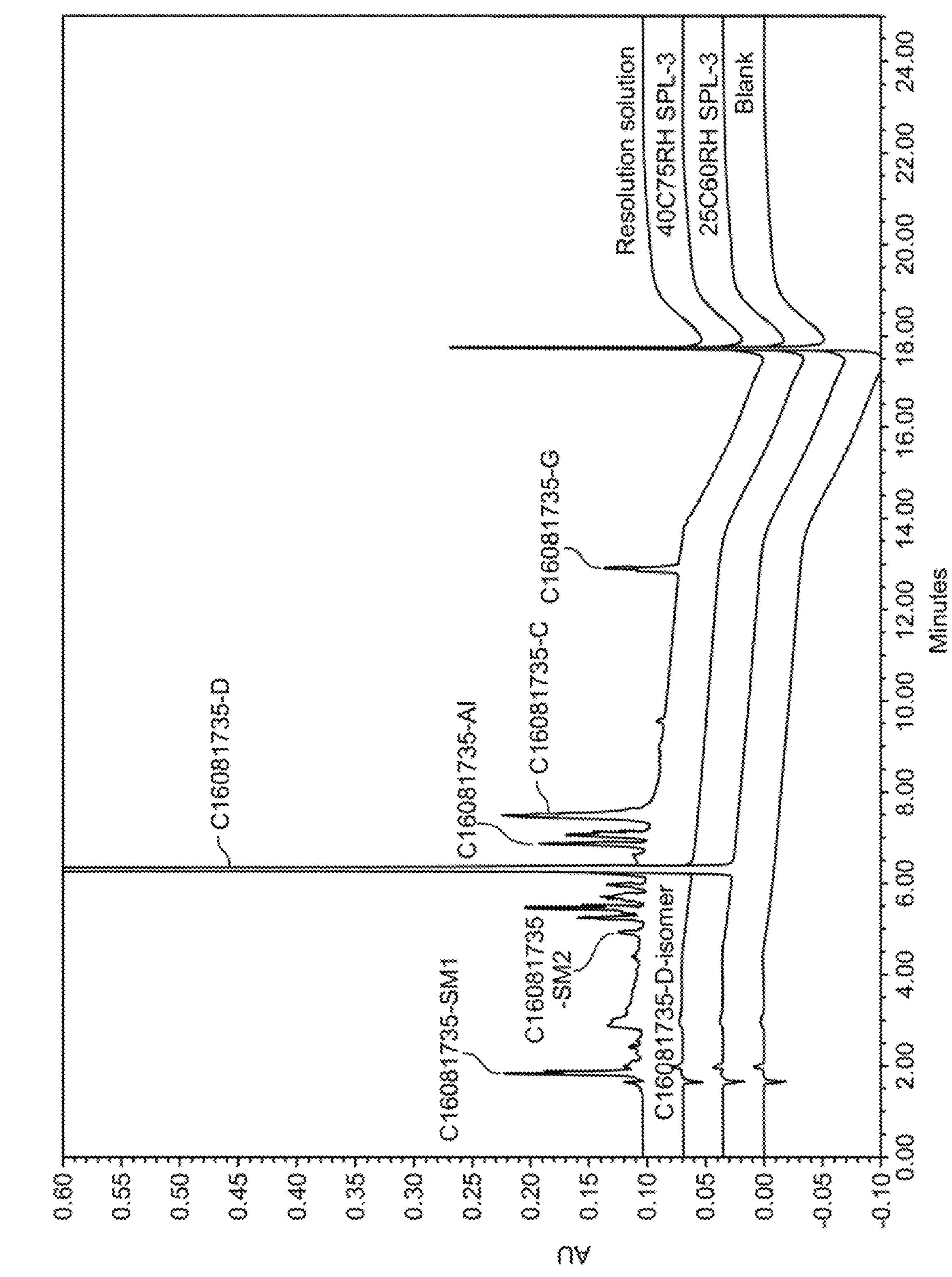
FIG. 112 is the representative overlaid chromatogram of blank, resolution solution and sample solution (6 M) for impurity test.

The result for the stability samples met the acceptance criteria of the specification. The representative overlaid chromatogram of blank, resolution solution and sample solution (6 M) for impurity test is provided in FIG. 112.

The embodiments described herein are intended to be exemplary. Persons skilled in the art will understand that variations and modifications may be made without departing from the scope of the invention encompassed by the claims below.

The invention claimed is:

1. A composition comprising a cyclo(-His-Pro) hydrate compound and a pharmaceutically acceptable carrier, said cyclo(-His-Pro) hydrate compound being characterized by an X-ray powder diffraction (XRPD) diffractogram comprising three or more peaks at 2θ values selected from the group consisting of 13.5°-13.9°, 16.9°-17.3°, 22.4°-22.6°, 24.1°–24.5°, and 27.2°-27.5°.

2. The composition of claim 1, wherein the XRPD diffractogram further comprises a peak at 2θ value at 17.9°-18.4°.

3. The composition of claim 1, wherein the XRPD diffractogram is substantially similar as shown in FIG. 2(*b*).

4. The composition of claim 1, wherein the cyclo(-His-Pro) hydrate compound comprises XRPD peaks at 2θ values at 13.5°-13.9°, 16.9°–17.3°, and 27.2°-27.5°.

5. The composition of claim 1, wherein the composition comprises about 1% to about 50% (w/w) of the cyclo(-His-Pro) hydrate compound based on the total weight of the composition.

6. The composition of claim 5, wherein the composition comprises about 1% to about 20% (w/w) of the cyclo(-His-Pro) hydrate compound.

7. The composition of claim 1, further comprising a metal or a metal compound wherein the metal is selected from the group consisting of copper, zinc, manganese, iron, cobalt, and chromium.

8. The composition of claim 7, wherein the metal is zinc.

9. The composition of claim 7, wherein the metal or metal compound is zinc element, zinc cation, zinc gluconate, zinc acetate, zinc sulfate, zinc picolinate, zinc orotate, or zinc citrate.

10. The composition of claim 1, which is lyophilized.

11. A method of treating a kidney disease in a subject in need thereof, comprising administering an effective amount of the composition comprising of claim 7 to the subject.

12. The method of claim 11, wherein the kidney disease is selected from the group consisting of acute kidney injury (AKI), chronic kidney disease (CKD), or kidney fibrosis.

13. The method of claim 11, wherein the composition is administered orally, topically, parenterally, intravenously, intradermally, colonically, rectally, intramuscularly, or intraperitoneally.

14. The method of claim 11, wherein the composition is formulated for parenteral administration by injection or continuous infusion.

15. The method of claim 11, wherein the composition further comprises a metal or a metal compound wherein the metal is selected from the group consisting of copper, zinc, manganese, iron, cobalt, and chromium.

16. The method of claim 15, wherein the metal is zinc.

17. The method of claim 15, wherein the metal or metal compound is zinc element, zinc cation, zinc gluconate, zinc acetate, zinc sulfate, zinc picolinate, zinc orotate, or zinc citrate.

18. The method of claim 11, wherein the composition is lyophilized.

* * * * *